(12) United States Patent
Watkins et al.

(10) Patent No.: US 7,279,549 B2
(45) Date of Patent: Oct. 9, 2007

(54) APHA-CONOTOXIN PEPTIDES

(75) Inventors: Maren Watkins, Salt Lake City, UT (US); Baldomero M. Olivera, Salt Lake City, UT (US); David R. Hillyard, Salt Lake City, UT (US); J. Michael McIntosh, Salt Lake City, UT (US); Robert M. Jones, Salt Lake City, UT (US)

(73) Assignees: The University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 320 days.

(21) Appl. No.: 10/895,372

(22) Filed: Jul. 21, 2004

(65) Prior Publication Data

US 2005/0032705 A1   Feb. 10, 2005

Related U.S. Application Data

(62) Division of application No. 09/493,795, filed on Jan. 28, 2000, now Pat. No. 6,797,808.

(60) Provisional application No. 60/118,381, filed on Jan. 29, 1999.

(51) Int. Cl.
*A61K 38/10* (2006.01)
*A61K 38/17* (2006.01)
*C07K 7/08* (2006.01)
*C07K 714/435* (2006.01)

(52) U.S. Cl. ............... 530/324; 514/12; 514/14; 530/327; 530/857

(58) Field of Classification Search ............ None
See application file for complete search history.

(56) References Cited

U.S. PATENT DOCUMENTS

| | | |
|---|---|---|
| 4,447,356 A | 5/1984 | Olivera et al. |
| 5,231,011 A | 7/1993 | Hillyard et al. |
| 5,432,155 A | 7/1995 | Olivera et al. |
| 5,514,774 A | 5/1996 | Olivera et al. |
| 5,595,972 A | 1/1997 | Olivera et al. |
| 5,670,622 A | 9/1997 | Shon et al. |
| 5,672,682 A | 9/1997 | Terlau et al. |
| 5,719,264 A | 2/1998 | Shon et al. |
| 5,739,276 A | 4/1998 | Shon et al. |
| 5,866,682 A | 2/1999 | McIntosh et al. |
| 5,889,147 A | 3/1999 | Cruz et al. |
| 5,969,096 A | 10/1999 | Shon et al. |

FOREIGN PATENT DOCUMENTS

| WO | WO9511256 A1 * | 4/1995 |
|---|---|---|
| WO | WO96/40211 A1 | 12/1996 |
| WO | WO98/22126 A1 | 5/1998 |

OTHER PUBLICATIONS

Result 8, Geneseq database search of Dec. 29, 2006, alignment of SEQ ID No. 244 with SEQ ID No. 12 of Oliveria et al., WO/95-11256 a1.*
Merriam-Webster Online Dictionary definition for "derivative," No. 4, http://m-w.com/dictionary/derivative, printed on Jan. 8, 2007.*
McIntosh, J.M. et al. (1999). *Ann Rev Biochem* 68:59-88.

* cited by examiner

*Primary Examiner*—Robert A. Wax
*Assistant Examiner*—Rosanne Kosson
(74) *Attorney, Agent, or Firm*—Rothwell, Figg, Ernst & Manbeck, P.C.

(57) ABSTRACT

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

8 Claims, No Drawings

APHA-CONOTOXIN PEPTIDES

CROSS-REFERENCE TO RELATED APPLICATION

The present application is a division of U.S. patent application Ser. No. 09/493,795 filed 28 Jan. 2000, now U.S. Pat. No. 6,797,808. U.S. patent application Ser. No. 09/493,795 is related to and claims priority under 35 U.S.C. § 119(e) to U.S. provisional patent application Ser. No. 60/118,381, filed 29 Jan. 1999. Each application is incorporated herein by reference.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The predatory cone snails (*Conus*) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these peptides are a large genus of venomous gastropods comprising approximately 500 species. All cone snail species are predators that inject venom to capture prey, and the spectrum of animals that the genus as a whole can envenomate is broad. A wide variety of hunting strategies are used; however, every *Conus* species uses fundamentally the same basic pattern of envenomation.

Several peptides isolated from *Conus* venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al., 1987). In addition, peptides named conantokins have been isolated from *Conus geographus* and *Conus tulipa* (Mena et al., 1990; Haack et al., 1990).

The α-conotoxins are small peptides highly specific for neuromuscular junction nicotinic acetylcholine receptors (Gray et al., 1981; Marshall and Harvey, 1990; Blount et al., 1992; Jacobsen et al., 1997) or highly specific for neuronal nicotinic acetylcholine receptors (Fainzilber et al., 1994; Johnson et al., 1995; Cartier et al., 1996; Luo et al., 1998). The α-conotoxins with specificity for neuromuscular junction nicotinic acetylcholine receptors are used as neuromuscular blocking agents for use in conjunction with surgery, as disclosed in U.S. patent application Ser. No. 09/488,799, filed 21 Jan. 2000, incorporated by reference herein. Additional α-conotoxins and uses for them have been described in U.S. Pat. Nos. 4,447,356 (Olivera et al., 1984); 5,432,155; 5,514,774, each incorporated herein by reference.

Additional uses for α-conotoxins are described in U.S. Ser. No. 09/219,446, filed 22 Dec. 1998, incorporated herein by reference. In this application, α-conotoxins with specificity for neuronal nicotinic acetylcholine receptors are used for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma.

It is desired to provide additional α-conotoxin peptides having uses as described herein.

SUMMARY OF THE INVENTION

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

More specifically, the present invention is directed to α-conotoxin peptides having the general formula I:

$Xaa_1$-$Xaa_2$-$Xaa_3$-$Xaa_4$-$Xaa_5$-Cys-Cys-$Xaa_6$-$Xaa_7$-$Xaa_8$-$Xaa_9$-Cys-$Xaa_{10}$-$Xaa_{11}$-$Xaa_{12}$-Cys-$Xaa_{13}$ (SEQ ID NO:1), wherein $Xaa_1$ is des-$Xaa_1$, Ile, Leu or Val; $Xaa_2$ is des-$Xaa_2$, Ala or Gly; $Xaa_3$ is des-$Xaa_3$, Gly, Trp (D or L), neo-Trp, halo-Trp or any unnatural aromatic amino acid; $Xaa_4$ is des-$Xaa_4$, Asp, Phe, Gly, Ala, Glu, γ-carboxy-Glu (Gla) or any unnatural aromatic amino acid; $Xaa_5$ is Glu, Gla, Asp, Ala, Thr, Ser, Gly, Ile, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_6$ is Ser, Thr, Arg, ornithine, homoarginine, Lys, N-methyl-Lys, N,N-dimethyl-Lys, N,N,N-trimethyl-Lys or any unnatural basic amino acid; $Xaa_7$ is Asp, Glu, Gla, Arg, ornithine, homoarginine, Lys, N-methyl-Lys, N,N-dimethyl-Lys, N,N,N-trimethyl-Lys or any unnatural basic amino acid; $Xaa_8$ is Ser, Thr, Asn, Ala, Gly, Arg, Lys, ornithine, homoarginine, N-methyl-Lys, N,N-dimethyl-Lys, N,N,N-trimethyl-Lys, any unnatural basic amino acid, His, halo-His, Pro or hydroxy-Pro; $Xaa_9$ is Thr, Ser, Ala, Asp, Asn, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_{10}$ is Gly, Ser, Thr, Ala, Asn, Arg, ornithine, homoarginine, Lys, N-methyl-Lys, N,N-dimethyl-Lys, N,N,N-trimethyl-Lys or any unnatural basic amino acid; $Xaa_{11}$ is Gln, Leu, His, halo-His, Trp (D or L), halo-Trp, neo-Trp, Tyr, nor-Tyr, mono-halo-Tyr, di-halo-Tyr, O-sulpho-Tyr, O-phospho-Tyr, nitro-Tyr, Arg, ornithine, homoarginine, Lys, N-methyl-Lys, N,N-dimethyl-Lys, N,N,N-trimethyl-Lys, any unnatural basic amino acid or any unnatural aromatic amino acid; $Xaa_{12}$ is Asn, His, halo-His, Ile, Leu, Val, Gln, Arg, ornithine, homoarginine, Lys, N-methyl-Lys, N,N-dimethyl-Lys, N,N, N-trimethyl-Lys or any unnatural basic amino acid; $Xaa_{13}$ is des-$Xaa_{13}$, Val, Ile, Leu, Arg, ornithine, homoarginine, Lys, N-methyl-Lys, N,N-dimethyl-Lys, N,N,N-trimethyl-Lys or any unnatural basic amino acid. The C-terminus may contain a free carboxyl group or an amide group. The halo is chlorine, bromine or iodine, preferably iodine for Tyr and His and preferably bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to α-conotoxin peptides having the general formula II:

$Xaa_1$-$Xaa_2$-$Xaa_3$-$Xaa_4$-Cys-Cys-$Xaa_5$-$Xaa_6$-$Xaa_7$-$Xaa_8$-Cys-$Xaa_9$-$Xaa_{10}$-$Xaa_{11}$-$Xaa_{12}$-$Xaa_{13}$-$Xaa_{14}$-Cys-$Xaa_{15}$-$Xaa_{16}$-$Xaa_{17}$ (SEQ ID NO:2), wherein $Xaa_1$ is des-$Xaa_1$, Asp, Glu or γ-carboxy-Glu (Gla); $Xaa_2$ is des-$Xaa_2$, Gln, Ala, Asp, Glu, Gla; $Xaa_3$ is des-$Xaa_3$, Gly, Ala, Asp, Glu, Gla, Pro or hydroxy-Pro; $Xaa_4$ is des-$Xaa_4$, Gly, Glu, Gla, Gln, Asp, Asn, Pro or hydroxy-Pro; $Xaa_5$ is Ser, Thr, Gly, Glu, Gla, Asn, Trp (D or L), neo-Trp, halo-Trp, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_6$ is Asp, Asn, His, halo-His, Thr, Ser, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_7$ is Pro or hydroxy-Pro; $Xaa_8$ is Ala, Ser, Thr, Asp, Val, Ile, Pro, hydroxy-Pro, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_9$ is Gly, Ile, Leu, Val, Ala, Thr, Ser, Pro, hydroxy-Pro, Phe, Trp (D or L), neo-Trp, halo-Trp, Arg, ornithine, homoarginine, Lys, N-methyl-Lys, N,N-dimethyl-Lys, N,N,N-trimethyl-Lys, any unnatural basic amino acid or any unnatural aromatic amino acid; $Xaa_{10}$ is Ala, Asn, Phe, Pro, hydroxy-Pro, Glu, Gla, Gln, His, halo-His, Val, Ser, Thr, Arg, ornithine, homoarginine, Lys, N-methyl-Lys, N,N-dimethyl-Lys, N,N,N-trimethyl-Lys or any unnatural basic amino acid; $Xaa_{11}$ is Thr, Ser, His, halo-His, Leu, Ile, Val, Asn, Met, Pro, hydroxy-Pro, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{12}$ is Asn, Pro, hydroxy-Pro, Gln, Ser, Thr, Arg, ornithine, homoarginine, Lys, N-methyl-Lys, N,N-dimethyl-Lys N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{13}$ is des-$Xaa_{13}$, Gly, Thr, Ser, Pro, hydroxy-Pro, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{14}$ is des-$Xaa_{14}$, Ile, Val, Asp, Leu, Phe, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; and $Xaa_{15}$ is des-$Xaa_{15}$, Gly, Ala, Met, Ser, Thr, Trp (D or L), neo-Trp, halo-Trp, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_{16}$ is des-$Xaa_{16}$, Trp (D or L), neo-Trp, halo-Trp, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_{17}$ is des-$Xaa_{17}$, Arg, ornithine, homoarginine, Lys, N-methyl-Lys, N,N-dimethyl-Lys, N,N,N-trimethyl-Lys or any unnatural basic amino acid. The C-terminus may contain a free carboxyl group or an amide group. The halo is preferably bromine, chlorine or iodine, more preferably iodine for His or Tyr and bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to α-conotoxin peptides having the general formula III:

$Xaa_1$-$Xaa_2$-$Xaa_3$-$Xaa_4$-$Xaa_5$-Cys-Cys-$Xaa_6$-$Xaa_7$-$Xaa_8$-$Xaa_9$-Cys-$Xaa_{10}$-$Xaa_{11}$-$Xaa_{12}$-$Xaa_{13}$-$Xaa_{14}$-$Xaa_{15}$-$Xaa_{16}$-Cys-$Xaa_{17}$-$Xaa_{18}$-$Xaa_{19}$-$Xaa_{20}$-$Xaa_{21}$-$Xaa_{22}$-$Xaa_{23}$-$Xaa_{24}$ (SEQ ID NO:3), wherein $Xaa_1$ is des-$Xaa_1$, Ser or Thr; $Xaa_2$ is des-$Xaa_2$, Asp, Glu, γ-carboxy-Glu (Gla), Asn, Ser or Thr; $Xaa_3$ is des-$Xaa_3$, Ala, Gly, Asn, Ser, Thr, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_4$ is des-$Xaa_4$, Ala, Val, Leu, Ile, Gly, Glu, Gla, Gln, Asp, Asn, Phe, Pro, hydroxy-Pro or any unnatural aromatic amino acid; $Xaa_5$ is des-$Xaa_5$, Thr, Ser, Asp, Glu, Gla, Gln, Gly, Val, Asp, Asn, Ala, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_6$ is Thr, Ser, Asp, Asn, Met, Val, Ala, Gly, Leu, Ile, Phe, any unnatural aromatic amino acid, Pro, hydroxy-Pro, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_7$ is Ile, Leu, Val, Ser, Thr, Gln, Asn, Asp, Arg, His, halo-His, Phe, any unnatural aromatic amino acid, homoarginine, ornithine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_8$ is Pro, hydroxy-Pro, Ser, Thr, Ile, Asp, Leu, Val, Gly, Ala, Phe, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_9$ is Val, Ala, Gly, Ile, Leu, Asp, Ser, Thr, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_{10}$ is His, halo-His, Arg, homoarginine, ornithine, Lys, N-methyl-Lys, N,N-dimethyl-Lys, N,N,N-trimethyl-Lys, any unnatural basic amino acid, Asn, Ala, Ser, Thr, Phe, Ile, Leu, Gly, Trp (D or L), neo-Trp, halo-Trp, any unnatural aromatic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{11}$ is Leu, Gln, Val, Ile, Gly, Met, Ala, Lys, N-methyl-Lys, N,N-dimethyl-Lys, N,N,N-trimethyl-Lys, Ser, Thr, Arg, homoarginine, ornithine, any unnatural basic amino acid, Asn, Glu, Gla, Gln, Phe, Trp (D or L), neo-Trp, halo-Trp or any unnatural aromatic amino acid; $Xaa_{12}$ is Glu, Gla, Gln, Asn, Asp, Pro, hydroxy-Pro, Ser, Gly, Thr, Lys, N-methyl-Lys, N,N-dimethyl-Lys, N,N,N-trimethyl-Lys, Arg, homoarginine, ornithine, any unnatural basic amino acid, Phe, His, halo-His, any unnatural aromatic amino acid, Leu, Met, Gly, Ala, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{13}$ is His, halo-His, Asn, Thr, Ser, Ile, Val, Leu, Phe, any unnatural aromatic amino acid, Arg, homoarginine, ornithine, Lys, N-methyl-Lys, N,N-dimethyl-Lys, N,N,N-trimethyl-Lys, any unnatural basic amino acid, Tyr, nor-Try, mono-halo-Tyr, di-halo-Tyr, O-sulpho-Tyr, O-phospho-Tyr, nitro-Tyr or any unnatural hydroxy containing amino acid; $Xaa_4$ is Ser, Thr, Ala, Gln, Pro, hydroxy-Pro, Gly, Ile, Leu, Arg, ornithine, homoarginine, Lys, N-methyl-Lys, N,N-dimethyl-Lys, N,N,N-trimethyl-Lys or any unnatural basic amino acid; $Xaa_{15}$ is Asn, Glu, Gla, Asp, Gly, His, halo-His, Ala, Leu, Gln, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{16}$ is Met, Ile, Thr, Ser, Val, Leu, Pro, hydroxy-Pro, Phe, any unnatural aromatic amino acid, Tyr, nor-Tyr, mono-halo-Tyr, di-halo-Tyr, O-sulpho-Tyr, O-phospho-Tyr, nitro-Tyr, any unnatural hydroxy containing amino acid, Glu, Gla, Ala, His, halo-His, Arg, ornithine, homoarginine, Lys, N-methyl-Lys, N,N-dimethyl-Lys, N,N,N-trimethyl-Lys or any unnatural basic amino acid; $Xaa_{17}$ is des-$Xaa_{17}$, Gly, Asp, Asn, Ala, Ile, Leu, Ser, Thr, His, halo-His, Arg, ornithine, homoarginine, Lys, N-methyl-Lys, N,N-dimethyl-Lys, N,N,N-trimethyl-Lys or any unnatural basic amino acid; $Xaa_{18}$ is des-$Xaa_{18}$, Gly, Glu, Gla, Gln, Trp (D or L), neo, halo-Trp, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_{19}$ is des-$Xaa_{19}$, Ser, Thr, Val, Ile, Ala, Arg, ornithine, homoarginine, Lys, N-methyl-Lys, N,N-dimethyl-Lys, N,N,N-trimethyl-Lys or any unnatural basic amino acid; $Xaa_{20}$ is des-$Xaa_{20}$, Val, Asp, His, halo-His, Arg, ornithine, homoarginine, Lys, N-methyl-Lys, N,N-dimethyl-Lys, N,N,N-trimethyl-Lys or any unnatural basic amino acid; $Xaa_{21}$ is des-$Xaa_{21}$, Asn, Pro or hydroxy-Pro; $Xaa_{22}$ is des-$Xaa_{22}$, Arg, ornithine, homoarginine, Lys, N-methyl-Lys, N,N-dimethyl-Lys, N,N,N-trimethyl-Lys or any unnatural basic amino acid; $Xaa_{23}$ is des-$Xaa_{23}$, Ser or Thr; $Xaa_{24}$ is des-$Xaa_{24}$, Leu, Ile or Val; with the proviso that (a) $Xaa_5$ is not Gly, when $Xaa_1$ is des-$Xaa_1$, $Xaa_2$ is des-$Xaa_2$, $Xaa_3$ is des-$Xaa_3$, $Xaa_4$ is des-$Xaa_4$, $Xaa_6$ is Ser, $Xaa_7$ is His, $Xaa_8$ is Pro, $Xaa_9$ is Ala, $Xaa_{10}$ is Ser, $Xaa_{11}$ is Val, $Xaa_{12}$ is Asn, $Xaa_{13}$ is Asn, $Xaa_{14}$ is Pro, $Xaa_{15}$ is Asp, $Xaa_{16}$ is Ile, $Xaa_{17}$ is des-$Xaa_{17}$, $Xaa_{18}$ is des-$Xaa_{18}$, $Xaa_{19}$ is des-$Xaa_{19}$, $Xaa_{20}$ is des-$Xaa_{20}$, $Xaa_{21}$ is des-$Xaa_{21}$, $Xaa_{22}$ is des-$Xaa_{22}$, $Xaa_{23}$ is des-$Xaa_{23}$, and $Xaa_{24}$ is des-$Xaa_{24}$. The C-terminus may contain a free carboxyl group or an amide group. The halo is preferably bromine, chlorine or iodine, more preferably iodine for His and Tyr and bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

The present invention is also directed to novel specific α-conotoxin peptides of general formula I having the formulas:

```
Asp-Xaa1-Cys-Cys-Ser-Asp-Ser-Arg-      (SEQ ID NO:4)
Cys-Gly-Xaa2-Asn-Cys-Leu;

Ala-Cys-Cys-Ser-Asp-Arg-Arg-Cys-Arg-   (SEQ ID N

The present invention is further directed to novel specific α-conotoxin peptides of general formula II having the formulas:

Cys-Cys-Ser-Asp-Xaa$_5$-Ala-Cys-Xaa$_2$-Gln-Thr-Xaa$_5$-Gly-Cys-Arg;   (SEQ ID NO:13)

Cys-Cys-Xaa$_1$-Asn-Xaa$_5$-Ala-Cys-Arg-His-Thr-Gln-Gly-Cys;   (SEQ ID NO:14)

Gly-Cys-Cys-Xaa$_3$-His-Xaa$_5$-Ala-Cys-Gly-Arg-His-Xaa$_4$-Cys;   (SEQ ID NO:15)

Ala-Xaa$_5$-Cys-Cys-Asn-Asn-Xaa$_5$-Ala-Cys-Val-Xaa$_2$-His-Arg-Cys;   (SEQ ID NO:16)

Ala-Xaa$_5$-Gly-Cys-Cys-Asn-Asn-Xaa$_5$-Ala-Cys-Val-Xaa$_2$-His-Arg-Cys;   (SEQ ID NO:17)

Xaa$_5$-Xaa$_5$-Cys-Cys-Asn-Asn-Xaa$_5$-Ala-Cys-Val-Xaa$_2$-His-Arg-Cys;   (SEQ ID NO:18)

Asp-Xaa$_1$-Asn-Cys-Cys-Xaa$_3$-Asn-Xaa$_5$-Ser-Cys-Xaa$_5$-Arg-Xaa$_5$-Arg-Cys-Thr;   (SEQ ID NO:19)

Gly-Cys-Cys-Ser-Thr-Xaa$_5$-Xaa$_5$-Cys-Ala-Val-Leu-Xaa$_4$-Cys;   (SEQ ID NO:20)

Gly-Cys-Cys-Gly-Asn-Xaa$_5$-Asp-Cys-Thr-Ser-His-Ser-Cys;   (SEQ ID NO:21)

Gly-Cys-Cys-Ser-Asn-Xaa$_5$-Xaa$_5$-Cys-Ala-His-Asn-Asn-Xaa$_5$-Asp-Cys-Arg;   (SEQ ID NO:42)

Gly-Cys-Cys-Xaa$_4$-Asn-Xaa$_5$-Val-Cys-Xaa$_2$-Xaa$_2$-Xaa$_4$-Xaa$_4$-Cys-Xaa$_3$-Xaa$_2$;   (SEQ ID NO:154)

Xaa$_6$-Xaa$_1$-Xaa$_5$-Gly-Cys-Cys-Arg-His-Xaa$_5$-Ala-Cys-Gly-Xaa$_2$-Asn-Arg-Cys;   (SEQ ID NO:155)

Cys-Cys-Ala-Asp-Xaa$_5$-Asp-Cys-Arg-Phe-Arg-Xaa$_5$-Gly-Cys;   (SEQ ID NO:156)

Gly-Cys-Cys-Xaa$_4$-Asn-Xaa$_5$-Ser-Cys-Xaa$_3$-Xaa$_5$-Xaa$_2$-Thr-Xaa$_4$-Cys-Ser-Xaa$_3$-Xaa$_2$;   (SEQ ID NO:157)

Cys-Cys-Ser-Asn-Xaa$_5$-Thr-Cys-Xaa$_2$-Xaa$_1$-Thr-Xaa$_4$-Gly-Cys;   (SEQ ID NO:158)

Cys-Cys-Ala-Asn-Xaa$_5$-Ile-Cys-Xaa$_2$-Asn-Thr-Xaa$_5$-Gly-Cys;   (SEQ ID NO:159)

Cys-Cys-Asn-Asn-Xaa$_5$-Thr-Cys-Xaa$_2$-Xaa$_1$-Thr-Xaa$_4$-Gly-Cys;   (SEQ ID NO:160)

Cys-Cys-Ser-Asn-Xaa$_5$-Val-Cys-Xaa$_2$-Xaa$_1$-Thr-Xaa$_4$-Gly-Cys;   (SEQ ID NO:161)

Gly-Gly-Cys-Cys-Ser-Xaa$_4$-Xaa$_5$-Xaa$_5$-Cys-Ile-Ala-Ser-Asn-Xaa$_5$-Xaa$_2$-Cys-Gly;   (SEQ ID NO:162)

Gly-Cys-Cys-Ser-His-Xaa$_5$-Val-Cys-Ser-Ala-Met-Ser-Xaa$_5$-Ile-Cys;   (SEQ ID NO:163)

Gly-Cys-Cys-Xaa$_2$-Asn-Xaa$_5$-Xaa$_4$-Cys-Gly-Ala-Ser-Xaa$_2$-Thr-Xaa$_4$-Cys;   (SEQ ID NO:164)

Gly-Cys-Cys-Ser-Xaa$_4$-Xaa$_5$-Xaa$_5$-Cys-Phe-Ala-Thr-Asn-Xaa$_5$-Asp-Cys;   (SEQ ID NO:165)

Gly-Gly-Cys-Cys-Ser-Xaa$_4$-Xaa$_5$-Xaa$_5$-Cys-Ile-Ala-Asn-Asn-Xaa$_5$-Leu-Cys-Ala;   (SEQ ID NO:166)

Gly-Gly-Cys-Cys-Ser-Xaa$_4$-Xaa$_5$-Xaa$_5$-Cys-Ile-Ala-Asn-Asn-Xaa$_5$-Phe-Cys-Ala;   (SEQ ID NO:167)

Asp-Cys-Cys-Ser-Asn-Xaa$_5$-Xaa$_5$-Cys-Ser-Gln-Asn-Asn-Xaa$_5$-Asp-Cys-Met;   (SEQ ID NO:168)

and

Asp-Cys-Cys-Ser-Asn-Xaa$_5$-Xaa$_5$-Cys-Ala-His-Asn-Asn-Xaa$_5$-Asp-Cys-Arg,   (SEQ ID NO:169)

wherein Xaa$_1$ is Glu or γ-carboxy-Glu (Gla); Xaa$_2$ is Lys, N-methyl-Lys, N,N-dimethyl-Lys or N,N,N-trimethyl-Lys; Xaa$_3$ is Trp (D or L), halo-Trp or neo-Trp; Xaa$_4$ is Tyr, nor-Tyr, mono-halo-Tyr, di-halo-Tyr, O-sulpho-Tyr, O-phospho-Tyr or nitro-Tyr; and Xaa$_5$ is Pro or hydroxy-Pro; and the C-terminus contains a carboxyl or amide group. The halo is preferably bromine, chlorine or iodine, more preferably iodine for Tyr and bromine for Trp. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe and Trp residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides of general formula II:

Sn1.1: SEQ ID NO: 13, wherein Xaa$_2$ is Lys and Xaa$_5$ is Pro;
Sn1.2: SEQ ID NO: 14, wherein Xaa$_1$ is Glu and Xaa$_5$ is Pro;
Sl1.3: SEQ ID NO: 15, wherein Xaa$_3$ is Trp, Xaa$_4$ is Tyr and Xaa$_5$ is Pro;
A1.2: SEQ ID NO: 16, wherein Xaa$_2$ is Lys and Xaa$_5$ is Pro;
Bu1.1: SEQ ID NO: 17, wherein Xaa$_2$ is Lys and Xaa$_5$ is Pro;
Bu1.2: SEQ ID NO: 18, wherein Xaa$_2$ is Lys and Xaa$_5$ is Pro;
Bu1.3: SEQ ID NO: 19, wherein Xaa$_1$ is Glu, Xaa$_3$ is Trp and Xaa$_5$ is Pro;
Bu1.4: SEQ ID NO: 20, wherein Xaa$_4$ is Tyr and Xaa$_5$ is Pro;
Cr1.3: SEQ ID NO: 21, wherein Xaa$_5$ is Pro;
Di1.1: SEQ ID NO: 42 wherein Xaa$_5$ is Pro;
Ms1.7: SEQ ID NO: 154, wherein Xaa$_2$ is Lys, Xaa$_3$ is Trp, Xaa$_4$ is Tyr and Xaa$_5$ is Pro;
P1.7: SEQ ID NO: 155, wherein Xaa$_1$ is Glu, Xaa$_2$ is Lys, Xaa$_5$ is Pro and Xaa$_6$ is Gln;
Ms1.2: SEQ ID NO: 156, wherein Xaa$_5$ is Pro;
Ms1.3: SEQ ID NO: 157, wherein Xaa$_2$ is Lys, Xaa$_3$ is Trp, Xaa$_4$ is Tyr and Xaa$_5$ is Pro;
Ms1.4: SEQ ID NO: 158, wherein Xaa$_1$ is Glu, Xaa$_2$ is Lys, Xaa$_4$ is Tyr and Xaa$_5$ is Pro;
Ms1.5: SEQ ID NO: 159, wherein Xaa$_2$ is Lys and Xaa$_5$ is Pro;
Ms1.8: SEQ ID NO: 160, wherein Xaa$_1$ is Glu, Xaa$_2$ is Lys, Xaa$_4$ is Tyr and Xaa$_5$ is Pro;
Ms1.9: SEQ ID NO: 161, wherein Xaa$_1$ is Glu, Xaa$_2$ is Lys, Xaa$_4$ is Tyr and Xaa$_5$ is Pro;
Bt1.7: SEQ ID NO: 162, wherein Xaa$_2$ is Lys, Xaa$_4$ is Tyr and Xaa$_5$ is Pro;
Lv1.5: SEQ ID NO: 163, wherein Xaa$_5$ is Pro;
Ms1.10: SEQ ID NO: 164, wherein Xaa$_2$ is Lys, Xaa$_4$ is Tyr and Xaa$_5$ is Pro;
Om1.1: SEQ ID NO: 165, wherein Xaa$_4$ is Tyr and Xaa$_5$ is Pro;
R1.6: SEQ ID NO: 166, wherein Xaa$_4$ is Tyr and Xaa$_5$ is Pro;
R1.7: SEQ ID NO: 167, wherein Xaa$_4$ is Tyr and Xaa$_5$ is Pro;
Vr1.1: SEQ ID NO: 168, wherein Xaa$_5$ is Pro; and
Vr1.2: SEQ ID NO: 169, wherein Xaa$_5$ is Pro.

The C-terminus preferably contains a carboxyl group for the peptides Sn1.1, Sn1.2, Cr1.3, Di1.1, Ms1.2, Ms1.4, Ms1.5, Ms1.8, Ms1.9, Vr1.1 and Vr1.2. The C-terminus of the other peptides preferably contains an amide group.

The present invention is also directed to novel specific α-conotoxin peptides of general formula III having the formulas:

Gly-Cys-Cys-Ser-Asn-Xaa$_5$-Val-Cys-His-Leu-Xaa$_1$-His-Ser-Asn-Met-Cys; (SEQ ID NO:22)

Gly-Cys-Cys-Ser-Asn-Xaa$_5$-Val-Cys-Arg-Gln-Asn-Asn-Ala-Xaa$_1$-Xaa$_4$-Cys-Arg; (SEQ ID NO:23)

Xaa$_5$-Gln-Cys-Cys-Ser-His-Xaa$_5$-Ala-Cys-Asn-Val-Asp-His-Xaa$_5$-Xaa$_1$-Ile-Cys-Arg; (SEQ ID NO:24)

Xaa$_5$-Xaa$_1$-Cys-Cys-Ser-His-Xaa$_5$-Ala-Cys-Asn-Val-Asp-His-Xaa$_5$-Xaa$_1$-Ile-Cys-Arg; (SEQ ID NO:25)

Xaa$_5$-Gln-Cys-Cys-Ser-His-Xaa$_5$-Ala-Cys-Asn-Val-Asp-His-Xaa$_5$-Xaa$_1$-Ile-Cys-Asp; (SEQ ID NO:26)

Xaa$_5$-Arg-Cys-Cys-Ser-His-Xaa$_5$-Ala-Cys-Asn-Val-Asp-His-Xaa$_5$-Xaa$_1$-Ile-Cys-Arg; (SEQ ID NO:27)

Xaa$_5$-Gln-Cys-Cys-Ser-His-Xaa$_5$-Ala-Cys-Asn-Val-Asp-His-Xaa$_5$-Gly-Ile-Cys-Arg; (SEQ ID NO:28)

Xaa$_5$-Gln-Cys-Cys-Ser-His-Xaa$_5$-Ala-Cys-Asn-Val-Asp-His-Xaa$_5$-Xaa$_1$-Thr-Cys-Arg; (SEQ ID NO:29)

Xaa$_5$-Gln-Cys-Cys-Ser-His-Xaa$_5$-Ala-Cys-Asn-Val-Asp-His-Xaa$_5$-Xaa$_1$-Val-Cys-Arg; (SEQ ID NO:30)

Xaa$_5$-Gln-Cys-Cys-Ser-His-Xaa$_5$-Ala-Cys-Asn-Ile-Asp-His-Xaa$_5$-Xaa$_1$-Ile-Cys-Arg; (SEQ ID NO:31)

Xaa$_5$-Gln-Cys-Cys-Ser-His-Xaa$_5$-Ala-Cys-Asn-Val-Asp-His-Xaa$_5$-Xaa$_1$-Ile-Cys-Arg-Arg-Arg-Arg; (SEQ ID NO:32)

Gly-Gly-Cys-Cys-Ser-His-Xaa$_5$-Ala-Cys-Ala-Val-Asn-His-Xaa$_5$-Xaa$_1$-Leu-Cys; (SEQ ID NO:33)

Gly-Cys-Cys-Ser-His-Xaa$_5$-Ala-Cys-Ser-Val-Asn-His-Xaa$_5$-Xaa$_1$-Leu-Cys; (SEQ ID NO:34)

Gly-Cys-Cys-Ser-His-Xaa$_5$-Ala-Cys-Asn-Val-Asp-His-Xaa$_5$-Xaa$_1$-Ile-Cys; (SEQ ID NO:35)

Gly-Cys-Cys-Ser-His-Xaa$_5$-Ala-Cys-Ser-Gly-Xaa$_2$-Thr-Gln-Xaa$_1$-Xaa$_5$-Cys-Arg-Xaa$_1$-Ser; (SEQ ID NO:36)

Xaa$_5$-Cys-Cys-Ser-His-Xaa$_5$-Ala-Cys-Ser-Gly-Asn-Asn-Xaa$_5$-Xaa$_1$-Phe-Cys-Arg-Gln; (SEQ ID NO:37)

Gly-Cys-Cys-Ser-His-Xaa$_5$-Ala-Cys-Ser-Gly-Asn-Asn-Xaa$_5$-Xaa$_1$-Phe-Cys-Arg-Gln; (SEQ ID NO:38)

Gly-Cys-Cys-Ser-His-Xaa$_5$-Xaa$_5$-Cys-Ala-Met-Asn-Asn-Xaa$_5$-Asp-Xaa$_4$-Cys; (SEQ ID NO:39)

Gly-Cys-Cys-Ser-His-Xaa$_5$-Xaa$_5$-Cys-Phe-Leu-Asn-Asn-Xaa$_5$-Asp-Xaa$_4$-Cys; (SEQ ID NO:40)

-continued

Gly-Cys-Cys-Ser-Asn-Xaa₅-Xaa₅-Cys-Ile-Ala-Xaa₂-Asn-Xaa₅-His-Met-Cys-Gly;  (SEQ ID NO:41)

Gly-Cys-Cys-Ser-Asn-Xaa₅-Ala-Cys-Ala-Gly-Asn-Asn-Xaa₅-His-Val-Cys-Arg-Gln;  (SEQ ID NO:43)

Gly-Cys-Cys-Ser-Arg-Xaa₅-Ala-Cys-Ile-Ala-Asn-Asn-Xaa₅-Asp-Leu-Cys;  (SEQ ID NO:44)

Gly-Cys-Cys-Ser-Asn-Xaa₅-Val-Cys-His-Val-Xaa₁-His-Xaa₅-Xaa₁-Leu-Cys-Arg-Arg-Arg;  (SEQ ID NO:45)

Gly-Gly-Cys-Cys-Ser-Phe-Xaa₅-Ala-Cys-Arg-Xaa₂-Xaa₅-Arg-Xaa₅-Xaa₁-Met-Cys-Gly;  (SEQ ID NO:46)

Xaa₅-Xaa₁-Cys-Cys-Ser-Asp-Xaa₅-Arg-Cys-Asn-Ser-Ser-His-Xaa₅-Xaa₁-Leu-Cys-Gly;  (SEQ ID NO:47)

Xaa₅-Gln-Cys-Cys-Ser-Asp-Xaa₅-Arg-Cys-Asn-Val-Gly-His-Xaa₅-Xaa₁-Leu-Cys-Gly;  (SEQ ID NO:48)

Xaa₆-Val-Cys-Cys-Ser-Asp-Xaa₅-Arg-Cys-Asn-Val-Gly-His-Xaa₅-Xaa₁-Ile-Cys-Gly;  (SEQ ID NO:49);

Gly-Cys-Cys-Ser-Arg-Xaa₅-Xaa₅-Cys-Ile-Ala-Asn-Asn-Xaa₅-Asp-Leu-Cys;  (SEQ ID NO:50)

Xaa₅-Gln-Cys-Cys-Ser-His-Leu-Ala-Cys-Asn-Val-Asp-His-Xaa₅-Xaa₁-Ile-Cys-Arg;  (SEQ ID NO:51)

Gly-Cys-Cys-Ser-Xaa₄-Phe-Asp-Cys-Arg-Met-Met-Phe-Xaa₅-Xaa₁-Met-Cys-Gly-Xaa₃-Arg;  (SEQ ID NO:52)

Gly-Gly-Cys-Cys-Ser-Phe-Ala-Ala-Cys-Arg-Xaa₂-Xaa₄-Arg-Xaa₅-Xaa₁-Met-Cys-Gly;  (SEQ ID NO:53)

Gly-Gly-Cys-Cys-Phe-His-Xaa₅-Val-Cys-Xaa₄-Ile-Asn-Leu-Leu-Xaa₁-Met-Cys-Arg-Gln-Arg;  (SEQ ID NO:54)

Ser-Ala-Thr-Cys-Cys-Asn-Xaa₄-Xaa₅-Xaa₅-Cys-Xaa₄-Xaa₁-Thr-Xaa₄-Xaa₅-Xaa₁-Ser-Cys-Leu;  (SEQ ID NO:55)

Ala-Cys-Cys-Ala-Xaa₄-Xaa₅-Xaa₅-Cys-Phe-Xaa₁-Ala-Xaa₄-Xaa₅-Xaa₁-Arg-Cys-Leu;  (SEQ ID NO:56)

Asn-Ala-Xaa₁-Cys-Cys-Xaa₄-Xaa₄-Xaa₅-Xaa₅-Cys-Xaa₄-Xaa₁-Ala-Xaa₄-Xaa₅-Xaa₁-Ile-Cys-Leu;  (SEQ ID NO:57)

Xaa₁-Cys-Cys-Thr-Asn-Xaa₅-Val-Cys-His-Ala-Xaa₁-His-Gln-Xaa₁-Leu-Cys-Ala-Arg-Arg-Arg;  (SEQ ID NO:170)

Gly-Cys-Cys-Ser-Asn-Xaa₅-Val-Cys-His-Leu-Xaa₁-His-Ser-Asn-Leu-Cys;  (SEQ ID NO:171)

Xaa₁-Cys-Cys-Thr-Asn-Xaa₅-Val-Cys-His-Val-Xaa₁-His-Gln-Xaa₁-Leu-Cys-Ala-Arg-Arg-Arg;  (SEQ ID NO:172)

Xaa₆-Xaa₁-Cys-Cys-Ser-Xaa₄-Xaa₅-Ala-Cys-Asn-Leu-Asp-His-Xaa₅-Xaa₁-Leu-Cys;  (SEQ ID NO:173)

Xaa₅-Xaa₁-Cys-Cys-Ser-Asp-Xaa₅-Arg-Cys-Asn-Ser-Thr-His-Xaa₅-Xaa₁-Leu-Cys-Gly;  (SEQ ID NO:174)

Leu-Asn-Cys-Cys-Met-Ile-Xaa₅-Xaa₅-Cys-Xaa₃-Xaa₂-Xaa₂-Xaa₄-Gly-Asp-Arg-Cys-Ser-Xaa₁-Val-Arg;  (SEQ ID NO:175)

Ala-Phe-Gly-Cys-Cys-Asp-Leu-Ile-Xaa₅-Cys-Leu-Xaa₁-Arg-Xaa₄-Gly-Asn-Arg-Cys-Asn-Xaa₁-Val-His;  (SEQ ID NO:176)

Leu-Gly-Cys-Cys-Asn-Val-Thr-Xaa₅-Cys-Xaa₃-Xaa₁-Xaa₂-Xaa₄-Gly-Asp-Xaa₂-Cys-Asn-Xaa₁-Val-Arg;  (SEQ ID NO:177)

Asp-Xaa₁-Cys-Cys-Ser-Asn-Xaa₅-Ala-Cys-Arg-Val-Asn-Asn-Xaa₅-His-Val-Cys-Arg-Arg-Arg;  (SEQ ID NO:178)

Leu-Asn-Cys-Cys-Ser-Ile-Xaa₅-Gly-Cys-Xaa₃-Asn-Xaa₁-Xaa₄-Xaa₂-Asp-Arg-Cys-Ser-Xaa₂-Val-Arg;  (SEQ ID NO:179)

Gly-Gly-Cys-Cys-Ser-His-Xaa₅-Val-Cys-Xaa₄-Phe-Asn-Asn-Xaa₅-Gln-Met-Cys-Arg;  (SEQ ID NO:180)

-continued

Gly-Gly-Cys-Cys-Ser-His-Xaa$_5$-Val-Cys-Asn-Leu-Asn-Asn-Xaa$_5$-Gln-Met-Cys-Arg; (SEQ ID NO:181)

Gly-Cys-Cys-Ser-His-Xaa$_5$-Xaa$_5$-Cys-Xaa$_4$-Ala-Asn-Asn-Gln-Ala-Xaa$_4$-Cys-Asn; (SEQ ID NO:182)

Gly-Gly-Cys-Cys-Ser-His-Xaa$_5$-Ala-Cys-Ser-Val-Thr-His-Xaa$_5$-Xaa$_1$-Leu-Cys; (SEQ ID NO:183)

Gly-Gly-Cys-Cys-Ser-Xaa$_4$-Xaa$_5$-Ala-Cys-Ser-Val-Xaa$_1$-His-Gln-Asp-Leu-Cys-Asp; (SEQ ID NO:184)

Val-Ser-Cys-Cys-Val-Val-Arg-Xaa$_5$-Cys-Xaa$_3$-Ile-Arg-Xaa$_4$-Gln-Xaa$_1$-Xaa$_1$-Cys-Leu-Xaa$_1$-Ala-Asp-Xaa$_5$-Arg-Thr-Leu; (SEQ ID NO:185)

Xaa$_6$-Asn-Cys-Cys-Ser-Ile-Xaa$_5$-Gly-Cys-Xaa$_3$-Xaa$_1$-Xaa$_2$-Xaa$_4$-Gly-Asp-Xaa$_2$-Cys-Ser-Xaa$_1$-Val-Arg; (SEQ ID NO:186)

Gly-Cys-Cys-Ser-Asn-Xaa$_5$-Val-Cys-His-Leu-Xaa$_1$-His-Xaa$_5$-Asn-Ala-Cys; (SEQ ID NO:187)

Gly-Cys-Cys-Ser-Asn-Xaa$_5$-Ile-Cys-Xaa$_4$-Phe-Asn-Asn-Xaa$_5$-Arg-Ile-Cys-Arg; (SEQ ID NO:188)

Xaa$_1$-Cys-Cys-Ser-Gln-Xaa$_5$-Xaa$_5$-Cys-Arg-Xaa$_3$-Xaa$_2$-His-Xaa$_5$-Xaa$_1$-Leu-Cys-Ser; (SEQ ID NO:189)

Gly-Cys-Cys-Ser-His-Xaa$_5$-Ala-Cys-Ala-Gly-Asn-Asn-Gln-His-Ile-Cys; (SEQ ID NO:190)

Gly-Cys-Cys-Ala-Val-Xaa$_5$-Ser-Cys-Arg-Leu-Arg-Asn-Xaa$_5$-Asp-Leu-Cys-Gly-Gly; (SEQ ID NO:191)

Gly-Cys-Cys-Ser-His-Xaa$_5$-Ala-Cys-Asn-Val-Asn-Asn-Xaa$_5$-His-Ile-Cys; (SEQ ID NO:192)

Thr-Xaa$_5$-Xaa$_1$-Xaa$_1$-Cys-Cys-Xaa$_5$-Asn-Xaa$_5$-Xaa$_5$-Cys-Phe-Ala-Thr-Asn-Ser-Asp-Ile-Cys-Gly; (SEQ ID NO:193)

Asp-Ala-Cys-Cys-Ser-Asp-Xaa$_5$-Arg-Cys-Ser-Gly-Xaa$_2$-His-Gln-Asp-Leu-Cys; (SEQ ID NO:194)

Xaa$_1$-Asp-Cys-Cys-Ser-Asp-Xaa$_5$-Arg-Cys-Ser-Val-Gly-His-Gln-Asp-Leu-Cys; (SEQ ID NO:195)

Gly-Cys-Cys-Ser-His-Xaa$_5$-Ala-Cys-Ala-Gly-Ser-Asn-Ala-His-Ile-Cys; (SEQ ID NO:196)

Xaa$_1$-Asp-Cys-Cys-Ser-Asp-Xaa$_5$-Arg-Cys-Ser-Val-Gly-His-Gln-Asp-Met-Cys; (SEQ ID NO:197)

Gly-Cys-Cys-Ser-His-Xaa$_5$-Ala-Cys-Ala-Gly-Asn-Asn-Xaa$_5$-His-Ile-Cys; (SEQ ID NO:198)

Gly-Cys-Cys-Gly-Asn-Xaa$_5$-Ser-Cys-Ser-Ile-His-Ile-Xaa$_5$-Xaa$_4$-Val-Cys-Asn; (SEQ ID NO:199)

Thr-Asp-Ser-Xaa$_1$-Xaa$_1$-Cys-Cys-Leu-Asp-Ser-Arg-Cys-Ala-Gly-Gln-His-Gln-Asp-Leu-Cys-Gly; (SEQ ID NO:200)

Gly-Cys-Cys-Ser-Asn-Xaa$_5$-Xaa$_5$-Cys-Xaa$_4$-Ala-Asn-Asn-Gln-Ala-Xaa$_4$-Cys-Asn; (SEQ ID NO:201)

Gly-Cys-Cys-Ser-His-Xaa$_5$-Ala-Cys-Ser-Val-Asn-Asn-Xaa$_5$-Asp-Ile-Cys; (SEQ ID NO:202)

Gly-Xaa$_2$-Cys-Cys-Ile-Asn-Asp-Ala-Cys-Arg-Ser-Xaa$_2$-His-Xaa$_5$-Gln-Xaa$_4$-Cys-Ser; (SEQ ID NO:203)

Gly-Cys-Cys-Xaa$_4$-Asn-Ile-Ala-Cys-Arg-Ile-Asn-Asn-Xaa$_5$-Arg-Xaa$_4$-Cys-Arg; (SEQ ID NO:204)

Gly-Cys-Cys-Ser-His-Xaa$_5$-Val-Cys-Arg-Phe-Asn-Xaa$_4$-Xaa$_5$-Xaa$_2$-Xaa$_4$-Cys-Gly; (SEQ ID NO:205)

Asp-Xaa$_1$-Cys-Cys-Ala-Ser-Xaa$_5$-Xaa$_5$-Cys-Arg-Leu-Asn-Asn-Xaa$_5$-Xaa$_4$-Val-Cys-His; (SEQ ID NO:206)

Gly-Cys-Cys-Ser-Asn-Xaa$_5$-Val-Cys-Xaa$_3$-Gln-Asn-Asn-Ala-Xaa$_1$-Xaa$_4$-Cys-Arg-Xaa$_1$-Ser; (SEQ ID NO:207)

Gly-Cys-Cys-Ser-His-Xaa$_5$-Xaa$_5$-Cys-Ala-Gln-Asn-Asn-Gln-Asp-Xaa$_4$-Cys; (SEQ ID NO:208)

| | |
|---|---|
| Gly-Cys-Cys-Ser-His-Xaa₅-Ala-Cys-Ser-Gly-Asn-Asn-Arg-Xaa₁-Xaa₄-Cys-Arg-Xaa₁-Ser; | (SEQ ID NO:209) |
| Asp-Xaa₅-Cys-Cys-Ser-Xaa₄-Xaa₅-Asp-Cys-Gly-Ala-Asn-His-Xaa₅-Xaa₁-Ile-Cys-Gly; | (SEQ ID NO:210) |
| Xaa₁-Cys-Cys-Ser-Gln-Xaa₅-Xaa₅-Cys-Arg-Xaa₃-Xaa₂-His-Xaa₅-Xaa₁-Leu-Cys-Ser; | (SEQ ID NO:211) |
| Gly-Cys-Cys-Ser-His-Xaa₅-Ala-Cys-Ala-Gly-Asn-Asn-Xaa₅-His-Ile-Cys; | (SEQ ID NO:212) |
| Gly-Cys-Cys-Ser-Asp-Xaa₅-Ser-Cys-Asn-Val-Asn-Asn-Xaa₅-Asp-Xaa₄-Cys; | (SEQ ID NO:213) |
| Xaa₁-Xaa₁-Cys-Cys-Ser-Asp-Xaa₅-Arg-Cys-Ser-Val-Gly-His-Gln-Asp-Met-Cys-Arg; | (SEQ ID NO:214) |
| Gly-Gly-Cys-Cys-Ser-Asn-Xaa₅-Ala-Cys-Leu-Val-Asn-His-Leu-Xaa₁-Met-Cys; | (SEQ ID NO:215) |
| Arg-Asp-Xaa₅-Cys-Cys-Phe-Asn-Xaa₅-Ala-Cys-Asn-Val-Asn-Asn-Xaa₅-Gln-Ile-Cys; | (SEQ ID NO:216) |
| Cys-Cys-Ser-Asp-Xaa₅-Ser-Cys-Xaa₃-Arg-Leu-His-Ser-Leu-Ala-Cys-Thr-Gly-Ile-Val-Asn-Arg; | (SEQ ID NO:217) |
| Cys-Cys-Thr-Asn-Xaa₅-Ala-Cys-Leu-Val-Asn-Asn-Ile-Arg-Phe-Cys-Gly; | (SEQ ID NO:218) |
| Asp-Xaa₁-Cys-Cys-Ser-Asp-Xaa₅-Arg-Cys-His-Gly-Asn-Asn-Arg-Asp-His-Cys-Ala; | (SEQ ID NO:219) |
| Asp-Cys-Cys-Ser-His-Xaa₅-Leu-Cys-Arg-Leu-Phe-Val-Xaa₅-Gly-Leu-Cys-Ile; | (SEQ ID NO:220) |
| Gly-Cys-Cys-Ser-His-Xaa₅-Val-Cys-Xaa₂-Val-Arg-Xaa₄-Xaa₅-Asp-Leu-Cys-Arg; | (SEQ ID NO:221) |
| Gly-Cys-Cys-Ser-His-Xaa₅-Ala-Cys-Asn-Val-Asn-Asn-Xaa₅-His-Ile-Cys; | (SEQ ID NO:222) |
| Gly-Cys-Cys-Ser-His-Xaa₅-Val-Cys-Xaa₂-Val-Arg-Xaa₄-Ser-Asp-Met-Cys; | (SEQ ID NO:223) |
| Gly-Gly-Cys-Cys-Ser-His-Xaa₅-Ala-Cys-Xaa₂-Val-His-Phe-Xaa₅-His-Ser-Cys; | (SEQ ID NO:224) |
| Val-Cys-Cys-Ser-Asn-Xaa₅-Val-Cys-His-Val-Asp-His-Xaa₅-Xaa₁-Leu-Cys-Arg-Arg-Arg-Arg; | (SEQ ID NO:225) |
| Gly-Cys-Cys-Ser-His-Xaa₅-Val-Cys-Asn-Leu-Ser-Asn-Xaa₅-Gln-Ile-Cys-Arg; | (SEQ ID NO:226) |
| Xaa₆-Xaa₁-Cys-Cys-Ser-His-Xaa₅-Ala-Cys-Asn-Val-Asp-His-Xaa₅-Xaa₁-Ile-Cys-Arg; | (SEQ ID NO:227) |
| Gly-Cys-Cys-Ser-Asn-Xaa₅-Ala-Cys-Leu-Val-Asn-His-Ile-Arg-Phe-Cys-Gly; | (SEQ ID NO:228) |
| Asp-Cys-Cys-Asp-Asp-Xaa₅-Ala-Cys-Thr-Val-Asn-Asn-Xaa₅-Gly-Leu-Cys-Thr; and | (SEQ ID NO:229) |
| Gly-Cys-Cys-Ser-Asn-Xaa₅-Xaa₅-Cys-Ile-Ala-Xaa₂-Asn-Xaa₅-His-Met-Cys-Gly-Gly-Arg-Arg, | (SEQ ID NO:230) | wherein Xaa₁ is Glu or γ-carboxy-Glu (Gla); Xaa₂ is Lys, N-methyl-Lys, N,N-dimethyl-Lys or N,N,N-trimethyl-Lys; Xaa₃ is Trp (D or L), halo-Trp or neo-Trp; Xaa₄ is Tyr, nor-Tyr, mono-halo-Tyr, di-halo-Tyr, O-sulpho-Tyr, O-phospho-Tyr or nitro-Tyr; and Xaa₅ is Pro or hydroxy-Pro; Xaa₆ is Gln or pyro-Glu; and the C-terminus contains a carboxyl or amide group. The halo is preferably bromine, chlorine or iodine, more preferably iodine for Tyr and bromine for Trp. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe and Trp residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides of general formula III:

| | |
|---|---|
| SmI: | SEQ ID NO: 22, wherein Xaa$_1$ is Glu and Xaa$_5$ is Pro; |
| OB-29: | SEQ ID NO: 23, wherein Xaa$_1$ is Glu, Xaa$_3$ is Tyr and Xaa$_5$ is Pro; |
| Tx1.1: | SEQ ID NO: 24, wherein Xaa$_1$ is Glu and Xaa$_5$ is Pro; |
| R1.1A: | SEQ ID NO: 25, wherein Xaa$_1$ is Glu and Xaa$_5$ is Pro; |
| R1.1B: | SEQ ID NO: 26, wherein Xaa$_1$ is Glu and Xaa$_5$ is Pro; |
| Om-9: | SEQ ID NO: 27, wherein Xaa$_1$ is Glu and Xaa$_5$ is Pro; |
| Om-10: | SEQ ID NO: 28, wherein Xaa$_5$ is Pro; |
| Om-21: | SEQ ID NO: 29, wherein Xaa$_1$ is Glu and Xaa$_5$ is Pro; |
| Om-25: | SEQ ID NO: 30, wherein Xaa$_1$ is Glu and Xaa$_5$ is Pro; |
| Om-27: | SEQ ID NO: 31, wherein Xaa$_1$ is Glu and Xaa$_5$ is Pro; |
| Om-28: | SEQ ID NO: 32, wherein Xaa$_1$ is Glu and Xaa$_5$ is Pro; |
| Bt1.2: | SEQ ID NO: 33, wherein Xaa$_1$ is Glu and Xaa$_5$ is Pro; |
| Bt1.4: | SEQ ID NO: 34, wherein Xaa$_1$ is Glu and Xaa$_5$ is Pro; |
| Da1.1: | SEQ ID NO: 35, wherein Xaa$_1$ is Glu and Xaa$_5$ is Pro; |
| OB-20: | SEQ ID NO: 36, wherein Xaa$_1$ is Glu, Xaa$_2$ is Lys and Xaa$_5$ is Pro; |
| TI: | SEQ ID NO: 37, wherein Xaa$_1$ is Glu and Xaa$_5$ is Pro; |
| TIB: | SEQ ID NO: 38, wherein Xaa$_1$ is Glu and Xaa$_5$ is Pro; |
| Pn1.1: | SEQ ID NO: 39, wherein Xaa$_5$ is Pro; |
| Pn1.2: | SEQ ID NO: 40, wherein Xaa$_1$ is Glu and Xaa$_5$ is Pro; |
| T1: | SEQ ID NO: 41, wherein Xaa$_2$ is Lys and Xaa$_5$ is Pro; |
| TIA: | SEQ ID NO: 43, wherein Xaa$_5$ is Pro; |
| Da1.2: | SEQ ID NO: 44, wherein Xaa$_5$ is Pro; |
| Cr1.2: | SEQ ID NO: 45, wherein Xaa$_1$ is Glu and Xaa$_5$ is Pro; |
| Sl1.2: | SEQ ID NO: 46, wherein Xaa$_1$ is Glu, Xaa$_2$ is Lys and Xaa$_5$ is Pro; |
| Tx1.3: | SEQ ID NO: 47, wherein Xaa$_1$ is Glu and Xaa$_5$ is Pro; |
| Da1.3: | SEQ ID NO: 48, wherein Xaa$_1$ is Glu and Xaa$_5$ is Pro; |
| Da1.4: | SEQ ID NO: 49, wherein Xaa$_1$ is Glu, Xaa$_5$ is Pro and Xaa$_6$ is Gln; |
| Tx1.2: | SEQ ID NO: 50, wherein Xaa$_5$ is Pro; |
| Om-35: | SEQ ID NO: 51, wherein Xaa$_1$ is Glu and Xaa$_5$ is Pro; |
| Sl1.1: | SEQ ID NO: 52, wherein Xaa$_1$ is Glu, Xaa$_3$ is Trp, Xaa$_4$ is Tyr and Xaa$_5$ is Pro; |
| Sl1.6: | SEQ ID NO: 53, wherein Xaa$_1$ is Glu, Xaa$_2$ is Lys, Xaa$_4$ is Tyr and Xaa$_5$ is Pro; |
| Sl1.7: | SEQ ID NO: 54, wherein Xaa$_1$ is Glu Xaa$_4$ is Tyr and Xaa$_5$ is Pro; |
| Bt1.1: | SEQ ID NO: 55, wherein Xaa$_1$ is Glu Xaa$_4$ is Tyr and Xaa$_5$ is Pro; |
| Bt: 1.3: | SEQ ID NO: 56, wherein Xaa$_1$ is Glu Xaa$_4$ is Tyr and Xaa$_5$ is Pro; |
| Bt1.5: | SEQ ID NO: 57, wherein Xaa$_1$ is Glu Xaa$_4$ is Tyr and Xaa$_5$ is Pro; |
| A1.4: | SEQ ID NO: 170, wherein Xaa$_1$ is Glu and Xaa$_5$ is Pro; |
| A1.5: | SEQ ID NO: 171, wherein Xaa$_1$ is Glu and Xaa$_5$ is Pro; |
| A1.6: | SEQ ID NO: 172, wherein Xaa$_1$ is Glu and Xaa$_5$ is Pro; |
| Af1.1: | SEQ ID NO: 173, wherein Xaa$_1$ is Glu Xaa$_4$ is Tyr, Xaa$_5$ is Pro and Xaa$_6$ is Gln; |
| Af1.2: | SEQ ID NO: 174, wherein Xaa$_1$ is Glu and Xaa$_5$ is Pro; |
| Ar1.2: | SEQ ID NO: 175, wherein Xaa$_1$ is Glu, Xaa$_2$ is Lys, Xaa$_3$ is Trp, Xaa$_4$ is Try and Xaa$_5$ is Pro; |
| Ar1.3: | SEQ ID NO: 176, wherein Xaa$_1$ is Glu, Xaa$_4$ is Tyr and Xaa$_5$ is Pro; |
| Ar1.4: | SEQ ID NO: 177, wherein Xaa$_1$ is Glu, Xaa$_2$ is Lys, Xaa$_3$ is Trp, Xaa$_4$ is Try and Xaa$_5$ is Pro; |
| Ar1.5: | SEQ ID NO: 178, wherein Xaa$_1$ is Glu, Xaa$_4$ is Tyr and Xaa$_5$ is Pro; |
| Ar1.6: | SEQ ID NO: 179, wherein Xaa$_1$ is Glu, Xaa$_2$ is Lys, Xaa$_3$ is Trp, Xaa$_4$ is Try and Xaa$_5$ is Pro; |
| Ay1.2: | SEQ ID NO: 180, wherein Xaa$_4$ is Tyr and Xaa$_5$ is Pro; |
| Ay1.3: | SEQ ID NO: 181, wherein Xaa$_5$ is Pro; |
| Bn1.4: | SEQ ID NO: 182, wherein Xaa$_4$ is Tyr and Xaa$_5$ is Pro; |
| Bt1.8: | SEQ ID NO: 183, wherein Xaa$_1$ is Glu and Xaa$_5$ is Pro; |
| Bt1.9: | SEQ ID NO: 184, wherein Xaa$_1$ is Glu, Xaa$_4$ is Tyr and Xaa$_5$ is Pro; |
| Ca1.3: | SEQ ID NO: 185, wherein Xaa$_1$ is Glu, Xaa$_3$ is Trp, Xaa$_4$ is Try and Xaa$_5$ is Pro; |
| Ca1.4: | SEQ ID NO: 186, wherein Xaa$_1$ is Glu, Xaa$_2$ is Lys, Xaa$_3$ is Trp, Xaa$_4$ is Try, Xaa$_5$ is Pro and Xaa$_6$ is Gln; |
| C1.2: | SEQ ID NO: 187, wherein Xaa$_1$ is Glu and Xaa$_5$ is Pro; |
| C1.3: | SEQ ID NO: 188, wherein Xaa$_4$ is Tyr and Xaa$_5$ is Pro; |
| Ep1.2: | SEQ ID NO: 189, wherein Xaa$_1$ is Glu, Xaa$_2$ is Lys, Xaa$_3$ is Trp and Xaa$_5$ is Pro; |
| G1.1: | SEQ ID NO: 190, wherein Xaa$_5$ is Pro; |
| G1.3: | SEQ ID NO: 191, wherein Xaa$_5$ is Pro; |
| Im1.3: | SEQ ID NO: 192, wherein Xaa$_5$ is Pro; |
| Lv1.2: | SEQ ID NO: 193, wherein Xaa$_1$ is Glu and Xaa$_5$ is Pro; |
| Lv1.3: | SEQ ID NO: 194, wherein Xaa$_2$ is Lys and Xaa$_5$ is Pro; |
| Lv1.4: | SEQ ID NO: 195, wherein Xaa$_1$ is Glu and Xaa$_5$ is Pro; |
| Lv1.6: | SEQ ID NO: 196, wherein Xaa$_5$ is Pro; |
| Lv1.7: | SEQ ID NO: 197, wherein Xaa$_1$ is Glu and Xaa$_5$ is Pro; |
| Lv1.8: | SEQ ID NO: 198, wherein Xaa$_5$ is Pro; |
| Lv1.9: | SEQ ID NO: 199, wherein Xaa$_4$ is Tyr and Xaa$_5$ is Pro; |
| Lv1.10: | SEQ ID NO: 200, wherein Xaa$_1$ is Glu; |
| Mr1.3: | SEQ ID NO: 201, wherein Xaa$_4$ is Tyr and Xaa$_5$ is Pro; |
| Mr1.4: | SEQ ID NO: 202, wherein Xaa$_5$ is Pro; |
| Ms1.1: | SEQ ID NO: 203, wherein Xaa$_2$ is Lys, Xaa$_4$ is Tyr and Xaa$_5$ is Pro; |
| Ms1.6: | SEQ ID NO: 204, wherein Xaa$_4$ is Tyr and Xaa$_5$ is Pro; |
| O1.1: | SEQ ID NO: 205, wherein Xaa$_2$ is Lys, Xaa$_4$ is Tyr and Xaa$_5$ is Pro; |
| O1.2: | SEQ ID NO: 206, wherein Xaa$_1$ is Glu, Xaa$_4$ is Tyr and Xaa$_5$ is Pro; |
| O1.4: | SEQ ID NO: 207, wherein Xaa$_1$ is Glu, Xaa$_3$ is Trp, Xaa$_4$ is Tyr and Xaa$_5$ is Pro; |
| O1.7: | SEQ ID NO: 208, wherein Xaa$_4$ is Tyr and Xaa$_5$ is Pro; |
| O1.8: | SEQ ID NO: 209, wherein Xaa$_1$ is Glu, Xaa$_4$ is Tyr and Xaa$_5$ is Pro; |
| Om1.2: | SEQ ID NO: 210, wherein Xaa$_1$ is Glu, Xaa$_4$ is Tyr and Xaa$_5$ is Pro; |
| Om1.3: | SEQ ID NO: 211, wherein Xaa$_1$ is Glu, Xaa$_2$ is Lys, Xaa$_3$ is Trp and Xaa$_5$ is Pro; |
| Om1.4: | SEQ ID NO: 212, wherein Xaa$_5$ is Pro; |
| Om1.5: | SEQ ID NO: 213, wherein Xaa$_4$ is Tyr and Xaa$_5$ is Pro; |
| Om1.6: | SEQ ID NO: 214, wherein Xaa$_1$ is Glu and Xaa$_5$ is Pro; |
| P1.4: | SEQ ID NO: 215, wherein Xaa$_1$ is Glu and Xaa$_5$ is Pro; |
| P1.5: | SEQ ID NO: 216, wherein Xaa$_5$ is Pro; |
| P1.6: | SEQ ID NO: 217, wherein Xaa$_3$ is Trp and Xaa$_5$ is Pro; |
| P1.8: | SEQ ID NO: 218, wherein Xaa$_5$ is Pro; |
| Rg1.1: | SEQ ID NO: 219, wherein Xaa$_1$ is Glu and Xaa$_5$ is Pro; |
| Rg1.3: | SEQ ID NO: 220, wherein Xaa$_5$ is Pro; |
| Rg1.4: | SEQ ID NO: 221, wherein Xaa$_2$ is Lys, Xaa$_4$ is Tyr and Xaa$_5$ is Pro; |
| Rg1.5: | SEQ ID NO: 222, wherein Xaa$_5$ is Pro; |
| Rg1.8: | SEQ ID NO: 223, wherein Xaa$_2$ is Lys, Xaa$_4$ is Tyr and Xaa$_5$ is Pro; |
| Sm1.4: | SEQ ID NO: 224, wherein Xaa$_2$ is Lys and Xaa$_5$ is Pro; |
| Sm1.5: | SEQ ID NO: 225, wherein Xaa$_1$ is Glu and Xaa$_5$ is Pro; |
| S1.5: | SEQ ID NO: 226, wherein Xaa$_5$ is Pro; |
| Tx1.5: | SEQ ID NO: 227, wherein Xaa$_1$ is Glu, Xaa$_5$ is Pro and Xaa$_6$ is Gln; |
| T1.1: | SEQ ID NO: 228, wherein Xaa$_5$ is Pro; |
| Vr1.3: | SEQ ID NO: 229, wherein Xaa$_5$ is Pro; and |
| Tb: | SEQ ID NO: 230, wherein Xaa$_2$ is Lys and Xaa$_5$ is Pro. |

The C-terminus preferably contains a carboxyl group for the peptides OB-29, Tx1.1, R1.1A, R1.1B, Om-9, Om-10, Om-21, Om-25, Om-27, Om-28, Cr1.2, Om-35, Bt1.1, Bt1.3, Bt1.5, A1.4, A1.6, Ar1.2, Ar1.3, Ar1.4, Ar1.5, Ar1.6, Ca1.3, Ca1.4, Ep1.2, Lv1.9, O1.2, Om1.3, Om1.6, P1.6, Rg1.1, Rg1.3, Rg1.4, Sm1.5, Tx1.5 and Vr1.3. The C-terminus of the other peptides preferably contains an amide group.

The present invention is also directed to the novel specific α-conotoxin peptides having the formulas:

Cys-Cys-Thr-Ile-Xaa$_5$-Ser-Cys-Xaa$_4$-  (SEQ ID NO:231)

Xaa$_1$-Xaa$_2$-Xaa$_2$-Xaa$_2$-Ile-Xaa$_2$-Ala-

Cys-Val-Phe and

Gly-Cys-Cys-Gly-Asn-Xaa$_5$-Ala-Cys-  (SEQ ID NO:232)

Ser-Gly-Ser-Ser-Xaa$_2$-Asp-Ala-Xaa$_5$-

Ser-Cys, wherein Xaa$_1$ is Glu or γ-carboxy-Glu (Gla); Xaa$_2$ is Lys, N-methyl-Lys, N,N-dimethyl-Lys or N,N,N-trimethyl-Lys; Xaa$_4$ is Tyr, nor-Tyr, mono-halo-Tyr, di-halo-Tyr, O-sulpho- Tyr, O-phospho-Tyr or nitro-Tyr; and $Xaa_5$ is Pro or hydroxy-Pro; and the C-terminus contains a carboxyl or amide group. The halo is preferably bromine, chlorine or iodine, more preferably iodine for Tyr. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides:

G1.2: SEQ ID NO:231, wherein $Xaa_1$ is Glu, $Xaa_2$ is Lys, $Xaa_4$ is Tyr and $Xaa_5$ is Pro; and Rg1.12: SEQ ID NO:232, wherein $Xaa_2$ is Lys and $Xaa_5$ is Pro.

The C-terminus of G1.2 preferably contains a carboxyl group, and the C-terminus of Rg1.12 preferably contains an amide group.

Examples of unnatural aromatic amino acid include, but are not limited to, such as nitro-Phe, 4-substituted-Phe wherein the substituent is $C_1$-$C_3$ alkyl, carboxyl, hydroxymethyl, sulphomethyl, halo, phenyl, 'CHO, —CN, —$SO_3H$ and —NHAc. Examples of unnatural hydroxy containing amino acid, include, but are not limited to, such as 4-hydroxymethyl-Phe, 4-hydroxyphenyl-Gly, 2,6-dimethyl-Tyr and 5-amino-Tyr. Examples of unnatural basic amino acids include, but are not limited to, N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala. These and other unnatural basic amino acids, unnatural hydroxy containing amino acids or unnatural aromatic amino acids are described in Building Block Index, Version 3.0 (1999 Catalog, pages 4-47 for hydroxy containing amino acids and aromatic amino acids and pages 66-87 for basic amino acids; see also website "amino-acids.com"), incorporated herein by reference, by and available from RSP Amino Acid Analogues, Inc., Worcester, Mass.

Optionally, in the peptides of general formulas I, II and III and the specific peptides described above, the Asn residues may be modified to contain an N-glycan and the Ser and Thr residues may be modified to contain an O-glycan. In accordance with the present invention, a glycan shall mean any N—, S— or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The glycan may also include similar polyhydroxy groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420,797, filed 19 Oct. 1999 (now U.S. Pat. No. 6,369,193) and in PCT Application No. PCT/US99/24380, filed 19 Oct. 1999, both incorporated herein by reference. A preferred glycan is Gal(β1-3)GalNAc(α1→).

Optionally, in the peptides of general formulas I and II and the specific peptides described above, pairs of Cys residues may be replaced pairwise with Ser/(Glu or Asp) or Lys/(Glu or Asp) combinations. Sequential coupling by known methods (Barnay et al., 2000; Hruby et al., 1994; Bitan et al., 1997) allows replacement of native Cys bridges with lactam bridges.

The present invention is further directed to propeptides and nucleic acid sequences encoding the propeptides or peptides as described in further detail herein.

DETAILED DESCRIPTION OF THE INVENTION

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

The present invention, in another aspect, relates to a pharmaceutical composition comprising an effective amount of an α-conotoxin peptide. Such a pharmaceutical composition has the capability of acting as antagonists for nicotinic acetylcholine receptors. In one aspect, the α-conotoxins with specificity for neuromuscular junction nicotinic acetylcholine receptors are used as neuromuscular blocking agents for use in conjunction with surgery, as disclosed in U.S. patent application Ser. No. 09/488,799, filed 21 Jan. 2000, incorporated by reference herein. In a second aspect, additional α-conotoxins and uses for them have been described in U.S. Pat. Nos. 4,447,356 (Olivera et al., 1984); 5,432,155; 5,514,774, each incorporated herein by reference.

In a third aspect additional uses for α-conotoxins are described in U.S. Ser. No. 09/219,446, filed 22 Dec. 1998, incorporated herein by reference. In this application, α-conotoxins with specificity for neuronal nicotinic acetylcholine receptors are used for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma.

The α-conotoxin peptides described herein are sufficiently small to be chemically synthesized. General chemical syntheses for preparing the foregoing α-conotoxin peptides are described hereinafter. Various ones of the α-conotoxin peptides can also be obtained by isolation and purification from specific *Conus* species using the technique described in U.S. Pat. No. 4,447,356 (Olivera et al., 1984), the disclosure of which is incorporated herein by reference.

Although the α-conotoxin peptides of the present invention can be obtained by purification from cone snails, because the amounts of α-conotoxin peptides obtainable from individual snails are very small, the desired substantially pure α-conotoxin peptides are best practically obtained in commercially valuable amounts by chemical synthesis using solid-phase strategy. For example, the yield from a single cone snail may be about 10 micrograms or less of α-conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active α-conotoxin peptides depends of course upon correct determination of the amino acid sequence.

The α-conotoxin peptides can also be produced by recombinant DNA techniques well known in the art. Such techniques are described by Sambrook et al. (1989). The peptides produced in this manner are isolated, reduced if necessary, and oxidized to form the correct disulfide bonds.

One method of forming disulfide bonds in the conantokin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino—and side chain—protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The FMOC protecting group is removed by treatment with a 20% solution of piperidine in dimethylformamide(DMF). Resins are subsequently washed with DMF (twice), followed by methanol and NMP.

Pharmaceutical compositions containing a compound of the present invention or its pharmaceutically acceptable salts as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*. Typically the conopeptides of the present invention exhibit their effect at a dosage range from about 0.001 mg/kg to about 250 mg/kg, preferably from about 0.05 mg/kg to about 100 mg/kg of the active ingredient, more preferably from a bout 0.1 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

EXAMPLES

The present invention is described by reference to the following Examples, which are offered by way of illustration and are not intended to limit the invention in any manner. Standard techniques well known in the art or the techniques specifically described below were utilized.

Example 1

Isolation of α-Conotoxins

Crude venom was extracted from venom ducts (Cruz et al., 1976), and the components were purified as previously described (Cartier et al., 1996a). The crude extract from venom ducts was purified by reverse phase liquid chromatography (RPLC) using a Vydac $C_{18}$ semi-preparative column (10×250 mm) and elution with a linear gradient of acetonitrile in 0.1% TFA. Further purification of bioactive peaks was done on a Vydac $C_{18}$ analytical column (4.6×220 mm) eluted with a gradient of acetonitrile in 0.1% TFA. The effluents were monitored at 220 nm. Peaks were collected, and aliquots were assayed for activity. Activity was monitored by assessing block of α3β4 nAChRs expressed in *Xenopus oocytes*.

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994).

In accordance with this method, peptides MII, AuIA, AuIB, AuIC, MAR-1, MAR-2, TI, OB-29, EpI, S1.1, Bn1.1, Bn1.2, Ca1.1, Ca1.2, Cn1.1, Cn1.2 and Sm1.3 were obtained.

Example 2

Synthesis of Conopeptides

The synthesis of conopeptides, either the mature toxins or the precursor peptides, was separately performed using conventional protection chemistry as described by Cartier et al. (1996). Briefly, the linear chains were built on Rink amide resin by Fmoc procedures with 2-(1H-benzotriol-1-yl)-1,1,3,3,-tetramethyluronium tetrafluoroborated coupling using an ABI model 430A peptide synthesizer with amino acid derivatives purchased from Bachem (Torrance Calif.). Orthogonal protection was used on cysteines: $Cys^3$ and $Cys^{16}$ were protected as the stable Cys(S-acetamidomethyl), while $Cys^2$ and $Cys^8$ were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except on $Cys^3$ and $Cys^{16}$. The peptides were dissolved in 0.1% TFA and 60% acetonitrile and purified by RPLC on a Vydac $C_{18}$ preparative column (22×250 mm) and eluted at a flow rate of 20 mL/min with a gradient of acetonitrile in 0.1% TFA.

The disulfide bridges in the three conopeptides were formed as described in Cartier et al. (1996). Briefly, the disulfide bridges between $Cys^2$ and $Cys^8$ were formed by air oxidation which was judged to be complete by analytical RPLC. The monocyclic peptides were purified by RPLC on a Vydac $C_{18}$ preparative column (22×250 mm) and eluted with a gradient of acetonitrile in 0.1% TFA. Removal of S-acetamidomethyl groups and closure of the disulfide bridge between $Cys^3$ and $Cys^{16}$ was carried out simultaneously be iodine oxidation. The cyclic peptides were purified by RPLC on a Vydac $C_{18}$ preparative column (22×250 mm) and eluted with a gradient of acetonitrile in 0.1% TFA.

Example 3

Isolation of DNA Encoding α-Conotoxins

DNA coding for α-conotoxins was isolated and cloned in accordance with conventional techniques using general procedures well known in the art, such as described in Olivera et al. (1996). Alternatively, cDNA libraries was prepared from *Conus* venom duct using conventional techniques. DNA from single clones was amplified by conventional techniques using primers which correspond approximately to the M13 universal priming site and the M13 reverse universal priming site. Clones having a size of approximately 300 nucleotides were sequenced and screened for similarity in sequence to known α-conotoxins. The DNA sequences and encoded propeptide or peptide sequences are set forth in Tables 1-134.

TABLE 1

DNA Sequence (SEQ ID NO:58) and Protein Sequence (SEQ ID NO:59) of MII

```
atg ttc acc gtg ttt ctg ttg gtt gtc ttg gca acc
Met Phe Thr Val Phe Leu Leu Val Val Leu Ala Thr act gtc gtt tcc ttc cct tca gat cgt gca tct gat
Thr Val Val Ser Phe Pro Ser Asp Arg Ala Ser Asp ggc agg aat gcc gca gcc aac gac aaa gcg tct gac
Gly Arg Asn Ala Ala Ala Asn Asp Lys Ala Ser Asp gtg atc acg ctg gcc ctc aag gga tgc tgt tcc aac
Val Ile Thr Leu Ala Leu Lys Gly Cys Cys Ser Asn cct gtc tgt cac ttg gag cat tca aac ctt tgt ggt
Pro Val Cys His Leu Glu His Ser Asn Leu Cys Gly aga aga cgc tgatgctcca ggaccctctg aaccacgacg
Arg Arg Arg ttcgagca
```

TABLE 2

DNA Sequence (SEQ ID NO:60) and Protein Sequence (SEQ ID NO:61) of AuIA

```
atg ttc acc gtg ttt ctg ttg gtt gtc ttg gca acc
Met Phe Thr Val Phe Leu Leu Val Val Leu Ala Thr acc gtc gtt tcc ttc act tca gat cgt gca tct gat
Thr Val Val Ser Phe Thr Ser Asp Arg Ala Ser Asp ggc agg aag gac gca gcg tct ggc ctg atc gct ctg
Gly Arg Lys Asp Ala Ala Ser Gly Leu Ile Ala Leu acc atc aag gga tgc tgt tct tat cct ccc tgt ttc
Thr Ile Lys Gly Cys Cys Ser Tyr Pro Pro Cys Phe gcg act aat tca gac tat tgt ggt tgacgacgct
Ala Thr Asn Ser Asp Tyr Cys Gly gatgctccag gaccctctga accacgacgt
```

TABLE 3

DNA Sequence (SEQ ID NO:62) and Protein Sequence (SEQ ID NO:63) of AuIB

```
atg ttc acc gtg ttt ctg ttg gtc gtc ttg gca acc
Met Phe Thr Val Phe Leu Leu Val Val Leu Ala Thr acc gtc gtt tcc ttc act tca gat cgt gca tct gat
Thr Val Val Ser Phe Thr Ser Asp Arg Ala Ser Asp ggc agg aag gac gca gcg tct ggc ctg att gct ctg
Gly Arg Lys Asp Ala Ala Ser Gly Leu Ile Ala Leu acc atg aag gga tgc tgt tct tat cct ccc tgt ttc
Thr Met Lys Gly Cys Cys Ser Tyr Pro Pro Cys Phe gcg act aat cca gac tgt ggt cga cga cgc tgatgctcca
Ala Thr Asn Pro Asp Cys Gly Arg Arg Arg ggaccctctg aaccacgacg t
```

TABLE 4

DNA Sequence (SEQ ID NO: 64) and Protein Sequence (SEQ ID NO: 65) of Tx1.3

```
atg ttc acc gtg ttt ctg ttg gtt gtc ttg gca acc
Met Phe Thr Val Phe Leu Leu Val Val Leu Ala Thr acc gtc gtt tcc ttc tct tca ggt cgt agt aca ttt
Thr Val Val Ser Phe Ser Ser Gly Arg Ser Thr Phe cgt ggc agg aat gcc gca gcc aaa gcg tct ggc ctg
Arg Gly Arg Asn Ala Ala Ala Lys Ala Ser Gly Leu gtc agt ctg act gac agg aga cca gaa tgc tgt agt
Val Ser Leu Thr Asp Arg Arg Pro Glu Cys Cys Ser gat cct cgc tgt aac tcg agt cat cca gaa ctt tgt
Asp Pro Arg Cys Asn Ser Ser His Pro Glu Leu Cys ggt gga aga cgc tgatgctcca ggaccctctg aaccacgacg t
Gly Gly Arg Arg
```

TABLE 5

DNA Sequence (SEQ ID NO: 66) and Protein Sequence (SEQ ID NO: 67) of Tx1.2

```
atg ttc acc gtg ttt ctg ttg gtt gtc ttg gca acc
Met Phe Thr Val Phe Leu Leu Val Val Leu Ala Thr gcc gtc gtt tcc ttc act tca gat cgt gca tct gat
Ala Val Val Ser Phe Thr Ser Asp Arg Ala Ser Asp gac ggg aaa gcc gct gcg tct gac ctg atc act ctg
Asp Gly Lys Ala Ala Ala Ser Asp Leu Ile Thr Leu acc atc aag gga tgc tgt tct cgt cct ccc tgt atc
Thr Ile Lys Gly Cys Cys Ser Arg Pro Pro Cys Ile gcg aat aat cca gac ttg tgt ggt tgacgacgct
Ala Asn Asn Pro Asp Leu Cys Gly gatgctccag aacggtctga accacgacgt tcgagcaatg ttcaccgtgt ttctgttggt tgtctt
```

TABLE 6

DNA Sequence (SEQ ID NO: 68) and Protein Sequence (SEQ ID NO: 69) of Tx1.1

```
atg ttc acc gtg ttt ctg ttg gtt gtc ttg gca acc
Met Phe Thr Val Phe Leu Leu Val Val Leu Ala Thr acc gtc gtt tcc ttc act tca ggt cgt agt aca ttt
Thr Val Val Ser Phe Thr Ser Gly Arg Ser Thr Phe cgt ggc agg aat gcc gca gcc aaa gcg tct ggc ctg
Arg Gly Arg Asn Ala Ala Ala Lys Ala Ser Gly Leu gtc agt ctg act gac agg aga cca caa tgc tgt tct
Val Ser Leu Thr Asp Arg Arg Pro Gln Cys Cys Ser cat cct gcc tgt aac gta gat cat cca gaa att tgt
His Pro Ala Cys Asn Val Asp His Pro Glu Ile Cys cgt tgaagacgct gatgctccag gaccctctga accacgacgt
Arg
```

TABLE 7

DNA Sequence (SEQ ID NO: 70) and
Protein Sequence (SEQ ID NO: 71) of R1.1A atg ttc acc gtg ttt ctg ttg gtt gtc ttg gca acc
Met Phe Thr Val Phe Leu Leu Val Val Leu Ala Thr acc gtc gtt tcc ttc act tca ggt cgt cgt aca ttt
Thr Val Val Ser Phe Thr Ser Gly Arg Arg Thr Phe cat ggc agg aat gcc gca gcc aaa gcg tct ggc ctg
His Gly Arg Asn Ala Ala Ala Lys Ala Ser Gly Leu gtc agt ctg act gac agg aga cca gaa tgc tgt tct
Val Ser Leu Thr Asp Arg Arg Pro Glu Cys Cys Ser cat cct gcc tgt aac gta gat cat cca gaa att tgt
His Pro Ala Cys Asn Val Asp His Pro Glu Ile Cys cgt tgaagacgct gatgctccag gaccctctga accacgacgt
Arg

TABLE 8

DNA Sequence (SEQ ID NO: 72) and
Protein Sequence (SEQ ID NO: 73) of R1.1B atg ttc acc gtg ttt ctg ttg gtt gtc ttg gca acc
Met Phe Thr Val Phe Leu Leu Val Val Leu Ala Thr acc gtc gtt tcc ttc act tca ggt cgt agt aca ttt
Thr Val Val Ser Phe Thr Ser Gly Arg Ser Thr Phe cgt ggc agg aat gcc gca gcc aaa gcg tct ggc ctg
Arg Gly Arg Asn Ala Ala Ala Lys Ala Ser Gly Leu gtc agt ctg act gac agg aga cca caa tgc tgt tct
Val Ser Leu Thr Asp Arg Arg Pro Gln Cys Cys Ser cat cct gcc tgt aac gta gat cat cca gaa att tgc
His Pro Ala Cys Asn Val Asp His Pro Glu Ile Cys gat tgaagacgct gatgctccag gaccctctga accacgacgt
Asp

TABLE 9

DNA Sequence (SEQ ID NO: 74) and
Protein Sequence (SEQ ID NO: 75) of S1.1 atg ttc act gtg ttt ctg ttg gtt gtc ttg gca atc
Met Phe Thr Val Phe Leu Leu Val Val Leu Ala Ile act gtc gtt tcc ttc cct tta gat cgt gaa tct gat
Thr Val Val Ser Phe Pro Leu Asp Arg Glu Ser Asp ggc gcg aat gcc gaa gcc cgc acc cac gat cat gag
Gly Ala Asn Ala Glu Ala Arg Thr His Asp His Glu aag cac gca ctg gac cgg aat gga tgc tgt agg aat
Lys His Ala Leu Asp Arg Asn Gly Cys Cys Arg Asn cct gcc tgt gag agc cac aga tgt ggt tgacgacgct
Pro Ala Cys Glu Ser His Arg Cys Gly gatgctccag gaccctctga accacgacgt tcgagca

TABLE 10

DNA Sequence (SEQ ID NO: 76) and
Protein Sequence (SEQ ID NO: 77) of Bn1.1 atg ttc acc atg ttt ctg ttg gtt gtc ttg gca acc
Met Phe Thr Met Phe Leu Leu Val Val Leu Ala Thr

TABLE 10-continued

DNA Sequence (SEQ ID NO: 76) and
Protein Sequence (SEQ ID NO: 77) of Bn1.1 act gtc gtt tcc ttc gct tca gat cgt gca tct gat
Thr Val Val Ser Phe Ala Ser Asp Arg Ala Ser Asp ggc agg aat gcc gca gcc aag gac aaa gcg tct gac
Gly Arg Asn Ala Ala Ala Lys Asp Lys Ala Ser Asp ctg gtc gct ctg acc gtc aag gga tgc tgt tct cat
Leu Val Ala Leu Thr Val Lys Gly Cys Cys Ser His cct gcc tgt agc gtg aat aat cca gac att tgt ggt
Pro Ala Cys Ser Val Asn Asn Pro Asp Ile Cys Gly tgaagacgct gatgctccag gaccctctga accacgacgt tcgagca

TABLE 11

DNA Sequence (SEQ ID NO: 78) and
Protein Sequence (SEQ ID NO: 79) of Bn1.2 aaa gaa tgc tgt act cat cct gcc tgt cac gtg agt
Lys Glu Cys Cys Thr His Pro Ala Cys His Val Ser cat cca gaa ctc tgt ggt tgaaaagcga cgtgacgctc
His Pro Glu Leu Cys Gly caggaccctc tgaaccacga cgttcgagca

TABLE 12

DNA Sequence (SEQ ID NO: 80) and
Protein Sequence (SEQ ID NO: 81) of Bn1.3 atg ttc acc gtg ttt ctg ttg gtt gtc ttg gca act
Met Phe Thr Val Phe Leu Leu Val Val Leu Ala Thr gct gtt ctt cca gtc act tta gat cgt gca tct gat
Ala Val Leu Pro Val Thr Leu Asp Arg Ala Ser Asp gga agg aat gca gca gcc aac gcc aaa acg cct cgc
Gly Arg Asn Ala Ala Ala Asn Ala Lys Thr Pro Arg ctg atc gcg cca ttc atc agg gat tat tgc tgt cat
Leu Ile Ala Pro Phe Ile Arg Asp Tyr Cys Cys His aga ggt ccc tgt atg gta tgg tgt ggt tgaagccgct
Arg Gly Pro Cys Met Val Trp Cys Gly gctgctccag gaccctctga accac

TABLE 13

DNA Sequence (SEQ ID NO: 82) and
Protein Sequence (SEQ ID NO: 83) of Ca1.1 atg ttc acc gtg ttt ctg ttg gtt gtc ttg gca acc
Met Phe Thr Val Phe Leu Leu Val Val Leu Ala Thr act gtg gtt tcc ttc act tca gat cgt gct tct gat
Thr Val Val Ser Phe Thr Ser Asp Arg Ala Ser Asp ggc agg aat gcc gca gcc aac gcg ttt gac ctg atc
Gly Arg Asn Ala Ala Ala Asn Ala Phe Asp Leu Ile gct ctg atc gcc agg caa aat tgc tgt agc att ccc
Ala Leu Ile Ala Arg Gln Asn Cys Cys Ser Ile Pro

TABLE 13-continued

**DNA Sequence (SEQ ID NO: 82) and
Protein Sequence (SEQ ID NO: 83) of Ca1.1** agc tgt tgg gag aaa tat aaa tgt agt taa
Ser Cys Trp Glu Lys Tyr Lys Cys Ser

TABLE 14

**DNA Sequence (SEQ ID NO: 84) and
Protein Sequence (SEQ ID NO: 85) of Ca1.2** atg ttc acc gtg ttt ctg ttg gtt gtc ttg gca acc
Met Phe Thr Val Phe Leu Leu Val Val Leu Ala Thr act gtg gtt tcc ttc act tca gat cgt gcg tct gaa
Thr Val Val Ser Phe Thr Ser Asp Arg Ala Ser Glu ggc agg aat gct gca gcc aag gac aaa gcg tct gac
Gly Arg Asn Ala Ala Ala Lys Asp Lys Ala Ser Asp ctg gtg gct ctg aca gtc agg gga tgc tgt gcc att
Leu Val Ala Leu Thr Val Arg Gly Cys Cys Ala Ile cgt gaa tgt cgc ttg cag aat gca gcg tat tgt ggt
Arg Glu Cys Arg Leu Gln Asn Ala Ala Tyr Cys Gly gga ata tac tgatgctcca ggaccctctg aaccacgacg
Gly Ile Tyr

TABLE 15

**DNA Sequence (SEQ ID NO: 86) and
Protein Sequence (SEQ ID NO: 87) of TIB** atg ttc acc gtg ttt ctg ttg gtt gtc ttg gca acc
Met Phe Thr Val Phe Leu Leu Val Val Leu Ala Thr act gtc gtt tcc ttc cct tca gat att gca act gag
Thr Val Val Ser Phe Pro Ser Asp Ile Ala Thr Glu ggc agg aat gcc gca gcc aaa gcg ttt gac ctg ata
Gly Arg Asn Ala Ala Ala Lys Ala Phe Asp Leu Ile tct tcg atc gtc aag aaa gga tgc tgt tcc cat cct
Ser Ser Ile Val Lys Lys Gly Cys Cys Ser His Pro gcc tgt tcg ggg aat aat cca gaa ttt tgt cgt caa
Ala Cys Ser Gly Asn Asn Pro Glu Phe Cys Arg Gln ggt cgc tgatgctcca ggaccctctg aaccacgacg t
Gly Arg

TABLE 16

**DNA Sequence (SEQ ID NO: 88) and
Protein Sequence (SEQ ID NO: 89) of TIA** atg ttc acc gtg ttt ctg ttg gtt gtc ttg gca acc
Met Phe Thr Val Phe Leu Leu Val Val Leu Ala Thr act gtc gtt tcc ttc cct tca gat ata gca act gag
Thr Val Val Ser Phe Pro Ser Asp Ile Ala Thr Glu ggc agg aat gcc gca gcc aaa gcg ttt gac ctg ata
Gly Arg Asn Ala Ala Ala Lys Ala Phe Asp Leu Ile tct tcg atc gtc agg aaa gga tgc tgt tcc aat ccc
Ser Ser Ile Val Arg Lys Gly Cys Cys Ser Asn Pro gcc tgt gcg ggg aat aat cca cat gtt tgt cgt caa
Ala Cys Ala Gly Asn Asn Pro His Val Cys Arg Gln

TABLE 16-continued

**DNA Sequence (SEQ ID NO: 88) and
Protein Sequence (SEQ ID NO: 89) of TIA** ggt cgc tgatgctcca ggaccctctg aaccacgacg t
Gly Arg

TABLE 17

**DNA Sequence (SEQ ID NO: 90) and
Protein Sequence (SEQ ID NO: 91) of Sl1.1** atg ttc acc gtg ttt ctg ttg gtt gtc ttg gca acc
Met Phe Thr Val Phe Leu Leu Val Val Leu Ala Thr acc gtc gtt tcc ttc aat tca gat cgt gat cca gca
Thr Val Val Ser Phe Asn Ser Asp Arg Asp Pro Ala tta ggt ggc agg aat gct gca gcc aaa gcg tct gac
Leu Gly Gly Arg Asn Ala Ala Ala Lys Ala Ser Asp aag atc gct tcg acc ctc aag aga aga gga tgc tgt
Lys Ile Ala Ser Thr Leu Lys Arg Arg Gly Cys Cys tcg tat ttt gac tgt aga atg atg ttt cca gaa atg
Ser Tyr Phe Asp Cys Arg Met Met Phe Pro Glu Met tgt ggt tgg cga ggc tgatgctcca ggaccctctg
Cys Gly Trp Arg Gly aaccacgacg t

TABLE 18

**DNA Sequence (SEQ ID NO: 92) and
Protein Sequence (SEQ ID NO: 93) of Sl1.2** atg ttc acc gtg ttt ctg ttg gtt gtc ttg gca acc
Met Phe Thr Val Phe Leu Leu Val Val Leu Ala Thr acc gtc gtt tcc ttc aat tca gat cgt gat cca gca
Thr Val Val Ser Phe Asn Ser Asp Arg Asp Pro Ala tta ggt ggc agg aat gct gca gcc ata gcg tct gac
Leu Gly Gly Arg Asn Ala Ala Ala Ile Ala Ser Asp aag atc gct tcg acc ctc agg aga gga gga tgc tgt
Lys Ile Ala Ser Thr Leu Arg Arg Gly Gly Cys Cys tct ttt cct gcc tgt aga aag tat cgt cca gaa atg
Ser Phe Pro Ala Cys Arg Lys Tyr Arg Pro Glu Met tgt ggt gga cga cgc tgatgctcca ggaccctctg
Cys Gly Gly Arg Arg aaccacgacg t

TABLE 19

**DNA Sequence (SEQ ID NO: 94) and
Protein Sequence (SEQ ID NO: 95) of Sl1.3** atg ttc acc gtg ttt ctg ttg gtt gtc ttg gca acc
Met Phe Thr Val Phe Leu Leu Val Val Leu Ala Thr acc gtc gtt tcc ttc act tca gat cat gaa tct gat
Thr Val Val Ser Phe Thr Ser Asp His Glu Ser Asp cgc ggt gat gcc caa acc atc caa gaa gtg ttt gag
Arg Gly Asp Ala Gln Thr Ile Gln Glu Val Phe Glu atg ttc gct ctg gac agc gat gga tgc tgt tgg cat

TABLE 19-continued

DNA Sequence (SEQ ID NO: 94) and
Protein Sequence (SEQ ID NO: 95) of Sl1.3

Met Phe Ala Leu Asp Ser Asp Gly Cys Cys Trp His cct gct tgt ggc aga cac tat tgt ggt cga aga cgc
Pro Ala Cys Gly Arg His Tyr Cys Gly Arg Arg Arg tgatgctcca ggaccctctg aaccacgacg t

TABLE 20

DNA Sequence (SEQ ID NO: 96) and
Protein Sequence (SEQ ID NO: 97) of Sl1.6 atg ttc acc gtg ttt ctg ttg gtt gtc ttg gca acc
Met Phe Thr Val Phe Leu Leu Val Val Leu Ala Thr acc gtc gtt tcc ttc aat tca gat cgt gat cca gca
Thr Val Val Ser Phe Asn Ser Asp Arg Asp Pro Ala tta ggt ggc agg aat gct gca gcc ata gcg tct gac
Leu Gly Gly Arg Asn Ala Ala Ala Ile Ala Ser Asp aag atc gct tcg acc ctc agg aga gga gga tgc tgt
Lys Ile Ala Ser Thr Leu Arg Arg Gly Gly Cys Cys tct ttt gct gcc tgt aga aag tat cgt cca gaa atg
Ser Phe Ala Ala Cys Arg Lys Tyr Arg Pro Glu Met tgt ggt gga cga cgc tgatgct
Cys Gly Gly Arg Arg

TABLE 21

DNA Sequence (SEQ ID NO: 98) and
Protein Sequence (SEQ ID NO: 99) of Sl1.7 atg ttc acc gtg ttt ctg ttg gtt ctc ttg gca acc
Met Phe Thr Val Phe Leu Leu Val Leu Leu Ala Thr acc gtc gtt tcc ttc aat tca gat cgt gca tta ggt
Thr Val Val Ser Phe Asn Ser Asp Arg Ala Leu Gly ggc agg aat gct gca gcc aaa gcg tct gac aag atc
Gly Arg Asn Ala Ala Ala Lys Ala Ser Asp Lys Ile ctt tcg aac ctc agg aga gga gga tgc tgt ttt cat
Leu Ser Asn Leu Arg Arg Gly Gly Cys Cys Phe His cct gtc tgt tac atc aat ctt cta gaa atg tgt cgt
Pro Val Cys Tyr Ile Asn Leu Leu Glu Met Cys Arg caa cga ggc tgatcgtcca ggaccctctg aaccacgacg t
Gln Arg Gly

TABLE 22

DNA Sequence (SEQ ID NO: 100) and
Protein Sequence (SEQ ID NO: 101) of Cn1.1 atg ttc acc gtg ttt ctg ttg gtt gtc ttg aca acc
Met Phe Thr Val Phe Leu Leu Val Val Leu Thr Thr act gtc gtt tcc ttc cct tca gat agt gca tct gat
Thr Val Val Ser Phe Pro Ser Asp Ser Ala Ser Asp gtc agg gat gac gaa gcc aaa gac gaa agg tct gac
Val Arg Asp Asp Glu Ala Lys Asp Glu Arg Ser Asp atg tac aaa tcg aaa cgg aat gga cgc tgt tgc cat
Met Tyr Lys Ser Lys Arg Asn Gly Arg Cys Cys His

TABLE 22-continued

DNA Sequence (SEQ ID NO: 100) and
Protein Sequence (SEQ ID NO: 101) of Cn1.1 cct gcc tgt ggc aaa cac ttt agt tgt gga cgc
Pro Ala Cys Gly Lys His Phe Ser Cys Gly Arg tgatgctcca ggaccctctg aaccacgacg t

TABLE 23

DNA Sequence (SEQ ID NO: 102) and
Protein Sequence (SEQ ID NO: 103) of SmI atg ttc acc gtg ttt ctg ttg gtt gtc ttg gca acc
Met Phe Thr Val Phe Leu Leu Val Val Leu Ala Thr act gtc gtt tcc tcc cct tca gat cgt gca tct gat
Thr Val Val Ser Ser Pro Ser Asp Arg Ala Ser Asp ggc agg aat gcc gca gcc aac gag aaa gcg tct gac
Gly Arg Asn Ala Ala Ala Asn Glu Lys Ala Ser Asp gtg atc gcg ctg gcc ctc aag gga tgc tgt tcc aac
Val Ile Ala Leu Ala Leu Lys Gly Cys Cys Ser Asn cct gtc tgt cac ctg gag cat tca aac atg tgt ggt
Pro Val Cys His Leu Glu His Ser Asn Met Cys Gly aga aga cgc tgatgctcca ggaccctctg aaccacgacg
Arg Arg Arg

TABLE 24

DNA Sequence (SEQ ID NO: 104) and
Protein Sequence (SEQ ID NO: 105) of Bt1.1 atg ttc tcc gtg ttt ctg ttg gtt gtc ttg gca acc
Met Phe Ser Val Phe Leu Leu Val Val Leu Ala Thr act gtc gtt tcc tcc act tca ggt ggt gca tct ggt
Thr Val Val Ser Ser Thr Ser Gly Gly Ala Ser Gly ggc agg aag gct gca gcc aaa gcg tct aac cgg atc
Gly Arg Lys Ala Ala Ala Lys Ala Ser Asn Arg Ile gct ctg acc gtc agg agt gca aca tgc tgt aat tat
Ala Leu Thr Val Arg Ser Ala Thr Cys

TABLE 25-continued

DNA Sequence (SEQ ID NO: 106) and
Protein Sequence (SEQ ID NO: 107) of Bt1.2 cat cct gcc t

TABLE 31-continued

DNA Sequence (SEQ ID NO: 118) and Protein Sequence (SEQ ID NO: 119) of Sm1.3 cct gcc tgt gag agc cac aga tgt ggt tgacgacgct
Pro Ala Cys Glu Ser His Arg Cys Gly gatgctccag gaccctctga accacgacg

TABLE 32

DNA Sequence (SEQ ID NO: 120) and Protein Sequence (SEQ ID NO: 121) of Crl.2 atg ttc acc gtg ttt ctg ttg gtt gtc ttg gca acc
Met Phe Thr Val Phe Leu Leu Val Val Leu Ala Thr act gtc gtt tcc ttc cct tca gat cgt gca tct gat
Thr Val Val Ser Phe Pro Ser Asp Arg Ala Ser Asp ggc agg aat gcc gca gcc agc gac aga gcg tct gac
Gly Arg Asn Ala Ala Ala Ser Asp Arg Ala Ser Asp gcg gcc cac cag gga tgc tgt tcc aac cct gtc tgt
Ala Ala His Gln Gly Cys Cys Ser Asn Pro Val Cys cac gtg gaa cat cca gaa ctt tgt cgt aga aga cgc
His Val Glu His Pro Glu Leu Cys Arg Arg Arg Arg tgatgctcca ggaccctctg aaccacgacg

TABLE 33

DNA Sequence (SEQ ID NO: 122) and Protein Sequence (SEQ ID NO: 123) of Crl.3 atg ttc acc gtg ttt ctg ttg gtt gtc ttg gca acc
Met Phe Thr Val Phe Leu Leu Val Val Leu Ala Thr act gtc gtt tcc ttc cct tca aat cgt gaa tct gat
Thr Val Val Ser Phe Pro Ser Asn Arg Glu Ser Asp ggc gcg aat gcc gaa gtc cgc acc gac gag cct gag
Gly Ala Asn Ala Glu Val Arg Thr Asp Glu Pro Glu gag cac gac gaa ctg ggc ggg aat gga tgc tgt ggg
Glu His Asp Glu Leu Gly Gly Asn Gly Cys Cys Gly aat cct gac tgt acg agc cac agt tgt gat tgacgacgct
Asn Pro Asp Cys Thr Ser His Ser Cys Asp gatgctccag gaccctctga accacgacg

TABLE 34

DNA Sequence (SEQ ID NO: 124) and Protein Sequence (SEQ ID NO: 125) of EpI atg ttc acc gtg ttt ctg ttg gtt gtc ttg gca acc
Met Phe Thr Val Phe Leu Leu Val Val Leu Ala Thr acc gtc gtt tcc ttc act tca gat cgt gca tct gat
Thr Val Val Ser Phe Thr Ser Asp Arg Ala Ser Asp agc agg aag gac gca gcg tct ggc ctg atc gct ctg
Ser Arg Lys Asp Ala Ala Ser Gly Leu Ile Ala Leu acc atc aag gga tgc tgt tct gat cct cgc tgt aac
Thr Ile Lys Gly Cys Cys Ser Asp Pro Arg Cys Asn

TABLE 34-continued

DNA Sequence (SEQ ID NO: 124) and Protein Sequence (SEQ ID NO: 125) of EpI atg aat aat cca gac tat tgt ggt tgacgacgct
Met Asn Asn Pro Asp Tyr Cys Gly gatgctccag gaccctctga accacgacg

TABLE 35

DNA Sequence (SEQ ID NO: 126) and Protein Sequence (SEQ ID NO: 127) of Sn1.1 atg tcc acc gtg ttt ctg ttg gtt gtc ctc gca acc
Met Ser Thr Val Phe Leu Leu Val Val Leu Ala Thr acc gtc gtt tcc ttc act gta gat cgt gca tct gat
Thr Val Val Ser Phe Thr Val Asp Arg Ala Ser Asp ggc agg gat gtc gca atc gac gac aga ttg gtg tct
Gly Arg Asp Val Ala Ile Asp Asp Arg Leu Val Ser ctc cct cag atc gcc cat gct gac tgt tgt tcc gat
Leu Pro Gln Ile Ala His Ala Asp Cys Cys Ser Asp cct gcc tgc aag cag acg ccc ggt tgt cgt taaagacgct
Pro Ala Cys Lys Gln Thr Pro Gly Cys Arg gctgctccag gaccctctga accacgacg

TABLE 36

DNA Sequence (SEQ ID NO: 128) and Protein Sequence (SEQ ID NO: 129) of Sn1.2 atg ttc acc gtg ttt ctg ttg gtt gtc ttg gca acc
Met Phe Thr Val Phe Leu Leu Val Val Leu Ala Thr acc gtc gct tcc ttc att atc gat gat cca tct gat
Thr Val Ala Ser Phe Ile Ile Asp Asp Pro Ser Asp ggc agg aat att gca gtc gac gac aga ggg ctt ttc
Gly Arg Asn Ile Ala Val Asp Asp Arg Gly Leu Phe tct acg ctc ttc cat gct gat tgc tgt gaa aat cct
Ser Thr Leu Phe His Ala Asp Cys Cys Glu Asn Pro gcc tgt aga cac acg cag ggt tgt tgatctttgt
Ala Cys Arg His Thr Gln Gly Cys tcttcaaaga cactgctggc ccaggaccct ctgaaccacg acg

TABLE 37

DNA Sequence (SEQ ID NO: 130) and Protein Sequence (SEQ ID NO: 131) of Da1.1 atg ttc acc gtg ttt ctg ttg gtt gtc ttg gca acc
Met Phe Thr Val Phe Leu Leu Val Val Leu Ala Thr acc gtc gtt tcc ttc act tca gat cgt gca ttt cgt
Thr Val Val Ser Phe Thr Ser Asp Arg Ala Phe Arg ggc agg aat gcc gca gcc aaa gag tct ggc ctg gtc
Gly Arg Asn Ala Ala Ala Lys Glu Ser Gly Leu Val ggt ctg acc gac aag acg cga gga tgc tgt tct cat
Gly Leu Thr Asp Lys Thr Arg Gly Cys Cys Ser His

TABLE 37-continued

DNA Sequence (SEQ ID NO: 130) and
Protein Sequence (SEQ ID NO: 131) of Da1.1 cct gcc tgt aac gta gat cat cca gaa att tgt ggt
Pro Ala Cys Asn Val Asp His Pro Glu Ile Cys Gly tgaagacgct gatgctccag gaccctctga accacgacgt

TABLE 38

DNA Sequence (SEQ ID NO: 132) and
Protein Sequence (SEQ ID NO: 133) of Da1.2 atg ttc acc gtg ttt ctg ttg gtt gtc ttg gca acc
Met Phe Thr Val Phe Leu Leu Val Val Leu Ala Thr acc gtc gtt tcc ttc act tca gat ggt gca tct gat
Thr Val Val Ser Phe Thr Ser Asp Gly Ala Ser Asp gac agg aaa gcc gct gcg tct gac ctg atc act ctg
Asp Arg Lys Ala Ala Ala Ser Asp Leu Ile Thr Leu acc atc aag gga tgc tgt tct cgt cct ccc tgt atc
Thr Ile Lys Gly Cys Cys Ser Arg Pro Pro Cys Ile gcg aat aat cca gac ttg tgt ggt cga cga cgc
Ala Asn Asn Pro Asp Leu Cys Gly Arg Arg Arg tgatgctcca ggaccctctg

TABLE 39

DNA Sequence (SEQ ID NO: 134) and
Protein Sequence (SEQ ID NO: 135) of Da1.3 atg ttc acc gtg ttt ctg ttg gtt gtc ttg gca acc
Met Phe Thr Val Phe Leu Leu Val Val Leu Ala Thr act gtc gtt tcc tcc act tca ggt cgt cgt gca ttt
Thr Val Val Ser Ser Thr Ser Gly Arg Arg Ala Phe cat ggc agg aat gcc gca gcc aaa gcg tct gga ctg
His Gly Arg Asn Ala Ala Ala Lys Ala Ser Gly Leu gtc ggt ctg act gac agg aga cca caa tgc tgt agt
Val Gly Leu Thr Asp Arg Arg Pro Gln Cys Cys Ser gat cct cgc tgt aac gta ggt cat cca gaa ctt tgt
Asp Pro Arg Cys Asn Val Gly His Pro Glu Leu Cys ggt gga aga cgc tgatgctcca ggaccctctg aaccacaacg t
Gly Gly Arg Arg

TABLE 40

DNA Sequence (SEQ ID NO: 136) and
Protein Sequence (SEQ ID NO: 137) of Da1.4 atg ttc acc gtg ttt ctg ttg gtt gtc ttg gca acc
Met Phe Thr Val Phe Leu Leu Val Val Leu Ala Thr act gtc gtt tcc tcc act tca ggt cgt gca ttt cat
Thr Val Val Ser Ser Thr Ser Gly Arg Ala Phe His ggc agg aat gcc gca gcc aaa gcg tct ggc ctg gtc
Gly Arg Asn Ala Ala Ala Lys Ala Ser Gly Leu Val ggt ctg acc gac aag agg caa gta tgc tgt agt gat
Gly Leu Thr Asp Lys Arg Gln Val Cys Cys Ser Asp cct cgc tgt aac gta ggt cat cca gaa att tgt ggt
Pro Arg Cys Asn Val Gly His Pro Glu Ile Cys Gly

TABLE 40-continued

DNA Sequence (SEQ ID NO: 136) and
Protein Sequence (SEQ ID NO: 137) of Da1.4 gga aga cgc tgatgctcca ggaccctctg aaccacgacg t
Gly Arg Arg

TABLE 41

DNA Sequence (SEQ ID NO: 138) and
Protein Sequence (SEQ ID NO: 139) of A1.2 atg ttc acc gtg ttt ctg ttg gtt gtc ttg aca acc
Met Phe Thr Val Phe Leu Leu Val Val Leu Thr Thr act gtc gtt tcc ttc cct tca gat agt gca tct ggt
Thr Val Val Ser Phe Pro Ser Asp Ser Ala Ser Gly ggc agg gat gac gag gcc aaa gac gaa agg tct gac
Gly Arg Asp Asp Glu Ala Lys Asp Glu Arg Ser Asp atg tac gaa ttg aaa cgg aat gga cgc tgt tgc cat
Met Tyr Glu Leu Lys Arg Asn Gly Arg Cys Cys His cct gcc tgt ggt ggc aaa tac gtt aaa tgt gga cgc
Pro Ala Cys Gly Gly Lys Tyr Val Lys Cys Gly Arg tgatgctcca ggaccctctc gaaccacg

TABLE 42

DNA Sequence (SEQ ID NO: 140) and
Protein Sequence (SEQ ID NO: 141) of Bu1.1 atg ttc acc gtg ttt ctg ttg gtt gtc ttg gca acc
Met Phe Thr Val Phe Leu Leu Val Val Leu Ala Thr act gtc gtt tcc ttc tct aca gat gat gaa tct gat
Thr Val Val Ser Phe Ser Thr Asp Asp Glu Ser Asp ggc tcg aat gaa gaa ccc agc gcc gac cag act gcc
Gly Ser Asn Glu Glu Pro Ser Ala Asp Gln Thr Ala agg tcc tca atg aac agg gcg cct gga tgc tgt aac
Arg Ser Ser Met Asn Arg Ala Pro Gly Cys Cys Asn aat cct gcc tgt gtg aag cac aga tgt gga tgacgctgat
Asn Pro Ala Cys Val Lys His Arg Cys Gly gctccaggac cctctgaacc acgacgt

TABLE 43

DNA Sequence (SEQ ID NO: 142) and
Protein Sequence (SEQ ID NO: 143) of Bu1.2 atg ttc acc gtg ttt ctg ttg gtt gtc ttg gca acc
Met Phe Thr Val Phe Leu Leu Val Val Leu Ala Thr act gtc gtt tcc ttc tct aca gat gat gaa tct gat
Thr Val Val Ser Phe Ser Thr Asp Asp Glu Ser Asp ggc tcg aat gaa gaa ccc agc gcc gac cag gct gcc
Gly Ser Asn Glu Glu Pro Ser Ala Asp Gln Ala Ala agg tcc gca atg aac agg ccg cct gga tgc tgt aac
Arg Ser Ala Met Asn Arg Pro Pro Gly Cys Cys Asn

TABLE 43-continued

DNA Sequence (SEQ ID NO: 142) and
Protein Sequence (SEQ ID NO: 143) of Bu1.2 aat cct gcc tgt gtg aag cac aga tgt ggt gga
Asn Pro Ala Cys Val Lys His Arg Cys Gly Gly tgacgctgat gctccaggac cctctgaacc acgacgt

TABLE 44

DNA Sequence (SEQ ID NO: 144) and
Protein Sequence (SEQ ID NO: 145) of Bu1.3 atg ttc acc gtg ttt ctg ttg gtt gtc ttg gca acc
Met Phe Thr Val Phe Leu Leu Val Val Leu Ala Thr act gtc gtt tcc ttc cct tca gat cgt gac tct gat
Thr Val Val Ser Phe Pro Ser Asp Arg Asp Ser Asp ggc gcg gat gcc gaa gcc agt gac gag cct gtt gag
Gly Ala Asp Ala Glu Ala Ser Asp Glu Pro Val Glu ttc gaa agg gac gag aat gga tgc tgt tgg aat cct
Phe Glu Arg Asp Glu Asn Gly Cys Cys Trp Asn Pro tcc tgt ccg agg ccc aga tgt aca gga cga cgc
Ser Cys Pro Arg Pro Arg Cys Thr Gly Arg Arg taatgctcca ggaccctctg aaccacgacg t

TABLE 45

DNA Sequence (SEQ ID NO: 146) and
Protein Sequence (SEQ ID NO: 170) of Bu1.4 atg ttc acc gtg ttt ctg ttg gtt gtc ttg aca acc
Met Phe Thr Val Phe Leu Leu Val Val Leu Thr Thr act gtc gtt tcc ttc cct tca gat cgt gca tct gat
Thr Val Val Ser Phe Pro Ser Asp Arg Ala Ser Asp ggc agg aat gcc gca gcc aac gac aaa gcg tct gac
Gly Arg Asn Ala Ala Ala Asn Asp Lys Ala Ser Asp gtg gtc acg ctg gtc ctc aag gga tgc tgt tcc acc
Val Val Thr Leu Val Leu Lys Gly Cys Cys Ser Thr cct ccc tgt gct gtg ctg tat tgt ggt aga aga cgc
Pro Pro Cys Ala Val Leu Tyr Cys Gly Arg Arg Arg tgatgctcca ggaccctctg aaccacgacg t

TABLE 46

DNA Sequence (SEQ ID NO: 148) and
Protein Sequence (SEQ ID NO: 149) of Di1.1 atg ttc acc gtg ttt ctg ttg gtt gtc ttc gca tcc
Met Phe Thr Val Phe Leu Leu Val Val Phe Ala Ser tct gtc acc tta gat cgt gca tct tat ggc agg tat
Ser Val Thr Leu Asp Arg Ala Ser Tyr Gly Arg Tyr gcc tca ccc gtc gac aga gcg tct gcc ctg atc gct
Ala Ser Pro Val Asp Arg Ala Ser Ala Leu Ile Ala cag gcc atc ctt cga gat tgc tgc tcc aat cct cct
Gln Ala Ile Leu Arg Asp Cys Cys Ser Asn Pro Pro

TABLE 46-continued

DNA Sequence (SEQ ID NO: 148) and
Protein Sequence (SEQ ID NO: 149) of Di1.1 tgt gcc cat aat aat cca gac tgt cgt taaagacgct
Cys Ala His Asn Asn Pro Asp Cys Arg gcttgctcca ggaccctctg aaccacgacg t

TABLE 47

DNA Sequence (SEQ ID NO: 150) and
Protein Sequence (SEQ ID NO: 151) of T1 gga tgc tgt tct aat cct ccc tgt atc gcg aag aat
Gly Cys Cys Ser Asn Pro Pro Cys Ile Ala Lys Asn cca cac atg tgt ggt gga aga cgc tga
Pro His Met Cys Gly Gly Arg Arg

TABLE 48

DNA Sequence (SEQ ID NO: 152) and
Protein Sequence (SEQ ID NO: 153) of Cn1.2 atg ttc acc gtg ttt ctg ttg gtt gtc ttg gca acc
Met Phe Thr Val Phe Leu Leu Val Val Leu Ala Thr act gtc gtt tcc ttc cct tca gat cgt gca tct gat
Thr Val Val Ser Phe Pro Ser Asp Arg Ala Ser Asp ggc agg aat gcc gca gcc aac gac aaa gcg tct gac
Gly Arg Asn Ala Ala Ala Asn Asp Lys Ala Ser Asp gtg atc acg ctg gcc ctc aag gga tgc tgt tcc aac
Val Ile Thr Leu Ala Leu Lys Gly Cys Cys Ser Asn cct gtc tgt cac ttg gag cat tca aac ctt tgt ggt
Pro Val Cys His Leu Glu His Ser Asn Leu Cys Gly aga aga cgc tgatgctcca ggaccctctg aaccacgacg t
Arg Arg Arg

TABLE 49

DNA Sequence (SEQ ID NO: 233) and
Protein Sequence (SEQ ID NO: 234) of Im1.1 tct gat gga aag agt gcc gcg gcc aaa gcc aaa ccg
Ser Asp Gly Lys Ser Ala Ala Ala Lys Ala Lys Pro tct cac ctg acg gct cca ttc atc agg gac gaa tgc
Ser His Leu Thr Ala Pro Phe Ile Arg Asp Glu Cys tgt tcc gat tct cgc tgt ggc aag aac tgt ctt tga
Cys Ser Asp Ser Arg Cys Gly Lys Asn Cys Leu

TABLE 50

DNA Sequence (SEQ ID NO: 235) and
Protein Sequence (SEQ ID NO: 236) of Im1.2 ttt gat gga agg aat gcc cca gcc gac gac aaa gcg
Phe Asp Gly Arg Asn Ala Pro Ala Asp Asp Lys Ala tct gac ctg atc gct caa atc gtc agg aga gca tgc
Ser Asp Leu Ile Ala Gln Ile Val Arg Arg Ala Cys

TABLE 50-continued

DNA Sequence (SEQ ID NO: 235) and
Protein Sequence (SEQ ID NO: 236) of Im1.2 tgt tcc gat cgt cgc tgt aga tgg agg tgt ggt tga
Cys Ser Asp Arg Arg Cys Arg Trp Arg Cys Gly

TABLE 51

DNA Sequence (SEQ ID NO: 237) and
Protein Sequence (SEQ ID NO: 238) of Rg1.2 tct gat gga agg aat gcc gca gcc gac gcc aga gcg
Ser Asp Gly Arg Asn Ala Ala Ala Asp Ala Arg Ala tct ccc cgg atc gct ctt ttc ctc agg ttc aca tgc
Ser Pro Arg Ile Ala Leu Phe Leu Arg Phe Thr Cys tgt agg aga ggt acc tgt tcc cag cac tgt ggt
Cys Arg Arg Gly Thr Cys Ser Gln His Cys Gly tgaagacact gctgctccag gaccctctga accacgacgt

TABLE 52

DNA Sequence (SEQ ID NO: 239) and
Protein Sequence (SEQ ID NO: 240) of Rg1.6 tct aat gga agg aat gcc gca gcc gac gcc aaa gcg
Ser Asn Gly Arg Asn Ala Ala Ala Asp Ala Lys Ala tct caa cgg atc gct cca ttc ctc agg gac tat tgc
Ser Gln Arg Ile Ala Pro Phe Leu Arg Asp Tyr Cys tgt agg aga cat gcc tgt acg ttg att tgt ggt
Cys Arg Arg His Ala Cys Thr Leu Ile Cys Gly tgaagacgct gctgctccag gaccctctga accacgacgt

TABLE 53

DNA Sequence (SEQ ID NO: 241) and
Protein Sequence (SEQ ID NO: 242) of Rg1.6A tct aat gga agg aat gcc gca gcc gac gcc aaa gcg
Ser Asn Gly Arg Asn Ala Ala Ala Asp Ala Lys Ala tct caa cgg atc gct cca ttc ctc agg gac tat tgc
Ser Gln Arg Ile Ala Pro Phe Leu Arg Asp Tyr Cys tgt agg aga cct ccc tgt acg ttg att tgt ggt
Cys Arg Arg Pro Pro Cys Thr Leu Ile Cys Gly tgaagacgct gctgctccag gaccctctga accacgacgt

TABLE 54

DNA Sequence (SEQ ID NO: 243) and
Protein Sequence (SEQ ID NO: 244) of Rg1.7 tct aat aaa agg aag aat gcc gca atg ctt gac atg
Ser Asn Lys Arg Lys Asn Ala Ala Met Leu Asp Met atc gct caa cac gcc ata agg ggt tgc tgt tcc gat
Ile Ala Gln His Ala Ile Arg Gly Cys Cys Ser Asp

TABLE 54-continued

DNA Sequence (SEQ ID NO: 243) and
Protein Sequence (SEQ ID NO: 244) of Rg1.7 cct cgc tgt aga tat aga tgt cgt tgaagacgct
Pro Arg Cys Arg Tyr Arg Cys Arg gctgctccag gaccctctga accacgacgt

TABLE 55

DNA Sequence (SEQ ID NO: 245) and
Protein Sequence (SEQ ID NO: 246) of Rg1.9 ttt aat gga agg agt gcc gca gcc gac caa aat gcg
Phe Asn Gly Arg Ser Ala Ala Ala Asp Gln Asn Ala cct ggc ctg atc gct caa gtc gtc aga gga ggg tgc
Pro Gly Leu Ile Ala Gln Val Val Arg Gly Gly Cys tgt tcc gat ccc cgc tgc gcc tgg aga tgt ggt
Cys Ser Asp Pro Arg Cys Ala Trp Arg Cys Gly tgaagacgtt gctgctccag gaccctctga accacgacgt

TABLE 56

DNA Sequence (SEQ ID NO: 247) and
Protein Sequence (SEQ ID NO: 248) of Rg1.10 ttt gat gga agg aat gcc gca gcc gac gcc aaa gtg
Phe Asp Gly Arg Asn Ala Ala Ala Asp Ala Lys Val att aac acg gtc gct cga atc gcc tgg gat ata tgc
Ile Asn Thr Val Ala Arg Ile Ala Trp Asp Ile Cys tgt tcc gaa cct gac tgt aac cat aaa tgt gtt
Cys Ser Glu Pro Asp Cys Asn His Lys Cys Val tgaagacgct tctgctccag gaccctctga accacgacgt

TABLE 57

DNA Sequence (SEQ ID NO: 249) and
Protein Sequence (SEQ ID NO: 250) of Rg1.11 tct aat aaa agg aag aat gcc gca atg ctt gac atg
Ser Asn Lys Arg Lys Asn Ala Ala Met Leu Asp Met atc gct caa cac gcc ata agg ggt tgc tgt tcc gat
Ile Ala Gln His Ala Ile Arg Gly Cys Cys Ser Asp cct cgc tgt aaa cat cag tgt ggt tgaagacgct
Pro Arg Cys Lys His Gln Cys Gly gctgctccag gaccctctga accacgacgt

TABLE 58

DNA Sequence (SEQ ID NO: 251) and
Protein Sequence (SEQ ID NO: 252) of Ms1.7 atc aag aat aca gca gcc agc aac aaa gcg tct agc
Ile Lys Asn Thr Ala Ala Ser Asn Lys Ala Ser Ser ctg gtg gct ctt gtt gtc agg gga tgc tgt tac aat
Leu Val Ala Leu Val Val Arg Gly Cys Cys Tyr Asn

TABLE 58-continued

DNA Sequence (SEQ ID NO: 251) and
Protein Sequence (SEQ ID NO: 252) of Ms1.7 cct gtc tgc aag aaa tat tat tgt tgg aaa ggc
Pro Val Cys Lys Lys Tyr Tyr Cys Trp Lys Gly tgatgctcca ggaccctctg aaccacgacg t

TABLE 59

DNA Sequence (SEQ ID NO: 253) and
Protein Sequence (SEQ ID NO: 254) of P1.7 tct gaa ggc agg aat gct gaa gcc atc gac aac gcc
Ser Glu Gly Arg Asn Ala Glu Ala Ile Asp Asn Ala tta gac cag agg gat cca aag cga cag gag ccg ggg
Leu Asp Gln Arg Asp Pro Lys Arg Gln Glu Pro Gly tgc tgt agg cat cct gcc tgt ggg aag aac aga tgt
Cys Cys Arg His Pro Ala Cys Gly Lys Asn Arg Cys gga aga cgc tgatgctcca ggaccctctg aaccacgacg t
Gly Arg Arg

TABLE 60

DNA Sequence (SEQ ID NO: 255) and
Protein Sequence (SEQ ID NO: 256) of Ms1.2 tct gat ggc agg aat att gca gtc gac gac aga tgg
Ser Asp Gly Arg Asn Ile Ala Val Asp Asp Arg Trp tct ttc tat acg ctc ttc cat gct act tgc tgt gcc
Ser Phe Tyr Thr Leu Phe His Ala Thr Cys Cys Ala gat cct gac tgt aga ttc cgg ccc ggt tgt tgatctttgt
Asp Pro Asp Cys Arg Phe Arg Pro Gly Cys tcttcaaaga cgctgctggc ccaggaccct ctgaaccacg acgt

TABLE 61

DNA Sequence (SEQ ID NO: 257) and
Protein Sequence (SEQ ID NO: 258) of Ms1.3 atc aag aat act gca gcc agc aac aaa gcg cct agc
Ile Lys Asn Thr Ala Ala Ser Asn Lys Ala Pro Ser ctg gtg gct att gcc gtc agg gga tgc tgt tac aat
Leu Val Ala Ile Ala Val Arg Gly Cys Cys Tyr Asn cct tcc tgt tgg ccg aaa aca tat tgt agt tggaaaggct
Pro Ser Cys Trp Pro Lys Thr Tyr Cys Ser gatgctccag gaccctctga accacgacgt

TABLE 62

DNA Sequence (SEQ ID NO: 259) and
Protein Sequence (SEQ ID NO: 260) of Ms1.4 tct gat agc agg aat gtc gca atc gag gac aga gtg
Ser Asp Ser Arg Asn Val Ala Ile Glu Asp Arg Val tct gac ctg cac tct atg ttc ttc gat gtt tct tgc
Ser Asp Leu His Ser Met Phe Phe Asp Val Ser Cys tgt agc aat cct acc tgt aaa gaa acg tat ggt tgt

TABLE 62-continued

DNA Sequence (SEQ ID NO: 259) and
Protein Sequence (SEQ ID NO: 260) of Ms1.4

Cys Ser Asn Pro Thr Cys Lys Glu Thr Tyr Gly Cys tgatcgttgg ttttgaagac gctgatgctc caggaccctc

TABLE 63

DNA Sequence (SEQ ID NO: 261) and
Protein Sequence (SEQ ID NO: 262) of Ms1.5 tct gtt ggc agg aat att gca gtc gac gac aga ggg
Ser Val Gly Arg Asn Ile Ala Val Asp Asp Arg Gly att ttc tct acg ctc ttc cat gct cat tgc tgt gcc
Ile Phe Ser Thr Leu Phe His Ala His Cys Cys Ala aat ccc atc tgt aaa aac acg ccc ggt tgt tgatctttgt
Asn Pro Ile Cys Lys Asn Thr Pro Gly Cys tcttcaaaga cgctgctggc ccaggaccct ctgaaccacg acgt

TABLE 64

DNA Sequence (SEQ ID NO: 263) and
Protein Sequence (SEQ ID NO: 264) of Ms1.8 tcc gat ggc agg aat gtc gca atc gac gac aga gtg
Ser Asp Gly Arg Asn Val Ala Ile Asp Asp Arg Val tct gac ctg cac tct atg ttc ttc gat att gct tgc
Ser Asp Leu His Ser Met Phe Phe Asp Ile Ala Cys tgt aac aat cct acc tgt aaa gaa acg tat ggt tgt
Cys Asn Asn Pro Thr Cys Lys Glu Thr Tyr Gly Cys tgatcgttgg ttttgaagac gctgatgctc caggaccctc tgaaccacga cgt

TABLE 65

DNA Sequence (SEQ ID NO: 265) and
Protein Sequence (SEQ ID NO: 266) of Ms1.9 tct gat ggc agg aat gtc gca atc gag gac aga gtg
Ser Asp Gly Arg Asn Val Ala Ile Glu Asp Arg Val tct gac ctg ctc tct atg ctc ttc gat gtt gct tgc
Ser Asp Leu Leu Ser Met Leu Phe Asp Val Ala Cys tgt agc aat cct gtc tgt aaa gaa acg tat ggt tgt
Cys Ser Asn Pro Val Cys Lys Glu Thr Tyr Gly Cys tgatcgttgg ttttgaagac gctgatgctc caggaccctc tgaaccacga cgt

TABLE 66

DNA Sequence (SEQ ID NO: 267) and
Protein Sequence (SEQ ID NO: 268) of Bt1.7 tat gat ggc agg aat gct gcc gcc gac gac aaa gct
Tyr Asp Gly Arg Asn Ala Ala Ala Asp Asp Lys Ala ttt gac ctg ctg gct atg acc ata agg gga gga tgc
Phe Asp Leu Leu Ala Met Thr Ile Arg Gly Gly Cys

TABLE 66-continued

DNA Sequence (SEQ ID NO: 267) and
Protein Sequence (SEQ ID NO: 268) of Bt1.7 tgt tcc tat cct ccc tgt atc gcg agt aat cct aaa
Cys Ser Tyr Pro Pro Cys Ile Ala Ser Asn Pro Lys tgt ggt g

TABLE 74

DNA Sequence (SEQ ID NO: 283) and
Protein Sequence (SEQ ID NO: 284) of A1.4 tct gat ggc agg aat gcc gca gcc aac gac aaa gcg
Ser Asp Gly Arg Asn Ala Ala Ala Asn Asp Lys Ala tct ggc atg agc gcg ctg gcc gtc aat gaa tgc tgt
Ser Gly Met Ser Ala Leu Ala Val Asn Glu Cys Cys acc aac cct gtc tgt cac gcg gaa cat caa gaa ctt
Thr Asn Pro Val Cys His Ala Glu His Gln Glu Leu tgt gct aga aga cgc tga
Cys Ala Arg Arg Arg

TABLE 75

DNA Sequence (SEQ ID NO: 285) and
Protein Sequence (SEQ ID NO: 286) of A1.5 tct gat ggc agg aat gcc gca gcc aac gac aaa gcg
Ser Asp Gly Arg Asn Ala Ala Ala Asn Asp Lys Ala tct gac gtg atc acg ctg gcc ctc aag gga tgc tgt
Ser Asp Val Ile Thr Leu Ala Leu Lys Gly Cys Cys tcc aac cct gtc tgt cac ttg gag cat tca aac ctt
Ser Asn Pro Val Cys His Leu Glu His Ser Asn Leu tgt ggt aga aga cgc tga
Cys Gly Arg Arg Arg

TABLE 76

DNA Sequence (SEQ ID NO: 287) and
Protein Sequence (SEQ ID NO: 288) of A1.6 tct gat ggc agg aat gcc gca gcc aac gac aaa gcg
Ser Asp Gly Arg Asn Ala Ala Ala Asn Asp Lys Ala tct ggc atg agc gcg ctg gcc gtc aat gaa tgc tgt
Ser Gly Met Ser Ala Leu Ala Val Asn Glu Cys Cys acc aac cct gtc tgt cac gtg gaa cat caa gaa ctt
Thr Asn Pro Val Cys His Val Glu His Gln Glu Leu tgt gct aga aga cgc tga
Cys Ala Arg Arg Arg

TABLE 77

DNA Sequence (SEQ ID NO: 289) and
Protein Sequence (SEQ ID NO: 290) of Af1.1 atg ttc acc gtg ttt ctg ttg gtt gtc ttg gca acc
Met Phe Thr Val Phe Leu Leu Val Val Leu Ala Thr acc gtc gtt tcc ttc act tca gat cgt gca ttt cgt
Thr Val Val Ser Phe Thr Ser Asp Arg Ala Phe Arg ggc agg aat gcc gca gcc aaa gcg tct ggc ctg gtc
Gly Arg Asn Ala Ala Ala Lys Ala Ser Gly Leu Val ggt ctg acc gac aag agg caa gaa tgc tgt tct tat
Gly Leu Thr Asp Lys Arg Gln Glu Cys Cys Ser Tyr cct gcc tgt aac cta gat cat cca gaa ctt tgt ggt
Pro Ala Cys Asn Leu Asp His Pro Glu Leu Cys Gly tgaagacgct gatgctccag gaccctctga accacgacgt

TABLE 78

DNA Sequence (SEQ ID NO: 291) and
Protein Sequence (SEQ ID NO: 292) of Af1.2 atg ttc acc gtg ttt ctg ttg gtt gtc ttg gca acc
Met Phe Thr Val Phe Leu Leu Val Val Leu Ala Thr act gtc gtt tcc tcc act tca ggt cgt cgt gca ttt
Thr Val Val Ser Ser Thr Ser Gly Arg Arg Ala Phe cgt ggc agg aat gcc gca gcc aaa gcg tct gga ctg
Arg Gly Arg Asn Ala Ala Ala Lys Ala Ser Gly Leu gtc ggt ctg act gac agg aga cca gaa tgc tgt agt
Val Gly Leu Thr Asp Arg Arg Pro Glu Cys Cys Ser gat cct cgc tgt aac tcg act cat cca gaa ctt tgt
Asp Pro Arg Cys Asn Ser Thr His Pro Glu Leu Cys ggt gga aga cgc tgatgctcca ggaccctctg aaccacgacg t
Gly Gly Arg Arg

TABLE 79

DNA Sequence (SEQ ID NO: 293) and
Protein Sequence (SEQ ID NO: 294) of Ar1.2 tct gat ggc agg aat gcc gca gcc aac gcg ttt gac
Ser Asp Gly Arg Asn Ala Ala Ala Asn Ala Phe Asp ctg atc gat ctg acc gcc agg cta aat tgc tgt atg
Leu Ile Asp Leu Thr Ala Arg Leu Asn Cys Cys Met att ccc ccc tgt tgg aag aaa tat gga gac aga tgt
Ile Pro Pro Cys Trp Lys Lys Tyr Gly Asp Arg Cys agt gaa gta cgc tgatgctcca ggaccctctg aaccacgacg t
Ser Glu Val Arg

TABLE 80

DNA Sequence (SEQ ID NO: 295) and
Protein Sequence (SEQ ID NO: 296) of Ar1.3 tct gat ggc agg aat gcc gca cgc aaa gcg ttt ggc
Ser Asp Gly Arg Asn Ala Ala Arg Lys Ala Phe Gly tgc tgc gac tta ata ccc tgt ttg gag aga tat ggt
Cys Cys Asp Leu Ile Pro Cys Leu Glu Arg Tyr Gly aac aga tgt aat gaa gtg cac tgatgctcca ggaccctctg
Asn Arg Cys Asn Glu Val His aaccacgcga cgt

TABLE 81

DNA Sequence (SEQ ID NO: 297) and
Protein Sequence (SEQ ID NO: 298) of Ar1.4 tct gat ggc agc aat gcc gca gcc aac gag ttt gac
Ser Asp Gly Ser Asn Ala Ala Ala Asn Glu Phe Asp ctg atc gct ctg acc gcc agg cta ggt tgc tgt aac
Leu Ile Ala Leu Thr Ala Arg Leu Gly Cys Cys Asn gtt aca ccc tgt tgg gag aaa tat gga gac aaa tgt
Val Thr Pro Cys Trp Glu Lys Tyr Gly Asp Lys Cys aat gaa gta cgc tgatgcttca ggaccctctg aaccacgacg T
Asn Glu Val Arg

TABLE 82

DNA Sequence (SEQ ID NO: 299) and
Protein Sequence (SEQ ID NO: 300) of Ar1.5 tct gat ggc agg aat gtc gca gca aaa gcg ttt cac
Ser Asp Gly Arg Asn Val Ala Ala Lys Ala Phe His cgg atc ggc cgg acc atc agg gat gaa tgc tgt tcc
Arg Ile Gly Arg Thr Ile Arg Asp Glu Cys Cys Ser aat cct gcc tgt agg gtg aat aat cca cac gtt tgt
Asn Pro Ala Cys Arg Val Asn Asn Pro His Val Cys aga cga cgc tgatgctcca ggaccctctg aaccacgacg t
Arg Arg Arg

TABLE 83

DNA Sequence (SEQ ID NO: 301) and
Protein Sequence (SEQ ID NO: 302) of Ar1.6 tct gat ggc agg aat gcc gca gcc aac gcg ttt gac
Ser Asp Gly Arg Asn Ala Ala Ala Asn Ala Phe Asp ctg atg cct ctg acc gcc agg cta aat tgc tgt agc
Leu Met Pro Leu Thr Ala Arg Leu Asn Cys Cys Ser att ccc ggc tgt tgg aac gaa tat aaa gac aga tgt
Ile Pro Gly Cys Trp Asn Glu Tyr Lys Asp Arg Cys agt aaa gta cgc tgatgctcca ggaccctctg aaccacgacg T
Ser Lys Val Arg

TABLE 84

DNA Sequence (SEQ ID NO:303) and Protein Sequence
(SEQ ID NO:304) of Ay1.2 tctgatggca ggaatgccgc agccgacgac aaagcgtctg acctggtcgc t ctg gtc gtc agg gga gga tgc tgt tcc
               Leu Val Val Arg Gly Gly Cys Cys Ser cac cct gtc tgt tac ttt aat aat cca caa atg tgt
His Pro Val Cys Tyr Phe Asn Asn Pro Gln Met Cys cgt gga aga cgc tgatgctcca ggaccctctg aaccacgacg t
Arg Gly Arg Arg

TABLE 85

DNA Sequence (SEQ ID NO:305) and Protein Sequence
(SEQ ID NO:306) of Ay1.3 tctgatggca ggaatgccgc agccgacgac aaagcgtctg acctggtcgc t ctg gcc gtc agg gga gga tgc tgt tcc
               Leu Ala Val Arg Gly Gly Cys Cys Ser cac cct gtc tgt aac ttg aat aat cca caa atg tgt
His Pro Val Cys Asn Leu Asn Asn Pro Gln Met Cys cgt gga aga cgc tgatgctcca ggaccctctg aaccacgacg t
Arg Gly Arg Arg

TABLE 86

DNA Sequence (SEQ ID NO:307) and Protein Sequence
(SEQ ID NO:308) of Bt1.8 ttt cgt ggc agg aat ccc gca gcc aac gac aaa agg
Phe Arg Gly Arg Asn Pro Ala Ala Asn Asp Lys Arg tct gac ctg gcc gct ctg agc gtc agg gga gga tgc
Ser Asp Leu Ala Ala Leu Ser Val Arg Gly Gly Cys tgt tcc cat cct gcc tgt agc gtg act cat cca gag
Cys Ser His Pro Ala Cys Ser Val Thr His Pro Glu ctt tgt ggc tgaagacgct gatgccccag gaccctctga
Leu Cys Gly accacgacgt

TABLE 87

DNA Sequence (SEQ ID NO:309) and Protein Sequence
(SEQ ID NO:310) of Bt1.9 tct gat ggc ggg aat gcc gca gcc aaa gcg tct gac
Ser Asp Gly Gly Asn Ala Ala Ala Lys Ala Ser Asp ctg atc gct cag acc atc agg gga gga tgc tgt tcc
Leu Ile Ala Gln Thr Ile Arg Gly Gly Cys Cys Ser tat cct gcc tgt agc gtg gaa cat caa gac ctt tgt
Tyr Pro Ala Cys Ser Val Glu His Gln Asp Leu Cys gat gga aga cgc tgatgctcca ggaccctctg aaccacgacg t
Asp Gly Arg Arg

TABLE 88

DNA Sequence (SEQ ID NO:311) and Protein Sequence
(SEQ ID NO:312) of Ca1.3 tct tat ggc agg aat gcc gca gcc aaa gcg ttt gaa gtg
agt tgc tgt
Ser Tyr Gly Arg Asn Ala Ala Ala Lys Ala Phe Glu Val
Ser Cys Cys gtc gtt cgc ccc tgt tgg att cgc tat caa gag gaa tgt
ctt gaa gca
Val Val Arg Pro Cys Trp Ile Arg Tyr Gln Glu Glu Cys
Leu Glu Ala gat ccc agg acc ctc tga
Asp Pro Arg Thr Leu

TABLE 89

DNA Sequence (SEQ ID NO:313) and Protein Sequence
(SEQ ID NO:314) of Ca1.4 tct gat ggc agg aat gcc gca gcc aac gcc ctt gac
Ser Asp Gly Arg Asn Ala Ala Ala Asn Ala Leu Asp ctg atc act ctg atc gcc agg caa aat tgc tgt agc
Leu Ile Thr Leu Ile Ala Arg Gln Asn Cys Cys Ser att ccc ggc tgt tgg gag aaa tat gga gac aaa tgt
Ile Pro Gly Cys Trp Glu Lys Tyr Gly Asp Lys Cys agt gaa gta cgc tga
Ser Glu Val Arg

TABLE 90

DNA Sequence (SEQ ID NO:315) and Protein Sequence (SEQ ID NO:316) of C1.2 tct gat ggc agg aat gaa gca gcc aac gac gaa gcg
Ser Asp Gly Arg Asn Glu Ala Ala Asn Asp Glu Ala tct gac gtg atc gag ctg gcc ctc aag gga tgc tgt
Ser Asp Val Ile Glu Leu Ala Leu Lys Gly Cys Cys tcc aac cct gtc tgt cac ttg gag cat cca aac gct
Ser Asn Pro Val Cys His Leu Glu His Pro Asn Ala tgt ggt aga aga cgc tgatgctcca ggaccctctg
Cys Gly Arg Arg Arg aaccacgacg t

TABLE 91

DNA Sequence (SEQ ID NO:317) and Protein Sequence (SEQ ID NO:318) of C1.3 tct gat ggc agg aat gcc gca gcc aac gac aaa gcg
Ser Asp Gly Arg Asn Ala Ala Ala Asn Asp Lys Ala tct gac ctg gtc gct ctg gcc gtc agg gga tgc tgt
Ser Asp Leu Val Ala Leu Ala Val Arg Gly Cys Cys tcc aac cct atc tgt tac ttt aat aat cca cga att
Ser Asn Pro Ile Cys Tyr Phe Asn Asn Pro Arg Ile tgt cgt gga aga cgc tgatgctcca ggaecctctg
Cys Arg Gly Arg Arg aaccacgacg t

TABLE 92

DNA Sequence (SEQ ID NO:319) and Protein Sequence (SEQ ID NO:320) of Ep1.2 tct cat ggc agg aat gcc gca cgc aaa gcg tct gac
Ser His Gly Arg Asn Ala Ala Arg Lys Ala Ser Asp ctg atc gct ctg acc gtc agg gaa tgc tgt tct cag
Leu Ile Ala Leu Thr Val Arg Glu Cys Cys Ser Gln cct ccc tgt cgc tgg aaa cat cca gaa ctt tgt agt
Pro Pro Cys Arg Trp Lys His Pro Glu Leu Cys Ser tga

TABLE 93

DNA Sequence (SEQ ID NO:321) and Protein Sequence (SEQ ID NO:322) of G1.1 tct gat ggc agg aat gac gca gcc aaa gcg ttt gac
Ser Asp Gly Arg Asn Asp Ala Ala Lys Ala Phe Asp ctg ata tct tcg acc gtc aag aaa gga tgc tgt tcc
Leu Ile Ser Ser Thr Val Lys Lys Gly Cys Cys Ser cat cct gcc tgt gcg ggg aat aat caa cat att tgt
His Pro Ala Cys Ala Gly Asn Asn Gln His Ile Cys ggc cga aga cgc tgatgctcca ggaccctctg aaccacgacg t
Gly Arg Arg Arg

TABLE 94

DNA Sequence (SEQ ID NO:323) and Protein Sequence (SEQ ID NO:324) of G1.3 tct gat ggc agg aat gcc gca gcc aac gac caa gcg
Ser Asp Gly Arg Asn Ala Ala Ala Asn Asp Gln Ala tct gac ctg atg gct gcg acc gtc agg gga tgc tgt
Ser Asp Leu Met Ala Ala Thr Val Arg Gly Cys Cys gcc gtt cct tcc tgt cgc ctc cgt aat cca gac ctt
Ala Val Pro Ser Cys Arg Leu Arg Asn Pro Asp Leu tgt ggt gga gga cgc tgatgctcca ggaccctctg
Cys Gly Gly Gly Arg aaccacgacg t

TABLE 95

DNA Sequence (SEQ ID NO:325) and Protein Sequence (SEQ ID NO:326) of Im1.3 ctt gat gaa agg aat gcc gca gcc gac gac aaa gcg
Leu Asp Glu Arg Asn Ala Ala Ala Asp Asp Lys Ala tct gac ctg atc gct caa atc gtc agg aga gga tgc
Ser Asp Leu Ile Ala Gln Ile Val Arg Arg Gly Cys tgt tcc cat cct gcc tgt aac gtg aat aat cca cac
Cys Ser His Pro Ala Cys Asn Val Asn Asn Pro His att tgt ggt tga
Ile Cys Gly

TABLE 96

DNA Sequence (SEQ ID NO:327) and Protein Sequence (SEQ ID NO:328) of Lv1.2 tct gat ggc agg aat act gca gcc aaa gtc aaa tat
Ser Asp Gly Arg Asn Thr Ala Ala Lys Val Lys Tyr tct aag acg ccg gag gaa tgc tgt ccc aat cct ccc
Ser Lys Thr Pro Glu Glu Cys Cys Pro Asn Pro Pro tgt ttc gcg aca aat tcg gat att tgt ggc gga aga
Cys Phe Ala Thr Asn Ser Asp Ile Cys Gly Gly Arg cgc tgatgctcca ggaccctctg aaccacgacg t
Arg

TABLE 97

DNA Sequence (SEQ ID NO:329) and Protein Sequence (SEQ ID NO:330) of Lv1.3 tct aat ggc agg aat gcc gca gcc aaa ttc aaa gcg
Ser Asn Gly Arg Asn Ala Ala Ala Lys Phe Lys Ala cct gcc ctg atg aag cgg acc gtc agg gat gct tgc
Pro Ala Leu Met Lys Arg Thr Val Arg Asp Ala Cys tgt tca gac cct cgc tgt tcc ggg aaa cat caa gac
Cys Ser Asp Pro Arg Cys Ser Gly Lys His Gln Asp ctg tgt ggc tgaagacgct gatgctccag gaccctctga
Leu Cys Gly accacgacgt

TABLE 98

DNA Sequence (SEQ ID NO:331) and Protein Sequence (SEQ ID NO:332) of Lv1.4 tct aat ggc agg aat gcc gca gcc aaa ttc aaa gcg
Ser Asn Gly Arg Asn Ala Ala Ala Lys Phe Lys Ala cct gcc ctg atg gag ctg acc gtc agg gaa gat tgc
Pro Ala Leu Met Glu Leu Thr Val Arg Glu Asp Cys tgt tca gac cct cgc tgt tcc gtg gga cat caa gac
Cys Ser Asp Pro Arg Cys Ser Val Gly His Gln Asp ctg tgt ggc tgaagacgct gatgctccag gaccctctga
Leu Cys Gly Accacgacgt

TABLE 99

DNA Sequence (SEQ ID NO:333) and Protein Sequence (SEQ ID NO:334) of Lv1.6 gca ttt gat ggc agg aat gct gca gcc agc gac aaa
Ala Phe Asp Gly Arg Asn Ala Ala Ala Ser Asp Lys gcg tcc gag ctg atg gct ctg gcc gtc agg gga tgc
Ala Ser Glu Leu Met Ala Leu Ala Val Arg Gly Cys tgt tcc cat cct gcc tgt gct ggg agt aat gca cat
Cys Ser His Pro Ala Cys Ala Gly Ser Asn Ala His atc tgt ggc aga aga cgc tgatgctcca ggaccctctg
Ile Cys Gly Arg Arg Arg aaccacgacg t

TABLE 100

DNA Sequence (SEQ ID NO:335) and Protein Sequence (SEQ ID NO:336) of Lv1.7 tct aat ggc agg aat gcc gca gcc aaa ttc aaa gcg
Ser Asn Gly Arg Asn Ala Ala Ala Lys Phe Lys Ala cct gcc ctg atg aag ctg acc gtc agg gag gat tgc
Pro Ala Leu Met Lys Leu Thr Val Arg Glu Asp Cys tgt tca gac cct cgc tgt tcc gtg gga cat caa gac
Cys Ser Asp Pro Arg Cys Ser Val Gly His Gln Asp atg tgt ggc tgaagacgct gatgctccag gaccctctga
Met Cys Gly atcacgacgt

TABLE 101

DNA Sequence (SEQ ID NO:337) and Protein Sequence (SEQ ID NO:338) of Lv1.8 ttt gaa tgc agg aat gct gca ggc aac gac aaa gcg
Phe Glu Cys Arg Asn Ala Ala Gly Asn Asp Lys Ala act gac ctg atg gct ctg act gtc agg gga tgc tgt
Thr Asp Leu Met Ala Leu Thr Val Arg Gly Cys Cys tcc cat cct gcc tgt gct ggg aat aat cca cat atc
Ser His Pro Ala Cys Ala Gly Asn Asn Pro His Ile

TABLE 101-continued

DNA Sequence (SEQ ID NO:337) and Protein Sequence (SEQ ID NO:338) of Lv1.8 tgc ggc tgaagacgct gatgctccag gaccctctga
Cys Gly accacgacgt

TABLE 102

DNA Sequence (SEQ ID NO:339) and Protein Sequence (SEQ ID NO:340) of Lv1.9 ttt gat ggc agg aac gcc gca gcc aac aac aaa gcg
Phe Asp Gly Arg Asn Ala Ala Ala Asn Asn Lys Ala act gat ctg atg gct ctg act gtc aga gga tgc tgt
Thr Asp Leu Met Ala Leu Thr Val Arg Gly Cys Cys ggc aat cct tca tgt agc atc cat att cct tac gtt
Gly Asn Pro Ser Cys Ser Ile His Ile Pro Tyr Val tgt aat tagagacact gatgctccag gaccctctga
Cys Asn accacgacgt

TABLE 103

DNA Sequence (SEQ ID NO:341) and Protein Sequence (SEQ ID NO:342) of Lv1.10 tct aat ggc agg aat gcc gca gcc aaa ttc aaa gcg
Ser Asn Gly Arg Asn Ala Ala Ala Lys Phe Lys Ala cct gcc ctg atg aag cgg acc gac agc gaa gaa tgc
Pro Ala Leu Met Lys Arg Thr Asp Ser Glu Glu Cys tgt tta gac tct cgc tgt gcc ggg caa cat caa gac
Cys Leu Asp Ser Arg Cys Ala Gly Gln His Gln Asp ctg tgt ggc gga aga cgc tgatgctcca ggaccctctg
Leu Cys Gly Gly Arg Arg aaccacgacg t

TABLE 104

DNA Sequence (SEQ ID NO:343) and Protein Sequence (SEQ ID NO:344) of Mr1.3 tct gat ggc agg aat gcc gca gcc aag gac aaa gcg
Ser Asp Gly Arg Asn Ala Ala Ala Lys Asp Lys Ala tct gac ctg gtc gct ctg acc gtc aag gga tgc tgt
Ser Asp Leu Val Ala Leu Thr Val Lys Gly Cys Cys tct aat cct ccc tgt tac gcg aat aat caa gcc tat
Ser Asn Pro Pro Cys Tyr Ala Asn Asn Gln Ala Tyr tgt aat gga aga cgc tga
Cys Asn Gly Arg Arg

TABLE 105

DNA Sequence (SEQ ID NO:345) and
Protein Sequence (SEQ ID NO:346) of Mr1.4 tct gat ggc agg aat gcc gca gcc aag gac aaa gcg
Ser Asp Gly Arg Asn Ala Ala Ala Lys Asp Lys Ala tct gac ctg gtc gct ctg acc gtc aag gga tgc tgt
Ser Asp Leu Val Ala Leu Thr Val Lys Gly Cys Cys tct cat cct gcc tgt agc gtg aat aat cca gac att
Ser His Pro Ala Cys Ser Val Asn Asn Pro Asp Ile tgt ggt tga
Cys Gly

TABLE 106

DNA Sequence (SEQ ID NO:347) and
Protein Sequence (SEQ ID NO:348) ofMs1.1 tct gat ggc agg aat gct gca gcc aac aac aaa gtg
Ser Asp Gly Arg Asn Ala Ala Ala Asn Asn Lys Val gct ttg acc atg agg gga aaa tgc tgt atc aat gat
Ala Leu Thr Met Arg Gly Lys Cys Cys Ile Asn Asp gcg tgt cgc tcg aaa cat cca cag tac tgt tct gga
Ala Cys Arg Ser Lys His Pro Gln Tyr Cys Ser Gly aga cgc tgatactcca ggaccctctg aaccacgacg t
Arg Arg

TABLE 107

DNA Sequence (SEQ ID NO:349) and Protein Sequence
(SEQ ID NO:350) of Ms1.6 tct gat ggc agg aat gct gca gcc aac gac aaa gtg
Ser Asp Gly Arg Asn Ala Ala Ala Asn Asp Lys Val tct gac cag atg gct ctg gtt gtc agg gga tgc tgt
Ser Asp Gln Met Ala Leu Val Val Arg Gly Cys Cys tac aat att gcc tgt aga att aat aat cca cgg tac
Tyr Asn Ile Ala Cys Arg Ile Asn Asn Pro Arg Tyr tgt cgt gga aaa cgc tgatgttcca ggaccctctg
Cys Arg Gly Lys Arg aaccacgacg t

TABLE 108

DNA Sequence (SEQ ID NO:351) and Protein Sequence
(SEQ ID NO:352) of O1.1 tctgaaggca ggaatgccgc agccaacgac aaagcgtctg acctgatggc t ctg aac gtc agg gga tgc tgt tcc cat
              Leu Asn Val Arg Gly Cys Cys Ser His cct gtc tgt cgc ttc aat tat cca aaa tat tgt ggt
Pro Val Cys Arg Phe Asn Tyr Pro Lys Tyr Cys Gly gga aga cgc tgatggtcca ggaccctctg aaccacgacg t
Gly Arg Arg

TABLE 109

DNA Sequence (SEQ ID NO:353) and Protein Sequence
(SEQ ID NO:354) of O1.2 tctgatggcg ggaatgccgc agcaaaagcg tttgatctaa tcact ctg gcc ctc agg gat gaa tgc tgt gcc agt cct ccc
Leu Ala Leu Arg Asp Glu Cys Cys Ala Ser Pro Pro tgt cgt ttg aat aat cca tac gta tgt cat tgacgacgct
Cys Arg Leu Asn Asn Pro Tyr Val Cys His gatgctccag gaccctctga accacgacgt

TABLE 110

DNA Sequence (SEQ ID NO:355) and Protein Sequence
(SEQ ID NO:356) of O1.4 atg ttc acc gtg ttt ctg ttg gtt gtc ttg gca acc
Met Phe Thr Val Phe Leu Leu Val Val Leu Ala Thr acc gtc gtt tcc ccc act tca gat cgt gca tct gat
Thr Val Val Ser Pro Thr Ser Asp Arg Ala Ser Asp agg agg aat gcc gca gcc aaa gcg ttt gac ctg aga
Arg Arg Asn Ala Ala Ala Lys Ala Phe Asp Leu Arg tat tcg acc gcc aag aga gga tgc tgt tcc aat cct
Tyr Ser Thr Ala Lys Arg Gly Cys Cys Ser Asn Pro gtc tgt tgg cag aat aat gca gaa tac tgt cgt gaa
Val Cys Trp Gln Asn Asn Ala Glu Tyr Cys Arg Glu agt ggc taatgctcca ggaccctctg aaccacgacg t
Ser Gly

TABLE 111

DNA Sequence (SEQ ID NO:357) and Protein Sequence
(SEQ ID NO:358) of O1.7 atg ttc acc gtg ttt ctg ttg gtt gtc ttg gca acc
Met Phe Thr Val Phe Leu Leu Val Val Leu Ala Thr acc gtc gtt tcc ttc act tca gat cgt gca tct gat
Thr Val Val Ser Phe Thr Ser Asp Arg Ala Ser Asp ggc ggg aat gtc gca gcg tct cac ctg atc gct ctg
Gly Gly Asn Val Ala Ala Ser His Leu Ile Ala Leu acc atc aag gga tgc tgt tct cac cct ccc tgt gcc
Thr Ile Lys Gly Cys Cys Ser His Pro Pro Cys Ala cag aat aat caa gac tat tgt ggt tgacgacgct
Gln Asn Asn Gln Asp Tyr Cys Gly gatgctccag gaccctctga accacgacgt

TABLE 112

DNA Sequence (SEQ ID NO:359) and Protein Sequence
(SEQ ID NO:360) of O1.8 atg ttc acc gtg ttt ctg ttg gtt gtc tta tca acc
Met Phe Thr Val Phe Leu Leu Val Val Leu Ser Thr acc gtc gtt tcc tcc act tca gat cgt gca tct gat
Thr Val Val Ser Ser Thr Ser Asp Arg Ala Ser Asp agg agg aat gcc gca gcc aaa gcg tct gac ctg atg
Arg Arg Asn Ala Ala Ala Lys Ala Ser Asp Leu Met

TABLE 112-continued

DNA Sequence (SEQ ID NO:359) and Protein Sequence
(SEQ ID NO:360) of O1.8

```
tat tcg acc gtc aag aaa gga tgt tgt tcc cat cct
Tyr Ser Thr Val Lys Lys Gly Cys Cys Ser His Pro gcc tgt tcg ggg aat aat cga gaa tat tgt cgt gaa
Ala Cys Ser Gly Asn Asn Arg Glu Tyr Cys Arg Clu agt ggc taatgctcca ggaccctctg aaccacgacg t
Ser Gly
```

TABLE 113

DNA Sequence (SEQ ID NO:361) and Protein Sequence
(SEQ ID NO:362) of Om1.2

```
tttgatggca ggaatgcctc agccgacagc aaagtggctg cccggatcgc t cag atc gac agg gat cca tgc tgt tcc
             Gln Ile Asp Arg Asp Pro Cys Cys Ser tat cct gac tgt ggc gcg aat cat cca gag att tgt
Tyr Pro Asp Cys Gly Ala Asn His Pro Glu Ile Cys ggt gga aaa cgc tgatgctcca ggaccctctg aaccacgacg t
Gly Gly Lys Arg
```

TABLE 114

DNA Sequence (SEQ ID NO:363) and Protein Sequence
(SEQ ID NO:364) of Om1.3

```
tctcatggca ggaatgccgc acgct ctg acc gtc agg gaa
                             Leu Thr Val Arg Glu tgc tgt tct cag cct cct tgt cgc tgg aaa cat cca
Cys Cys Ser Gln Pro Pro Cys Arg Trp Lys His Pro gaa ctt tgt agt tgaagacgct gatgctccag gaccctctga
Glu Leu Cys Ser accacgacgt
```

TABLE 115

DNA Sequence (SEQ ID NO:365) and Protein Sequence
(SEQ ID NO:366) of Om1.4

```
tttgatggca ggaatgctgc agccagcgac aaagcgtctg agctgatggc t ctg gcc gtc agg gga tgc tgt tcc cat
               Leu Ala Val Arg Gly Cys Cys Ser His cct gcc tgt gct ggg aat aat cca cat atc tgt ggc
Pro Ala Cys Ala Gly Asn Asn Pro His Ile Cys Gly aga aga cgc tgatgctcca ggaccctctg aaccacgacg t
Arg Arg Arg
```

TABLE 116

DNA Sequence (SEQ ID NO:367) and Protein Sequence
(SEQ ID NO:368) of Om1.5

```
tctggtgtca ggaaagacgc agcgcctggc ctgatcgct ctg acc
                                             Leu Thr atc aag gga tgc tgt tct gat cct agc tgt aac gtg
Ile Lys Gly Cys Cys Ser Asp Pro Ser Cys Asn Val
```

TABLE 116-continued

DNA Sequence (SEQ ID NO:367) and Protein Sequence
(SEQ ID NO:368) of Om1.5

```
aat aat cca gac tat tgt ggt tgacgacgct gatgctccag
Asn Asn Pro Asp Tyr Cys Gly gaccctctga accacgacgt
```

TABLE 117

DNA Sequence (SEQ ID NO:369) and Protein Sequence
(SEQ ID NO:370) of Om1.6

```
tctaatggca ggaatgccgc agccaaattc aaagcgcctg ccctgatgga g ctg acc gtc agg gaa gaa tgc tgt tca
                Leu Thr Val Arg Glu Glu Cys Cys Ser gac cct cgc tgt tcc gtg gga cat caa gat atg tgt
Asp Pro Arg Cys Ser Val Gly His Gln Asp Met Cys cgg tgaagcacgt gatgctccag gaccctctga accacgacgt
Arg
```

TABLE 118

DNA Sequence (SEQ ID NO:371) and Protein Sequence
(SEQ ID NO:372) of P1.4

```
act gat ggc agg aat gct gca gcc ata gcg ctt gac
Thr Asp Gly Arg Asn Ala Ala Ala Ile Ala Leu Asp ctg atc gct ccg gcc gtc agg gga gga tgc tgt tcc
Leu Ile Ala Pro Ala Val Arg Gly Gly Cys Cys Ser aat cct gcc tgt tta gtg aat cat cta gaa atg tgt
Asn Pro Ala Cys Leu Val Asn His Leu Glu Met Cys ggt aaa aga cgc tgatgcccca ggaccctctg aaccacgacg
Gly Lys Arg Arg t
```

TABLE 119

DNA Sequence (SEQ ID NO:373) and Protein Sequence
(SEQ ID NO:374) of P1.5

```
tct gat ggc agg gat gcc gca gcc aac gac aaa gcg
Ser Asp Gly Arg Asp Ala Ala Ala Asn Asp Lys Ala tct gac ctg atc gct ctg acc gcc agg aga gat cca
Ser Asp Leu Ile Ala Leu Thr Ala Arg Arg Asp Pro tgc tgt ttc aat cct gcc tgt aac gtg aat aat cca
Cys Cys Phe Asn Pro Ala Cys Asn Val Asn Asn Pro cag att tgt ggt tgaagacgct gatgctccag gaccctctga
Gln Ile Cys Gly accacgacgt
```

TABLE 120

DNA Sequence (SEQ ID NO:375) and Protein Sequence
(SEQ ID NO:376) of P1.6

```
tct gat ggc agg gat gct gag aaa aca ggc ttt gac
Ser Asp Gly Arg Asp Ala Glu Lys Thr Gly Phe Asp
```

TABLE 120-continued

DNA Sequence (SEQ ID NO:375) and Protein Sequence (SEQ ID NO:376) of P1.6 acg acc att gtg ccg gaa gac tgc tgt tcg gat cct
Thr Thr Ile Val Pro Glu Asp Cys Cys Ser Asp Pro tcc tgt tgg agg ctg cat agt tta gct tgt act gga
Ser Cys Trp Arg Leu His Ser Leu Ala Cys Thr Gly att gta aac cgc tgatgctcca ggaccctctg aaccacgacg
Ile Val Asn Arg t

TABLE 121

DNA Sequence (SEQ ID NO:377) and Protein Sequence (SEQ ID NO:378) of P1.8 act gat ggc agg agt gct gca gcc ata gcg ttt gcc
Thr Asp Gly Arg Ser Ala Ala Ala Ile Ala Phe Ala ctg atc gct ccg acc gtc tgc tgt act aat cct gcc
Leu Ile Ala Pro Thr Val Cys Cys Thr Asn Pro Ala tgt ctc gtg aat aat ata cgc ttt tgt ggt gga aga
Cys Leu Val Asn Asn Ile Arg Phe Cys Gly Gly Arg cgc tgatgcccca ggaccctctg aaccacgacg t
Arg

TABLE 122

DNA Sequence (SEQ ID NO:379) and Protein Sequence (SEQ ID NO:380) of Rg1.1 tct gat gga aga aat gcc gca agc gac gcc aaa gcg
Ser Asp Gly Arg Asn Ala Ala Ser Asp Ala Lys Ala ttt ccc cgg atc gct cca atc gtc agg gac gaa tgc
Phe Pro Arg Ile Ala Pro Ile Val Arg Asp Glu Cys tgt agc gat cct agg tgt cac ggg aat aat cgg gac
Cys Ser Asp Pro Arg Cys His Gly Asn Asn Arg Asp cac tgt gct tgaagacgct gctgctccag gaccctctga
His Cys Ala accacgacgt

TABLE 123

DNA Sequence (SEQ ID NO:381) and Protein Sequence (SEQ ID NO:382) of Rg1.3 tct gat ggc agg aat acc gcg gcc gac gaa aaa gcg
Ser Asp Gly Arg Asn Thr Ala Ala Asp Glu Lys Ala tcc gac ctg atc tct caa act gtc aag aga gat tgc
Ser Asp Leu Ile Ser Gln Thr Val Lys Arg Asp Cys tgt tcc cat cct ctc tgt aga tta ttt gtt cca gga
Cys Ser His Pro Leu Cys Arg Leu Phe Val Pro Gly ctt tgt att tgaagacgct gctgctccag gaccctctga
Leu Cys Ile Accacgact

TABLE 124

DNA Sequence (SEQ ID NO:383) and Protein Sequence (SEQ ID NO:384) of Rg1.4 tct gat ggc agg aat gcc gca gcc gac aac aaa gcg
Ser Asp Gly Arg Asn Ala Ala Ala Asp Asn Lys Ala tct gac cta atc gct caa atc gtc agg aga gga tgc
Ser Asp Leu Ile Ala Gln Ile Val Arg Arg Gly Cys tgt tcc cat cct gtc tgt aaa gtg agg tat cca gac
Cys Ser His Pro Val Cys Lys Val Arg Tyr Pro Asp ctg tgt cgt tgaagacgct gctgctccag gaccctctga
Leu Cys Arg Accacgacgt

TABLE 125

DNA Sequence (SEQ ID NO:385) and Protein Sequence (SEQ ID NO:386) of Rg1.5 tct gat ggc agg aat gcc gca gcc gac aac aga gcg
Ser Asp Gly Arg Asn Ala Ala Ala Asp Asn Arg Ala tct gac cta atc gct caa atc gtc agg aga gga tgc
Ser Asp Leu Ile Ala Gln Ile Val Arg Arg Gly Cys tgt tcc cat cct gcc tgt aat gtg aat aat cca cac
Cys Ser His Pro Ala Cys Asn Val Asn Asn Pro His att tgt ggt tgaagacgct gctgctccag gaccctctga
Ile Cys Gly accacgacgt

TABLE 126

DNA Sequence (SEQ ID NO:387) and Protein Sequence (SEQ ID NO:388) of Rg1.8 tct gat ggc agg aat gcc gca gcc gac aac aaa ccg
Ser Asp Gly Arg Asn Ala Ala Ala Asp Asn Lys Pro tct gac cta atc gct caa atc gtc agg aga gga tgc
Ser Asp Leu Ile Ala Gln Ile Val Arg Arg Gly Cys tgt tcg cat cct gtc tgt aaa gtg agg tat tca gac
Cys Ser His Pro Val Cys Lys Val Arg Tyr Ser Asp atg tgt ggt tgaagacgct gctgctccag gaccctctga
Met Cys Gly accacgacgt

TABLE 127

DNA Sequence (SEQ ID NO:389) and Protein Sequence (SEQ ID NO:390) of Sm1.4 tct gat ggc agg aat gca gag cga cga caa agc gtc
Ser Asp Gly Arg Asn Ala Glu Arg Arg Gln Ser Val tgt cct ggt cgc tct ggc ccc agg gga gga tgt tgt
Cys Pro Gly Arg Ser Gly Pro Arg Gly Gly Cys Cys tcc cac cct gcc tgt aag gtg cat ttt cca cac agt
Ser His Pro Ala Cys Lys Val His Phe Pro His Ser

TABLE 127-continued

DNA Sequence (SEQ ID NO:389) and Protein Sequence (SEQ ID NO:390) of Sm1.4 tgt ggt tgacgacgct gatgctccag gaccctctga
Cys Gly accacgacgt

TABLE 128

DNA Sequence (SEQ ID NO:391) and Protein Sequence (SEQ ID NO:392) of Sm1.5 tct gat ggc agg aat gcc gca gcc agc gac aga gcg
Ser Asp Gly Arg Asn Ala Ala Ala Ser Asp Arg Ala tct gac gcg gcc cac cag gta tgc tgt tcc aac cct
Ser Asp Ala Ala His Gln Val Cys Cys Ser Asn Pro gtc tgt cac gtg gat cat cca gaa ctt tgt cgt aga
Val Cys His Val Asp His Pro Glu Leu Cys Arg Arg aga cgc tgatgctcca ggaccctctg aaccacgacg t
Arg Arg

TABLE 129

DNA Sequence (SEQ ID NO:393) and Protein Sequence (SEQ ID NO:394) of S1.5 tct gat ggc agg aat gcc gcg gcc aac gac aaa gcg
Ser Asp Gly Arg Asn Ala Ala Ala Asn Asp Lys Ala tct gac ctg gtc gct ccg gcc atc agg gga tgc tgt
Ser Asp Leu Val Ala Pro Ala Ile Arg Gly Cys Cys tcc cac cct gtc tgt aac ttg agt aat cca caa att
Ser His Pro Val Cys Asn Leu Ser Asn Pro Gln Ile tgt cgt gga aga cgc tgatgctcca ggaccctctg
Cys Arg Gly Arg Arg aaccacgacg t

TABLE 130

DNA Sequence (SEQ ID NO:395) and Protein Sequence (SEQ ID NO:396) of Tx1.5 ttt cat ggc agg aat gcc gca gcc aaa gcg tct ggc
Phe His Gly Arg Asn Ala Ala Ala Lys Ala Ser Gly ctg gtc ggt ctg acc gac aag agg caa gaa tgc tgt
Leu Val Gly Leu Thr Asp Lys Arg Gln Glu Cys Cys tct cat cct gcc tgt aac gta gat cat cca gaa att
Ser His Pro Ala Cys Asn Val Asp His Pro Glu Ile tgt cgt tga
Cys Arg

TABLE 131

DNA Sequence (SEQ ID NO:397) and Protein Sequence (SEQ ID NO:398) of T1.1 act gat ggc agg agt gct gca gcc ata gcg ttt gcc
Thr Asp Gly Arg Ser Ala Ala Ala Ile Ala Phe Ala

TABLE 131-continued

DNA Sequence (SEQ ID NO:397) and Protein Sequence (SEQ ID NO:398) of T1.1 ctg atc gct ccg acc gtc tgg gaa gga tgc tgt tct
Leu Ile Ala Pro Thr Val Trp Glu Gly Cys Cys Ser aat cct gcc tgt ctc gtg aat cat ata cgc ttt tgt
Asn Pro Ala Cys Leu Val Asn His Ile Arg Phe Cys ggt gga aga cgc tgatgcccca ggaccctctg aaccacgacg t
Gly Gly Arg Arg

TABLE 132

DNA Sequence (SEQ ID NO:399) and Protein Sequence (SEQ ID NO:400) of Vr1.3 tct aat ggc atg aat gcc gca gcc atc agg aaa gcg
Ser Asn Gly Met Asn Ala Ala Ala Ile Arg Lys Ala tct gcc ctg gtg gct cag atc gcc cat cga gac tgc
Ser Ala Leu Val Ala Gln Ile Ala His Arg Asp Cys tgt gac gat cct gcc tgc acc gtg aat aat cca ggc
Cys Asp Asp Pro Ala Cys Thr Val Asn Asn Pro Gly ctt tgc act tgaagatgct gctgccccag gaccctctga
Leu Cys Thr accacgacgt

TABLE 133

DNA Sequence (SEQ ID NO:401) and Protein Sequence (SEQ ID NO:402) of G1.2 tct gat ggc ggg aat gcc gca gca aaa gag tct gac
Ser Asp Gly Gly Asn Ala Ala Ala Lys Glu Ser Asp gtg atc gct ctg acc gtc tgg aaa tgc tgt acc att
Val Ile Ala Leu Thr Val Trp Lys Cys Cys Thr Ile cct tcc tgt tat gag aaa aaa aaa att aaa gca tgt
Pro Ser Cys Tyr Glu Lys Lys Lys Ile Lys Ala Cys gtc ttt tgacgacgct gatgctccag gaccctctga
Val Phe accacgacgt

TABLE 134

DNA Sequence (SEQ ID NO:403) and Protein Sequence (SEQ ID NO:404) of Rg1.12 tct gat ggc gca gtc gac gac aaa gcg ttg gat cga
Ser Asp Gly Ala Val Asp Asp Lys Ala Leu Asp Arg atc gct gaa atc gtc agg aga gga tgc tgt ggc aat
Ile Ala Glu Ile Val Arg Arg Gly Cys Cys Gly Asn cct gcc tgt agc ggc tcc tcg aaa gat gca ccc tct
Pro Ala Cys Ser Gly Ser Ser Lys Asp Ala Pro Ser tgt ggt tgaagacgct gctgctccag gaccctctga
Cys Gly accacgacgt It will be appreciated that the methods and compositions of the instant invention can be incorporated in the form of a variety of embodiments, only a few of which are disclosed

BIBLIOGRAPHY

Bamay, G. et al. (2000). *J. Med. Chem.*
Bitan, G. et al. (1997). *J. Peptide Res.* 49:421-426.
Blount, K. et al. (1992). *Toxicon* 30:835-842.
Bodansky et al. (1966). *Chem. Ind.* 38:1597-98.
Cartier, G. E. et al. (1996). *J. Biol. Chem.* 271:7522-7528.
Cruz, L. J. at al. (1976). *Verliger* 18:302-308.
Cruz, L. J. et al. (1987). *J. Biol. Chem.* 260:9280-9288.
Fainzilber, M. et al. (1994). *Biochemistry* 33:9523-9529.
Gray, W. R. et al. (1981). *J. Biol. Chem.* 256:4734-4740.
Haack, J. A. et al. (1990). *J. Biol. Chem.* 265:6025-6029.
Horiki, K. et al. (1978). *Chemistry Letters* 165-68.
Hubry, V. et al. (1994). *Reactive Polymers* 22:231-241.
Jacobsen, R. et al. (1997). *J. Biol. Chem.* 272:22531-22537.
Johnson, D. S. et al. (1995). *Mol. Pharmacol.* 48:194-199.
Kapoor (1970). *J. Pharm. Sci.* 59:1-27.
Kornreich, W. D. et al. (1986). U.S. Pat. No. 4,569,967.
Luo, S. et al. (1998). *J. Neurosci.* 18:8571-8679.
Marshall, I. G. and Harvey, A. L. (1990). *Toxicon* 28:231-234.
Martinez, J. S. et al. (1995). *Biochem.* 34:14519-14526.
McIntosh, J. M. et al. (1982). *Arch. Biochem. Biophys.* 218:329-334.
Mena, E. E. et al. (1990). *Neurosci. Lett.* 118:241-244.
*Methoden der Organischen Chemie (Houben-Weyl): Synthese von Peptiden*, E. Wunsch (Ed.), Georg Thieme Verlag, Stuttgart, Ger. (1974).
Myers, R. A. et al. (1991). *Biochemistry* 30:9370-9377.
Nishiuchi, Y. et al. (1993). *Int. J. Pept. Protein Res.* 42:533-538.
Nowak, L. et al. (1984). *Nature* 307:462-465.
Olivera, B. M. et al. (1984). U.S. Pat. No. 4,447,356.
Olivera, B. M. et al. (1985). *Science* 230:1338-1343.
Olivera, B. M. et al. (1996). U.S. Pat. No. 5,514,774.
Rivier, J. R. et al. (1978). *Biopolymers* 17:1927-38.
Rivier, J. R. et al. (1987). *Biochem.* 26:8508-8512.
Sambrook, J. et al. (1989). *Molecular Cloning: A Laboratory Manual*, 2nd Ed., Cold Spring Harbor Laboratory, Cold Spring Harbor, N.Y.
Schroder & Lubke (1965). *The Peptides* 1:72-75, Academic Press, N.Y.
Shon, K.-J. et al. (1994). *Biochemistry* 33:11420-11425.
Stewart and Young, *Solid-Phase Peptide Synthesis*, Freeman & Co., San Francisco, Calif. (1969).
Vale et al. (1978). U.S. Pat. No. 4,105,603.
Van de Steen, P. et al. (1998). *Critical Rev. in Biochem. and Mol. Biol.* 33:151-208.
Zafaralla, G. C. et al. (1988). *Biochemistry* 27:7102-7105.
Zhou L. M., et al. (1996). *J. Neurochem.* 66:620-628.
U.S. Pat. No. 3,972,859.
U.S. Pat. No. 3,842,067.
U.S. Pat. No. 3,862,925.
U.S. Pat. No. 5,550,050.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.

SEQUENCE LISTING

```
<160> NUMBER OF SEQ ID NOS: 404

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:Alpha-
      Conotoxin Peptide Generic Formula I
<220> FEATURE:
<221> NAME/KEY: SITE
<222> LOCATION: (1)..(3)
<223> OTHER INFORMATION: Xaa at residue 1 is des-Xaa, Ile, Leu or Val;
      Xaa at residue 2 is des-Xaa, Ala or Gly; Xaa at residue 3 is
      des-Xaa, Gly, Trp (D or L), neo-Trp, halo-Trp or any unnatural
      aromatic amino acid.
<220> FEATURE:
<221> NAME/KEY: SITE
<222> LOCATION: (4)..(5)
<223> OTHER INFORMATION: N-methyl-Lys, Xaa at residue 4 is des-Xaa, Gly,
      Trp (D or L), neo-Trp, halo-Trp or any unnatural
      aromatic amino acid; Xaa at residue 5 is Glu,
      gamma-carboxy-Glu (Gla), Asp, Ala, Thr, Ser, Gly,
<220> FEATURE:
<221> NAME/KEY: SITE
<222> LOCATION: (5)..(8)
<223> OTHER INFORMATION: Ile, Tyr, nor-Tyr, mono-halo-Tyr, di-halo-Tyr,
      O-sulpho-Tyr, O-phospho-Tyr, nitro-Tyr or any
      unnatural hydroxy containing amino acid; Xaa at
      residue 8 is Ser, Thr, Arg, ornithine,
```

```
<220> FEATURE:
<221> NAME/KEY: SITE
<222> LOCATION: (8)..(9)
<223> OTHER INFORMATION: homoarginine, Lys, N,N-dimethyl-Lys, N,N,N-
      trimethyl-Lys or any unnatural basic amino acid;
      Xaa at residue 9 is Asp, Glu, Gla, Arg, ornithine,
      homoarginine, Lys, N-methyl-Lys,N,N-dimethyl-
<220> FEATURE:
<221> NAME/KEY: SITE
<222> LOCATION: (9)..(10)
<223> OTHER INFORMATION: Lys, N,N,N-trimethyl-Lys or any unnatural basic
      amino acid; Xaa at residue 10 is Ser, Thr, Asn,
      Ala, Gly, Arg, Lys, ornithine, homoarginine,
      N-methyl-Lys, N,N-dimethyl-Lys, N,N,N-trimethyl-
<220> FEATURE:
<221> NAME/KEY: SITE
<222> LOCATION: (10)..(11)
<223> OTHER INFORMATION: Lys, any unnatural basic amino acid, His, halo-
      His, Pro or hydroxy-Pro; Xaa at residue 11 is
      Thr, Ser, Ala, Asp, Asn, Pro, hydroxy-Pro, Arg,
      ornithine, homoarginine, Lys, N-methyl-Lys,
<220> FEATURE:
<221> NAME/KEY: SITE
<222> LOCATION: (11)..(13)
<223> OTHER INFORMATION: N,N-dimethyl-Lys, N,N,N-trimethyl-Lys or any
      unnatural basic amino acid; Xaa at residue 13 is
      Gly, Ser, Thr, Ala, Asn, Arg, ornithine,
      homoarginine, Lys, N-methyl-Lys,
<220> FEATURE:
<221> NAME/KEY: SITE
<222> LOCATION: (13)..(14)
<223> OTHER INFORMATION: N,N-dimethyl-Lys, N,N,N-trimethyl-Lys or any
      unnatural basic amino acid; Xaa at residue 14 is
      Gln, Leu, His, halo-His, Trp (D or L), halo-Trp,
      neo-Trp, Tyr, nor-Tyr, mono-halo-Tyr, di-halo-
<220> FEATURE:
<221> NAME/KEY: SITE
<222> LOCATION: (14)
<223> OTHER INFORMATION: Tyr, O-sulpho-Tyr, O-phospho-Tyr, nitro-Tyr,
      Arg, ornithine, homoarginine, Lys, N-methyl-Lys, N,N-dimethyl-Lys,
      N,N,N-trimethyl-Lys, any unnatural basic amino acid or any
      unnatural aromatic amino
<220> FEATURE:
<221> NAME/KEY: SITE
<222> LOCATION: (14)..(15)
<223> OTHER INFORMATION: acid; Xaa at residue 15 is Asn, His, halo-His,
      Ile, Leu, Val, Gln, Arg, ornithine, homoarginine,
      Lys, N-methyl-Lys, N,N-dimethyl-Lys, N,N,N-
      trimethyl-Lys or any unnatural basic amino acid;
<220> FEATURE:
<221> NAME/KEY: SITE
<222> LOCATION: (17)
<223> OTHER INFORMATION: Xaa at residue 17 is des-Xaa, Val, Ile, Leu,
      Arg, ornithine, homoarginine, Lys, N-methyl-Lys, N,N-dimethyl-Lys,
      N,N,N-trimethyl-Lys or any unnatural basic amino acid.

<400> SEQUENCE: 1

Xaa Xaa Xaa Xaa Xaa Cys Cys Xaa Xaa Xaa Xaa Cys Xaa Xaa Xaa Cys
 1               5                  10                  15

Xaa

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence:Alpha-
      Conotoxin Peptide Generic Formula II.
<220> FEATURE:
<221> NAME/KEY: SITE
<222> LOCATION: (1)..(3)
<223> OTHER INFORMATION: Xaa at residue 1 is des-Xaa, Asp, Glu or gamma-
      carboxy-Glu (Gla); Xaa at residue 2 is des-Xaa,
      Gln, Ala, Asp, Glu, Gla; Xaa at residue 3 is des-
      Xaa, Gly, Ala, Asp, Glu, Gla, Pro or hydroxy-Pro.
<220> FEATURE:
```

```
<221> NAME/KEY: SITE
<222> LOCATION: (4)..(7)
<223> OTHER INFORMATION: Xaa at residue 4 is des-Xaa, Gly, Glu, Gla,
      Gln, Asp, Asn, Pro or hydroxy-Pro; Xaa at residue 7 is Ser, Thr,
      Gly, Glu, Gla, Asn, Trp (D or L), neo-Trp, halo-Trp, Arg,
      ornithine, homoarginine,
<220> FEATURE:
<221> NAME/KEY: SITE
<222> LOCATION: (7)
<223> OTHER INFORMATION: Lys, N-methyl-Lys, N,N-dimethyl-Lys, N,N,N-
      trimethyl-Lys, any unnatural basic amino acid,
      Tyr, nor-Tyr, mono-halo-Tyr, di-halo-Tyr,
      O-sulpho-Tyr, O-phospho-Tyr, nitro-Tyr or any
<220> FEATURE:
<221> NAME/KEY: SITE
<222> LOCATION: (7)..(8)
<223> OTHER INFORMATION: unnatural hydroxy containing amino acid; Xaa at
      residue 8 is Asp, Asn, His, halo-His, Thr, Ser,
      Tyr, nor-Tyr, mono-halo-Tyr, di-halo-Tyr,
      O-sulpho-Tyr, O-phospho-Tyr, nitro-Tyr or any
<220> FEATURE:
<221> NAME/KEY: SITE
<222> LOCATION: (8)..(10)
<223> OTHER INFORMATION: unnatural hydroxy containing amino acid; Xaa at
      residue 9 is Pro or hydroxy-Pro; Xaa at residue
      10 is Ala, Ser, Thr, Asp, Val, Ile, Pro, hydroxyl-
      Pro, Tyr, nor-Tyr, mono-halo-Tyr, di-halo-Tyr,
<220> FEATURE:
<221> NAME/KEY: SITE
<222> LOCATION: (10)..(12)
<223> OTHER INFORMATION: O-sulpho-Tyr, O-phospho-Tyr, nitro-Tyr or any
      unnatural hydroxy containing amino acid; Xaa at
      residue 12 is Gly, Ile, Leu, Val, Ala, Thr, Ser,
      Pro, hydroxy-Pro, Phe, Trp (D or L), neo-Trp,
<220> FEATURE:
<221> NAME/KEY: SITE
<222> LOCATION: (12)..(13)
<223> OTHER INFORMATION: halo-Trp, Arg, ornithine, homoarginine, Lys, N-
      methyl-Lys, N,N-dimethyl-Lys, N,N,N-trimethyl-
      Lys, any unnatural basic amino acid or any
      unnatural aromatic amino acid; Xaa at residue 13
<220> FEATURE:
<221> NAME/KEY: SITE
<222> LOCATION: (13)
<223> OTHER INFORMATION: is Ala, Asn, Phe, Pro, hydroxy-Pro, Glu, Gla,
      Gln, His, halo-His, Val, Ser, Thr, Arg,
      ornithine, homoarginine, Lys, N-methyl-Lys, N,N-
      dimethyl-Lys, N,N,N-trimethyl-Lys or any
<220> FEATURE:
<221> NAME/KEY: SITE
<222> LOCATION: (13)..(14)
<223> OTHER INFORMATION: unnatural basic amino acid; Xaa at residue 14
      is Thr, Ser, His, halo-His, Leu, Ile, Val, Asn, Met, Pro,
      hydroxy-Pro, Arg, ornithine, homoarginine, Lys, N-methyl-Lys,
      N,N-dimethyl-Lys, N,N,N-
<220> FEATURE:
<221> NAME/KEY: SITE
<222> LOCATION: (14)..(15)
<223> OTHER INFORMATION: trimethyl-Lys, any unnatural basic amino acid,
      Tyr, nor-Tyr, mono-halo-Tyr, di-halo-Tyr,
      O-sulpho-Tyr, O-phospho-Tyr, nitro-Tyr or any
      unnatural hydroxy containing amino acid; Xaa at
<220> FEATURE:
<221> NAME/KEY: SITE
<222> LOCATION: (15)
<223> OTHER INFORMATION: residue 15 is Asn, Pro, hydroxy-Pro, Gln, Ser,
      Thr, Arg, ornithine, homoarginine, Lys, N-methyl-
      Lys, N,N-dimethyl-Lys N,N,N-trimethyl-Lys, any
      unnatural basic amino acid, Tyr, nor-Tyr, mono-
<220> FEATURE:
<221> NAME/KEY: SITE
<222> LOCATION: (15)..(16)
<223> OTHER INFORMATION: halo-Tyr, di-halo-Tyr, O-sulpho-Tyr, O-phospho-
      Tyr, nitro-Tyr or any unnatural hydroxy contain-
      ing amino acid; Xaa at residue 16 is des-Xaa,
      Gly, Thr, Ser, Pro, hydroxy-Pro, Tyr, nor-Tyr,
<220> FEATURE:
<221> NAME/KEY: SITE
<222> LOCATION: (16)..(17)
```

```
<223> OTHER INFORMATION: mono-halo-Tyr, di-halo-Tyr, O-sulpho-Tyr,
      O-phospho-Tyr, nitro-Tyr or any unnatural hydroxy
      containing amino acid; Xaa at residue 17 is des-
      Xaa, Ile, Val, Asp, Leu, Phe, Arg, ornithine,
<220> FEATURE:
<221> NAME/KEY: SITE
<222> LOCATION: (17)
<223> OTHER INFORMATION: homoarginine, Lys, N-methyl-Lys, N,N-dimethyl-
      Lys, N,N,N-trimethyl-Lys, any unnatural basic
      amino acid, Tyr, nor-Tyr, mono-halo-Tyr, di-halo-
      Tyr, O-sulpho-Tyr, O-phospho-Tyr, nitro-Tyr or
<220> FEATURE:
<221> NAME/KEY: SITE
<222> LOCATION: (17)..(19)
<223> OTHER INFORMATION: any unnatural hydroxy containing amino acid;
      Xaa at residue 19 is des-Xaa, Gly, Ala, Met, Ser, Thr, Trp (D or
      L), neo-Trp, halo-Trp, any unnatural aromatic amino acid, Arg,
      ornithine,
<220> FEATURE:
<221> NAME/KEY: SITE
<222> LOCATION: (19)..(20)
<223> OTHER INFORMATION: homoarginine, Lys, N-methyl-Lys, N,N-dimethyl-
      Lys, N,N,N-trimethyl-Lys or any unnatural basic
      amino acid; Xaa at residue 20 is des-Xaa, Trp
      (D or L), neo-Trp, halo-Trp, any unnatural
<220> FEATURE:
<221> NAME/KEY: SITE
<222> LOCATION: (20)..(21)
<223> OTHER INFORMATION: aromatic amino acid, Arg, ornithine, homo-
      arginine, Lys, N-methyl-Lys, N,N-dimethyl-Lys,
      N,N,N-trimethyl-Lys or any unnatural basic amino
      acid; Xaa at residue 21 is des-Xaa, Arg,
<220> FEATURE:
<221> NAME/KEY: SITE
<222> LOCATION: (21)
<223> OTHER INFORMATION: ornithine, homoarginine, Lys, N-methyl-Lys,
      N,N-dimethyl-Lys, N,N,N-trimethyl-Lys or any
      unnatural basic amino acid.

<400> SEQUENCE: 2

Xaa Xaa Xaa Xaa Cys Cys Xaa X

```
<223> OTHER INFORMATION: arginine, Lys, N-methyl-Lys, N,N-dimethyl-Lys,
      N,N,N-trimethyl-Lys or any unnatural basic amino
      acid; Xaa at residue 8 is Thr, Ser, Asp, Asn, Met,
      Val, Ala, Gly, Leu, Ile, Phe, any unnatural
<220> FEATURE:
<221> NAME/KEY: SITE
<222> LOCATION: (8)..(9)
<223> OTHER INFORMATION: aromatic amino acid, Pro, hydroxy-Pro, Tyr,
      nor-Tyr, mono-halo-Tyr, di-halo-Tyr, O-sulpho-Tyr, O-phospho-Tyr,
      nitro-Tyr or any unnatural hydroxy containing amino acid; Xaa at
      residue 9 is Ile,
<220> FEATURE:
<221> NAME/KEY: SITE
<222> LOCATION: (9)
<223> OTHER INFORMATION: Leu, Val, Ser, Thr, Gln, Asn, Asp, Arg, His,
      halo-His, Phe,  any unnatural aromatic amino
      acid, homoarginine, ornithine, Lys, N-methyl-Lys,
      N,N-dimethyl-Lys, N,N,N-trimethyl-Lys, any
<220> FEATURE:
<221> NAME/KEY: SITE
<222> LOCATION: (9)..(10)
<223> OTHER INFORMATION: unnatural basic amino acid, Tyr, nor-Tyr, mono-
      halo-Tyr, di-halo-Tyr, O-sulpho-Tyr, O-phospho-
      Tyr, nitro-Tyr or any unnatural hydroxy contain-
      ing amino acid; Xaa at residue 10 is Pro, hyroxy-
<220> FEATURE:
<221> NAME/KEY: SITE
<222> LOCATION: (10)
<223> OTHER INFORMATION: Pro, Ser, Thr, Ile, Asp, Leu, Val, Gly, Ala,
      Phe, any unnatural aromatic amino acid, Arg, ornithine,
      homoarginine, Lys, N-methyl-Lys, N,N-dimethyl-Lys,
      N,N,N-trimethyl-Lys or any unnatural basic amino
<220> FEATURE:
<221> NAME/KEY: SITE
<222> LOCATION: (11)
<223> OTHER INFORMATION: acid; Xaa at residue 11 is Val, Ala, Gly, Ile,
      Leu, Asp, Ser, Thr, Pro, hydroxy-Pro, Arg,
      ornithine, homoarginine, Lys, N-methyl-Lys,
      N,N-dimethyl-Lys, N,N,N-trimethyl-Lys or any
<220> FEATURE:
<221> NAME/KEY: SITE
<222> LOCATION: (11)..(13)
<223> OTHER INFORMATION: unnatural basic amino acid; Xaa at residue 13
      is His, halo-His, Arg, homoarginine, ornithine, Lys, N-methyl-Lys,
      N,N-dimethyl-Lys, N,N,N-trimethyl-Lys, any unnatural basic amino
      acid, Asn, Ala,
<220> FEATURE:
<221> NAME/KEY: SITE
<222> LOCATION: (13)
<223> OTHER INFORMATION: Ser, Thr, Phe, Ile, Leu, Gly, Trp (D or L),
      neo-Trp, halo-Trp, any unnatural aromatic amino acid, Tyr,
      nor-Tyr, mono-halo-Tyr, di-halo-Tyr, O-sulpho-Tyr, O-phospho-Tyr,
      nitro-Tyr or any
<220> FEATURE:
<221> NAME/KEY: SITE
<222> LOCATION: (13)..(14)
<223> OTHER INFORMATION: unnatural hydroxy containing amino acid; Xaa at
      residue 14 is Leu, Gln, Val, Ile, Gly, Met, Ala,
      Lys, N-methyl-Lys, N,N-dimethyl-Lys, N,N,N-tri-
      Methyl-Lys, Ser, Thr, Arg, homoarginine, orni-
<220> FEATURE:
<221> NAME/KEY: SITE
<222> LOCATION: (14)..(15)
<223> OTHER INFORMATION: thine, any unnatural basic amino acid, Asn,
      Glu, Gla, Gln, Phe, Trp (D or L), neo-Trp, halo-Trp or any
      unnatural aromatic amino acid; Xaa at residue 15 is Glu, Gla, Gln,
      Asn, Asp, Pro, hydroxy-Pro,
<220> FEATURE:
<221> NAME/KEY: SITE
<222> LOCATION: (15)
<223> OTHER INFORMATION: Ser, Gly, Thr, Lys, N-methyl-Lys, N,N-dimethyl-
      Lys, N,N,N-trimethyl-Lys, Arg, homoarginine,
      ornithine, any unnatural basic amino acid, Phe,
      His, halo-His, any unnatural aromatic acid, Leu,
<220> FEATURE:
<221> NAME/KEY: SITE
<222> LOCATION: (15)..(16)
<223> OTHER INFORMATION: Met, Gly, Ala, Tyr, nor-Tyr, mono-halo-Tyr, di-
      halo-Tyr, O-sulpho-Tyr, O-phospho-Tyr, nitro-Tyr
```

```
        or any unnatural hydroxy containing amino acid;
        Xaa at residue 16 is His, halo-His, Asn, Thr,
<220>  FEATURE:
<221>  NAME/KEY: SITE
<222>  LOCATION: (16)
<223>  OTHER INFORMATION: Ser, Ile, Val, Leu, Phe, any unnatural aromatic
        amino acid, Arg, homoarginine, ornithine, Lys, N-
        methyl-Lys, N,N-dimethyl-Lys, N,N,N-trimethyl-Lys,
        any unnatural basic amino acid, Tyr, nor-Tyr,
<220>  FEATURE:
<221>  NAME/KEY: SITE
<222>  LOCATION: (16)..(17)
<223>  OTHER INFORMATION: mono-halo-Tyr, di-halo-Tyr, O-sulpho-Tyr,
        O-phospho-Tyr, nitro-Tyr or any unnatural hydroxy
        containing amino acid; Xaa at residue 17 is Ser,
        Thr, Ala, Gln, Pro, hydroxy-Pro, Gly, Ile, Leu,
<220>  FEATURE:
<221>  NAME/KEY: SITE
<222>  LOCATION: (17)..(18)
<223>  OTHER INFORMATION: Arg, ornithine, homoarginine, Lys,
        N-methyl-Lys, N,N-dimethyl-Lys, N,N,N-trimethyl-Lys or any
        unnatural basic amino acid; Xaa at residue 18 is
        Asn, Glu, Gla, Asp, Gly, His, halo-His, Ala, Leu,
<220>  FEATURE:
<221>  NAME/KEY: SITE
<222>  LOCATION: (18)
<223>  OTHER INFORMATION: Gln, Arg,  ornithine, homoarginine, Lys,
        N-methyl- Lys, N,N-dimethyl-Lys, N,N,N-trimethyl-Lys, any
        unnatural basic amino acid, Tyr, nor-Tyr, mono-
        halo-Tyr, di-halo-Tyr, O-sulpho-Tyr, O-phospho-
<220>  FEATURE:
<221>  NAME/KEY: SITE
<222>  LOCATION: (18)..(19)
<223>  OTHER INFORMATION: Tyr, nitro-Tyr or any unnatural hydroxy
        containing amino acid; Xaa at residue 19 is Met, Ile, Thr,
        Ser, Val, Leu, Pro, hydroxy-Pro, Phe, any
        unnatural aromatic amino acid, Tyr, nor-Tyr, mono-
<220>  FEATURE:
<221>  NAME/KEY: SITE
<222>  LOCATION: (19)
<223>  OTHER INFORMATION: halo-Tyr, di-halo-Tyr, O-sulpho-Tyr, O-phospho-
        Tyr, nitro-Tyr, any unnatural hydroxy containing
        amino acid, Glu, Gla, Ala, His, halo-His, Arg,
        ornithine, homoarginine, Lys, N-methyl-Lys, N,N-
<220>  FEATURE:
<221>  NAME/KEY: SITE
<222>  LOCATION: (21)
<223>  OTHER INFORMATION: dimethyl-Lys, N,N,N-trimethyl-Lys or any
        unnatural basic amino acid; Xaa at residue 21 is des-Xaa,
        Gly, Asp, Asn, Ala, Ile, Leu, Ser, Thr, His, halo-
        His, Arg, ornithine, homoarginine, Lys, N-methyl-
<220>  FEATURE:
<221>  NAME/KEY: SITE
<222>  LOCATION: (21)..(22)
<223>  OTHER INFORMATION: Lys, N,N-dimethyl-Lys, N,N,N-trimethyl-Lys or
        any unnatural basic amino acid; Xaa at residue 22 is
        des-Xaa, Gly, Glu, Gla, Gln, Trp (D or L), neo-Trp,
        halo-Trp, any unnatural aromatic amino acid, Arg,
<220>  FEATURE:
<221>  NAME/KEY: SITE
<222>  LOCATION: (22)..(23)
<223>  OTHER INFORMATION: ornithine, homoarginine, Lys, N-methyl-Lys,
        N,N-dimethyl-Lys, N,N,N-trimethyl-Lys or any unnatural
        basic amino acid; Xaa at residue 23 is des-Xaa,
        Ser, Thr, Val, Ile, Ala, Arg, ornithine, homo-
<220>  FEATURE:
<221>  NAME/KEY: SITE
<222>  LOCATION: (23)..(24)
<223>  OTHER INFORMATION: arginine, Lys, N-methyl-Lys, N,N-dimethyl-Lys,
        N,N,N-trimethyl-Lys or any unnatural basic amino
        acid; Xaa at residue 24 is des-Xaa, Val, Asp, His,
        halo-His, Arg, ornithine, homoarginine, Lys, N-
<220>  FEATURE:
<221>  NAME/KEY: SITE
<222>  LOCATION: (24)..(26)
<223>  OTHER INFORMATION: methyl-Lys, N,N-dimethyl-Lys,
        N,N,N-trimethyl-Lys or any unnatural basic amino acid; Xaa at
        residue 25 is des-Xaa, Asn, Pro or hydroxy-Pro; Xaa at
        residue 26 is des-Xaa, Arg, ornithine, homo-
```

```
<220> FEATURE:
<221> NAME/KEY: SITE
<222> LOCATION: (26)..(28)
<223> OTHER INFORMATION: arginine, Lys, N-methyl-Lys, N,N-dimethyl-Lys,
      N,N,N-trimethyl-Lys or any unnatural basic amino
      acid; Xaa at residue 27 is des-Xaa, Ser or Thr;
      Xaa at residue 28 is des-Xaa, Leu, Ile or Val.

<400> SEQUENCE: 3

Xaa Xaa Xaa Xaa Xaa Cys Cys Xaa Xaa Xaa Xaa Cys Xaa Xaa Xaa Xaa
 1               5                  10                  15

Xaa Xaa Xaa Cys Xaa Xaa Xaa Xaa Xaa Xaa Xaa Xaa
            20                  25

<210> SEQ ID NO 4
<211> LENGTH: 14
<212> TYPE: PRT
<213> ORGANISM: Conus imperialis
<220> FEATURE:
<221> NAME/KEY: SITE
<222> LOCATION: (2)..(11)
<223> OTHER INFORMATION: Xaa at residue 2 is Glu or gamma-carboxy-Glu;
      Xaa at residue 11 is Lys, N-methyl-Lys, N,N-dimethyl-Lys or
      N,N,N-trimethyl-Lys.

<400> SEQUENCE: 4

Asp Xaa Cys Cys Ser Asp Ser Arg Cys Gly Xaa Asn Cys Leu
 1               5                  10

<210> SEQ ID NO 5
<211> LENGTH: 12
<212> TYPE: PRT
<213> ORGANISM: Conus imperialis
<220> FEATURE:
<221> NAME/KEY: SITE
<222> LOCATION: (10)
<223> OTHER INFORMATION: Xaa at residue 10 is Trp (D or L) or halo-Trp.

<400> SEQUENCE: 5

Ala Cys Cys Ser Asp Arg Arg Cys Arg Xaa Arg Cys
 1               5                  10

<210> SEQ ID NO 6
<211> LENGTH: 13
<212> TYPE: PRT
<213> ORGANISM: Conus regius

<400> SEQUENCE: 6

Phe Thr Cys Cys Arg Arg Gly Thr Cys Ser Gln His Cys
 1               5                  10

<210> SEQ ID NO 7
<211> LENGTH: 13
<212> TYPE: PRT
<213> ORGANISM: Conus regius
<220> FEATURE:
<221> NAME/KEY: SITE
<222> LOCATION: (2)
<223> OTHER INFORMATION: Xaa at residue 2 is Tyr, nor-Tyr,
      mono-halo-Tyr, di-halo-Tyr, O-sulpho-Tyr, O-phospho-Tyr or
      nitro-Tyr.

<400> SEQUENCE: 7

Asp Xaa Cys Cys Arg Arg His Ala Cys Thr Leu Ile Cys
 1               5                  10

<210> SEQ ID NO 8
<211> LENGTH: 13
```

```
<212> TYPE: PRT
<213> ORGANISM: Conus regius
<220> FEATURE:
<221> NAME/KEY: SITE
<222> LOCATION: (2)..(8)
<223> OTHER INFORMATION: Xaa at residue 2 is Tyr, nor-Tyr,
      mono-halo-Tyr, di-halo-Tyr, O-sulpho-Tyr, O-phospho-Tyr or
      nitro-Tyr; Xaa at residues 7 and 8 is Pro or hydroxy-Pro.

<400> SEQUENCE: 8

Asp Xaa Cys Cys Arg Arg Xaa Xaa Cys Thr Leu Ile Cys
 1

```
<222> LOCATION: (6)..(9)
<223> OTHER INFORMATION: Xaa at residue 6 is Pro or hydroxy-Pro; Xaa at
      residue 9 is Lys, N-methyl-Lys, N,N-dimethyl-Lys
      or N,N,N-trimethyl-Lys.

<400> SEQUENCE: 12

Gly Cys Cys Ser Asp Xaa Arg Cys Xaa His Gln Cys
 1               5                   10

<210> SEQ ID NO 13
<211> LENGTH: 14
<212> TYPE: PRT
<213> ORGANISM: Conus sponsalis
<220> FEATURE:
<221> NAME/KEY: SITE
<222> LOCATION: (5)..(11)
<223> OTHER INFORMATION: Xaa at residues 5 and 11 is Pro or hydroxy-Pro;
      Xaa at residue 8 is Lys, N-methyl-Lys,
      N.N-dimethyl-Lys or N.N.N-trimethyl-Lys.

<400> SEQUENCE: 13

Cys Cys Ser Asp Xaa Ala Cys Xaa Gln Thr Xaa Gly Cys Arg
 1               5                   10

<210> SEQ ID NO 14
<211> LENGTH: 13
<212> TYPE: PRT
<213> ORGANISM: Conus sponsalis
<220> FEATURE:
<221> NAME/KEY: SITE
<222> LOCATION: (3)..(5)
<223> OTHER INFORMATION: Xaa at residue 3 is Glu or gamma-carboxy-Glu;
      Xaa at residue 5 is Pro or hydroxy-Pro.

<400> SEQUENCE: 14

Cys Cys Xaa Asn Xaa Ala Cys Arg His Thr Gln Gly Cys
 1               5                   10

<210> SEQ ID NO 15
<211> LENGTH: 13
<212> TYPE: PRT
<213> ORGANISM: Conus sulcatus
<220> FEATURE:
<221> NAME/KEY: SITE
<222> LOCATION: (4)..(12)
<223> OTHER INFORMATION: Xaa at residue 4 is Trp or halo-Trp; Xaa at
      residue 6 is Pro or hydroxy-Pro; Xaa at residue 12
      is Tyr, nor-Tyr, mono-halo-Tyr, di-halo-Tyr,
      O-sulpho-Tyr, O-phospho-Tyr or nitro-Tyr.

<400> SEQUENCE: 15

Gly Cys Cys Xaa His Xaa Ala Cys Gly Arg His Xaa Cys
 1               5                   10

<210> SEQ ID NO 16
<211> LENGTH: 14
<212> TYPE: PRT
<213> ORGANISM: Conus achatinus
<220> FEATURE:
<221> NAME/KEY: SITE
<222> LOCATION: (2)..(11)
<223> OTHER INFORMATION: Xaa at residues 2 and 7 is Pro or hydroxy-Pro;
      Xaa at residue 11 is Lys, N-methyl-Lys, N,N-dimethyl-Lys or
      N,N,N-trimethyl-Lys.

<400> SEQUENCE: 16

Ala Xaa Cys Cys Asn Asn Xaa Ala Cys Val Xaa His Arg Cys
 1               5                   10
```

<210> SEQ ID NO 17
<211> LENGTH: 15
<212> TYPE: PRT
<213> ORGANISM: Conus bullatus
<220> FEATURE:
<221> NAME/KEY: SITE
<222> LOCATION: (2)..(12)
<223> OTHER INFORMATION: Xaa at residues 2 and 8 is Pro or hydroxy-Pro;
    Xaa at residue 12 is Lys, N-methyl-Lys, N,N-dimethyl-Lys or
    N,N,N-trimethyl-Lys.

<400> SEQUENCE: 17

Ala Xaa Gly Cys Cys Asn Asn Xaa Ala Cys Val Xaa His Arg Cys
 1               5                  10                  15

<210> SEQ ID NO 18
<211> LENGTH: 14
<212> TYPE: PRT
<213> ORGANISM: Conus bullatus
<220> FEATURE:
<221> NAME/KEY: SITE
<222> LOCATION: (1)..(11)
<223> OTHER INFORMATION: Xaa at residues 1, 2 and 7 is Pro or
    hydroxy-Pro; Xaa at residue 11 is Lys, N-methyl-Lys,
    N,N-dimethyl-Lys or N,N,N-trimethyl-Lys.

<400> SEQUENCE: 18

Xaa Xaa Cys Cys Asn Asn Xaa Ala Cys Val Xaa His Arg Cys
 1               5                  10

<210> SEQ ID NO 19
<211> LENGTH: 16
<212> TYPE: PRT
<213> ORGANISM: Conus bullatus
<220> FEATURE:
<221> NAME/KEY: SITE
<222> LOCATION: (2)..(13)
<223> OTHER INFORMATION: Xaa at residue 2 is Glu or gamma-carboxy-Glu;
    Xaa at residue 6 is Trp or halo-Trp; Xaa at residues 8
    11 and 13 is Pro or hydroxy-Pro.

<400> SEQUENCE: 19

Asp Xaa Asn Cys Cys Xaa Asn Xaa Ser Cys Xaa Arg Xaa Arg Cys Thr
 1               5                  10                  15

<210> SEQ ID NO 20
<211> LENGTH: 13
<212> TYPE: PRT
<213> ORGANISM: Conus bullatus
<220> FEATURE:
<221> NAME/KEY: SITE
<222> LOCATION: (6)..(12)
<223> OTHER INFORMATION: Xaa at residues 6 and 7 is Pro or hydroxy-Pro;
    Xaa at residue 12 is Tyr, nor-Tyr, mono-halo-Tyr, di-halo-Tyr,
    O-sulpho-Tyr, O-phospho-Tyr or nitro-Tyr.

<400> SEQUENCE: 20

Gly Cys Cys Ser Arg Xaa Xaa Cys Ala Val Leu Xaa Cys
 1               5                  10

<210> SEQ ID NO 21
<211> LENGTH: 13
<212> TYPE: PRT
<213> ORGANISM: Conus circumcisus
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 21

```
Gly Cys Cys Gly Asn Xaa Asp Cys Thr Ser His Ser Cys
 1               5                  10
```

<210> SEQ ID NO 22
<211> LENGTH: 16
<212> TYPE: PRT
<213> ORGANISM: Conus stercusmuscarum
<220> FEATURE:
<221> NAME/KEY: SITE
<222> LOCATION: (6)..(11)
<223> OTHER INFORMATION: Xaa at residue 6 is Pro or hydroxy-Pro; Xaa at
      residue 11 is Glu or gamma-carboxy-Glu.

<400> SEQUENCE: 22

```
Gly Cys Cys Ser Asn Xaa Val Cys His Leu Xaa His Ser Asn Met Cys
 1               5                  10                  15
```

<210> SEQ ID NO 23
<211> LENGTH: 17
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residue 6 is Pro or hydroxy-Pro; Xaa at
      residue 14 is Glu or gamma-carboxy-Glu; Xaa at
      residue 15 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (15)
<223> OTHER INFORMATION: nitro-Tyr.

<400> SEQUENCE: 23

```
Gly Cys Cys Ser Asn Xaa Val Cys Arg Gln Asn Asn Ala Xaa Xaa Cys
 1               5                  10                  15

Arg
```

<210> SEQ ID NO 24
<211> LENGTH: 18
<212> TYPE: PRT
<213> ORGANISM: Conus textile
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 24

```
Xaa Gln Cys Cys Ser His Xaa Ala Cys Asn Val Asp His Xaa Xaa Ile
 1               5                  10                  15

Cys Arg
```

<210> SEQ ID NO 25
<211> LENGTH: 18
<212> TYPE: PRT
<213> ORGANISM: Conus radiatus
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residues 2 and 15 is Glu or gamma-carboxy-Glu.

<400> SEQUENCE: 25

```
Xaa Xaa Cys Cys Ser His Xaa Ala Cys Asn Val Asp His Xaa Xaa Ile
 1               5                  10                  15

Cys Arg
```

```
<210> SEQ ID NO 26
<211> LENGTH: 18
<212> TYPE: PRT
<213> ORGANISM: Conus radiatus
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 26

Xaa Gln Cys Cys Ser His Xaa Ala Cys Asn Val Asp His Xaa Xaa Ile
 1               5                  10                  15

Cys Asp

<210> SEQ ID NO 27
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 27

Xaa Arg Cys Cys Ser His Xaa Ala Cys Asn Val Asp His Xaa Xaa Ile
 1               5                  10                  15

Cys Arg

<210> SEQ ID NO 28
<211> LENGTH: 18
<212> TYPE: PRT
<213> ORGANISM: Conus omaria
<220> FEATURE:
<221> NAME/KEY: SITE
<222> LOCATION: (1)..(14)
<223> OTHER INFORMATION: Xaa at residues 1, 7 and 14 is Pro or
      hydroxy-Pro.

<400> SEQUENCE: 28

Xaa Gln Cys Cys Ser His Xaa Ala Cys Asn Val Asp His Xaa Gly Ile
 1               5                  10                  15

Cys Arg

<210> SEQ ID NO 29
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 29

Xaa Gln Cys Cys Ser His Xaa Ala Cys Asn Val Asp His Xaa Xaa Thr
 1               5                  10                  15

Cys Arg

<210> SEQ ID NO 30
<211> LENGTH: 18
<212> TYPE: PRT
<213> ORGANISM: Conus omaria
<220> FEATURE:
<221> NAME/KEY: SITE
```

-continued

```
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 30

Xaa Gln Cys Cys Ser His Xaa Ala Cys Asn Val Asp His Xaa Xaa Val
 1               5                   10                  15

Cys Arg

<210> SEQ ID NO 31
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 31

Xaa Gln Cys Cys Ser His Xaa Ala Cys Asn Ile Asp His Xaa Xaa Ile
 1               5                   10                  15

Cys Arg

<210> SEQ ID NO 32
<211> LENGTH: 21
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 32

Xaa Gln Cys Cys Ser His Xaa Ala Cys Asn Val Asp His Xaa Xaa Ile
 1               5                   10                  15

Cys Arg Arg Arg Arg
            20

<210> SEQ ID NO 33
<211> LENGTH: 17
<212> TYPE: PRT
<213> ORGANISM: Conus betulinus
<220> FEATURE:
<221> NAME/KEY: SITE
<222> LOCATION: (7)..(15)
<223> OTHER INFORMATION: Xaa at residues 7 and 14 is Pro or
      hydroxy-Pro; Xaa at residue 15 is Glu or gamma-carboxy-Glu.

<400> SEQUENCE: 33

Gly Gly Cys Cys Ser His Xaa Ala Cys Ala Val Asn His Xaa Xaa Leu
 1               5                   10                  15

Cys

<210> SEQ ID NO 34
<211> LENGTH: 16
<212> TYPE: PRT
<213> ORGANISM: Conus betulinus
<220> FEATURE:
<221> NAME/KEY: SITE
<222> LOCATION: (6)..(14)
<223> OTHER INFORMATION: Xaa at residues 6 and 13 is Pro or hydroxy-Pro;
      Xaa at residue 14 is Glu or gamma-carboxy-Glu.

<400> SEQUENCE: 34
```

Gly Cys Cys Ser His Xaa Ala Cys Ser Val Asn His Xaa Xaa Leu Cys
 1               5                  10                  15

<210> SEQ ID NO 35
<211> LENGTH: 16
<212> TYPE: PRT
<213> ORGANISM: Conus dalli
<220> FEATURE:
<221> NAME/KEY: SITE
<222> LOCATION: (6)..(14)
<223> OTHER INFORMATION: Xaa at residues 6 and 13 is Pro or hydroxy-Pro;
      Xaa at residue 14 is Glu or gamma-carboxy-Glu.

<400> SEQUENCE: 35

Gly Cys Cys Ser His Xaa Ala Cys Asn Val Asp His Xaa Xaa Ile Cys
 1               5                  10                  15

<210> SEQ ID NO 36
<211> LENGTH: 19
<212> TYPE: PRT
<213> ORGANISM: Conus obscurus
<220> FEATURE:
<221> NAME/KEY: SITE
<222> LOCATION: (6)..(18)
<223> OTHER INFORMATION: Xaa at residues 6 and 15 is Pro or hydroxy-Pro;
      Xaa at reside 11 is Lys, N-methyl-Lys,
      N,N-dimethyl-Lys or N,N,N-trimethyl-Lys; Xaa at
      residues 14 and 18 is Glu or gamma-carboxy-Glu.

<400> SEQUENCE: 36

Gly Cys Cys Ser His Xaa Ala Cys Ser Gly Xaa Thr Gln Xaa Xaa Cys
 1               5                  10                  15

Arg Xaa Ser

<210> SEQ ID NO 37
<211> LENGTH: 18
<212> TYPE: PRT
<213> ORGANISM: Conus tulipa
<220> FEATURE:
<221> NAME/KEY: SITE
<222> LOCATION: (1)..(14)
<223> OTHER INFORMATION: Xaa at residues 1, 6 and 13 is Pro or
      hydroxy-Pro; Xaa at residue 14 is Glu or gamma-carboxy-Glu.

<400> SEQUENCE: 37

Xaa Cys Cys Ser His Xaa Ala Cys Ser Gly Asn Asn Xaa Xaa Phe Cys
 1               5                  10                  15

Arg Gln

<210> SEQ ID NO 38
<211> LENGTH: 18
<212> TYPE: PRT
<213> ORGANISM: Conus tulipa
<220> FEATURE:
<221> NAME/KEY: SITE
<222> LOCATION: (6)..(14)
<223> OTHER INFORMATION: Xaa at residues 6 and 13 is Pro or
      hydroxy-Pro; Xaa at residue 14 is Glu or gamma-carboxy-Glu.

<400> SEQUENCE: 38

Gly Cys Cys Ser His Xaa Ala Cys Ser Gly Asn Asn Xaa Xaa Phe Cys
 1               5                  10                  15

Arg Gln

<210> SEQ ID NO 39
<211> LENGTH: 16
<212> TYPE: PRT

```
<213> ORGANISM: Conus pennaceus
<220> FEATURE:
<221> NAME/KEY: SITE
<222> LOCATION: (6)..(15)
<223> OTHER INFORMATION: Xaa at residues 6, 7 and 13 is Pro or
      hydroxy-Pro; Xaa at residue 15 is Tyr, nor-Tyr, mono-halo-Tyr,
      di-halo-Tyr, O-sulpho-Tyr, O-phospho-Tyr or nitro-Tyr.

<400> SEQUENCE: 39

Gly Cys Cys Ser His Xaa Xaa Cys Ala Met Asn Asn Xaa Asp Xaa Cys
 1               5                  10                  15

<210> SEQ ID NO 40
<211> LENGTH: 16
<212> TYPE: PRT
<213> ORGANISM: Conus pennaceus
<220> FEATURE:
<221> NAME/KEY: SITE
<222> LOCATION: (6)..(15)
<223> OTHER INFORMATION: Xaa at residuew 6, 7 and 13 is Pro or
      hydroxy-Pro; Xaa at residue 15 is Tyr, nor-Tyr, mono-halo-Tyr,
      di-halo-Tyr, O-sulpho-Tyr, O-phospho-Tyr or nitro-Tyr.

<400> SEQUENCE: 40

Gly Cys Cys Ser His Xaa Xaa Cys Phe Leu Asn Asn Xaa Asp Xaa Cys
 1               5                  10                  15

<210> SEQ ID NO 41
<211> LENGTH: 17
<212> TYPE: PRT
<213> ORGANISM: Conus textile
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro; Xaa at residue 11 is Lys, N-methyl-Lys,
      N,N-dimethyl-Lys or N.N.N-trimethyl-Lys.

<400> SEQUENCE: 41

Gly Cys Cys Ser Asn Xaa Xaa Cys Ile Ala Xaa Asn Xaa His Met Cys
 1               5                  10                  15

Gly

<210> SEQ ID NO 42
<211> LENGTH: 16
<212> TYPE: PRT
<213> ORGANISM: Conus distans
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro.

<400> SEQUENCE: 42

Gly Cys Cys Ser Asn Xaa Xaa Cys Ala His Asn Asn Xaa Asp Cys Arg
 1               5                  10                  15

<210> SEQ ID NO 43
<211> LENGTH: 17
<212> TYPE: PRT
<213> ORGANISM: Conus tulipa
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 43

Gly Cys Cys Ser Asn Xaa Ala Cys Ala Gly Asn Asn Xaa His Val Cys
 1               5                  10                  15
```

Arg

<210> SEQ ID NO 44
<211> LENGTH: 16
<212> TYPE: PRT
<213> ORGANISM: Conus dalli
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 44

Gly Cys Cys Ser Arg Xaa Ala Cys Ile Ala Asn Asn Xaa Asp Leu Cys
 1               5                  10                  15

<210> SEQ ID NO 45
<211> LENGTH: 20
<212> TYPE: PRT
<213> ORGANISM: Conus circumcisus
<220> FEATURE:
<221> NAME/KEY: SITE
<222> LOCATION: (6)..(14)
<223> OTHER INFORMATION: Xaa at residues 6 and 13 is Pro or hydroxy-Pro;
      Xaa at residues 11 and 14 is Glu or
      gamma-carboxy-Glu.

<400> SEQUENCE: 45

Gly Cys Cys Ser Asn Xaa Val Cys His Val Xaa His Xaa Xaa Leu Cys
 1               5                  10                  15

Arg Arg Arg Arg
            20

<210> SEQ ID NO 46
<211> LENGTH: 18
<212> TYPE: PRT
<213> ORGANISM: Conus sulcatus
<220> FEATURE:
<221> NAME/KEY: SITE
<222> LOCATION: (7)..(15)
<223> OTHER INFORMATION: Xaa at residues 7, 12 and 14 is Pro or
      hydroxy-Pro; Xaa at residue 11 is Lys,
      N-methyl-Lys, N,N-dimethyl-Lys or
      N,N,N-trimethyl-Lys; Xaa at residue 15 is Glu or
<220> FEATURE:
<221> NAME/KEY: SITE
<222> LOCATION: (7)..(15)
<223> OTHER INFORMATION: gamma-carboxy-Glu.

<400> SEQUENCE: 46

Gly Gly Cys Cys Ser Phe Xaa Ala Cys Arg Xaa Xaa Arg Xaa Xaa Met
 1               5                  10                  15

Cys Gly

<210> SEQ ID NO 47
<211> LENGTH: 18
<212> TYPE: PRT
<213> ORGANISM: Conus textile
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residues 2 and 15 is Glu or gamma-carboxy-Glu.

<400> SEQUENCE: 47

Xaa Xaa Cys Cys Ser Asp Xaa Arg Cys Asn Ser Ser His Xaa Xaa Leu
 1               5                  10                  15

Cys Arg

```
<210> SEQ ID NO 48
<211> LENGTH: 18
<212> TYPE: PRT
<213> ORGANISM: Conus dalli
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 48

Xaa Gln Cys Cys Ser Asp Xaa Arg Cys Asn Val Gly His Xaa Xaa Leu
 1               5                  10                  15

Cys Gly

<210> SEQ ID NO 49
<211> LENGTH: 18
<212> TYPE: PRT
<213> ORGANISM: Conus dalli
<220> FEATURE:
<221> NAME/KEY: SITE
<222> LOCATION: (1)..(15)
<223> OTHER INFORMATION: Xaa at residue 1 is Gln or pyro-Glu; Xaa at
      residues 7 and 14 is Pro or hydroxy-Pro; Xaa at
      residue 15 is Glu or gamma-carboxy-Glu.

<400> SEQUENCE: 49

Xaa Val Cys Cys Ser Asp Xaa Arg Cys Asn Val Gly His Xaa Xaa Ile
 1               5                  10                  15

Cys Gly

<210> SEQ ID NO 50
<211> LENGTH: 16
<212> TYPE: PRT
<213> ORGANISM: Conus textile
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro.

<400> SEQUENCE: 50

Gly Cys Cys Ser Arg Xaa Xaa Cys Ile Ala Asn Asn Xaa Asp Leu Cys
 1               5                  10                  15

<210> SEQ ID NO 51
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1 and 14 is Pro or hydroxy-Pro;
      Xaa at residue 15 is Glu or gamma-carboxy-Glu.

<400> SEQUENCE: 51

Xaa Gln Cys Cys Ser His Leu Ala Cys Asn Val Asp His Xaa Xaa Ile
 1               5                  10                  15

Cys Arg

<210> SEQ ID NO 52
<211> LENGTH: 19
<212> TYPE: PRT
<213> ORGANISM: Conus sulcatus
<220> FEATURE:
<221> NAME/KEY: SITE
```

```
<222> LOCATION: (5)..(14)
<223> OTHER INFORMATION: Xaa at residue 5 is Tyr, nor-Tyr,
      mono-halo-Tyr, di-halo-Tyr, O-sulpho-Tyr, O-phospho-Tyr or
      nitro-Tyr; Xaa at residue 13 is Pro or
      hydroxy-Pro; Xaa at residue 14 is Glu or
<220> FEATURE:
<221> NAME/KEY: SITE
<222> LOCATION: (14)..(18)
<223> OTHER INFORMATION: gamma-carboxy-Glu; Xaa at residue 18 is Trp or
      halo-Trp.

<400> SEQUENCE: 52

Gly Cys Cys Ser Xaa Phe Asp Cys Arg Met Met Phe Xaa Xaa Met Cys
 1               5                  10                  15

Gly Xaa Arg

<210> SEQ ID NO 53
<211> LENGTH: 18
<212> TYPE: PRT
<213> ORGANISM: Conus sulcatus
<220> FEATURE:
<221> NAME/KEY: SITE
<222> LOCATION: (11)..(12)
<223> OTHER INFORMATION: Xaa at residue 11 is Lys, N-methyl-Lys,
      N,N-dimethyl-Lys or N,N,N-trimethyl-Lys; Xaa at
      residue 12 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (12)..(15)
<223> OTHER INFORMATION: nitro-Tyr; Xaa at residue 14 is Pro or
      hydroxyl-Pro; Xaa at residue 15 is Glu or gamma-carboxy-Glu.

<400> SEQUENCE: 53

Gly Gly Cys Cys Ser Phe Ala Ala Cys Arg Xaa Xaa Arg Xaa Xaa Met
 1               5                  10                  15

Cys Gly

<210> SEQ ID NO 54
<211> LENGTH: 20
<212> TYPE: PRT
<213> ORGANISM: Conus sulcatus
<220> FEATURE:
<221> NAME/KEY: SITE
<222> LOCATION: (7)..(15)
<223> OTHER INFORMATION: Xaa at residue 7 is Pro or hydroxy-Pro; Xaa at
      residue 10 is Tyr, nor-Tyr, mono-halo-Tyr,
      di-halo-Tyr, O-sulpho-Tyr, O-phospho-Tyr or
      nitro-Tyr; Xaa at residue 15 is Glu or
<220> FEATURE:
<221> NAME/KEY: SITE
<222> LOCATION: (7)..(15)
<223> OTHER INFORMATION: gamma-carboxy-Glu.

<400> SEQUENCE: 54

Gly Gly Cys Cys Phe His Xaa Val Cys Xaa Ile Asn Leu Leu Xaa Met
 1               5                  10                  15

Cys Arg Gln Arg
            20

<210> SEQ ID NO 55
<211> LENGTH: 19
<212> TYPE: PRT
<213> ORGANISM: Conus betulinus
<220> FEATURE:
<221> NAME/KEY: SITE
<222> LOCATION: (7)..(15)
<223> OTHER INFORMATION: Xaa at residues 7, 11 and 14 is Tyr, nor-Tyr,
      mono-halo-Tyr, di-halo-Tyr, O-sulpho-Tyr,
      O-phospho-Tyr; Xaa at residues 8, 9 and 15 is Pro
```

```
          or hydroxy-Pro.
<220> FEATURE:
<221> NAME/KEY: SITE
<222> LOCATION: (12)..(16)
<223> OTHER INFORMATION: Xaa at residues 12 and 16 is Glu or
      gamma-carboxy-Glu.

<400> SEQUENCE: 55

Ser Ala Thr Cys Cys Asn Xaa Xaa Xaa Cys Xaa Xaa Thr Xaa Xaa Xaa
 1               5                  10                  15

Ser Cys Leu

<210> SEQ ID NO 56
<211> LENGTH: 17
<212> TYPE: PRT
<213> ORGANISM: Conus betulinus
<220> FEATURE:
<221> NAME/KEY: SITE
<222> LOCATION: (5)..(13)
<223> OTHER INFORMATION: Xaa at residues 5 and 12 is Tyr, nor-Tyr,
      mono-halo-Tyr, di-halo-Tyr, O-sulpho-Tyr,
      O-phospho-Tyr or nitro-Tyr; Xaa at residues 6, 7
      and 13 is Pro or hydroxy-Pro.
<220> FEATURE:
<221> NAME/KEY: SITE
<222> LOCATION: (10)..(14)
<223> OTHER INFORMATION: Xaa at residues 10 and 14 is Glu or
      gamma-carboxy-Glu.

<400> SEQUENCE: 56

Ala Cys Cys Ala Xaa Xaa Xaa Cys Phe Xaa Ala Xaa Xaa Xaa Arg Cys
 1               5                  10                  15

Leu

<210> SEQ ID NO 57
<211> LENGTH: 19
<212> TYPE: PRT
<213> ORGANISM: Conus betulinus
<220> FEATURE:
<221> NAME/KEY: SITE
<222> LOCATION: (3)..(16)
<223> OTHER INFORMATION: Xaa at residues 3, 12 and 16 is Glu or
      gamma-carboxy-Glu; Xaa at residues 6, 7, 11 and 14
      is Tyr, nor-Tyr, mono-halo-Tyr, di-halo-Tyr,
      O-sulpho-Tyr, O-phospho-Tyr or nitro-Tyr.
<220> FEATURE:
<221> NAME/KEY: SITE
<222> LOCATION: (8)..(15)
<223> OTHER INFORMATION: Xaa at residues 8, 9 and 15 is Pro or
      hydroxy-Pro.

<400> SEQUENCE: 57

Asn Ala Xaa Cys Cys Xaa Xaa Xaa Xaa Cys Xaa Xaa Ala Xaa Xaa Xaa
 1               5                  10                  15

Ile Cys Leu

<210> SEQ ID NO 58
<211> LENGTH: 227
<212> TYPE: DNA
<213> ORGANISM: Conus magus
<220> FEATURE:
<221> NAME/KEY: CDS
<222> LOCATION: (1)..(189)

<400> SEQUENCE: 58 atg ttc acc gtg ttt ctg ttg gtt gtc ttg gca acc act gtc gtt tcc      48
Met Phe Thr Val Phe Leu Leu Val Val Leu Ala Thr Thr Val Val Ser
 1               5                  10                  15
```

```
ttc cct tca gat cgt gca tct gat ggc agg aat gcc gca gcc aac gac      96
Phe Pro Ser Asp Arg Ala Ser Asp Gly Arg Asn Ala Ala Ala Asn Asp
             20                  25                  30 aaa gcg tct gac gtg atc acg ctg gcc ctc aag gga tgc tgt tcc aac     144
Lys Ala Ser Asp Val Ile Thr Leu Ala Leu Lys Gly Cys Cys Ser Asn
         35                  40                  45 cct gtc tgt cac ttg gag cat tca aac ctt tgt ggt aga aga cgc         189
Pro Val Cys His Leu Glu His Ser Asn Leu Cys Gly Arg Arg Arg
     50                  55                  60 tgatgctcca ggaccctctg aaccacgacg ttcgagca                            227

<210> SEQ ID NO 59
<211> LENGTH: 63
<212> TYPE: PRT
<213> ORGANISM: Conus magus

<400> SEQUENCE: 59

Met Phe Thr Val Phe Leu Leu Val Val Leu Ala Thr Thr Val Val Ser
 1               5                  10                  15

Phe Pro Ser Asp Arg Ala Ser Asp Gly Arg Asn Ala Ala Ala Asn Asp
             20                  25                  30

Lys Ala Ser Asp Val Ile Thr Leu Ala Leu Lys Gly Cys Cys Ser Asn
         35                  40                  45

Pro Val Cys His Leu Glu His Ser Asn Leu Cys Gly Arg Arg Arg
     50                  55                  60

<210> SEQ ID NO 60
<211> LENGTH: 208
<212> TYPE: DNA
<213> ORGANISM: Conus aulicus
<220> FEATURE:
<221> NAME/KEY: CDS
<222> LOCATION: (1)..(168)

<400> SEQUENCE: 60 atg ttc acc gtg ttt ctg ttg gtt gtc ttg gca acc acc gtc gtt tcc     48
Met Phe Thr Val Phe Leu Leu Val Val Leu Ala Thr Thr Val Val Ser
 1               5                  10                  15 ttc act tca gat cgt gca tct gat ggc agg aag gac gca gcg tct ggc     96
Phe Thr Ser Asp Arg Ala Ser Asp Gly Arg Lys Asp Ala Ala Ser Gly
             20                  25                  30 ctg atc gct ctg acc atc aag gga tgc tgt tct tat cct ccc tgt ttc    144
Leu Ile Ala Leu Thr Ile Lys Gly Cys Cys Ser Tyr Pro Pro Cys Phe
         35                  40                  45 gcg act aat tca gac tat tgt ggt tgacgacgct gatgctccag gaccctctga   198
Ala Thr Asn Ser Asp Tyr Cys Gly
     50                  55 accacgacgt                                                          208

<210> SEQ ID NO 61
<211> LENGTH: 56
<212> TYPE: PRT
<213> ORGANISM: Conus aulicus

<400> SEQUENCE: 61

Met Phe Thr Val Phe Leu Leu Val Val Leu Ala Thr Thr Val Val Ser
 1               5                  10                  15

Phe Thr Ser Asp Arg Ala Ser Asp Gly Arg Lys Asp Ala Ala Ser Gly
             20                  25                  30

Leu Ile Ala Leu Thr Ile Lys Gly Cys Cys Ser Tyr Pro Pro Cys Phe
         35                  40                  45
```

```
Ala Thr Asn Ser Asp Tyr Cys Gly
    50                  55

<210> SEQ ID NO 62
<211> LENGTH: 205
<212> TYPE: DNA
<213> ORGANISM: Conus aulicus
<220> FEATURE:
<221> NAME/KEY: CDS
<222> LOCATION: (1)..(174)

<400> SEQUENCE: 62 atg ttc acc gtg ttt ctg ttg gtc gtc ttg gca acc acc gtc gtt tcc      48
Met Phe Thr Val Phe Leu Leu Val Val Leu Ala Thr Thr Val Val Ser
1               5                   10                  15 ttc act tca gat cgt gca tct gat ggc agg aag gac gca gcg tct ggc      96
Phe Thr Ser Asp Arg Ala Ser Asp Gly Arg Lys Asp Ala Ala Ser Gly
                20                  25                  30 ctg att gct ctg acc atg aag gga tgc tgt tct tat cct ccc tgt ttc     144
Leu Ile Ala Leu Thr Met Lys Gly Cys Cys Ser Tyr Pro Pro Cys Phe
            35                  40                  45 gcg act aat cca gac tgt ggt cga cga cgc tgatgctcca ggaccctctg       194
Ala Thr Asn Pro Asp Cys Gly Arg Arg Arg
        50                  55 aaccacgacg t                                                         205

<210> SEQ ID NO 63
<211> LENGTH: 58
<212> TYPE: PRT
<213> ORGANISM: Conus aulicus

<400> SEQUENCE: 63

Met Phe Thr Val Phe Leu Leu Val Val Leu Ala Thr Thr Val Val Ser
1               5                   10                  15

Phe Thr Ser Asp Arg Ala Ser Asp Gly Arg Lys Asp Ala Ala Ser Gly
                20                  25                  30

Leu Ile Ala Leu Thr Met Lys Gly Cys Cys Ser Tyr Pro Pro Cys Phe
            35                  40                  45

Ala Thr Asn Pro Asp Cys Gly Arg Arg Arg
        50                  55

<210> SEQ ID NO 64
<211> LENGTH: 223
<212> TYPE: DNA
<213> ORGANISM: Conus textile
<220> FEATURE:
<221> NAME/KEY: CDS
<222> LOCATION: (1)..(192)

<400> SEQUENCE: 64 atg ttc acc gtg ttt ctg ttg gtt gtc ttg gca acc acc gtc gtt tcc      48
Met Phe Thr Val Phe Leu Leu Val Val Leu Ala Thr Thr Val Val Ser
1               5                   10                  15 ttc tct tca ggt cgt agt aca ttt cgt ggc agg aat gcc gca gcc aaa      96
Phe Ser Ser Gly Arg Ser Thr Phe Arg Gly Arg Asn Ala Ala Ala Lys
                20                  25                  30 gcg tct ggc ctg gtc agt ctg act gac agg aga cca gaa tgc tgt agt     144
Ala Ser Gly Leu Val Ser Leu Thr Asp Arg Arg Pro Glu Cys Cys Ser
            35                  40                  45 gat cct cgc tgt aac tcg agt cat cca gaa ctt tgt ggt gga aga cgc     192
Asp Pro Arg Cys Asn Ser Ser His Pro Glu Leu Cys Gly Gly Arg Arg
        50                  55                  60
```

```
<210> SEQ ID NO 65
<211> LENGTH: 64
<212> TYPE: PRT
<213> ORGANISM: Conus textile

<400> SEQUENCE: 65

Met Phe Thr Val Phe Leu Leu Val Val Leu Ala Thr Thr Val Val Ser
 1               5                  10                  15

Phe Ser Ser Gly Arg Ser Thr Phe Arg Gly Arg Asn Ala Ala Ala Lys
            20                  25                  30

Ala Ser Gly Leu Val Ser Leu Thr Asp Arg Arg Pro Glu Cys Cys Ser
        35                  40                  45

Asp Pro Arg Cys Asn Ser Ser His Pro Glu Leu Cys Gly Gly Arg Arg
    50                  55                  60

<210> SEQ ID NO 66
<211> LENGTH: 244
<212> TYPE: DNA
<213> ORGANISM: Conus textile
<220> FEATURE:
<221> NAME/KEY: CDS
<222> LOCATION: (1)..(168)

<400> SEQUENCE: 66 atg ttc acc gtg ttt ctg ttg gtt gtc ttg gca acc gcc gtc gtt tcc      48
Met Phe Thr Val Phe Leu Leu Val Val Leu Ala Thr Ala Val Val Ser
 1               5                  10                  15 ttc act tca gat cgt gca tct gat gac ggg aaa gcc gct gcg tct gac      96
Phe Thr Ser Asp Arg Ala Ser Asp Asp Gly Lys Ala Ala Ala Ser Asp
            20                  25                  30 ctg atc act ctg acc atc aag gga tgc tgt tct cgt cct ccc tgt atc     144
Leu Ile Thr Leu Thr Ile Lys Gly Cys Cys Ser Arg Pro Pro Cys Ile
        35                  40                  45 gcg aat aat cca gac ttg tgt ggt tgacgacgct gatgctccag aacggtctga    198
Ala Asn Asn Pro Asp Leu Cys Gly
    50                  55 accacgacgt tcgagcaatg ttcaccgtgt ttctgttggt tgtctt                   244

<210> SEQ ID NO 67
<211> LENGTH: 56
<212> TYPE: PRT
<213> ORGANISM: Conus textile

<400> SEQUENCE: 67

Met Phe Thr Val Phe Leu Leu Val Val Leu Ala Thr Ala Val Val Ser
 1               5                  10                  15

Phe Thr Ser Asp Arg Ala Ser Asp Asp Gly Lys Ala Ala Ala Ser Asp
            20                  25                  30

Leu Ile Thr Leu Thr Ile Lys Gly Cys Cys Ser Arg Pro Pro Cys Ile
        35                  40                  45

Ala Asn Asn Pro Asp Leu Cys Gly
    50                  55

<210> SEQ ID NO 68
<211> LENGTH: 223
<212> TYPE: DNA
<213> ORGANISM: Conus textile
<220> FEATURE:
<221> NAME/KEY: CDS
```
tgatgctcca ggaccctctg aaccacgacg t                                   223

-continued

```
<222> LOCATION: (1)..(183)

<400> SEQUENCE: 68 atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc act tca ggt cgt agt aca ttt cgt ggc agg aat gcc gca gcc aaa      96
Phe Thr Ser Gly Arg Ser Thr Phe Arg Gly Arg Asn Ala Ala Ala Lys
             20                  25                  30 gcg tct ggc ctg gtc agt ctg act gac agg aga cca caa tgc tgt tct     144
Ala Ser Gly Leu Val Ser Leu Thr Asp Arg Arg Pro Gln Cys Cys Ser
         35                  40                  45 cat cct gcc tgt aac gta gat cat cca gaa att tgt cgt tgaagacgct      193
His Pro Ala Cys Asn Val Asp His Pro Glu Ile Cys Arg
     50                  55                  60 gatgctccag gaccctctga accacgacgt                                    223

<210> SEQ ID NO 69
<211> LENGTH: 61
<212> TYPE: PRT
<213> ORGANISM: Conus textile

<400> SEQUENCE: 69

Met Phe Thr Val Phe Leu Leu Val Val Leu Ala Thr Thr Val Val Ser
 1               5                  10                  15

Phe Thr Ser Gly Arg Ser Thr Phe Arg Gly Arg Asn Ala Ala Ala Lys
             20                  25                  30

Ala Ser Gly Leu Val Ser Leu Thr Asp Arg Arg Pro Gln Cys Cys Ser
         35                  40                  45

His Pro Ala Cys Asn Val Asp His Pro Glu Ile Cys Arg
     50                  55                  60

<210> SEQ ID NO 70
<211> LENGTH: 223
<212> TYPE: DNA
<213> ORGANISM: Conus radiatus
<220> FEATURE:
<221> NAME/KEY: CDS
<222> LOCATION: (1)..(183)

<400> SEQUENCE: 70 atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc act tca ggt cgt cgt aca ttt cat ggc agg aat gcc gca gcc aaa      96
Phe Thr Ser Gly Arg Arg Thr Phe His Gly Arg Asn Ala Ala Ala Lys
             20                  25                  30 gcg tct ggc ctg gtc agt ctg act gac agg aga cca gaa tgc tgt tct     144
Ala Ser Gly Leu Val Ser Leu Thr Asp Arg Arg Pro Glu Cys Cys Ser
         35                  40                  45 cat cct gcc tgt aac gta gat cat cca gaa att tgt cgt tgaagacgct      193
His Pro Ala Cys Asn Val Asp His Pro Glu Ile Cys Arg
     50                  55                  60 gatgctccag gaccctctga accacgacgt                                    223

<210> SEQ ID NO 71
<211> LENGTH: 61
<212> TYPE: PRT
<213> ORGANISM: Conus radiatus

<400> SEQUENCE: 71
```

```
Met Phe Thr Val Phe Leu Leu Val Val Leu Ala Thr Thr Val Val Ser
  1               5                  10                  15

Phe Thr Ser Gly Arg Arg Thr Phe His Gly Arg Asn Ala Ala Ala Lys
             20                  25                  30

Ala Ser Gly Leu Val Ser Leu Thr Asp Arg Arg Pro Glu Cys Cys Ser
         35                  40                  45

His Pro Ala Cys Asn Val Asp His Pro Glu Ile Cys Arg
     50                  55                  60
```

<210> SEQ ID NO 72
<211> LENGTH: 223
<212> TYPE: DNA
<213> ORGANISM: Conus radiatus
<220> FEATURE:
<221> NAME/KEY: CDS
<222> LOCATION: (1)..(183)

<400> SEQUENCE: 72

```
atg ttc acc gtg ttt ctg ttg gtt gtc ttg gca acc acc gtc gtt tcc         48
Met Phe Thr Val Phe Leu Leu Val Val Leu Ala Thr Thr Val Val Ser
  1               5                  10                  15 ttc act tca ggt cgt agt aca ttt cgt ggc agg aat gcc gca gcc aaa         96
Phe Thr Ser Gly Arg Ser Thr Phe Arg Gly Arg Asn Ala Ala Ala Lys
             20                  25                  30 gcg tct ggc ctg gtc agt ctg act gac agg aga cca caa tgc tgt tct        144
Ala Ser Gly Leu Val Ser Leu Thr Asp Arg Arg Pro Gln Cys Cys Ser
         35                  40                  45 cat cct gcc tgt aac gta gat cat cca gaa att tgc gat tgaagacgct        193
His Pro Ala Cys Asn Val Asp His Pro Glu Ile Cys Asp
     50                  55                  60 gatgctccag gaccctctga accacgacgt                                        223
```

<210> SEQ ID NO 73
<211> LENGTH: 61
<212> TYPE: PRT
<213> ORGANISM: Conus radiatus

<400> SEQUENCE: 73

```
Met Phe Thr Val Phe Leu Leu Val Val Leu Ala Thr Thr Val Val Ser
  1               5                  10                  15

Phe Thr Ser Gly Arg Ser Thr Phe Arg Gly Arg Asn Ala Ala Ala Lys
             20                  25                  30

Ala Ser Gly Leu Val Ser Leu Thr Asp Arg Arg Pro Gln Cys Cys Ser
         35                  40                  45

His Pro Ala Cys Asn Val Asp His Pro Glu Ile Cys Asp
     50                  55                  60
```

<210> SEQ ID NO 74
<211> LENGTH: 218
<212> TYPE: DNA
<213> ORGANISM: Conus striatus
<220> FEATURE:
<221> NAME/KEY: CDS
<222> LOCATION: (1)..(171)

<400> SEQUENCE: 74

```
atg ttc act gtg ttt ctg ttg gtt gtc ttg gca atc act gtc gtt tcc         48
Met Phe Thr Val Phe Leu Leu Val Val Leu Ala Ile Thr Val Val Ser
  1               5                  10                  15 ttc cct tta gat cgt gaa tct gat ggc gcg aat gcc gaa gcc cgc acc         96
Phe Pro Leu Asp Arg Glu Ser Asp Gly Ala Asn Ala Glu Ala Arg Thr
             20                  25                  30
```

```
cac gat cat gag aag cac gca ctg gac cgg aat gga tgc tgt agg aat        144
His Asp His Glu Lys His Ala Leu Asp Arg Asn Gly Cys Cys Arg Asn
         35                  40                  45 cct gcc tgt gag agc cac aga tgt ggt tgacgacgct gatgctccag              191
Pro Ala Cys Glu Ser His Arg Cys Gly
 50                  55 gaccctctga accacgacgt tcgagca                                          218
```

<210> SEQ ID NO 75
<211> LENGTH: 57
<212> TYPE: PRT
<213> ORGANISM: Conus striatus

<400> SEQUENCE: 75

```
Met Phe Thr Val Phe Leu Leu Val Val Leu Ala Ile Thr Val Val Ser
  1               5                  10                  15

Phe Pro Leu Asp Arg Glu Ser Asp Gly Ala Asn Ala Glu Ala Arg Thr
                 20                  25                  30

His Asp His Glu Lys His Ala Leu Asp Arg Asn Gly Cys Cys Arg Asn
         35                  40                  45

Pro Ala Cys Glu Ser His Arg Cys Gly
 50                  55
```

<210> SEQ ID NO 76
<211> LENGTH: 227
<212> TYPE: DNA
<213> ORGANISM: Conus bandanus
<220> FEATURE:
<221> NAME/KEY: CDS
<222> LOCATION: (1)..(180)

<400> SEQUENCE: 76

```
atg ttc acc atg ttt ctg ttg gtt gtc ttg gca acc act gtc gtt tcc        48
Met Phe Thr Met Phe Leu Leu Val Val Leu Ala Thr Thr Val Val Ser
  1               5                  10                  15 ttc gct tca gat cgt gca tct gat ggc agg aat gcc gca gcc aag gac        96
Phe Ala Ser Asp Arg Ala Ser Asp Gly Arg Asn Ala Ala Ala Lys Asp
                 20                  25                  30 aaa gcg tct gac ctg gtc gct ctg acc gtc aag gga tgc tgt tct cat       144
Lys Ala Ser Asp Leu Val Ala Leu Thr Val Lys Gly Cys Cys Ser His
         35                  40                  45 cct gcc tgt agc gtg aat aat cca gac att tgt ggt tgaagacgct            190
Pro Ala Cys Ser Val Asn Asn Pro Asp Ile Cys Gly
 50                  55                  60 gatgctccag gaccctctga accacgacgt tcgagca                              227
```

<210> SEQ ID NO 77
<211> LENGTH: 60
<212> TYPE: PRT
<213> ORGANISM: Conus bandanus

<400> SEQUENCE: 77

```
Met Phe Thr Met Phe Leu Leu Val Val Leu Ala Thr Thr Val Val Ser
  1               5                  10                  15

Phe Ala Ser Asp Arg Ala Ser Asp Gly Arg Asn Ala Ala Ala Lys Asp
                 20                  25                  30

Lys Ala Ser Asp Leu Val Ala Leu Thr Val Lys Gly Cys Cys Ser His
         35                  40                  45

Pro Ala Cys Ser Val Asn Asn Pro Asp Ile Cys Gly
 50                  55                  60
```

<210> SEQ ID NO 78
<211> LENGTH: 104
<212> TYPE: DNA
<213> ORGANISM: Conus bandanus
<220> FEATURE:
<221> NAME/KEY: CDS
<222> LOCATION: (1)..(54)

<400> SEQUENCE: 78

```
aaa gaa tgc tgt act cat cct gcc tgt cac gtg agt cat cca gaa ctc        48
Lys Glu Cys Cys Thr His Pro Ala Cys His Val Ser His Pro Glu Leu
  1               5                  10                  15 tgt ggt tgaaaagcga cgtgacgctc caggaccctc tgaaccacga cgttcgagca        104
Cys Gly
```

<210> SEQ ID NO 79
<211> LENGTH: 18
<212> TYPE: PRT
<213> ORGANISM: Conus bandanus

<400> SEQUENCE: 79

Lys Glu Cys Cys Thr His Pro Ala Cys His Val Ser His Pro Glu Leu
  1               5                  10                  15

Cys Gly

<210> SEQ ID NO 80
<211> LENGTH: 206
<212> TYPE: DNA
<213> ORGANISM: Conus bandanus
<220> FEATURE:
<221> NAME/KEY: CDS
<222> LOCATION: (1)..(171)

<400> SEQUENCE: 80

```
atg ttc acc gtg ttt ctg ttg gtt gtc ttg gca act gct gtt ctt cca        48
Met Phe Thr Val Phe Leu Leu Val Val Leu Ala Thr Ala Val Leu Pro
  1               5                  10                  15 gtc act tta gat cgt gca tct gat gga agg aat gca gca gcc aac gcc        96
Val Thr Leu Asp Arg Ala Ser Asp Gly Arg Asn Ala Ala Ala Asn Ala
                 20                  25                  30 aaa acg cct cgc ctg atc gcg cca ttc atc agg gat tat tgc tgt cat       144
Lys Thr Pro Arg Leu Ile Ala Pro Phe Ile Arg Asp Tyr Cys Cys His
             35                  40                  45 aga ggt ccc tgt atg gta tgg tgt ggt tgaagccgct gctgctccag            191
Arg Gly Pro Cys Met Val Trp Cys Gly
         50                  55 gaccctctga accac                                                      206
```

<210> SEQ ID NO 81
<211> LENGTH: 57
<212> TYPE: PRT
<213> ORGANISM: Conus bandanus

<400> SEQUENCE: 81

Met Phe Thr Val Phe Leu Leu Val Val Leu Ala Thr Ala Val Leu Pro
  1               5                  10                  15

Val Thr Leu Asp Arg Ala Ser Asp Gly Arg Asn Ala Ala Ala Asn Ala
                 20                  25                  30

Lys Thr Pro Arg Leu Ile Ala Pro Phe Ile Arg Asp Tyr Cys Cys His
             35                  40                  45

Arg Gly Pro Cys Met Val Trp Cys Gly

<210> SEQ ID NO 82
<211> LENGTH: 174
<212> TYPE: DNA
<213> ORGANISM: Conus caracteristicus
<220> FEATURE:
<221> NAME/KEY: CDS
<222> LOCATION: (1)..(171)

<400> SEQUENCE: 82

```
atg ttc acc gtg ttt ctg ttg gtt gtc ttg gca acc act gtg gtt tcc      48
Met Phe Thr Val Phe Leu Leu Val Val Leu Ala Thr Thr Val Val Ser
  1               5                  10                  15 ttc act tca gat cgt gct tct gat ggc agg aat gcc gca gcc aac gcg      96
Phe Thr Ser Asp Arg Ala Ser Asp Gly Arg Asn Ala Ala Ala Asn Ala
             20                  25                  30 ttt gac ctg atc gct ctg atc gcc agg caa aat tgc tgt agc att ccc     144
Phe Asp Leu Ile Ala Leu Ile Ala Arg Gln Asn Cys Cys Ser Ile Pro
         35                  40                  45 agc tgt tgg gag aaa tat aaa tgt agt taa                             174
Ser Cys Trp Glu Lys Tyr Lys Cys Ser
     50                  55
```

<210> SEQ ID NO 83
<211> LENGTH: 57
<212> TYPE: PRT
<213> ORGANISM: Conus caracteristicus

<400> SEQUENCE: 83

```
Met Phe Thr Val Phe Leu Leu Val Val Leu Ala Thr Thr Val Val Ser
  1               5                  10                  15

Phe Thr Ser Asp Arg Ala Ser Asp Gly Arg Asn Ala Ala Ala Asn Ala
             20                  25                  30

Phe Asp Leu Ile Ala Leu Ile Ala Arg Gln Asn Cys Cys Ser Ile Pro
         35                  40                  45

Ser Cys Trp Glu Lys Tyr Lys Cys Ser
     50                  55
```

<210> SEQ ID NO 84
<211> LENGTH: 219
<212> TYPE: DNA
<213> ORGANISM: Conus caracteristicus
<220> FEATURE:
<221> NAME/KEY: CDS
<222> LOCATION: (1)..(189)

<400> SEQUENCE: 84

```
atg ttc acc gtg ttt ctg ttg gtt gtc ttg gca acc act gtg gtt tcc      48
Met Phe Thr Val Phe Leu Leu Val Val Leu Ala Thr Thr Val Val Ser
  1               5                  10                  15 ttc act tca gat cgt gcg tct gaa ggc agg aat gct gca gcc aag gac      96
Phe Thr Ser Asp Arg Ala Ser Glu Gly Arg Asn Ala Ala Ala Lys Asp
             20                  25                  30 aaa gcg tct gac ctg gtg gct ctg aca gtc agg gga tgc tgt gcc att     144
Lys Ala Ser Asp Leu Val Ala Leu Thr Val Arg Gly Cys Cys Ala Ile
         35                  40                  45 cgt gaa tgt cgc ttg cag aat gca gcg tat tgt ggt gga ata tac         189
Arg Glu Cys Arg Leu Gln Asn Ala Ala Tyr Cys Gly Gly Ile Tyr
     50                  55                  60 tgatgctcca ggaccctctg aaccacgacg                                    219
```

```
<210> SEQ ID NO 85
<211> LENGTH: 63
<212> TYPE: PRT
<213> ORGANISM: Conus caracteristicus

<400> SEQUENCE: 85

Met Phe Thr Val Phe Leu Leu Val Val Leu Ala Thr Thr Val Val Ser
 1               5                  10                  15

Phe Thr Ser Asp Arg Ala Ser Glu Gly Arg Asn Ala Ala Ala Lys Asp
             20                  25                  30

Lys Ala Ser Asp Leu Val Ala Leu Thr Val Arg Gly Cys Cys Ala Ile
         35                  40                  45

Arg Glu Cys Arg Leu Gln Asn Ala Ala Tyr Cys Gly Ile Tyr
     50                  55                  60

<210> SEQ ID NO 86
<211> LENGTH: 217
<212> TYPE: DNA
<213> ORGANISM: Conus tulipa
<220> FEATURE:
<221> NAME/KEY: CDS
<222> LOCATION: (1)..(186)

<400> SEQUENCE: 86 atg ttc acc gtg ttt ctg ttg gtt gtc ttg gca acc act gtc gtt tcc      48
Met Phe Thr Val Phe Leu Leu Val Val Leu Ala Thr Thr Val Val Ser
 1               5                  10                  15 ttc cct tca gat att gca act gag ggc agg aat gcc gca gcc aaa gcg      96
Phe Pro Ser Asp Ile Ala Thr Glu Gly Arg Asn Ala Ala Ala Lys Ala
             20                  25                  30 ttt gac ctg ata tct tcg atc gtc aag aaa gga tgc tgt tcc cat cct     144
Phe Asp Leu Ile Ser Ser Ile Val Lys Lys Gly Cys Cys Ser His Pro
         35                  40                  45 gcc tgt tcg ggg aat aat cca gaa ttt tgt cgt caa ggt cgc              186
Ala Cys Ser Gly Asn Asn Pro Glu Phe Cys Arg Gln Gly Arg
     50                  55                  60 tgatgctcca ggaccctctg aaccacgacg t                                   217

<210> SEQ ID NO 87
<211> LENGTH: 62
<212> TYPE: PRT
<213> ORGANISM: Conus tulipa

<400> SEQUENCE: 87

Met Phe Thr Val Phe Leu Leu Val Val Leu Ala Thr Thr Val Val Ser
 1               5                  10                  15

Phe Pro Ser Asp Ile Ala Thr Glu Gly Arg Asn Ala Ala Ala Lys Ala
             20                  25                  30

Phe Asp Leu Ile Ser Ser Ile Val Lys Lys Gly Cys Cys Ser His Pro
         35                  40                  45

Ala Cys Ser Gly Asn Asn Pro Glu Phe Cys Arg Gln Gly Arg
     50                  55                  60

<210> SEQ ID NO 88
<211> LENGTH: 217
<212> TYPE: DNA
<213> ORGANISM: Conus tulipa
<220> FEATURE:
<221> NAME/KEY: CDS
<222> LOCATION: (1)..(186)

<400> SEQUENCE: 88
```

```
atg ttc acc gtg ttt ctg ttg gtt gtc ttg gca acc act gtc gtt tcc      48
Met Phe Thr Val Phe Leu Leu Val Val Leu Ala Thr Thr Val Val Ser
1               5                   10                  15 ttc cct tca gat ata gca act gag ggc agg aat gcc gca gcc aaa gcg      96
Phe Pro Ser Asp Ile Ala Thr Glu Gly Arg Asn Ala Ala Ala Lys Ala
            20                  25                  30 ttt gac ctg ata tct tcg atc gtc agg aaa gga tgc tgt tcc aat ccc     144
Phe Asp Leu Ile Ser Ser Ile Val Arg Lys Gly Cys Cys Ser Asn Pro
        35                  40                  45 gcc tgt gcg ggg aat aat cca cat gtt tgt cgt caa ggt cgc             186
Ala Cys Ala Gly Asn Asn Pro His Val Cys Arg Gln Gly Arg
    50                  55                  60 tgatgctcca ggaccctctg aaccacgacg t                                  217
```

<210> SEQ ID NO 89
<211> LENGTH: 62
<212> TYPE: PRT
<213> ORGANISM: Conus tulipa

<400> SEQUENCE: 89

```
Met Phe Thr Val Phe Leu Leu Val Val Leu Ala Thr Thr Val Val Ser
1               5                   10                  15

Phe Pro Ser Asp Ile Ala Thr Glu Gly Arg Asn Ala Ala Ala Lys Ala
            20                  25                  30

Phe Asp Leu Ile Ser Ser Ile Val Arg Lys Gly Cys Cys Ser Asn Pro
        35                  40                  45

Ala Cys Ala Gly Asn Asn Pro His Val Cys Arg Gln Gly Arg
    50                  55                  60
```

<210> SEQ ID NO 90
<211> LENGTH: 226
<212> TYPE: DNA
<213> ORGANISM: Conus sulcatus
<220> FEATURE:
<221> NAME/KEY: CDS
<222> LOCATION: (1)..(195)

<400> SEQUENCE: 90

```
atg ttc acc gtg ttt ctg ttg gtt gtc ttg gca acc acc gtc gtt tcc      48
Met Phe Thr Val Phe Leu Leu Val Val Leu Ala Thr Thr Val Val Ser
1               5                   10                  15 ttc aat tca gat cgt gat cca gca tta ggt ggc agg aat gct gca gcc      96
Phe Asn Ser Asp Arg Asp Pro Ala Leu Gly Gly Arg Asn Ala Ala Ala
            20                  25                  30 aaa gcg tct gac aag atc gct tcg acc ctc aag aga aga gga tgc tgt    144
Lys Ala Ser Asp Lys Ile Ala Ser Thr Leu Lys Arg Arg Gly Cys Cys
        35                  40                  45 tcg tat ttt gac tgt aga atg atg ttt cca gaa atg tgt ggt tgg cga    192
Ser Tyr Phe Asp Cys Arg Met Met Phe Pro Glu Met Cys Gly Trp Arg
    50                  55                  60 ggc tgatgctcca ggaccctctg aaccacgacg t                              226
Gly
65
```

<210> SEQ ID NO 91
<211> LENGTH: 65
<212> TYPE: PRT
<213> ORGANISM: Conus sulcatus

<400> SEQUENCE: 91

```
Met Phe Thr Val Phe Leu Leu Val Val Leu Ala Thr Thr Val Val Ser
1               5                   10                  15
```

```
Phe Asn Ser Asp Arg Asp Pro Ala Leu Gly Gly Arg Asn Ala Ala Ala
             20                  25                  30

Lys Ala Ser Asp Lys Ile Ala Ser Thr Leu Lys Arg Arg Gly Cys Cys
         35                  40                  45

Ser Tyr Phe Asp Cys Arg Met Met Phe Pro Glu Met Cys Gly Trp Arg
 50                  55                  60

Gly
 65
```

```
<210> SEQ ID NO 92
<211> LENGTH: 226
<212> TYPE: DNA
<213> ORGANISM: Conus sulcatus
<220> FEATURE:
<221> NAME/KEY: CDS
<222> LOCATION: (1)..(195)

<400> SEQUENCE: 92
```

```
atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc aat tca gat cgt gat cca gca tta ggt ggc agg aat gct gca gcc      96
Phe Asn Ser Asp Arg Asp Pro Ala Leu Gly Gly Arg Asn Ala Ala Ala
             20                  25                  30 ata gcg tct gac aag atc gct tcg acc ctc agg aga gga gga tgc tgt     144
Ile Ala Ser Asp Lys Ile Ala Ser Thr Leu Arg Arg Gly Gly Cys Cys
         35                  40                  45 tct ttt cct gcc tgt aga aag tat cgt cca gaa atg tgt ggt gga cga     192
Ser Phe Pro Ala Cys Arg Lys Tyr Arg Pro Glu Met Cys Gly Gly Arg
 50                  55                  60 cgc tgatgctcca ggaccctctg aaccacgacg t                              226
Arg
 65
```

```
<210> SEQ ID NO 93
<211> LENGTH: 65
<212> TYPE: PRT
<213> ORGANISM: Conus sulcatus

<400> SEQUENCE: 93
```

```
Met Phe Thr Val Phe Leu Leu Val Val Leu Ala Thr Thr Val Val Ser
 1               5                  10                  15

Phe Asn Ser Asp Arg Asp Pro Ala Leu Gly Gly Arg Asn Ala Ala Ala
             20                  25                  30

Ile Ala Ser Asp Lys Ile Ala Ser Thr Leu Arg Arg Gly Gly Cys Cys
         35                  40                  45

Ser Phe Pro Ala Cys Arg Lys Tyr Arg Pro Glu Met Cys Gly Gly Arg
 50                  55                  60

Arg
 65
```

```
<210> SEQ ID NO 94
<211> LENGTH: 211
<212> TYPE: DNA
<213> ORGANISM: Conus sulcatus
<220> FEATURE:
<221> NAME/KEY: CDS
<222> LOCATION: (1)..(180)

<400> SEQUENCE: 94
```

```
atg ttc acc gtg ttt ctg ttg gtt gtc ttg gca acc acc gtc gtt tcc      48
```

```
Met Phe Thr Val Phe Leu Leu Val Val Leu Ala Thr Thr Val Val Ser
 1               5                  10                  15 ttc act tca gat cat gaa tct gat cgc ggt gat gcc caa acc atc caa      96
Phe Thr Ser Asp His Glu Ser Asp Arg Gly Asp Ala Gln Thr Ile Gln
                 20                  25                  30 gaa gtg ttt gag atg ttc gct ctg gac agc gat gga tgc tgt tgg cat     144
Glu Val Phe Glu Met Phe Ala Leu Asp Ser Asp Gly Cys Cys Trp His
             35                  40                  45 cct gct tgt ggc aga cac tat tgt ggt cga aga cgc tgatgctcca           190
Pro Ala Cys Gly Arg His Tyr Cys Gly Arg Arg Arg
         50                  55                  60 ggaccctctg aaccacgacg t                                              211

<210> SEQ ID NO 95
<211> LENGTH: 60
<212> TYPE: PRT
<213> ORGANISM: Conus sulcatus

<400> SEQUENCE: 95

Met Phe Thr Val Phe Leu Leu Val Val Leu Ala Thr Thr Val Val Ser
 1               5                  10                  15

Phe Thr Ser Asp His Glu Ser Asp Arg Gly Asp Ala Gln Thr Ile Gln
                 20                  25                  30

Glu Val Phe Glu Met Phe Ala Leu Asp Ser Asp Gly Cys Cys Trp His
             35                  40                  45

Pro Ala Cys Gly Arg His Tyr Cys Gly Arg Arg Arg
         50                  55                  60

<210> SEQ ID NO 96
<211> LENGTH: 202
<212> TYPE: DNA
<213> ORGANISM: Conus sulcatus
<220> FEATURE:
<221> NAME/KEY: CDS
<222> LOCATION: (1)..(195)

<400> SEQUENCE: 96 atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc aat tca gat cgt gat cca gca tta ggt ggc agg aat gct gca gcc      96
Phe Asn Ser Asp Arg Asp Pro Ala Leu Gly Gly Arg Asn Ala Ala Ala
                 20                  25                  30 ata gcg tct gac aag atc gct tcg acc ctc agg aga gga gga tgc tgt     144
Ile Ala Ser Asp Lys Ile Ala Ser Thr Leu Arg Arg Gly Gly Cys Cys
             35                  40                  45 tct ttt gct gcc tgt aga aag tat cgt cca gaa atg tgt ggt gga cga     192
Ser Phe Ala Ala Cys Arg Lys Tyr Arg Pro Glu Met Cys Gly Gly Arg
         50                  55                  60 cgc tgatgct                                                          202
Arg
 65

<210> SEQ ID NO 97
<211> LENGTH: 65
<212> TYPE: PRT
<213> ORGANISM: Conus sulcatus

<400> SEQUENCE: 97

Met Phe Thr Val Phe Leu Leu Val Val Leu Ala Thr Thr Val Val Ser
 1               5                  10                  15
```

-continued

```
Phe Asn Ser Asp Arg Asp Pro Ala Leu Gly Gly Arg Asn Ala Ala Ala
             20                  25                  30

Ile Ala Ser Asp Lys Ile Ala Ser Thr Leu Arg Arg Gly Gly Cys Cys
         35                  40                  45

Ser Phe Ala Ala Cys Arg Lys Tyr Arg Pro Glu Met Cys Gly Gly Arg
     50                  55                  60

Arg
 65
```

<210> SEQ ID NO 98
<211> LENGTH: 220
<212> TYPE: DNA
<213> ORGANISM: Conus sulcatus
<220> FEATURE:
<221> NAME/KEY: CDS
<222> LOCATION: (1)..(189)

<400> SEQUENCE: 98

```
atg ttc acc gtg ttt ctg ttg gtt ctc ttg gca acc acc gtc gtt tcc        48
Met Phe Thr Val Phe Leu Leu Val Leu Leu Ala Thr Thr Val Val Ser
 1               5                  10                  15 ttc aat tca gat cgt gca tta ggt ggc agg aat gct gca gcc aaa gcg        96
Phe Asn Ser Asp Arg Ala Leu Gly Gly Arg Asn Ala Ala Ala Lys Ala
             20                  25                  30 tct gac aag atc ctt tcg aac ctc agg aga gga gga tgc tgt ttt cat       144
Ser Asp Lys Ile Leu Ser Asn Leu Arg Arg Gly Gly Cys Cys Phe His
         35                  40                  45 cct gtc tgt tac atc aat ctt cta gaa atg tgt cgt caa cga ggc           189
Pro Val Cys Tyr Ile Asn Leu Leu Glu Met Cys Arg Gln Arg Gly
     50                  55                  60 tgatcgtcca ggaccctctg aaccacgacg t                                    220
```

<210> SEQ ID NO 99
<211> LENGTH: 63
<212> TYPE: PRT
<213> ORGANISM: Conus sulcatus

<400> SEQUENCE: 99

```
Met Phe Thr Val Phe Leu Leu Val Leu Leu Ala Thr Thr Val Val Ser
 1               5                  10                  15

Phe Asn Ser Asp Arg Ala Leu Gly Gly Arg Asn Ala Ala Ala Lys Ala
             20                  25                  30

Ser Asp Lys Ile Leu Ser Asn Leu Arg Arg Gly Gly Cys Cys Phe His
         35                  40                  45

Pro Val Cys Tyr Ile Asn Leu Leu Glu Met Cys Arg Gln Arg Gly
     50                  55                  60
```

<210> SEQ ID NO 100
<211> LENGTH: 208
<212> TYPE: DNA
<213> ORGANISM: Conus consors
<220> FEATURE:
<221> NAME/KEY: CDS
<222> LOCATION: (1)..(177)

<400> SEQUENCE: 100

```
atg ttc acc gtg ttt ctg ttg gtt gtc ttg aca acc act gtc gtt tcc        48
Met Phe Thr Val Phe Leu Leu Val Val Leu Thr Thr Thr Val Val Ser
 1               5                  10                  15 ttc cct tca gat agt gca tct gat gtc agg gat gac gaa gcc aaa gac        96
Phe Pro Ser Asp Ser Ala Ser Asp Val Arg Asp Asp Glu Ala Lys Asp
             20                  25                  30
```

```
gaa agg tct gac atg tac aaa tcg aaa cgg aat gga cgc tgt tgc cat    144
Glu Arg Ser Asp Met Tyr Lys Ser Lys Arg Asn Gly Arg Cys Cys His
        35                  40                  45 cct gcc tgt ggc aaa cac ttt agt tgt gga cgc tgatgctcca ggaccctctg  197
Pro Ala Cys Gly Lys His Phe Ser Cys Gly Arg
    50                  55 aaccacgacg t                                                        208

<210> SEQ ID NO 101
<211> LENGTH: 59
<212> TYPE: PRT
<213> ORGANISM: Conus consors

<400> SEQUENCE: 101

Met Phe Thr Val Phe Leu Leu Val Val Leu Thr Thr Val Val Ser
 1               5                  10                  15

Phe Pro Ser Asp Ser Ala Ser Asp Val Arg Asp Asp Glu Ala Lys Asp
                20                  25                  30

Glu Arg Ser Asp Met Tyr Lys Ser Lys Arg Asn Gly Arg Cys Cys His
        35                  40                  45

Pro Ala Cys Gly Lys His Phe Ser Cys Gly Arg
    50                  55

<210> SEQ ID NO 102
<211> LENGTH: 219
<212> TYPE: DNA
<213> ORGANISM: Conus stercusmuscarum
<220> FEATURE:
<221> NAME/KEY: CDS
<222> LOCATION: (1)..(189)

<400> SEQUENCE: 102 atg ttc acc gtg ttt ctg ttg gtt gtc ttg gca acc act gtc gtt tcc    48
Met Phe Thr Val Phe Leu Leu Val Val Leu Ala Thr Thr Val Val Ser
 1               5                  10                  15 tcc cct tca gat cgt gca tct gat ggc agg aat gcc gca gcc aac gag    96
Ser Pro Ser Asp Arg Ala Ser Asp Gly Arg Asn Ala Ala Ala Asn Glu
                20                  25                  30 aaa gcg tct gac gtg atc gcg ctg gcc ctc aag gga tgc tgt tcc aac   144
Lys Ala Ser Asp Val Ile Ala Leu Ala Leu Lys Gly Cys Cys Ser Asn
        35                  40                  45 cct gtc tgt cac ctg gag cat tca aac atg tgt ggt aga aga cgc       189
Pro Val Cys His Leu Glu His Ser Asn Met Cys Gly Arg Arg Arg
    50                  55                  60 tgatgctcca ggaccctctg aaccacgacg                                   219

<210> SEQ ID NO 103
<211> LENGTH: 63
<212> TYPE: PRT
<213> ORGANISM: Conus stercusmuscarum

<400> SEQUENCE: 103

Met Phe Thr Val Phe Leu Leu Val Val Leu Ala Thr Thr Val Val Ser
 1               5                  10                  15

Ser Pro Ser Asp Arg Ala Ser Asp Gly Arg Asn Ala Ala Ala Asn Glu
                20                  25                  30

Lys Ala Ser Asp Val Ile Ala Leu Ala Leu Lys Gly Cys Cys Ser Asn
        35                  40                  45

Pro Val Cys His Leu Glu His Ser Asn Met Cys Gly Arg Arg Arg
    50                  55                  60
```

<210> SEQ ID NO 104
<211> LENGTH: 248
<212> TYPE: DNA
<213> ORGANISM: Conus betulinus
<220> FEATURE:
<221> NAME/KEY: CDS
<222> LOCATION: (1)..(180)

<400> SEQUENCE: 104

```
atg ttc tcc gtg ttt ctg ttg gtt gtc ttg gca acc act gtc gtt tcc       48
Met Phe Ser Val Phe Leu Leu Val Val Leu Ala Thr Thr Val Val Ser
  1               5                  10                  15 tcc act tca ggt ggt gca tct ggt ggc agg aag gct gca gcc aaa gcg       96
Ser Thr Ser Gly Gly Ala Ser Gly Gly Arg Lys Ala Ala Ala Lys Ala
             20                  25                  30 tct aac cgg atc gct ctg acc gtc agg agt gca aca tgc tgt aat tat      144
Ser Asn Arg Ile Ala Leu Thr Val Arg Ser Ala Thr Cys Cys Asn Tyr
         35                  40                  45 cct ccc tgt tac gag act tat cca gaa agt tgt ctg taacgtgaat           190
Pro Pro Cys Tyr Glu Thr Tyr Pro Glu Ser Cys Leu
     50                  55                  60 catccagagc tttgtggctg aagacactga tgctccagga ccctctgaac cacgacgt      248
```

<210> SEQ ID NO 105
<211> LENGTH: 60
<212> TYPE: PRT
<213> ORGANISM: Conus betulinus

<400> SEQUENCE: 105

```
Met Phe Ser Val Phe Leu Leu Val Val Leu Ala Thr Thr Val Val Ser
  1               5                  10                  15

Ser Thr Ser Gly Gly Ala Ser Gly Gly Arg Lys Ala Ala Ala Lys Ala
             20                  25                  30

Ser Asn Arg Ile Ala Leu Thr Val Arg Ser Ala Thr Cys Cys Asn Tyr
         35                  40                  45

Pro Pro Cys Tyr Glu Thr Tyr Pro Glu Ser Cys Leu
     50                  55                  60
```

<210> SEQ ID NO 106
<211> LENGTH: 223
<212> TYPE: DNA
<213> ORGANISM: Conus betulinus
<220> FEATURE:
<221> NAME/KEY: CDS
<222> LOCATION: (1)..(183)

<400> SEQUENCE: 106

```
atg ttc acc gtg ttt ctg ttg gtt gtc ttg gca acc act gtg gtt tcc       48
Met Phe Thr Val Phe Leu Leu Val Val Leu Ala Thr Thr Val Val Ser
  1               5                  10                  15 ttc act tca ggt cgt gca ttt cgt ggc agg aat cgc gca gcc gac gac       96
Phe Thr Ser Gly Arg Ala Phe Arg Gly Arg Asn Arg Ala Ala Asp Asp
             20                  25                  30 aaa agg tct gac ctg gcc gct ctg agc gtc agg gga gga tgc tgt tcc      144
Lys Arg Ser Asp Leu Ala Ala Leu Ser Val Arg Gly Gly Cys Cys Ser
         35                  40                  45 cat cct gcc tgt gcg gtg aat cat cca gag ctt tgt ggc tgaagacgct       193
His Pro Ala Cys Ala Val Asn His Pro Glu Leu Cys Gly
     50                  55                  60 gatgccccag gaccctctga accacgacgt                                     223
```

-continued

<210> SEQ ID NO 107
<211> LENGTH: 61
<212> TYPE: PRT
<213> ORGANISM: Conus betulinus

<400> SEQUENCE: 107

Met Phe Thr Val Phe Leu Leu Val Val Leu Ala Thr Thr Val Val Ser
1               5                   10                  15

Phe Thr Ser Gly Arg Ala Phe Arg Gly Arg Asn Arg Ala Ala Asp Asp
            20                  25                  30

Lys Arg Ser Asp Leu Ala Ala Leu Ser Val Arg Gly Gly Cys Cys Ser
        35                  40                  45

His Pro Ala Cys Ala Val Asn His Pro Glu Leu Cys Gly
    50                  55                  60

<210> SEQ ID NO 108
<211> LENGTH: 248
<212> TYPE: DNA
<213> ORGANISM: Conus betulinus
<220> FEATURE:
<221> NAME/KEY: CDS
<222> LOCATION: (1)..(180)

<400> SEQUENCE: 108 atg ttc acc gtg ttt ctg ttg gtt gtc ttg gca acc act gtc gtt tcc      48
Met Phe Thr Val Phe Leu Leu Val Val Leu Ala Thr Thr Val Val Ser
1               5                   10                  15 ttc act tca ggt cgt gca tct ggt ggc agg aat gct gca gcc aaa gcg      96
Phe Thr Ser Gly Arg Ala Ser Gly Gly Arg Asn Ala Ala Ala Lys Ala
            20                  25                  30 tct aac cgg atc gct atg gcc atc agc agt gga gca tgc tgt gca tat     144
Ser Asn Arg Ile Ala Met Ala Ile Ser Ser Gly Ala Cys Cys Ala Tyr
        35                  40                  45 cct ccc tgt ttc gag gct tat cca gaa aga tgt ctg taacgtgaat          190
Pro Pro Cys Phe Glu Ala Tyr Pro Glu Arg Cys Leu
    50                  55                  60 catccagacc tttgtggctg aagacgctga tgccccagga ccctctgaac cacgacgt 248

<210> SEQ ID NO 109
<211> LENGTH: 60
<212> TYPE: PRT
<213> ORGANISM: Conus betulinus

<400> SEQUENCE: 109

Met Phe Thr Val Phe Leu Leu Val Val Leu Ala Thr Thr Val Val Ser
1 5 10 15

Phe Thr Ser Gly Arg Ala Ser Gly Gly Arg Asn Ala Ala Ala Lys Ala
20 25 30

Ser Asn Arg Ile Ala Met Ala Ile Ser Ser Gly Ala Cys Cys Ala Tyr
35 40 45

Pro Pro Cys Phe Glu Ala Tyr Pro Glu Arg Cys Leu
50 55 60

<210> SEQ ID NO 110
<211> LENGTH: 223
<212> TYPE: DNA
<213> ORGANISM: Conus betulinus
<220> FEATURE:
<221> NAME/KEY: CDS
<222> LOCATION: (1)..(192)

<400> SEQUENCE: 110

```
atg ttc acc gtg ttt ctg ttg gtt gtc ttg gca acc act gtc gtt tcc        48
Met Phe Thr Val Phe Leu Leu Val Val Leu Ala Thr Thr Val Val Ser
 1               5                  10                  15 ttc act tca gat cgt gca ttt cgt ggc agg aat tcc gca gcc aac gac        96
Phe Thr Ser Asp Arg Ala Phe Arg Gly Arg Asn Ser Ala Ala Asn Asp
             20                  25                  30 aaa agg tct gac ctg gcc gct ctg agc gtc agg aga gga tgc tgc tcc       144
Lys Arg Ser Asp Leu Ala Ala Leu Ser Val Arg Arg Gly Cys Cys Ser
 35                  40                  45 cat ccc gcc tgt agc gtg aat cat cca gag ctt tgt ggt aga aga cgc       192
His Pro Ala Cys Ser Val Asn His Pro Glu Leu Cys Gly Arg Arg Arg
 50                  55                  60 tgatgcccca ggaccctctg aaccacgacg t                                    223
```

<210> SEQ ID NO 111
<211> LENGTH: 64
<212> TYPE: PRT
<213> ORGANISM: Conus betulinus

<400> SEQUENCE: 111

```
Met Phe Thr Val Phe Leu Leu Val Val Leu Ala Thr Thr Val Val Ser
 1               5                  10                  15

Phe Thr Ser Asp Arg Ala Phe Arg Gly Arg Asn Ser Ala Ala Asn Asp
             20                  25                  30

Lys Arg Ser Asp Leu Ala Ala Leu Ser Val Arg Arg Gly Cys Cys Ser
 35                  40                  45

His Pro Ala C

```
Phe Thr Ser Gly Arg Ala Ser Gly Gly Arg Asn Ala Ala Lys Ala
            20                  25                  30

Ser Asn Arg Ile Ala Leu Ile Val Arg Asn Ala Glu Cys Cys Tyr Tyr
            35                  40                  45

Pro Pro Cys Tyr Glu Ala Tyr Pro Glu Ile Cys Leu
            50                  55                  60

<210> SEQ ID NO 114
<211> LENGTH: 207
<212> TYPE: DNA
<213> ORGANISM: Conus pennaceus
<220> FEATURE:
<221> NAME/KEY: CDS
<222> LOCATION: (1)..(168)

<400> SEQUENCE: 114 atg ttc acc gtg ttt ctg ttg gtt gtc ttg gca acc acc gtc att tcc      48
Met Phe Thr Val Phe Leu Leu Val Val Leu Ala Thr Thr Val Ile Ser
 1               5                  10                  15 ttc act tca gat cgt gca tct gat ggc ggg aat gcc gca gcg tct gac      96
Phe Thr Ser Asp Arg Ala Ser Asp Gly Gly Asn Ala Ala Ala Ser Asp
            20                  25                  30 ctg atc gct ctg acc atc aag gga tgc tgt tct cat cct ccc tgt gcc     144
Leu Ile Ala Leu Thr Ile Lys Gly Cys Cys Ser His Pro Pro Cys Ala
        35                  40                  45 atg aat aat cca gac tat tgt ggt tgacgacgct gatgctccag gaccctctga   198
Met Asn Asn Pro Asp Tyr Cys Gly
        50                  55 accacgacg                                                             207

<210> SEQ ID NO 115
<211> LENGTH: 56
<212> TYPE: PRT
<213> ORGANISM: Conus pennaceus

<400> SEQUENCE: 115

Met Phe Thr Val Phe Leu Leu Val Val Leu Ala Thr Thr Val Ile Ser
 1               5                  10                  15

Phe Thr Ser Asp Arg Ala Ser Asp Gly Gly Asn Ala Ala Ala Ser Asp
            20                  25                  30

Leu Ile Ala Leu Thr Ile Lys Gly Cys Cys Ser His Pro Pro Cys Ala
        35                  40                  45

Met Asn Asn Pro Asp Tyr Cys Gly
        50                  55

<210> SEQ ID NO 116
<211> LENGTH: 207
<212> TYPE: DNA
<213> ORGANISM: Conus pennaceus
<220> FEATURE:
<221> NAME/KEY: CDS
<222> LOCATION: (1)..(168)

<400> SEQUENCE: 116 atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc act tca gat cgt gca tct gat ggc ggg aat gcc gca atg tct gac      96
Phe Thr Ser Asp Arg Ala Ser Asp Gly Gly Asn Ala Ala Met Ser Asp
            20                  25                  30 ctg atc gct ctg acc atc aag gga tgc tgt tct cat cct ccc tgt ttc     144
Leu Ile Ala Leu Thr Ile Lys Gly Cys Cys Ser His Pro Pro Cys Phe
```

```
                35                  40                  45
ctg aat aat cca gac tat tgt ggt tgacgacgct gatgctccag gaccctctga      198
Leu Asn Asn Pro Asp Tyr Cys Gly
        50                  55 accacgacg                                                              207

<210> SEQ ID NO 117
<211> LENGTH: 56
<212> TYPE: PRT
<213> ORGANISM: Conus pennaceus

<400> SEQUENCE: 117

Met Phe Thr Val Phe Leu Leu Val Val Leu Ala Thr Thr Val Val Ser
 1               5                  10                  15

Phe Thr Ser Asp Arg Ala Ser Asp Gly Gly Asn Ala Ala Met Ser Asp
            20                  25                  30

Leu Ile Ala Leu Thr Ile Lys Gly Cys Cys Ser His Pro Pro Cys Phe
        35                  40                  45

Leu Asn Asn Pro Asp Tyr Cys Gly
    50                  55

<210> SEQ ID NO 118
<211> LENGTH: 210
<212> TYPE: DNA
<213> ORGANISM: Conus stercusmuscarum
<220> FEATURE:
<221> NAME/KEY: CDS
<222> LOCATION: (1)..(171)

<400> SEQUENCE: 118 atg ttc acc gtg ttt ctg ttg gtt gtc ttg gca acc act gtc gtt tcc       48
Met Phe Thr Val Phe Leu Leu Val Val Leu Ala Thr Thr Val Val Ser
 1               5                  10                  15 ttc cct tca gat cgt gaa tct gat ggc gcg aat gac gaa gcc cgc acc       96
Phe Pro Ser Asp Arg Glu Ser Asp Gly Ala Asn Asp Glu Ala Arg Thr
            20                  25                  30 gac gag cct gag gag cac gga ccg gac agg aat gga tgc tgt agg aat      144
Asp Glu Pro Glu Glu His Gly Pro Asp Arg Asn Gly Cys Cys Arg Asn
        35                  40                  45 cct gcc tgt gag agc cac aga tgt ggt tgacgacgct gatgctccag            191
Pro Ala Cys Glu Ser His Arg Cys Gly
    50                  55 gaccctctga accacgacg                                                  210

<210> SEQ ID NO 119
<211> LENGTH: 57
<212> TYPE: PRT
<213> ORGANISM: Conus stercusmuscarum

<400> SEQUENCE: 119

Met Phe Thr Val Phe Leu Leu Val Val Leu Ala Thr Thr Val Val Ser
 1               5                  10                  15

Phe Pro Ser Asp Arg Glu Ser Asp Gly Ala Asn Asp Glu Ala Arg Thr
            20                  25                  30

Asp Glu Pro Glu Glu His Gly Pro Asp Arg Asn Gly Cys Cys Arg Asn
        35                  40                  45

Pro Ala Cys Glu Ser His Arg Cys Gly
    50                  55

<210> SEQ ID NO 120
```

```
<211> LENGTH: 210
<212> TYPE: DNA
<213> ORGANISM: Conus circumcisus
<220> FEATURE:
<221> NAME/KEY: CDS
<222> LOCATION: (1)..(180)

<400> SEQUENCE: 120 atg ttc acc gtg ttt ctg ttg gtt gtc ttg gca acc act gtc gtt tcc    48
Met Phe Thr Val Phe Leu Leu Val Val Leu Ala Thr Thr Val Val Ser
 1               5                  10                  15 ttc cct tca gat cgt gca tct gat ggc agg aat gcc gca gcc agc gac    96
Phe Pro Ser Asp Arg Ala Ser Asp Gly Arg Asn Ala Ala Ala Ser Asp
             20                  25                  30 aga gcg tct gac gcg gcc cac cag gga tgc tgt tcc aac cct gtc tgt   144
Arg Ala Ser Asp Ala Ala His Gln Gly Cys Cys Ser Asn Pro Val Cys
         35                  40                  45 cac gtg gaa cat cca gaa ctt tgt cgt aga aga cgc tgatgctcca        190
His Val Glu His Pro Glu Leu Cys Arg Arg Arg
     50                  55                  60 ggaccctctg aaccacgacg                                              210

<210> SEQ ID NO 121
<211> LENGTH: 60
<212> TYPE: PRT
<213> ORGANISM: Conus circumcisus

<400> SEQUENCE: 121

Met Phe Thr Val Phe Leu Leu Val Val Leu Ala Thr Thr Val Val Ser
 1               5                  10                  15

Phe Pro Ser Asp Arg Ala Ser Asp Gly Arg Asn Ala Ala Ala Ser Asp
             20                  25                  30

Arg Ala Ser Asp Ala Ala His Gln Gly Cys Cys Ser Asn Pro Val Cys
         35                  40                  45

His Val Glu His Pro Glu Leu Cys Arg Arg Arg
     50                  55                  60

<210> SEQ ID NO 122
<211> LENGTH: 213
<212> TYPE: DNA
<213> ORGANISM: Conus circumcisus
<220> FEATURE:
<221> NAME/KEY: CDS
<222> LOCATION: (1)..(174)

<400> SEQUENCE: 122 atg ttc acc gtg ttt ctg ttg gtt gtc ttg gca acc act gtc gtt tcc    48
Met Phe Thr Val Phe Leu Leu Val Val Leu Ala Thr Thr Val Val Ser
 1               5                  10                  15 ttc cct tca aat cgt gaa tct gat ggc gcg aat gcc gaa gtc cgc acc    96
Phe Pro Ser Asn Arg Glu Ser Asp Gly Ala Asn Ala Glu Val Arg Thr
             20                  25                  30 gac gag cct gag gag cac gac gaa ctg ggc ggg aat gga tgc tgt ggg   144
Asp Glu Pro Glu Glu His Asp Glu Leu Gly Gly Asn Gly Cys Cys Gly
         35                  40                  45 aat cct gac tgt acg agc cac agt tgt gat tgacgacgct gatgctccag     194
Asn Pro Asp Cys Thr Ser His Ser Cys Asp
     50                  55 gaccctctga accacgacg                                               213

<210> SEQ ID NO 123
<211> LENGTH: 58
```

-continued

<212> TYPE: PRT
<213> ORGANISM: Conus circumcisus

<400> SEQUENCE: 123

Met Phe Thr Val Phe Leu Leu Val Val Leu Ala Thr Thr Val Val Ser
 1               5                  10                  15

Phe Pro Ser Asn Arg Glu Ser Asp Gly Ala Asn Ala Glu Val Arg Thr
            20                  25                  30

Asp Glu Pro Glu Glu His Asp Glu Leu Gly Gly Asn Gly Cys Cys Gly
        35                  40                  45

Asn Pro Asp Cys Thr Ser His Ser Cys Asp
    50                  55

<210> SEQ ID NO 124
<211> LENGTH: 207
<212> TYPE: DNA
<213> ORGANISM: Conus episcopatus
<220> FEATURE:
<221> NAME/KEY: CDS
<222> LOCATION: (1)..(168)

<400> SEQUENCE: 124 atg ttc acc gtg ttt ctg ttg gtt gtc ttg gca acc acc gtc gtt tcc      48
Met Phe Thr Val Phe Leu Leu Val Val Leu Ala Thr Thr Val Val Ser
 1               5                  10                  15 ttc act tca gat cgt gca tct gat agc agg aag gac gca gcg tct ggc      96
Phe Thr Ser Asp Arg Ala Ser Asp Ser Arg Lys Asp Ala Ala Ser Gly
            20                  25                  30 ctg atc gct ctg acc atc aag gga tgc tgt tct gat cct cgc tgt aac     144
Leu Ile Ala Leu Thr Ile Lys Gly Cys Cys Ser Asp Pro Arg Cys Asn
        35                  40                  45 atg aat aat cca gac tat tgt ggt tgacgacgct gatgctccag gaccctctga    198
Met Asn Asn Pro Asp Tyr Cys Gly
    50                  55 accacgacg                                                           207

<210> SEQ ID NO 125
<211> LENGTH: 56
<212> TYPE: PRT
<213> ORGANISM: Conus episcopatus

<400> SEQUENCE: 125

Met Phe Thr Val Phe Leu Leu Val Val Leu Ala Thr Thr Val Val Ser
 1               5                  10                  15

Phe Thr Ser Asp Arg Ala Ser Asp Ser Arg Lys Asp Ala Ala Ser Gly
            20                  25                  30

Leu Ile Ala Leu Thr Ile Lys Gly Cys Cys Ser Asp Pro Arg Cys Asn
        35                  40                  45

Met Asn Asn Pro Asp Tyr Cys Gly
    50                  55

<210> SEQ ID NO 126
<211> LENGTH: 213
<212> TYPE: DNA
<213> ORGANISM: Conus sponsalis
<220> FEATURE:
<221> NAME/KEY: CDS
<222> LOCATION: (1)..(174)

<400> SEQUENCE: 126 atg tcc acc gtg ttt ctg ttg gtt gtc ctc gca acc acc gtc gtt tcc      48
Met Ser Thr Val Phe Leu Leu Val Val Leu Ala Thr Thr Val Val Ser

```
ttc act gta gat cgt gca tct gat ggc agg gat gtc gca atc gac gac      96
Phe Thr Val Asp Arg Ala Ser Asp Gly Arg Asp Val Ala Ile Asp Asp
             20                  25                  30 aga ttg gtg tct ctc cct cag atc gcc cat gct gac tgt tgt tcc gat     144
Arg Leu Val Ser Leu Pro Gln Ile Ala His Ala Asp Cys Cys Ser Asp
         35                  40                  45 cct gcc tgc aag cag acg ccc ggt tgt cgt taaagacgct gctgctccag       194
Pro Ala Cys Lys Gln Thr Pro Gly Cys Arg
     50                  55 gaccctctga accacgacg                                                213
```

<210> SEQ ID NO 127
<211> LENGTH: 58
<212> TYPE: PRT
<213> ORGANISM: Conus sponsalis

<400> SEQUENCE: 127

```
Met Ser Thr Val Phe Leu Leu Val Val Leu Ala Thr Thr Val Ser
 1               5                  10                  15

Phe Thr Val Asp Arg Ala Ser Asp Gly Arg Asp Val Ala Ile Asp Asp
             20                  25                  30

Arg Leu Val Ser Leu Pro Gln Ile Ala His Ala Asp Cys Cys Ser Asp
         35                  40                  45

Pro Ala Cys Lys Gln Thr Pro Gly Cys Arg
     50                  55
```

<210> SEQ ID NO 128
<211> LENGTH: 221
<212> TYPE: DNA
<213> ORGANISM: Conus sponsalis
<220> FEATURE:
<221> NAME/KEY: CDS
<222> LOCATION: (1)..(168)

<400> SEQUENCE: 128

```
atg ttc acc gtg ttt ctg ttg gtt gtc ttg gca acc acc gtc gct tcc      48
Met Phe Thr Val Phe Leu Leu Val Val Leu Ala Thr Thr Val Ala Ser
 1               5                  10                  15 ttc att atc gat gat cca tct gat ggc agg aat att gca gtc gac gac     96
Phe Ile Ile Asp Asp Pro Ser Asp Gly Arg Asn Ile Ala Val Asp Asp
             20                  25                  30 aga ggg ctt ttc tct acg ctc ttc cat gct gat tgc tgt gaa aat cct    144
Arg Gly Leu Phe Ser Thr Leu Phe His Ala Asp Cys Cys Glu Asn Pro
         35                  40                  45 gcc tgt aga cac acg cag ggt tgt tgatctttgt tcttcaaaga cactgctggc   198
Ala Cys Arg His Thr Gln Gly Cys
     50                  55 ccaggaccct ctgaaccacg acg                                          221
```

<210> SEQ ID NO 129
<211> LENGTH: 56
<212> TYPE: PRT
<213> ORGANISM: Conus sponsalis

<400> SEQUENCE: 129

```
Met Phe Thr Val Phe Leu Leu Val Val Leu Ala Thr Thr Val Ala Ser
 1               5                  10                  15

Phe Ile Ile Asp Asp Pro Ser Asp Gly Arg Asn Ile Ala Val Asp Asp
             20                  25                  30
```

```
<210> SEQ ID NO 130
<211> LENGTH: 220
<212> TYPE: DNA
<213> ORGANISM: Conus dalli
<220> FEATURE:
<221> NAME/KEY: CDS
<222> LOCATION: (1)..(180)

<400> SEQUENCE: 130
```

| | | | | | | | | | | | | | | | | |
|---|---|---|---|---|---|---|---|---|---|---|---|---|---|---|---|---|
| atg | ttc | acc | gtg | ttt | ctg | ttg | gtt | gtc | ttg | gca | acc | acc | gtc | gtt | tcc | 48 |
| Met | Phe | Thr | Val | Phe | Leu | Leu | Val | Val | Leu | Ala | Thr | Thr | Val | Val | Ser | |
| 1 | | | | 5 | | | | | 10 | | | | | 15 | | |
| ttc | act | tca | gat | cgt | gca | ttt | cgt | ggc | agg | aat | gcc | gca | gcc | aaa | gag | 96 |
| Phe | Thr | Ser | Asp | Arg | Ala | Phe | Arg | Gly | Arg | Asn | Ala | Ala | Ala | Lys | Glu | |
| | | | 20 | | | | | 25 | | | | | 30 | | | |
| tct | ggc | ctg | gtc | ggt | ctg | acc | gac | aag | acg | cga | gga | tgc | tgt | tct | cat | 144 |
| Ser | Gly | Leu | Val | Gly | Leu | Thr | Asp | Lys | Thr | Arg | Gly | Cys | Cys | Ser | His | |
| | | 35 | | | | | 40 | | | | | 45 | | | | |
| cct | gcc | tgt | aac | gta | gat | cat | cca | gaa | att | tgt | ggt | tgaagacgct | | | | 190 |
| Pro | Ala | Cys | Asn | Val | Asp | His | Pro | Glu | Ile | Cys | Gly | | | | | |
| | 50 | | | | | 55 | | | | | 60 | | | | | |
| gatgctccag gaccctctga accacgacgt | | | | | | | | | | | | | | | | 220 |

```
<210> SEQ ID NO 131
<211> LENGTH: 60
<212> TYPE: PRT
<213> ORGANISM: Conus dalli

<400> SEQUENCE: 131
```

Met Phe Thr Val Phe Leu Leu Val Val Leu Ala Thr Thr Val Val Ser
1               5                   10                  15

Phe Thr Ser Asp Arg Ala Phe Arg Gly Arg Asn Ala Ala Ala Lys Glu
            20                  25                  30

Ser Gly Leu Val Gly Leu Thr Asp Lys Thr Arg Gly Cys Cys Ser His
        35                  40                  45

Pro Ala Cys Asn Val Asp His Pro Glu Ile Cys Gly
    50                  55                  60

```
<210> SEQ ID NO 132
<211> LENGTH: 208
<212> TYPE: DNA
<213> ORGANISM: Conus dalli
<220> FEATURE:
<221> NAME/KEY: CDS
<222> LOCATION: (1)..(177)

<400> SEQUENCE: 132
```

| | | | | | | | | | | | | | | | | |
|---|---|---|---|---|---|---|---|---|---|---|---|---|---|---|---|---|
| atg | ttc | acc | gtg | ttt | ctg | ttg | gtt | gtc | ttg | gca | acc | acc | gtc | gtt | tcc | 48 |
| Met | Phe | Thr | Val | Phe | Leu | Leu | Val | Val | Leu | Ala | Thr | Thr | Val | Val | Ser | |
| 1 | | | | 5 | | | | | 10 | | | | | 15 | | |
| ttc | act | tca | gat | ggt | gca | tct | gat | gac | agg | aaa | gcc | gct | gcg | tct | gac | 96 |
| Phe | Thr | Ser | Asp | Gly | Ala | Ser | Asp | Asp | Arg | Lys | Ala | Ala | Ala | Ser | Asp | |
| | | | 20 | | | | | 25 | | | | | 30 | | | |
| ctg | atc | act | ctg | acc | atc | aag | gga | tgc | tgt | tct | cgt | cct | ccc | tgt | atc | 144 |
| Leu | Ile | Thr | Leu | Thr | Ile | Lys | Gly | Cys | Cys | Ser | Arg | Pro | Pro | Cys | Ile | |
| | | 35 | | | | | 40 | | | | | 45 | | | | |
| gcg | aat | aat | cca | gac | ttg | tgt | ggt | cga | cga | cgc | tgatgctcca | ggaccctctg | | | | 197 |

```
Ala Asn Asn Pro Asp Leu Cys Gly Arg Arg Arg
    50              55 aaccacgacg t                                                              208

<210> SEQ ID NO 133
<211> LENGTH: 59
<212> TYPE: PRT
<213> ORGANISM: Conus dalli

<400> SEQUENCE: 133

Met Phe Thr Val Phe Leu Leu Val Val Leu Ala Thr Thr Val Val Ser
1               5                   10                  15

Phe Thr Ser Asp Gly Ala Ser Asp Asp Arg Lys Ala Ala Ala Ser Asp
            20                  25                  30

Leu Ile Thr Leu Thr Ile Lys Gly Cys Cys Ser Arg Pro Pro Cys Ile
        35                  40                  45

Ala Asn Asn Pro Asp Leu Cys Gly Arg Arg Arg
    50              55

<210> SEQ ID NO 134
<211> LENGTH: 223
<212> TYPE: DNA
<213> ORGANISM: Conus dalli
<220> FEATURE:
<221> NAME/KEY: CDS
<222> LOCATION: (1)..(192)

<400> SEQUENCE: 134 atg ttc acc gtg ttt ctg ttg gtt gtc ttg gca acc act gtc gtt tcc          48
Met Phe Thr Val Phe Leu Leu Val Val Leu Ala Thr Thr Val Val Ser
1               5                   10                  15 tcc act tca ggt cgt cgt gca ttt cat ggc agg aat gcc gca gcc aaa          96
Ser Thr Ser Gly Arg Arg Ala Phe His Gly Arg Asn Ala Ala Ala Lys
            20                  25                  30 gcg tct gga ctg gtc ggt ctg act gac agg aga cca caa tgc tgt agt         144
Ala Ser Gly Leu Val Gly Leu Thr Asp Arg Arg Pro Gln Cys Cys Ser
        35                  40                  45 gat cct cgc tgt aac gta ggt cat cca gaa ctt tgt ggt gga aga cgc         192
Asp Pro Arg Cys Asn Val Gly His Pro Glu Leu Cys Gly Gly Arg Arg
    50              55                      60 tgatgctcca ggaccctctg aaccacaacg t                                       223

<210> SEQ ID NO 135
<211> LENGTH: 64
<212> TYPE: PRT
<213> ORGANISM: Conus dalli

<400> SEQUENCE: 135

Met Phe Thr Val Phe Leu Leu Val Val Leu Ala Thr Thr Val Val Ser
1               5                   10                  15

Ser Thr Ser Gly Arg Arg Ala Phe His Gly Arg Asn Ala Ala Ala Lys
            20                  25                  30

Ala Ser Gly Leu Val Gly Leu Thr Asp Arg Arg Pro Gln Cys Cys Ser
        35                  40                  45

Asp Pro Arg Cys Asn Val Gly His Pro Glu Leu Cys Gly Gly Arg Arg
    50              55                  60

<210> SEQ ID NO 136
<211> LENGTH: 220
<212> TYPE: DNA
<213> ORGANISM: Conus dalli
```

```
<220> FEATURE:
<221> NAME/KEY: CDS
<222> LOCATION: (1)..(189)

<400> SEQUENCE: 136 atg ttc acc gtg ttt ctg ttg gtt gtc ttg gca acc act gtc gtt tcc       48
Met Phe Thr Val Phe Leu Leu Val Val Leu Ala Thr Thr Val Val Ser
 1               5                  10                  15 tcc act tca ggt cgt gca ttt cat ggc agg aat gcc gca gcc aaa gcg       96
Ser Thr Ser Gly Arg Ala Phe His Gly Arg Asn Ala Ala Ala Lys Ala
                20                  25                  30 tct ggc ctg gtc ggt ctg acc gac aag agg caa gta tgc tgt agt gat      144
Ser Gly Leu Val Gly Leu Thr Asp Lys Arg Gln Val Cys Cys Ser Asp
            35                  40                  45 cct cgc tgt aac gta ggt cat cca gaa att tgt ggt gga aga cgc          189
Pro Arg Cys Asn Val Gly His Pro Glu Ile Cys Gly Gly Arg Arg
        50                  55                  60 tgatgctcca ggaccctctg aaccacgacg t                                   220

<210> SEQ ID NO 137
<211> LENGTH: 63
<212> TYPE: PRT
<213> ORGANISM: Conus dalli

<400> SEQUENCE: 137

Met Phe Thr Val Phe Leu Leu Val Val Leu Ala Thr Thr Val Val Ser
 1               5                  10                  15

Ser Thr Ser Gly Arg Ala Phe His Gly Arg Asn Ala Ala Ala Lys Ala
                20                  25                  30

Ser Gly Leu Val Gly Leu Thr Asp Lys Arg Gln Val Cys Cys Ser Asp
            35                  40                  45

Pro Arg Cys Asn Val Gly His Pro Glu Ile Cys Gly Gly Arg Arg
        50                  55                  60

<210> SEQ ID NO 138
<211> LENGTH: 208
<212> TYPE: DNA
<213> ORGANISM: Conus achatinus
<220> FEATURE:
<221> NAME/KEY: CDS
<222> LOCATION: (1)..(180)

<400> SEQUENCE: 138 atg ttc acc gtg ttt ctg ttg gtt gtc ttg aca acc act gtc gtt tcc       48
Met Phe Thr Val Phe Leu Leu Val Val Leu Thr Thr Thr Val Val Ser
 1               5                  10                  15 ttc cct tca gat agt gca tct ggt ggc agg gat gac gag gcc aaa gac       96
Phe Pro Ser Asp Ser Ala Ser Gly Gly Arg Asp Asp Glu Ala Lys Asp
                20                  25                  30 gaa agg tct gac atg tac gaa ttg aaa cgg aat gga cgc tgt tgc cat      144
Glu Arg Ser Asp Met Tyr Glu Leu Lys Arg Asn Gly Arg Cys Cys His
            35                  40                  45 cct gcc tgt ggt ggc aaa tac gtt aaa tgt gga cgc tgatgctcca           190
Pro Ala Cys Gly Gly Lys Tyr Val Lys Cys Gly Arg
        50                  55                  60 ggaccctctc gaaccacg                                                  208

<210> SEQ ID NO 139
<211> LENGTH: 60
<212> TYPE: PRT
<213> ORGANISM: Conus achatinus
```

```
<400> SEQUENCE: 139

Met Phe Thr Val Phe Leu Leu Val Val Leu Thr Thr Val Val Ser
 1               5                  10                  15

Phe Pro Ser Asp Ser Ala Ser Gly Gly Arg Asp Asp Glu Ala Lys Asp
                20                  25                  30

Glu Arg Ser Asp Met Tyr Glu Leu Lys Arg Asn Gly Arg Cys Cys His
            35                  40                  45

Pro Ala Cys Gly Gly Lys Tyr Val Lys Cys Gly Arg
        50                  55                  60

<210> SEQ ID NO 140
<211> LENGTH: 211
<212> TYPE: DNA
<213> ORGANISM: Conus bullatus
<220> FEATURE:
<221> NAME/KEY: CDS
<222> LOCATION: (1)..(174)

<400> SEQUENCE: 140 atg ttc acc gtg ttt ctg ttg gtt gtc ttg gca acc act gtc gtt tcc      48
Met Phe Thr Val Phe Leu Leu Val Val Leu Ala Thr Thr Val Val Ser
 1               5                  10                  15 ttc tct aca gat gat gaa tct gat ggc tcg aat gaa gaa ccc agc gcc      96
Phe Ser Thr Asp Asp Glu Ser Asp Gly Ser Asn Glu Glu Pro Ser Ala
                20                  25                  30 gac cag act gcc agg tcc tca atg aac agg gcg cct gga tgc tgt aac     144
Asp Gln Thr Ala Arg Ser Ser Met Asn Arg Ala Pro Gly Cys Cys Asn
            35                  40                  45 aat cct gcc tgt gtg aag cac aga tgt gga tgacgctgat gctccaggac       194
Asn Pro Ala Cys Val Lys His Arg Cys Gly
        50                  55 cctctgaacc acgacgt                                                  211

<210> SEQ ID NO 141
<211> LENGTH: 58
<212> TYPE: PRT
<213> ORGANISM: Conus bullatus

<400> SEQUENCE: 141

Met Phe Thr Val Phe Leu Leu Val Val Leu Ala Thr Thr Val Val Ser
 1               5                  10                  15

Phe Ser Thr Asp Asp Glu Ser Asp Gly Ser Asn Glu Glu Pro Ser Ala
                20                  25                  30

Asp Gln Thr Ala Arg Ser Ser Met Asn Arg Ala Pro Gly Cys Cys Asn
            35                  40                  45

Asn Pro Ala Cys Val Lys His Arg Cys Gly
        50                  55

<210> SEQ ID NO 142
<211> LENGTH: 214
<212> TYPE: DNA
<213> ORGANISM: Conus bullatus
<220> FEATURE:
<221> NAME/KEY: CDS
<222> LOCATION: (1)..(177)

<400> SEQUENCE: 142 atg ttc acc gtg ttt ctg ttg gtt gtc ttg gca acc act gtc gtt tcc      48
Met Phe Thr Val Phe Leu Leu Val Val Leu Ala Thr Thr Val Val Ser
 1               5                  10                  15 ttc tct aca gat gat gaa tct gat ggc tcg aat gaa gaa ccc agc gcc      96
```

```
Phe Ser Thr Asp Asp Glu Ser Asp Gly Ser Asn Glu Glu Pro Ser Ala
             20                  25                  30 gac cag gct gcc agg tcc gca atg aac agg ccg cct gga tgc tgt aac      144
Asp Gln Ala Ala Arg Ser Ala Met Asn Arg Pro Pro Gly Cys Cys Asn
         35                  40                  45 aat cct gcc tgt gtg aag cac aga tgt ggt gga tgacgctgat gctccaggac    197
Asn Pro Ala Cys Val Lys His Arg Cys Gly Gly
     50                  55 cctctgaacc acgacgt                                                   214

<210> SEQ ID NO 143
<211> LENGTH: 59
<212> TYPE: PRT
<213> ORGANISM: Conus bullatus

<400> SEQUENCE: 143

Met Phe Thr Val Phe Leu Leu Val Val Leu Ala Thr Thr Val Val Ser
 1               5                  10                  15

Phe Ser Thr Asp Asp Glu Ser Asp Gly Ser Asn Glu Glu Pro Ser Ala
             20                  25                  30

Asp Gln Ala Ala Arg Ser Ala Met Asn Arg Pro Pro Gly Cys Cys Asn
         35                  40                  45

Asn Pro Ala Cys Val Lys His Arg Cys Gly Gly
     50                  55

<210> SEQ ID NO 144
<211> LENGTH: 208
<212> TYPE: DNA
<213> ORGANISM: Conus bullatus
<220> FEATURE:
<221> NAME/KEY: CDS
<222> LOCATION: (1)..(177)

<400> SEQUENCE: 144 atg ttc acc gtg ttt ctg ttg gtt gtc ttg gca acc act gtc gtt tcc      48
Met Phe Thr Val Phe Leu Leu Val Val Leu Ala Thr Thr Val Val Ser
 1               5                  10                  15 ttc cct tca gat cgt gac tct gat ggc gcg gat gcc gaa gcc agt gac      96
Phe Pro Ser Asp Arg Asp Ser Asp Gly Ala Asp Ala Glu Ala Ser Asp
             20                  25                  30 gag cct gtt gag ttc gaa agg gac gag aat gga tgc tgt tgg aat cct      144
Glu Pro Val Glu Phe Glu Arg Asp Glu Asn Gly Cys Cys Trp Asn Pro
         35                  40                  45 tcc tgt ccg agg ccc aga tgt aca gga cga cgc taatgctcca ggaccctctg    197
Ser Cys Pro Arg Pro Arg Cys Thr Gly Arg Arg
     50                  55 aaccacgacg t                                                         208

<210> SEQ ID NO 145
<211> LENGTH: 59
<212> TYPE: PRT
<213> ORGANISM: Conus bullatus

<400> SEQUENCE: 145

Met Phe Thr Val Phe Leu Leu Val Val Leu Ala Thr Thr Val Val Ser
 1               5                  10                  15

Phe Pro Ser Asp Arg Asp Ser Asp Gly Ala Asp Ala Glu Ala Ser Asp
             20                  25                  30

Glu Pro Val Glu Phe Glu Arg Asp Glu Asn Gly Cys Cys Trp Asn Pro
         35                  40                  45
```

```
Ser Cys Pro Arg Pro Arg Cys Thr Gly Arg Arg
    50                  55
```

<210> SEQ ID NO 146
<211> LENGTH: 211
<212> TYPE: DNA
<213> ORGANISM: Conus bullatus
<220> FEATURE:
<221> NAME/KEY: CDS
<222> LOCATION: (1)..(180)

<400> SEQUENCE: 146

```
atg ttc acc gtg ttt ctg ttg gtt gtc ttg aca acc act gtc gtt tcc        48
Met Phe Thr Val Phe Leu Leu Val Val Leu Thr Thr Thr Val Val Ser
 1               5                  10                  15 ttc cct tca gat cgt gca tct gat ggc agg aat gcc gca gcc aac gac        96
Phe Pro Ser Asp Arg Ala Ser Asp Gly Arg Asn Ala Ala Ala Asn Asp
             20                  25                  30 aaa gcg tct gac gtg gtc acg ctg gtc ctc aag gga tgc tgt tcc acc       144
Lys Ala Ser Asp Val Val Thr Leu Val Leu Lys Gly Cys Cys Ser Thr
         35                  40                  45 cct ccc tgt gct gtg ctg tat tgt ggt aga aga cgc tgatgctcca            190
Pro Pro Cys Ala Val Leu Tyr Cys Gly Arg Arg Arg
     50                  55                  60 ggaccctctg aaccacgacg t                                               211
```

<210> SEQ ID NO 147
<211> LENGTH: 60
<212> TYPE: PRT
<213> ORGANISM: Conus bullatus

<400> SEQUENCE: 147

```
Met Phe Thr Val Phe Leu Leu Val Val Leu Thr Thr Thr Val Val Ser
 1               5                  10                  15

Phe Pro Ser Asp Arg Ala Ser Asp Gly Arg Asn Ala Ala Ala Asn Asp
             20                  25                  30

Lys Ala Ser Asp Val Val Thr Leu Val Leu Lys Gly Cys Cys Ser Thr
         35                  40                  45

Pro Pro Cys Ala Val Leu Tyr Cys Gly Arg Arg Arg
     50                  55                  60
```

<210> SEQ ID NO 148
<211> LENGTH: 212
<212> TYPE: DNA
<213> ORGANISM: Conus distans
<220> FEATURE:
<221> NAME/KEY: CDS
<222> LOCATION: (1)..(171)

<400> SEQUENCE: 148

```
atg ttc acc gtg ttt ctg ttg gtt gtc ttc gca tcc tct gtc acc tta        48
Met Phe Thr Val Phe Leu Leu Val Val Phe Ala Ser Ser Val Thr Leu
 1               5                  10                  15 gat cgt gca tct tat ggc agg tat gcc tca ccc gtc gac aga gcg tct        96
Asp Arg Ala Ser Tyr Gly Arg Tyr Ala Ser Pro Val Asp Arg Ala Ser
             20                  25                  30 gcc ctg atc gct cag gcc atc ctt cga gat tgc tgc tcc aat cct cct       144
Ala Leu Ile Ala Gln Ala Ile Leu Arg Asp Cys Cys Ser Asn Pro Pro
         35                  40                  45 tgt gcc cat aat aat cca gac tgt cgt taaagacgct gcttgctcca             191
Cys Ala His Asn Asn Pro Asp Cys Arg
     50                  55
```

-continued ggaccctctg aaccacgacg t    212

<210> SEQ ID NO 149
<211> LENGTH: 57
<212> TYPE: PRT
<213> ORGANISM: Conus distans

<400> SEQUENCE: 149

Met Phe Thr Val Phe Leu Leu Val Val Phe Ala Ser Ser Val Thr Leu
1               5                   10                  15

Asp Arg Ala Ser Tyr Gly Arg Tyr Ala Ser Pro Val Asp Arg Ala Ser
            20                  25                  30

Ala Leu Ile Ala Gln Ala Ile Leu Arg Asp Cys Cys Ser Asn Pro Pro
        35                  40                  45

Cys Ala His Asn Asn Pro Asp Cys Arg
    50                  55

<210> SEQ ID NO 150
<211> LENGTH: 63
<212> TYPE: DNA
<213> ORGANISM: Conus textile
<220> FEATURE:
<221> NAME/KEY: CDS
<222> LOCATION: (1)..(60)

<400> SEQUENCE: 150 gga tgc tgt tct aat cct ccc tgt atc gcg aag aat cca cac atg tgt    48
Gly Cys Cys Ser Asn Pro Pro Cys Ile Ala Lys Asn Pro His Met Cys
1               5                   10                  15 ggt gga aga cgc tga    63
Gly Gly Arg Arg
            20

SEQ ID NO 151
LENGTH: 20
TYPE: PRT
ORGANISM: Conus textile

<400> SEQUENCE: 151

Gly Cys Cys Ser Asn Pro Pro Cys Ile Ala Lys Asn Pro His Met Cys
1               5                   10                  15

Gly Gly Arg Arg
            20

<210> SEQ ID NO 152
<211> LENGTH: 220
<212> TYPE: DNA
<213> ORGANISM: Conus consors
<220> FEATURE:
<221> NAME/KEY: CDS
<222> LOCATION: (1)..(189)

<400> SEQUENCE: 152 atg ttc acc gtg ttt ctg ttg gtt gtc ttg gca acc act gtc gtt tcc    48
Met Phe Thr Val Phe Leu Leu Val Val Leu Ala Thr Thr Val Val Ser
1               5                   10                  15 ttc cct tca gat cgt gca tct gat ggc agg aat gcc gca gcc aac gac    96
Phe Pro Ser Asp Arg Ala Ser Asp Gly Arg Asn Ala Ala Ala Asn Asp
            20                  25                  30 aaa gcg tct gac gtg atc acg ctg gcc ctc aag gga tgc tgt tcc aac    144
Lys Ala Ser Asp Val Ile Thr Leu Ala Leu Lys Gly Cys Cys Ser Asn
        35                  40                  45 cct gtc tgt cac ttg gag cat tca aac ctt tgt ggt aga aga cgc    189

```
Pro Val Cys His Leu Glu His Ser Asn Leu Cys Gly Arg Arg Arg
    50                  55                  60 tgatgctcca ggaccctctg aaccacgacg t                                          220

<210> SEQ ID NO 153
<211> LENGTH: 63
<212> TYPE: PRT
<213> ORGANISM: Conus consors

<400> SEQUENCE: 153

Met Phe Thr Val Phe Leu Leu Val Val Leu Ala Thr Thr Val Ser
1               5                   10                  15

Phe Pro Ser Asp Arg Ala Ser Asp Gly Arg Asn Ala Ala Ala Asn Asp
            20                  25                  30

Lys Ala Ser Asp Val Ile Thr Leu Ala Leu Lys Gly Cys Cys Ser Asn
        35                  40                  45

Pro Val Cys His Leu Glu His Ser Asn Leu Cys Gly Arg Arg Arg
    50                  55                  60

<210> SEQ ID NO 154
<211> LENGTH: 15
<212> TYPE: PRT
<213> ORGANISM: Conus musicus
<220> FEATURE:
<221> NAME/KEY: SITE
<222> LOCATION: (4)..(12)
<223> OTHER INFORMATION: Xaa at residues 4, 11 and 12 is Tyr, nor-Tyr,
      mono-halo-Tyr, di-halo-Tyr, O-sulpho-Tyr,
      O-phospho-Tyr or nitro-Tyr. Xaa at residue 6 is
      Pro or hydroxy-Pro.
<220> FEATURE:
<221> NAME/KEY: SITE
<222> LOCATION: (9)..(15)
<223> OTHER INFORMATION: Xaa at residues 9, 10 and 15 is Lys,
      N-methyl-Lys, N,N-dimethyl-Lys or N,N,N-trimethyl-Lys; Xaa at
      residue 14 is Trp (D or L) or halo-Trp.

<400> SEQUENCE: 154

Gly Cys Cys Xaa Asn Xaa Val Cys Xaa Xaa Xaa Xaa Cys Xaa Xaa
1               5                   10                  15

<210> SEQ ID NO 155
<211> LENGTH: 16
<212> TYPE: PRT
<213> ORGANISM: Conus purpurascens
<220> FEATURE:
<221> NAME/KEY: SITE
<222> LOCATION: (1)..(3)
<223> OTHER INFORMATION: Xaa at residue 1 is Gln or pyro-Glu; Xaa at
      residue 2 is Glu or gamma-carboxy-Glu; Xaa at
      residues 3 and 9 is Pro or hydroxy-Pro.
<220> FEATURE:
<221> NAME/KEY: SITE
<222> LOCATION: (13)
<223> OTHER INFORMATION: Xaa at residue 13 is Lys, N-methyl-Lys,
      N,N-dimethyl-Lys or N,N,N-trimethyl-Lys.

<400> SEQUENCE: 155

Xaa Xaa Xaa Gly Cys Cys Arg His Xaa Ala Cys Gly Xaa Asn Arg Cys
1               5                   10                  15

<210> SEQ ID NO 156
<211> LENGTH: 13
<212> TYPE: PRT
<213> ORGANISM: Conus musicus
<220> FEATURE:
<221> NAME/KEY: SITE
<222> LOCATION: (5)..(11)
```

<223> OTHER INFORMATION: Xaa at residues 5 and 11 is Pro or hydroxy-Pro.

<400> SEQUENCE: 156

Cys Cys Ala Asp Xaa Asp Cys Arg Phe Arg Xaa Gly Cys
 1               5                   10

<210> SEQ ID NO 157
<211> LENGTH: 17
<212> TYPE: PRT
<213> ORGANISM: Conus musicus
<220> FEATURE:
<221> NAME/KEY: SITE
<222> LOCATION: (4)..(13)
<223> OTHER INFORMATION: Xaa at residues 4 and 13 is Tyr, nor-Tyr,
      mono-halo-Tyr, di-halo-Tyr, O-sulpho-Tyr,
      O-phospho-Tyr or nitro-Tyr; Xaa at residues 6 and
      10 is Pro or hydroxy-Pro.
<220> FEATURE:
<221> NAME/KEY: SITE
<222> LOCATION: (9)..(17)
<223> OTHER INFORMATION: Xaa at residues 9 and 16 is Trp (D or L) or
      halo-Trp; Xaa at residues 11 and 17 is Lys,
      N-methyl-Lys, N,N-dimethyl-Lys or
      N,N,N-trimethyl-Lys.

<400> SEQUENCE: 157

Gly Cys Cys Xaa Asn Xaa Ser Cys Xaa Xaa Xaa Thr Xaa Cys Ser Xaa
 1               5                   10                  15

Xaa

<210> SEQ ID NO 158
<211> LENGTH: 13
<212> TYPE: PRT
<213> ORGANISM: Conus musicus
<220> FEATURE:
<221> NAME/KEY: SITE
<222> LOCATION: (5)..(8)
<223> OTHER INFORMATION: Xaa at residue 5 is Pro or hydroxy-Pro; Xaa at
      residue 8 is Lys, N-methyl-Lys, N,N-dimethyl-Lys
      or N,N,N-trimethyl-Lys.
<220> FEATURE:
<221> NAME/KEY: SITE
<222> LOCATION: (9)..(11)
<223> OTHER INFORMATION: Xaa at residue 9 is Glu or gamma-carboxy-Glu;
      Xaa at residue 11 is Tyr, nor-Tyr, mono-halo-Tyr, di-halo-Tyr,
      O-sulpho-Tyr, O-phospho-Tyr or nitro-Tyr.

<400> SEQUENCE: 158

Cys Cys Ser Asn Xaa Thr Cys Xaa Xaa Thr Xaa Gly Cys
 1               5                   10

<210> SEQ ID NO 159
<211> LENGTH: 13
<212> TYPE: PRT
<213> ORGANISM: Conus musicus
<220> FEATURE:
<221> NAME/KEY: SITE
<222> LOCATION: (5)..(11)
<223> OTHER INFORMATION: Xaa at residues 5 and 11 is Pro or hydroxy-Pro;
      Xaa at residue 8 is Lys, N-methyl-Lys,
      N,N-dimethyl-Lys or N,N,N-trimethyl-Lys.

<400> SEQUENCE: 159

Cys Cys Ala Asn Xaa Ile Cys Xaa Asn Thr Xaa Gly Cys
 1               5                   10

<210> SEQ ID NO 160
<211> LENGTH: 13
<212> TYPE: PRT
<213> ORGANISM: Conus musicus

```
<220> FEATURE:
<221> NAME/KEY: SITE
<222> LOCATION: (5)..(8)
<223> OTHER INFORMATION: Xaa at residue 5 is Pro or hydroxy-Pro; Xaa at
      residue 8 is Lys, N-methyl-Lys, N,N-dimethyl-Lys
      or N,N,N-trimethyl-Lys.
<220> FEATURE:
<221> NAME/KEY: SITE
<222> LOCATION: (9)..(11)
<223> OTHER INFORMATION: Xaa at residue 9 is Glu or gamma-carboxy-Glu;
      Xaa at residue 11 is Tyr, mono-halo-Tyr, di-halo-Tyr,
      O-sulpho-Tyr, O-phospho-Tyr or nitro-Tyr.

<400> SEQUENCE: 160

Cys Cys Asn Asn Xaa Thr Cys Xaa Xaa Thr Xaa Gly Cys
  1               5                  10

<210> SEQ ID NO 161
<211> LENGTH: 13
<212> TYPE: PRT
<213> ORGANISM: Conus musicus
<220> FEATURE:
<221> NAME/KEY: SITE
<222> LOCATION: (5)..(8)
<223> OTHER INFORMATION: Xaa at residue 5 is Pro or hydroxy-Pro; Xaa at
      residue 8 is Lys, N-methyl-Lys, N,N-dimethyl-Lys
      or N,N,N-trimethyl-Lys.
<220> FEATURE:
<221> NAME/KEY: SITE
<222> LOCATION: (9)..(11)
<223> OTHER INFORMATION: Xaa at residue 9 is Glu or gamma-carboxy-Glu;
      Xaa at residue 11 is Tyr, nor-Tyr, mono-halo-Tyr, di-halo-Tyr,
      O-sulpho-Tyr, O-phospho-Tyr or nitro-Tyr.

<400> SEQUENCE: 161

Cys Cys Ser Asn Xaa Val Cys Xaa Xaa Thr Xaa Gly Cys
  1               5                  10

<210> SEQ ID NO 162
<211> LENGTH: 17
<212> TYPE: PRT
<213> ORGANISM: Conus betulinus
<220> FEATURE:
<221> NAME/KEY: SITE
<222> LOCATION: (6)..(14)
<223> OTHER INFORMATION: Xaa at residue 6 is Tyr, nor-Tyr,
      mono-halo-Tyr, di-halo-Tyr, O-sulpho-Tyr, O-phospho-Tyr or
      nitro-Tyr; Xaa at residues 7, 8 and 14 is Pro or hydroxy-Pro.
<220> FEATURE:
<221> NAME/KEY: SITE
<222> LOCATION: (15)
<223> OTHER INFORMATION: Xaa at residue 15 is Lys, N-methyl-Lys,
      N,N-dimethyl-Lys or N,N,N-trimethyl-Lys.

<400> SEQUENCE: 162

Gly Gly Cys Cys Ser Xaa Xaa Xaa Cys Ile Ala Ser Asn Xaa Xaa Cys
  1               5                  10                  15

Gly

<210> SEQ ID NO 163
<211> LENGTH: 15
<212> TYPE: PRT
<213> ORGANISM: Conus lividus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 163

Gly Cys Cys Ser His Xaa Val Cys Ser Ala Met Ser Xaa Ile Cys
  1               5                  10                  15
```

-continued

```
<210> SEQ ID NO 164
<211> LENGTH: 15
<212> TYPE: PRT
<213> ORGANISM: Conus musicus
<220> FEATURE:
<221> NAME/KEY: SITE
<222> LOCATION: (4)..(12)
<223> OTHER INFORMATION: Xaa at residues 4 and 12 is Lys, N-methyl-Lys,
      N,N-dimethyl-Lys or N,N,N-trimethyl-Lys; Xaa at
      residue 6 is Pro or hydroxy-Pro.
<220> FEATURE:
<221> NAME/KEY: SITE
<222> LOCATION: (7)..(14)
<223> OTHER INFORMATION: Xaa at residues 7 and 14 is Tyr, mono-halo-Tyr,
      di-halo-Tyr, O-sulpho-Tyr, O-phospho-Tyr or
      nitro-Tyr.

<400> SEQUENCE: 164

Gly Cys Cys Xaa Asn Xaa Xaa Cys Gly Ala Ser Xaa Thr Xaa Cys
  1               5                  10                  15

<210> SEQ ID NO 165
<211> LENGTH: 15
<212> TYPE: PRT
<213> ORGANISM: Conus omaria
<220> FEATURE:
<221> NAME/KEY: SITE
<222> LOCATION: (5)..(13)
<223> OTHER INFORMATION: Xaa at residue 5 is Tyr, nor-Tyr,
      mono-halo-Tyr, di-halo-Tyr, O-sulpho-Tyr, O-phospho-Tyr or
      nitro-Tyr; Xaa at residues 6, 7 and 13 is Pro or hydroxy-Pro.

<400> SEQUENCE: 165

Gly Cys Cys Ser Xaa Xaa Xaa Cys Phe Ala Thr Asn Xaa Asp Cys
  1               5                  10                  15

<210> SEQ ID NO 166
<211> LENGTH: 17
<212> TYPE: PRT
<213> ORGANISM: Conus radiatus
<220> FEATURE:
<221> NAME/KEY: SITE
<222> LOCATION: (6)..(14)
<223> OTHER INFORMATION: Xaa at residue 6 is Tyr, nor-Tyr,
      mono-halo-Tyr, di-halo-Tyr, O-sulpho-Tyr, O-phospho-Tyr or
      nitro-Tyr; Xaa at residues 7, 8 and 14 is Pro or hydroxy-Pro.

<400> SEQUENCE: 166

Gly Gly Cys Cys Ser Xaa Xaa Xaa Cys Ile Ala Asn Asn Xaa Leu Cys
  1               5                  10                  15
Ala

<210> SEQ ID NO 167
<211> LENGTH: 17
<212> TYPE: PRT
<213> ORGANISM: Conus radiatus
<220> FEATURE:
<221> NAME/KEY: SITE
<222> LOCATION: (6)..(14)
<223> OTHER INFORMATION: Xaa at residue 6 is Tyr, nor-Tyr,
      mono-halo-Tyr, di-halo-Tyr, O-sulpho-Tyr, O-phospho-Tyr or
      nitro-Tyr; Xaa at residues 7, 8 and 14 is Pro or hydroxy-Pro.

<400> SEQUENCE: 167

Gly Gly Cys Cys Ser Xaa Xaa Xaa Cys Ile Ala Asn Asn Xaa Phe Cys
  1               5                  10                  15
Ala
```

```
<210> SEQ ID NO 168
<211> LENGTH: 16
<212> TYPE: PRT
<213> ORGANISM: Conus virgo
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro.

<400> SEQUENCE: 168

Asp Cys Cys Ser Asn Xaa Xaa Cys Ser Gln Asn Asn Xaa Asp Cys Met
 1               5                  10                  15

<210> SEQ ID NO 169
<211> LENGTH: 16
<212> TYPE: PRT
<213> ORGANISM: Conus virgo
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro.

<400> SEQUENCE: 169

Asp Cys Cys Ser Asn Xaa Xaa Cys Ala His Asn Asn Xaa Asp Cys Arg
 1               5                  10                  15

<210> SEQ ID NO 170
<211> LENGTH: 20
<212> TYPE: PRT
<213> ORGANISM: Conus achatinus
<220> FEATURE:
<221> NAME/KEY: SITE
<222> LOCATION: (1)..(14)
<223> OTHER INFORMATION: Xaa at residues 1, 11 and 14 is Glu or
      gamma-carboxy-Glu; Xaa at residue 6 is Pro or
      hydroxy-Pro.

<400> SEQUENCE: 170

Xaa Cys Cys Thr Asn Xaa Val Cys His Ala Xaa His Gln Xaa Leu Cys
 1               5                  10                  15

Ala Arg Arg Arg
            20

<210> SEQ ID NO 171
<211> LENGTH: 16
<212> TYPE: PRT
<213> ORGANISM: Conus achatinus
<220> FEATURE:
<221> NAME/KEY: SITE
<222> LOCATION: (6)..(10)
<223> OTHER INFORMATION: Xaa at residue 6 is Pro or hydroxy-Pro; Xaa at
      residue 11 is Glu or gamma-carboxy-Glu.

<400> SEQUENCE: 171

Gly Cys Cys Ser Asn Xaa Val Cys His Leu Xaa His Ser Asn Leu Cys
 1               5                  10                  15

<210> SEQ ID NO 172
<211> LENGTH: 20
<212> TYPE: PRT
<213> ORGANISM: Conus achatinus
<220> FEATURE:
<221> NAME/KEY: SITE
<222> LOCATION: (1)..(14)
<223> OTHER INFORMATION: Xaa at residues 1, 11 and 14 is Glu or
      gamma-carboxy-Glu; Xaa at residue 6 is Pro or
      hydroxy-Pro.
```

```
<400> SEQUENCE: 172

Xaa Cys Cys Thr Asn Xaa Val Cys His Val Xaa His Gln Xaa Leu Cys
 1               5                   10                  15

Ala Arg Arg Arg
            20

<210> SEQ ID NO 173
<211> LENGTH: 17
<212> TYPE: PRT
<213> ORGANISM: Conus ammiralis
<220> FEATURE:
<221> NAME/KEY: SITE
<222> LOCATION: (1)..(15)
<223> OTHER INFORMATION: Xaa at residue 1 is Gln or pyro-Glu; Xaa at
      residues 2 and 15 is Glu or gamma-carboxy-Glu; Xaa
      at residue 6 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (6)..(14)
<223> OTHER INFORMATION: nitro-Tyr; Xaa at residues 7 and 14 is Pro or
      hydroxy-Pro.

<400> SEQUENCE: 173

Xaa Xaa Cys Cys Ser Xaa Xaa Ala Cys Asn Leu Asp His Xaa Xaa Leu
 1               5                   10                  15

Cys

<210> SEQ ID NO 174
<211> LENGTH: 18
<212> TYPE: PRT
<213> ORGANISM: Conus ammiralis
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residues 2 and 15 is Glu or gamma-carboxy-Glu.

<400> SEQUENCE: 174

Xaa Xaa Cys Cys Ser Asp Xaa Arg Cys Asn Ser Thr His Xaa Xaa Leu
 1               5                   10                  15

Cys Gly

<210> SEQ ID NO 175
<211> LENGTH: 21
<212> TYPE: PRT
<213> ORGANISM: Conus arenatus
<220> FEATURE:
<221> NAME/KEY: SITE
<222> LOCATION: (7)..(12)
<223> OTHER INFORMATION: Xaa at residues 7 and 8 is Pro or hydroxy-Pro;
      Xaa at residue 10 is Trp (D or L) or halo-Trp; Xaa at residues 11
      and 12 is Lys, N-methyl-Lys, N,N-dimethyl-Lys or
      N,N,N-trimethyl-Lys.
<220> FEATURE:
<221> NAME/KEY: SITE
<222> LOCATION: (13)..(19)
<223> OTHER INFORMATION: Xaa at residue 13 is Tyr, nor-Tyr,
      mono-halo-Tyr, di-halo-Tyr, O-sulpho-Tyr, O-phospho-Tyr or
      nitro-Tyr ; Xaa at residue 19 is Glu or gamma-carboxy-Glu.

<400> SEQUENCE: 175

Leu Asn Cys Cys Met Ile Xaa Xaa Cys Xaa Xaa Xaa Xaa Gly Asp Arg
 1               5                   10                  15

Cys Ser Xaa Val Arg
            20
```

```
<210> SEQ ID NO 176
<211> LENGTH: 22
<212> TYPE: PRT
<213> ORGANISM: Conus arenatus
<220> FEATURE:
<221> NAME/KEY: SITE
<222> LOCATION: (9)..(20)
<223> OTHER INFORMATION: Xaa at residue 9 is Pro or hydroxy-Pro; Xaa at
      residues 12 and 20 is Glu or gamma-carboxy-Glu;
      Xaa at residue 14 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (9)..(20)
<223> OTHER INFORMATION: nitro-Tyr.

<400> SEQUENCE: 176

Ala Phe Gly Cys Cys Asp Leu Ile Xaa Cys Leu Xaa Arg Xaa Gly Asn
 1               5                  10                  15

Arg Cys Asn Xaa Val His
            20

<210> SEQ ID NO 177
<211> LENGTH: 21
<212> TYPE: PRT
<213> ORGANISM: Conus arenatus
<220> FEATURE:
<221> NAME/KEY: SITE
<222> LOCATION: (8)..(16)
<223> OTHER INFORMATION: Xaa at residue 8 is Pro or hydroxy-Pro; Xaa at
      residue 10 is Trp (D or L) or halo-Trp; Xaa at
      residues 12 and 16 is Lys, N-methyl-Lys,
      N,N-dimethyl-Lys or N,N,N-trimethyl-Lys.
<220> FEATURE:
<221> NAME/KEY: SITE
<222> LOCATION: (11)..(19)
<223> OTHER INFORMATION: Xaa at residues 11 and 19 is Glu or
      gamma-carboxy-Glu; Xaa at residue 13 is Tyr,
      mono-halo-Tyr, di-halo-Tyr, O-sulpho-Tyr,
      O-phospho-Tyr or nitro-Tyr.

<400> SEQUENCE: 177

Leu Gly Cys Cys Asn Val Thr Xaa Cys Xaa Xaa Xaa Xaa Gly Asp Xaa
 1               5                  10                  15

Cys Asn Xaa Val Arg
            20

<210> SEQ ID NO 178
<211> LENGTH: 20
<212> TYPE: PRT
<213> ORGANISM: Conus arenatus
<220> FEATURE:
<221> NAME/KEY: SITE
<222> LOCATION: (2)..(14)
<223> OTHER INFORMATION: Xaa at residue 2 is Glu or gamma-carboxy-Glu;
      Xaa at residues 7 and 14 is Pro or hydroxy-Pro.

<400> SEQUENCE: 178

Asp Xaa Cys Cys Ser Asn Xaa Ala Cys Arg Val Asn Asn Xaa His Val
 1               5                  10                  15

Cys Arg Arg Arg
            20

<210> SEQ ID NO 179
<211> LENGTH: 21
<212> TYPE: PRT
<213> ORGANISM: Conus arenatus
<220> FEATURE:
<221> NAME/KEY: SITE
```

```
<222> LOCATION: (7)..(13)
<223> OTHER INFORMATION: Xaa at residue 7 is Pro or hydroxy-Pro; Xaa at
      residue 10 is Trp (D or L) or halo-Trp; Xaa at
      residue 12 is Glu or gamma-carboxy-Glu; Xaa at
      residue 13 is Tyr, nor-Tyr, mono-halo-Tyr,
<220> FEATURE:
<221> NAME/KEY: SITE
<222> LOCATION: (13)..(19)
<223> OTHER INFORMATION: di-halo-Tyr, O-sulpho-Tyr, O-phospho-Tyr or
      nitro-Tyr; Xaa at residues 14 and 19 is Lys,
      N-methyl-Lys, N,N-dimethyl-Lys or
      N,N,N-trimethyl-Lys.

<400> SEQUENCE: 179

Leu Asn Cys Cys Ser Ile Xaa Gly Cys Xaa Asn Xaa Xaa Xaa Asp Arg
 1               5                  10                  15

Cys Ser Xaa Val Arg
            20

<210> SEQ ID NO 180
<211> LENGTH: 18
<212> TYPE: PRT
<213> ORGANISM: Conus aurisiacus
<220> FEATURE:
<221> NAME/KEY: SITE
<222> LOCATION: (7)..(14)
<223> OTHER INFORMATION: Xaa at residues 7 and 14 is Pro or hydroxy-Pro;
      Xaa at residue 10 is Tyr, mono-halo-Tyr,
      di-halo-Tyr, O-sulpho-Tyr, O-phospho-Tyr or
      nitro-Tyr.

<400> SEQUENCE: 180

Gly Gly Cys Cys Ser His Xaa Val Cys Xaa Phe Asn Asn Xaa Gln Met
 1               5                  10                  15

Cys Arg

<210> SEQ ID NO 181
<211> LENGTH: 18
<212> TYPE: PRT
<213> ORGANISM: Conus aurisiacus
<220> FEATURE:
<221> NAME/KEY: SITE
<222> LOCATION: (7)..(14)
<223> OTHER INFORMATION: Xaa at residues 7 and 14 is Pro or hydroxy-Pro.

<400> SEQUENCE: 181

Gly Gly Cys Cys Ser His Xaa Val Cys Asn Leu Asn Asn Xaa Gln Met
 1               5                  10                  15

Cys Arg

<210> SEQ ID NO 182
<211> LENGTH: 17
<212> TYPE: PRT
<213> ORGANISM: Conus bandanus
<220> FEATURE:
<221> NAME/KEY: SITE
<222> LOCATION: (6)..(15)
<223> OTHER INFORMATION: Xaa at residues 6 and 7 is Pro or hydroxy-Pro;
      Xaa at residues 9 and 15 is Tyr, mono-halo-Tyr, di-halo-Tyr,
      O-sulpho-Tyr, O-phospho-Tyr or nitro-Tyr.

<400> SEQUENCE: 182

Gly Cys Cys Ser His Xaa Xaa Cys Xaa Ala Asn Asn Gln Ala Xaa Cys
 1               5                  10                  15

Asn

<210> SEQ ID NO 183
```

```
<211> LENGTH: 17
<212> TYPE: PRT
<213> ORGANISM: Conus betulinus
<220> FEATURE:
<221> NAME/KEY: SITE
<222> LOCATION: (7)..(15)
<223> OTHER INFORMATION: Xaa at residues 7 and 14 is Pro and
      hydroxy-Pro; Xaa at residue 15 is Glu or gamma-carboxy-Glu.

<400

-continued

```
<221> NAME/KEY: SITE
<222> LOCATION: (12)..(16)
<223> OTHER INFORMATION: Xaa at residues 12 and 16 is Lys, N-methyl-Lys,
      N,N-dimethyl-Lys or N,N,N-trimethyl-Lys; Xaa at
      residue 13 is Tyr, mono-halo-Tyr, di-halo-Tyr,
      O-sulpho-Tyr, O-phospho-Tyr or nitro-Tyr.

<400> SEQUENCE: 186

Xaa Asn Cys Cys Ser Ile Xaa Gly Cys Xaa Xaa Xaa Xaa Gly Asp Xaa
 1               5                  10                  15

Cys Ser Xaa Val Arg
            20

<210> SEQ ID NO 187
<211> LENGTH: 16
<212> TYPE: PRT
<213> ORGANISM: Conus catus
<220> FEATURE:
<221> NAME/KEY: SITE
<222> LOCATION: (6)..(13)
<223> OTHER INFORMATION: Xaa at residues 6 and 13 is Pro or hydroxy-Pro;
      Xaa at residue 11 is Glu or gamma-carboxy-Glu.

<400> SEQUENCE: 187

Gly Cys Cys Ser Asn Xaa Val Cys His Leu Xaa His Xaa Asn Ala Cys
 1               5                  10                  15

<210> SEQ ID NO 188
<211> LENGTH: 17
<212> TYPE: PRT
<213> ORGANISM: Conus catus
<220> FEATURE:
<221> NAME/KEY: SITE
<222> LOCATION: (6)..(13)
<223> OTHER INFORMATION: Xaa at residues 6 and 13 is Pro or hydroxy-Pro;
      Xaa at residue 9 is Tyr, nor-Tyr, mono-halo-Tyr,
      di-halo-Tyr, O-sulpho-Tyr, O-phospho-Tyr or
      nitro-Tyr.

<400> SEQUENCE: 188

Gly Cys Cys Ser Asn Xaa Ile Cys Xaa Phe Asn Asn Xaa Arg Ile Cys
 1               5                  10                  15

Arg

<210> SEQ ID NO 189
<211> LENGTH: 17
<212> TYPE: PRT
<213> ORGANISM: Conus episcopatus
<220> FEATURE:
<221> NAME/KEY: SITE
<222> LOCATION: (1)..(14)
<223> OTHER INFORMATION: Xaa at residues 1 and 14 is Glu or
      gamma-carboxy-Glu; Xaa at residues 6, 7 and 13 is
      Pro or hydroxy-Pro; Xaa at residue 10 is Trp (D or
      L) or halo-Trp.
<220> FEATURE:
<221> NAME/KEY: SITE
<222> LOCATION: (11)
<223> OTHER INFORMATION: Xaa at residue 11 is Lys, N-methyl-Lys,
      N,N-dimethyl-Lys or N,N,N-trimethyl-Lys.

<400> SEQUENCE: 189

Xaa Cys Cys Ser Gln Xaa Xaa Cys Arg Xaa Xaa His Xaa Xaa Leu Cys
 1               5                  10                  15

Ser

<210> SEQ ID NO 190
<211> LENGTH: 16
```

```
<212> TYPE: PRT
<213> ORGANISM: Conus geographus
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 190

Gly Cys Cys Ser His Xaa Ala Cys Ala Gly Asn Asn Gln His Ile Cys
 1               5                  10                  15

<210> SEQ ID NO 191
<211> LENGTH: 18
<212> TYPE: PRT
<213> ORGANISM: Conus geographus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 191

Gly Cys Cys Ala Val Xaa Ser Cys Arg Leu Arg Asn Xaa Asp Leu Cys
 1               5                  10                  15

Gly Gly

<210> SEQ ID NO 192
<211> LENGTH: 16
<212> TYPE: PRT
<213> ORGANISM: Conus imperialis
<220> FEATURE:
<221> NAME/KEY: NP_BIND
<222> LOCATION: (6)..(13)
<223> OTHER INFORMATION: Xaa at residues 6 and 13 is Pro or hydroxy-Pro.

<400> SEQUENCE: 192

Gly Cys Cys Ser His Xaa Ala Cys Asn Val Asn Asn Xaa His Ile Cys
 1               5                  10                  15

<210> SEQ ID NO 193
<211> LENGTH: 20
<212> TYPE: PRT
<213> ORGANISM: Conus lividus
<220> FEATURE:
<221> NAME/KEY: SITE
<222> LOCATION: (2)..(10)
<223> OTHER INFORMATION: Xaa at residues 2, 7, 9 and 10 is Pro or
      hydroxy-Pro; Xaa at residues 3 and 4 is Glu or
      gamma-carboxy-Glu.

<400> SEQUENCE: 193

Thr Xaa Xaa Xaa Cys Cys Xaa Asn Xaa Xaa Cys Phe Ala Thr Asn Ser
 1               5                  10                  15

Asp Ile Cys Gly
            20

<210> SEQ ID NO 194
<211> LENGTH: 17
<212> TYPE: PRT
<213> ORGANISM: Conus lividus
<220> FEATURE:
<221> NAME/KEY: SITE
<222> LOCATION: (7)..(12)
<223> OTHER INFORMATION: Xaa at residue 7 is Pro or hydroxy-Pro; Xaa at
      residue 12 is Lys, N-methyl-Lys, N,N-dimethyl-Lys
      or N,N,N-trimethyl-Lys.

<400> SEQUENCE: 194

Asp Ala Cys Cys Ser Asp Xaa Arg Cys Ser Gly Xaa His Gln Asp Leu
```

-continued

```
                1               5                  10                 15
Cys

<210> SEQ ID NO 195
<211> LENGTH: 17
<212> TYPE: PRT
<213> ORGANISM: Conus lividus
<220> FEATURE:
<221> NAME/KEY: SITE
<222> LOCATION: (1)..(7)
<223> OTHER INFORMATION: Xaa at residue 1 is Glu or gamma-carboxy-Glu;
      Xaa at residue 7 is Pro or hydroxy-Pro.

<400> SEQUENCE: 195

Xaa Asp Cys Cys Ser Asp Xaa Arg Cys Ser Val Gly His Gln Asp Leu
  1               5                  10                 15
Cys

<210> SEQ ID NO 196
<211> LENGTH: 16
<212> TYPE: PRT
<213> ORGANISM: Conus lividus
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 196

Gly Cys Cys Ser His Xaa Ala Cys Ala Gly Ser Asn Ala His Ile Cys
  1               5                  10                 15

<210> SEQ ID NO 197
<211> LENGTH: 17
<212> TYPE: PRT
<213> ORGANISM: Conus lividus
<220> FEATURE:
<221> NAME/KEY: SITE
<222> LOCATION: (1)..(7)
<223> OTHER INFORMATION: Xaa at residue 1 is Glu or gamma-carboxy-Glu;
      Xaa at residue 7 is Pro or hydroxy-Pro.

<400> SEQUENCE: 197

Xaa Asp Cys Cys Ser Asp Xaa Arg Cys Ser Val Gly His Gln Asp Met
  1               5                  10                 15
Cys

<210> SEQ ID NO 198
<211> LENGTH: 16
<212> TYPE: PRT
<213> ORGANISM: Conus lividus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 198

Gly Cys Cys Ser His Xaa Ala Cys Ala Gly Asn Asn Xaa His Ile Cys
  1               5                  10                 15

<210> SEQ ID NO 199
<211> LENGTH: 17
<212> TYPE: PRT
<213> ORGANISM: Conus lividus
<220> FEATURE:
<221> NAME/KEY: SITE
<222> LOCATION: (6)..(14)
<223> OTHER INFORMATION: Xaa at residues 6 and 13 is Pro or hydroxy-Pro;
```

```
    Xaa at residue 14 is Tyr, mono-halo-Tyr,
    di-halo-Tyr, O-sulpho-Tyr, O-phospho-Tyr or
    nitro-Tyr.

<400> SEQUENCE: 199

Gly Cys Cys Gly Asn Xaa Ser Cys Ser Ile His Ile Xaa Xaa Val Cys
  1               5                  10                  15
Asn

<210> SEQ ID NO 200
<211> LENGTH: 21
<212> TYPE: PRT
<213> ORGANISM: Conus lividus
<220> FEATURE:
<221> NAME/KEY: SITE
<222> LOCATION: (4)..(5)
<223> OTHER INFORMATION: Xaa at residues 4 and 5 is Glu or
      gamma-carboxy-Glu.

<400> SEQUENCE: 200

Thr Asp Ser Xaa Xaa Cys Cys Leu Asp Ser Arg Cys Ala Gly Gln His
  1               5                  10                  15
Gln Asp Leu Cys Gly
            20

<210> SEQ ID NO 201
<211> LENGTH: 17
<212> TYPE: PRT
<213> ORGANISM: Conus marmoreus
<220> FEATURE:
<221> NAME/KEY: SITE
<222> LOCATION: (6)..(15)
<223> OTHER INFORMATION: Xaa at residues 6 and 7 is Pro or hydroxy-Pro;
      Xaa at residues 9 and 15 is Tyr, mono-halo-Tyr, di-halo-Tyr,
      O-sulpho-Tyr, O-phospho-Tyr or nitro-Tyr.

<400> SEQUENCE: 201

Gly Cys Cys Ser Asn Xaa Xaa Cys Xaa Ala Asn Asn Gln Ala Xaa Cys
  1               5                  10                  15
Asn

<210> SEQ ID NO 202
<211> LENGTH: 16
<212> TYPE: PRT
<213> ORGANISM: Conus marmoreus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 202

Gly Cys Cys Ser His Xaa Ala Cys Ser Val Asn Asn Xaa Asp Ile Cys
  1               5                  10                  15

<210> SEQ ID NO 203
<211> LENGTH: 18
<212> TYPE: PRT
<213> ORGANISM: Conus musicus
<220> FEATURE:
<221> NAME/KEY: SITE
<222> LOCATION: (2)..(15)
<223> OTHER INFORMATION: Xaa at residues 2 and 12 is Lys, N-methyl-Lys,
      N,N-dimethyl-Lys or N,N-trimethyl-Lys; Xaa at
      residue 14 is Pro or hydroxy-Pro.
<220> FEATURE:
<221> NAME/KEY: SITE
<222> LOCATION: (16)
<223> OTHER INFORMATION: Xaa at residue 16 is Tyr, mono-halo-Tyr,
```

```
        di-halo-Tyr, O-sulpho-Tyr, O-phospho-Tyr or
        nitro-Tyr.

<400> SEQUENCE: 203

Gly Xaa Cys Cys Ile Asn Asp Ala Cys Arg Ser Xaa His Xaa Gln Xaa
 1               5                  10                  15

Cys Ser

<210> SEQ ID NO 204
<211> LENGTH: 17
<212> TYPE: PRT
<213> ORGANISM: Conus musicus
<220> FEATURE:
<221> NAME/KEY: SITE
<222> LOCATION: (4)..(15)
<223> OTHER INFORMATION: Xaa at residues 4 and 15 is Tyr, nor-Tyr,
        mono-halo-Tyr, di-halo-Tyr, O-sulpho-Tyr,
        O-phospho-Tyr or nitro-Tyr; Xaa at residue 13 is
        Pro or hydroxy-Pro.

<400> SEQUENCE: 204

Gly Cys Cys Xaa Asn Ile Ala Cys Arg Ile Asn Asn Xaa Arg Xaa Cys
 1               5                  10                  15

Arg

<210> SEQ ID NO 205
<211> LENGTH: 17
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residues 6 and 13 is Pro or hydroxy-Pro;
        Xaa at residues 12 and 15 is Tyr, nor-Tyr,
        mono-halo-Tyr, di-halo-Tyr, O-sulpho-Tyr,
        O-phospho-Tyr or nitro-Tyr.
<220> FEATURE:
<221> NAME/KEY: SITE
<222> LOCATION: (14)
<223> OTHER INFORMATION: Xaa at residue 14 is Lys, N-methyl-Lys,
        N,N-dimethyl-Lys or N,N,N-trimethyl-Lys.

<400> SEQUENCE: 205

Gly Cys Cys Ser His Xaa Val Cys Arg Phe Asn Xaa Xaa Xaa Xaa Cys
 1               5                  10                  15

Gly

<210> SEQ ID NO 206
<211> LENGTH: 18
<212> TYPE: PRT
<213> ORGANISM: Conus obscurus
<220> FEATURE:
<221> NAME/KEY: SITE
<222> LOCATION: (2)..(15)
<223> OTHER INFORMATION: Xaa at residue 2 is Glu or gamma-carboxy-Glu;
        Xaa at residues 7, 8 and 14 is Pro or hydroxy-Pro; Xaa at residue
        15 is Tyr, nor-Tyr, mono-halo-Tyr, di-halo-Tyr, O-sulpho-Tyr,
        O-phospho-Tyr or
<220> FEATURE:
<221> NAME/KEY: SITE
<222> LOCATION: (2)..(15)
<223> OTHER INFORMATION: nitro-Tyr

<400> SEQUENCE: 206

Asp Xaa Cys Cys Ala Ser Xaa Xaa Cys Arg Leu Asn Asn Xaa Xaa Val
 1               5                  10                  15

Cys His
```

```
<210> SEQ ID NO 207
<211> LENGTH: 19
<212> TYPE: PRT
<213> ORGANISM: Conus obscurus
<220> FEATURE:
<221> NAME/KEY: SITE
<222> LOCATION: (6)..(18)
<223> OTHER INFORMATION: Xaa at residue 6 is Pro or hydroxy-Pro; Xaa at
      residue 9 is Trp (D or L) or halo-Trp; Xaa at
      residues 14 and 18 is Glu or gamma-carboxy-Glu.
<220> FEATURE:
<221> NAME/KEY: SITE
<222> LOCATION: (15)
<223> OTHER INFORMATION: Xaa at residue 15 is Tyr, nor-Tyr,
      mono-halo-Tyr, di-halo-Tyr, O-sulpho-Tyr, O-phospho-Tyr or
      nitro-Tyr.

<400> SEQUENCE: 207

Gly Cys Cys Ser Asn Xaa Val Cys Xaa Gln Asn Asn Ala Xaa Xaa Cys
 1               5                  10                  15

Arg Xaa Ser

<210> SEQ ID NO 208
<211> LENGTH: 16
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residues 6 and 7 is Pro or hydroxy-Pro;
      Xaa at residue 15 is Tyr, nor-Tyr, mono-halo-Tyr, di-halo-Tyr,
      O-sulpho-Tyr, O-phospho-Tyr or nitro-Tyr.

<400> SEQUENCE: 208

Gly Cys Cys Ser His Xaa Xaa Cys Ala Gln Asn Asn Gln Asp Xaa Cys
 1               5                  10                  15

<210> SEQ ID NO 209
<211> LENGTH: 19
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residue 6 is Pro or hydroxy-Pro; Xaa at
      residues 14 and 18 is Glu or gamma-carboxy-Glu;
      Xaa at residue 15 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (6)..(15)
<223> OTHER INFORMATION: nitro-Tyr.

<400> SEQUENCE: 209

Gly Cys Cys Ser His Xaa Ala Cys Ser Gly Asn Asn Arg Xaa Xaa Cys
 1               5                  10                  15

Arg Xaa Ser

<210> SEQ ID NO 210
<211> LENGTH: 18
<212> TYPE: PRT
<213> ORGANISM: Conus omaria
<220> FEATURE:
<221> NAME/KEY: SITE
<222> LOCATION: (2)..(15)
<223> OTHER INFORMATION: Xaa at residues 2, 7 and 14 is Pro or
      hydroxy-Pro; Xaa at residue 6 is Tyr, nor-Tyr, mono-halo-Tyr,
      di-halo-Tyr, O-sulpho-Tyr, O-phospho-Tyr or nitro-Tyr; Xaa at
      residue 15 is Glu or
<220> FEATURE:
```

```
<221> NAME/KEY: SITE
<222> LOCATION: (2)..(15)
<223> OTHER INFORMATION: gamma-carboxy-Glu

<400> SEQUENCE: 210

Asp Xaa Cys Cys Ser Xaa Xaa Asp Cys Gly Ala Asn His Xaa Xaa Ile
 1               5                  10                  15
Cys Gly

<210> SEQ ID NO 211
<211> LENGTH: 17
<212> TYPE: PRT
<213> ORGANISM: Conus omaria
<220> FEATURE:
<221> NAME/KEY: SITE
<222> LOCATION: (1)..(14)
<223> OTHER INFORMATION: Xaa at residues 1 and 14 is Glu or
      gamma-carboxy-Glu; Xaa at residues 6, 7 and 13 is
      Pro or hydroxy-Pro; Xaa at residue 10 is Trp (D or
      L) or halo-Trp.
<220> FEATURE:
<221> NAME/KEY: SITE
<222> LOCATION: (11)
<223> OTHER INFORMATION: Xaa at residue 11 is Lys, N-methyl-Lys,
      N,N-dimethyl-Lys or N,N,N-trimethyl-Lys.

<400> SEQUENCE: 211

Xaa Cys Cys Ser Gln Xaa Xaa Cys Arg Xaa Xaa His Xaa Xaa Leu Cys
 1               5                  10                  15
Ser

<210> SEQ ID NO 212
<211> LENGTH: 16
<212> TYPE: PRT
<213> ORGANISM: Conus omaria
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 212

Gly Cys Cys Ser His Xaa Ala Cys Ala Gly Asn Asn Xaa His Ile Cys
 1               5                  10                  15

<210> SEQ ID NO 213
<211> LENGTH: 16
<212> TYPE: PRT
<213> ORGANISM: Conus omaria
<220> FEATURE:
<221> NAME/KEY: SITE
<222> LOCATION: (6)..(15)
<223> OTHER INFORMATION: Xaa at residues 6 and 13 is Pro or hydroxy-Pro;
      Xaa at residue 15 is Tyr, nor-Tyr, mono-halo-Tyr,
      di-halo-Tyr, O-sulpho-Tyr, O-phospho-Tyr or
      nitro-Tyr.

<400> SEQUENCE: 213

Gly Cys Cys Ser Asp Xaa Ser Cys Asn Val Asn Asn Xaa Asp Xaa Cys
 1               5                  10                  15

<210> SEQ ID NO 214
<211> LENGTH: 18
<212> TYPE: PRT
<213> ORGANISM: Conus omaria
<220> FEATURE:
<221> NAME/KEY: SITE
<222> LOCATION: (1)..(7)
<223> OTHER INFORMATION: Xaa at residues 1 and 2 is Glu or
      gamma-carboxy-Glu; Xaa at residue 7 is Pro or
``` hydroxy-Pro.

<400> SEQUENCE: 214

Xaa Xaa Cys Cys Ser Asp Xaa Arg Cys Ser Val Gly His Gln Asp Met
 1               5                  10                  15

Cys Arg

<210> SEQ ID NO 215
<211> LENGTH: 17
<212> TYPE: PRT
<213> ORGANISM: Conus purpurascens
<220> FEATURE:
<221> NAME/KEY: SITE
<222> LOCATION: (7)..(15)
<223> OTHER INFORMATION: Xaa at residue 7 is Pro or hydroxy-Pro; Xaa at
      residue 15 is Glu or gamma-carboxy-Glu.

<400> SEQUENCE: 215

Gly Gly Cys Cys Ser Asn Xaa Ala Cys Leu Val Asn His Leu Xaa Met
 1               5                  10                  15

Cys

<210> SEQ ID NO 216
<211> LENGTH: 18
<212> TYPE: PRT
<213> ORGANISM: Conus purpurascens
<220> FEATURE:
<221> NAME/KEY: SITE
<222> LOCATION: (3)..(15)
<223> OTHER INFORMATION: Xaa at residues 3, 8 and 15 is Pro or
      hydroxy-Pro.

<400> SEQUENCE: 216

Arg Asp Xaa Cys Cys Phe Asn Xaa Ala Cys Asn Val Asn Asn Xaa Gln
 1               5                  10                  15

Ile Cys

<210> SEQ ID NO 217
<211> LENGTH: 21
<212> TYPE: PRT
<213> ORGANISM: Conus purpurascens
<220> FEATURE:
<221> NAME/KEY: SITE
<222> LOCATION: (5)..(8)
<223> OTHER INFORMATION: Xaa at residue 5 is Pro or hydroxy-Pro; Xaa at
      residue 8 is Trp (D or L) or halo-Trp.

<400> SEQUENCE: 217

Cys Cys Ser Asp Xaa Ser Cys Xaa Arg Leu His Ser Leu Ala Cys Thr
 1               5                  10                  15

Gly Ile Val Asn Arg
            20

<210> SEQ ID NO 218
<211> LENGTH: 16
<212> TYPE: PRT
<213> ORGANISM: Conus purpurascens
<220> FEATURE:
<221> NAME/KEY: SITE
<222> LOCATION: (5)
<223> OTHER INFORMATION: Xaa at residue 5 is Pro or hydroxy-Pro.

<400> SEQUENCE: 218

Cys Cys Thr Asn Xaa Ala Cys Leu Val Asn Asn Ile Arg Phe Cys Gly
 1               5                  10                  15

```
<210> SEQ ID NO 219
<211> LENGTH: 18
<212> TYPE: PRT
<213> ORGANISM: Conus regius
<220> FEATURE:
<221> NAME/KEY: SITE
<222> LOCATION: (2)..(7)
<223> OTHER INFORMATION: Xaa at residue 2 is Glu or gamma-carboxy-Glu;
      Xaa at residue 7 is Pro or hydroxy-Pro.

<400> SEQUENCE: 219

Asp Xaa Cys Cys Ser Asp Xaa Arg Cys His Gly Asn Asn Arg Asp His
 1               5                  10                  15

Cys Ala

<210> SEQ ID NO 220
<211> LENGTH: 17
<212> TYPE: PRT
<213> ORGANISM: Conus regius
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 220

Asp Cys Cys Ser His Xaa Leu Cys Arg Leu Phe Val Xaa Gly Leu Cys
 1               5                  10                  15

Ile

<210> SEQ ID NO 221
<211> LENGTH: 17
<212> TYPE: PRT
<213> ORGANISM: Conus regius
<220> FEATURE:
<221> NAME/KEY: SITE
<222> LOCATION: (6)..(13)
<223> OTHER INFORMATION: Xaa at residues 6 and 13 is Pro or hydroxy-Pro;
      Xaa at residue 9 is Lys, N-methyl-Lys,
      N,N-dimethyl-Lys or N,N,N-trimethyl-Lys.
<220> FEATURE:
<221> NAME/KEY: SITE
<222> LOCATION: (12)
<223> OTHER INFORMATION: Xaa at residue 12 is Tyr, nor-Tyr,
      mono-halo-Tyr, di-halo-Tyr, O-sulpho-Tyr, O-phospho-Tyr or
      nitro-Tyr.

<400> SEQUENCE: 221

Gly Cys Cys Ser His Xaa Val Cys Xaa Val Arg Xaa Xaa Asp Leu Cys
 1               5                  10                  15

Arg

<210> SEQ ID NO 222
<211> LENGTH: 16
<212> TYPE: PRT
<213> ORGANISM: Conus regius
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 222

Gly Cys Cys Ser His Xaa Ala Cys Asn Val Asn Asn Xaa His Ile Cys
 1               5                  10                  15

<210> SEQ ID NO 223
<211> LENGTH: 16
<212> TYPE: PRT
```

<213> ORGANISM: Conus regius
<220> FEATURE:
<221> NAME/KEY: SITE
<222> LOCATION: (6)..(12)
<223> OTHER INFORMATION: Xaa at residue 6 is Pro or hydroxy-Pro; Xaa at
      residue 12 is Tyr, nor-Tyr, nor-Tyr,
      mono-halo-Tyr, di-halo-Tyr, O-sulpho-Tyr,
      O-phospho-Tyr or nitro-Tyr.
<220> FEATURE:
<221> NAME/KEY: SITE
<222> LOCATION: (9)
<223> OTHER INFORMATION: Xaa at residue 9 is Lys, N-methyl-Lys,
      N,N-dimethyl-Lys or N,N,N-trimethyl-Lys.

<400> SEQUENCE: 223

Gly Cys Cys Ser His Xaa Val Cys Xaa Val Arg Xaa Ser Asp Met Cys
 1               5                  10                  15

<210> SEQ ID NO 224
<211> LENGTH: 17
<212> TYPE: PRT
<213> ORGANISM: Conus stercusmuscarum
<220> FEATURE:
<221> NAME/KEY: SITE
<222> LOCATION: (7)..(14)
<223> OTHER INFORMATION: Xaa at residues 7 and 14 is Pro or hydroxy-Pro;
      Xaa at residue 10 is Lys, N-methyl-Lys,
      N,N-dimethyl-Lys or N,N,N-trimethyl-Lys.

<400> SEQUENCE: 224

Gly Gly Cys Cys Ser His Xaa Ala Cys Xaa Val His Phe Xaa His Ser
 1               5                  10                  15

Cys

<210> SEQ ID NO 225
<211> LENGTH: 20
<212> TYPE: PRT
<213> ORGANISM: Conus stercusmuscarum
<220> FEATURE:
<221> NAME/KEY: SITE
<222> LOCATION: (6)..(14)
<223> OTHER INFORMATION: Xaa at residues 6 and 13 is Pro or hydroxy-Pro;
      Xaa at residue 14 is Glu or gamma-carboxy-Glu.

<400> SEQUENCE: 225

Val Cys Cys Ser Asn Xaa Val Cys His Val Asp His Xaa Xaa Leu Cys
 1               5                  10                  15

Arg Arg Arg Arg
            20

<210> SEQ ID NO 226
<211> LENGTH: 17
<212> TYPE: PRT
<213> ORGANISM: Conus striatus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 226

Gly Cys Cys Ser His Xaa Val Cys Asn Leu Ser Asn Xaa Gln Ile Cys
 1               5                  10                  15

Arg

<210> SEQ ID NO 227
<211> LENGTH: 18
<212> TYPE: PRT
<213> ORGANISM: Conus textile

```
<220> FEATURE:
<221> NAME/KEY: SITE
<222> LOCATION: (1)..(15)
<223> OTHER INFORMATION: Xaa at residue 1 is Gln or pyro-Glu; Xaa at
      residues 2 and 15 is Glu or gamma-carboxy-Glu; Xaa
      at residues 7 and 14 is Pro or hydroxy-Pro.

<400> SEQUENCE: 227

Xaa Xaa Cys Cys Ser His Xaa Ala Cys Asn Val Asp His Xaa Xaa Ile
 1               5                  10                  15

Cys Arg

<210> SEQ ID NO 228
<211> LENGTH: 17
<212> TYPE: PRT
<213> ORGANISM: Conus tulipa
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 228

Gly Cys Cys Ser Asn Xaa Ala Cys Leu Val Asn His Ile Arg Phe Cys
 1               5                  10                  15

Gly

<210> SEQ ID NO 229
<211> LENGTH: 17
<212> TYPE: PRT
<213> ORGANISM: Conus virgo
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 229

Asp Cys Cys Asp Asp Xaa Ala Cys Thr Val Asn Asn Xaa Gly Leu Cys
 1               5                  10                  15

Thr

<210> SEQ ID NO 230
<211> LENGTH: 20
<212> TYPE: PRT
<213> ORGANISM: Conus textile
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro; Xaa at residue 11 is Lys, N-methyl-Lys,
      N,N-dimethyl-Lys or N,N,N-trimethyl-Lys.

<400> SEQUENCE: 230

Gly Cys Cys Ser Asn Xaa Xaa Cys Ile Ala Xaa Asn Xaa His Met Cys
 1               5                  10                  15

Gly Gly Arg Arg
         20

<210> SEQ ID NO 231
<211> LENGTH: 18
<212> TYPE: PRT
<213> ORGANISM: Conus geographus
<220> FEATURE:
<221> NAME/KEY: SITE
<222> LOCATION: (5)..(9)
<223> OTHER INFORMATION: Xaa at residue 5 is Pro or hydroxy-Pro; Xaa at
      residue 8 is Tyr, nor-Tyr, mono-halo-Tyr,
      di-halo-Tyr, O-sulpho-Tyr, O-phospho-Tyr or
```

```
        nitro-Tyr; Xaa at residue 9 is Glu or
<220> FEATURE:
<221> NAME/KEY: SITE
<222> LOCATION: (9)..(14)
<223> OTHER INFORMATION: gamma-carboxy-Glu; Xaa at residues 10, 11, 12
        and 14 is Lys, N-methyl-Lys, N,N-dimethyl-Lys or
        N,N,N-trimethyl-Lys.

<400> SEQUENCE: 231

Cys Cys Thr Ile Xaa Ser Cys Xaa Xaa Xaa Xaa Xaa Ile Xaa Ala Cys
 1               5                  10                  15

Val Phe

<210> SEQ ID NO 232
<211> LENGTH: 18
<212> TYPE: PRT
<213> ORGANISM: Conus regius
<220> FEATURE:
<221> NAME/KEY: SITE
<222> LOCATION: (6)..(16)
<223> OTHER INFORMATION: Xaa at residues 6 and 16 is Pro or hydroxy-Pro;
        Xaa at residue 13 is Lys, N-methyl-Lys,
        N,N-dimethyl-Lys or N,N,N-trimethyl-Lys.

<400> SEQUENCE: 232

Gly Cys Cys Gly Asn Xaa Ala Cys Ser Gly Ser Ser Xaa Asp Ala Xaa
 1               5                  10                  15

Ser Cys

<210> SEQ ID NO 233
<211> LENGTH: 108
<212> TYPE: DNA
<213> ORGANISM: Conus imperialis
<220> FEATURE:
<221> NAME/KEY: CDS
<222> LOCATION: (1)..(105)

<400> SEQUENCE: 233 tct gat gga aag agt gcc gcg gcc aaa gcc aaa ccg tct cac ctg acg        48
Ser Asp Gly Lys Ser Ala Ala Ala Lys Ala Lys Pro Ser His Leu Thr
 1               5                  10                  15 gct cca ttc atc agg gac gaa tgc tgt tcc gat tct cgc tgt ggc aag        96
Ala Pro Phe Ile Arg Asp Glu Cys Cys Ser Asp Ser Arg Cys Gly Lys
                20                  25                  30 aac tgt ctt tga                                                       108
Asn Cys Leu
        35

<210> SEQ ID NO 234
<211> LENGTH: 35
<212> TYPE: PRT
<213> ORGANISM: Conus imperialis

<400> SEQUENCE: 234

Ser Asp Gly Lys Ser Ala Ala Ala Lys Ala Lys Pro Ser His Leu Thr
 1               5                  10                  15

Ala Pro Phe Ile Arg Asp Glu Cys Cys Ser Asp Ser Arg Cys Gly Lys
                20                  25                  30

Asn Cys Leu
        35

Y<210> SEQ ID NO 235
<211> LENGTH: 108
<212> TYPE: DNA
<213> ORGANISM: Conus imperialis
```

```
<220> FEATURE:
<221> NAME/KEY: CDS
<222> LOCATION: (1)..(105)

<400> SEQUENCE: 235 ttt gat gga agg aat gcc cca gcc gac gac aaa gcg tct gac ctg atc      48
Phe Asp Gly Arg Asn Ala Pro Ala Asp Asp Lys Ala Ser Asp Leu Ile
 1               5                  10                  15 gct caa atc gtc agg aga gca tgc tgt tcc gat cgt cgc tgt aga tgg      96
Ala Gln Ile Val Arg Arg Ala Cys Cys Ser Asp Arg Arg Cys Arg Trp
            20                  25                  30 agg tgt ggt tga                                                     108
Arg Cys Gly
        35

<210> SEQ ID NO 236
<211> LENGTH: 35
<212> TYPE: PRT
<213> ORGANISM: Conus imperialis

<400> SEQUENCE: 236

Phe Asp Gly Arg Asn Ala Pro Ala Asp Asp Lys Ala Ser Asp Leu Ile
 1               5                  10                  15

Ala Gln Ile Val Arg Arg Ala Cys Cys Ser Asp Arg Arg Cys Arg Trp
            20                  25                  30

Arg Cys Gly
        35

Y<210> SEQ ID NO 237
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 237 tct gat gga agg aat gcc gca gcc gac gcc aga gcg tct ccc cgg atc      48
Ser Asp Gly Arg Asn Ala Ala Ala Asp Ala Arg Ala Ser Pro Arg Ile
 1               5                  10                  15 gct ctt ttc ctc agg ttc aca tgc tgt agg aga ggt acc tgt tcc cag      96
Ala Leu Phe Leu Arg Phe Thr Cys Cys Arg Arg Gly Thr Cys Ser Gln
            20                  25                  30 cac tgt ggt tgaagacact gctgctccag gaccctctga accacgacgt             145
His Cys Gly
        35

<210> SEQ ID NO 238
<211> LENGTH: 35
<212> TYPE: PRT
<213> ORGANISM: Conus regius

<400> SEQUENCE: 238

Ser Asp Gly Arg Asn Ala Ala Ala Asp Ala Arg Ala Ser Pro Arg Ile
 1               5                  10                  15

Ala Leu Phe Leu Arg Phe Thr Cys Cys Arg Arg Gly Thr Cys Ser Gln
            20                  25                  30

His Cys Gly
        35

Y<210> SEQ ID NO 239
<211> LENGTH: 145
<212> TYPE: DNA
```

<213> ORGANISM: Conus regius
<220> FEATURE:
<221> NAME/KEY: CDS
<222> LOCATION: (1)..(105)

<400> SEQUENCE: 239

```
tct aat gga agg aat gcc gca gcc gac gcc aaa gcg tct caa cgg atc      48
Ser Asn Gly Arg Asn Ala Ala Ala Asp Ala Lys Ala Ser Gln Arg Ile
 1               5                  10                  15 gct cca ttc ctc agg gac tat tgc tgt agg aga cat gcc tgt acg ttg      96
Ala Pro Phe Leu Arg Asp Tyr Cys Cys Arg Arg His Ala Cys Thr Leu
            20                  25                  30 att tgt ggt tgaagacgct gctgctccag gaccctctga accacgacgt             145
Ile Cys Gly
        35
```

<210> SEQ ID NO 240
<211> LENGTH: 35
<212> TYPE: PRT
<213> ORGANISM: Conus regius

<400> SEQUENCE: 240

```
Ser Asn Gly Arg Asn Ala Ala Ala Asp Ala Lys Ala Ser Gln Arg Ile
 1               5                  10                  15

Ala Pro Phe Leu Arg Asp Tyr Cys Cys Arg Arg His Ala Cys Thr Leu
            20                  25                  30

Ile Cys Gly
        35
```

Y<210> SEQ ID NO 241
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 241

```
tct aat gga agg aat gcc gca gcc gac gcc aaa gcg tct caa cgg atc      48
Ser Asn Gly Arg Asn Ala Ala Ala Asp Ala Lys Ala Ser Gln Arg Ile
 1               5                  10                  15 gct cca ttc ctc agg gac tat tgc tgt agg aga cct ccc tgt acg ttg      96
Ala Pro Phe Leu Arg Asp Tyr Cys Cys Arg Arg Pro Pro Cys Thr Leu
            20                  25                  30 att tgt ggt tgaagacgct gctgctccag gaccctctga accacgacgt             145
Ile Cys Gly
        35
```

<210> SEQ ID NO 242
<211> LENGTH: 35
<212> TYPE: PRT
<213> ORGANISM: Conus regius

<400> SEQUENCE: 242

```
Ser Asn Gly Arg Asn Ala Ala Ala Asp Ala Lys Ala Ser Gln Arg Ile
 1               5                  10                  15

Ala Pro Phe Leu Arg Asp Tyr Cys Cys Arg Arg Pro Pro Cys Thr Leu
            20                  25                  30

Ile Cys Gly
        35
```

Y<210> SEQ ID NO 243
<211> LENGTH: 136

<212> TYPE: DNA
<213> ORGANISM: Conus regius
<220> FEATURE:
<221> NAME/KEY: CDS
<222> LOCATION: (1)..(96)

<400> SEQUENCE: 243

```
tct aat aaa agg aag aat gcc gca atg ctt gac atg atc gct caa cac      48
Ser Asn Lys Arg Lys Asn Ala Ala Met Leu Asp Met Ile Ala Gln His
 1               5                  10                  15 gcc ata agg ggt tgc tgt tcc gat cct cgc tgt aga tat aga tgt cgt      96
Ala Ile Arg Gly Cys Cys Ser Asp Pro Arg Cys Arg Tyr Arg Cys Arg
             20                  25                  30 tgaagacgct gctgctccag gaccctctga accacgacgt                         136
```

<210> SEQ ID NO 244
<211> LENGTH: 32
<212> TYPE: PRT
<213> ORGANISM: Conus regius

<400> SEQUENCE: 244

```
Ser Asn Lys Arg Lys Asn Ala Ala Met Leu Asp Met Ile Ala Gln His
 1               5                  10                  15

Ala Ile Arg Gly Cys Cys Ser Asp Pro Arg Cys Arg Tyr Arg Cys Arg
             20                  25                  30
```

<210> SEQ ID NO 245
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 245

```
ttt aat gga agg agt gcc gca gcc gac caa aat gcg cct ggc ctg atc      48
Phe Asn Gly Arg Ser Ala Ala Ala Asp Gln Asn Ala Pro Gly Leu Ile
 1               5                  10                  15 gct caa gtc gtc aga gga ggg tgc tgt tcc gat ccc cgc tgc gcc tgg      96
Ala Gln Val Val Arg Gly Gly Cys Cys Ser Asp Pro Arg Cys Ala Trp
             20                  25                  30 aga tgt ggt tgaagacgtt gctgctccag gaccctctga accacgacgt            145
Arg Cys Gly
         35
```

<210> SEQ ID NO 246
<211> LENGTH: 35
<212> TYPE: PRT
<213> ORGANISM: Conus regius

<400> SEQUENCE: 246

```
Phe Asn Gly Arg Ser Ala Ala Ala Asp Gln Asn Ala Pro Gly Leu Ile
 1               5                  10                  15

Ala Gln Val Val Arg Gly Gly Cys Cys Ser Asp Pro Arg Cys Ala Trp
             20                  25                  30

Arg Cys Gly
         35
```

<210> SEQ ID NO 247
<211> LENGTH: 145
<212> TYPE: DNA
<213> ORGANISM: Conus regius
<220> FEATURE:
<221> NAME/KEY: CDS

```
<222> LOCATION: (1)..(105)

<400> SEQUENCE: 247 ttt gat gga agg aat gcc gca gcc gac gcc aaa gtg att aac acg gtc      48
Phe Asp Gly Arg Asn Ala Ala Ala Asp Ala Lys Val Ile Asn Thr Val
  1               5                  10                  15 gct cga atc gcc tgg gat ata tgc tgt tcc gaa cct gac tgt aac cat      96
Ala Arg Ile Ala Trp Asp Ile Cys Cys Ser Glu Pro Asp Cys Asn His
             20                  25                  30 aaa tgt gtt tgaagacgct tctgctccag gaccctctga accacgacgt             145
Lys Cys Val
         35

<210> SEQ ID NO 248
<211> LENGTH: 35
<212> TYPE: PRT
<213> ORGANISM: Conus regius

<400> SEQUENCE: 248

Phe Asp Gly Arg Asn Ala Ala Ala Asp Ala Lys Val Ile Asn Thr Val
  1               5                  10                  15

Ala Arg Ile Ala Trp Asp Ile Cys Cys Ser Glu Pro Asp Cys Asn His
             20                  25                  30

Lys Cys Val
         35

<210> SEQ ID NO 249
<211> LENGTH: 136
<212> TYPE: DNA
<213> ORGANISM: Conus regius
<220> FEATURE:
<221> NAME/KEY: CDS
<222> LOCATION: (1)..(96)

<400> SEQUENCE: 249 tct aat aaa agg aag aat gcc gca atg ctt gac atg atc gct caa cac      48
Ser Asn Lys Arg Lys Asn Ala Ala Met Leu Asp Met Ile Ala Gln His
  1               5                  10                  15 gcc ata agg ggt tgc tgt tcc gat cct cgc tgt aaa cat cag tgt ggt      96
Ala Ile Arg Gly Cys Cys Ser Asp Pro Arg Cys Lys His Gln Cys Gly
             20                  25                  30 tgaagacgct gctgctccag gaccctctga accacgacgt                         136

<210> SEQ ID NO 250
<211> LENGTH: 32
<212> TYPE: PRT
<213> ORGANISM: Conus regius

<400> SEQUENCE: 250

Ser Asn Lys Arg Lys Asn Ala Ala Met Leu Asp Met Ile Ala Gln His
  1               5                  10                  15

Ala Ile Arg Gly Cys Cys Ser Asp Pro Arg Cys Lys His Gln Cys Gly
             20                  25                  30

<210> SEQ ID NO 251
<211> LENGTH: 136
<212> TYPE: DNA
<213> ORGANISM: Conus musicus
<220> FEATURE:
<221> NAME/KEY: CDS
<222> LOCATION: (1)..(105)

<400> SEQUENCE: 251
```

```
atc aag aat aca gca gcc agc aac aaa gcg tct agc ctg gtg gct ctt      48
Ile Lys Asn Thr Ala Ala Ser Asn Lys Ala Ser Ser Leu Val Ala Leu
 1               5                  10                  15 gtt gtc agg gga tgc tgt tac aat cct gtc tgc aag aaa tat tat tgt      96
Val Val Arg Gly Cys Cys Tyr Asn Pro Val Cys Lys Lys Tyr Tyr Cys
             20                  25                  30 tgg aaa ggc tgatgctcca ggaccctctg aaccacgacg t                      136
Trp Lys Gly
        35
```

<210> SEQ ID NO 252
<211> LENGTH: 35
<212> TYPE: PRT
<213> ORGANISM: Conus musicus

<400> SEQUENCE: 252

```
Ile Lys Asn Thr Ala Ala Ser Asn Lys Ala Ser Ser Leu Val Ala Leu
 1               5                  10                  15

Val Val Arg Gly Cys Cys Tyr Asn Pro Val Cys Lys Lys Tyr Tyr Cys
             20                  25                  30

Trp Lys Gly
        35
```

<210> SEQ ID NO 253
<211> LENGTH: 148
<212> TYPE: DNA
<213> ORGANISM: Conus purpurascens
<220> FEATURE:
<221> NAME/KEY: CDS
<222> LOCATION: (1)..(117)

<400> SEQUENCE: 253

```
tct gaa ggc agg aat gct gaa gcc atc gac aac gcc tta gac cag agg      48
Ser Glu Gly Arg Asn Ala Glu Ala Ile Asp Asn Ala Leu Asp Gln Arg
 1               5                  10                  15 gat cca aag cga cag gag ccg ggg tgc tgt agg cat cct gcc tgt ggg      96
Asp Pro Lys Arg Gln Glu Pro Gly Cys Cys Arg His Pro Ala Cys Gly
             20                  25                  30 aag aac aga tgt gga aga cgc tgatgctcca ggaccctctg aaccacgacg t      148
Lys Asn Arg Cys Gly Arg Arg
        35
```

<210> SEQ ID NO 254
<211> LENGTH: 39
<212> TYPE: PRT
<213> ORGANISM: Conus purpurascens

<400> SEQUENCE: 254

```
Ser Glu Gly Arg Asn Ala Glu Ala Ile Asp Asn Ala Leu Asp Gln Arg
 1               5                  10                  15

Asp Pro Lys Arg Gln Glu Pro Gly Cys Cys Arg His Pro Ala Cys Gly
             20                  25                  30

Lys Asn Arg Cys Gly Arg Arg
        35
```

<210> SEQ ID NO 255
<211> LENGTH: 156
<212> TYPE: DNA
<213> ORGANISM: Conus musicus
<220> FEATURE:
<221> NAME/KEY: CDS
<222> LOCATION: (1)..(102)

<400> SEQUENCE: 255

```
tct gat ggc agg aat att gca gtc gac gac aga tgg tct ttc tat acg      48
Ser Asp Gly Arg Asn Ile Ala Val Asp Asp Arg Trp Ser Phe Tyr Thr
 1               5                  10                  15 ctc ttc cat gct act tgc tgt gcc gat cct gac tgt aga ttc cgg ccc      96
Leu Phe His Ala Thr Cys Cys Ala Asp Pro Asp Cys Arg Phe Arg Pro
             20                  25                  30 ggt tgt tgatctttgt tcttcaaaga cgctgctggc ccaggaccct ctgaaccacg      152
Gly Cys acgt                                                                 156
```

```
<210> SEQ ID NO 256
<211> LENGTH: 34
<212> TYPE: PRT
<213> ORGANISM: Conus musicus

<400> SEQUENCE: 256

Ser Asp Gly Arg Asn Ile Ala Val Asp Asp Arg Trp Ser Phe Tyr Thr
 1               5                  10                  15

Leu Phe His Ala Thr Cys Cys Ala Asp Pro Asp Cys Arg Phe Arg Pro
             20                  25                  30

Gly Cys

<210> SEQ ID NO 257
<211> LENGTH: 142
<212> TYPE: DNA
<213> ORGANISM: Conus musicus
<220> FEATURE:
<221> NAME/KEY: CDS
<222> LOCATION: (1)..(102)

<400> SEQUENCE: 257 atc aag aat act gca gcc agc aac aaa gcg cct agc ctg gtg gct att      48
Ile Lys Asn Thr Ala Ala Ser Asn Lys Ala Pro Ser Leu Val Ala Ile
 1               5                  10                  15 gcc gtc agg gga tgc tgt tac aat cct tcc tgt tgg ccg aaa aca tat      96
Ala Val Arg Gly Cys Cys Tyr Asn Pro Ser Cys Trp Pro Lys Thr Tyr
             20                  25                  30 tgt agt tggaaaggct gatgctccag gaccctctga accacgacgt               142
Cys Ser
```

```
<210> SEQ ID NO 258
<211> LENGTH: 34
<212> TYPE: PRT
<213> ORGANISM: Conus musicus

<400> SEQUENCE: 258

Ile Lys Asn Thr Ala Ala Ser Asn Lys Ala Pro Ser Leu Val Ala Ile
 1               5                  10                  15

Ala Val Arg Gly Cys Cys Tyr Asn Pro Ser Cys Trp Pro Lys Thr Tyr
             20                  25                  30

Cys Ser

<210> SEQ ID NO 259
<211> LENGTH: 161
<212> TYPE: DNA
<213> ORGANISM: Conus musicus
<220> FEATURE:
<221> NAME/KEY: CDS
<222> LOCATION: (1)..(108)

<400> SEQUENCE: 259
```

```
tct gat agc agg aat gtc gca atc gag gac aga gtg tct gac ctg cac    48
Ser Asp Ser Arg Asn Val Ala Ile Glu Asp Arg Val Ser Asp Leu His
 1               5                  10                  15 tct atg ttc ttc gat gtt tct tgc tgt agc aat cct acc tgt aaa gaa    96
Ser Met Phe Phe Asp Val Ser Cys Cys Ser Asn Pro Thr Cys Lys Glu
                20                  25                  30 acg tat ggt tgt tgatcgttgg ttttgaagac gctgatgctc caggaccctc       148
Thr Tyr Gly Cys
            35 tgaaccacga cgt                                                    161

<210> SEQ ID NO 260
<211> LENGTH: 36
<212> TYPE: PRT
<213> ORGANISM: Conus musicus

<400> SEQUENCE: 260

Ser Asp Ser Arg Asn Val Ala Ile Glu Asp Arg Val Ser Asp Leu His
 1               5                  10                  15

Ser Met Phe Phe Asp Val Ser Cys Cys Ser Asn Pro Thr Cys Lys Glu
                20                  25                  30

Thr Tyr Gly Cys
            35

<210> SEQ ID NO 261
<211> LENGTH: 156
<212> TYPE: DNA
<213> ORGANISM: Conus musicus
<220> FEATURE:
<221> NAME/KEY: CDS
<222> LOCATION: (1)..(102)

<400> SEQUENCE: 261 tct gtt ggc agg aat att gca gtc gac gac aga ggg att ttc tct acg    48
Ser Val Gly Arg Asn Ile Ala Val Asp Asp Arg Gly Ile Phe Ser Thr
 1               5                  10                  15 ctc ttc cat gct cat tgc tgt gcc aat ccc atc tgt aaa aac acg ccc    96
Leu Phe His Ala His Cys Cys Ala Asn Pro Ile Cys Lys Asn Thr Pro
                20                  25                  30 ggt tgt tgatctttgt tcttcaaaga cgctgctggc ccaggaccct ctgaaccacg    152
Gly Cys acgt                                                              156

<210> SEQ ID NO 262
<211> LENGTH: 34
<212> TYPE: PRT
<213> ORGANISM: Conus musicus

<400> SEQUENCE: 262

Ser Val Gly Arg Asn Ile Ala Val Asp Asp Arg Gly Ile Phe Ser Thr
 1               5                  10                  15

Leu Phe His Ala His Cys Cys Ala Asn Pro Ile Cys Lys Asn Thr Pro
                20                  25                  30

Gly Cys

<210> SEQ ID NO 263
<211> LENGTH: 161
<212> TYPE: DNA
<213> ORGANISM: Conus musicus
<220> FEATURE:
<221> NAME/KEY: CDS
<222> LOCATION: (1)..(108)
```

<400> SEQUENCE: 263

| tcc | gat | ggc | agg | aat | gtc | gca | atc | gac | gac | aga | gtg | tct | gac | ctg | cac | 48 |
| Ser | Asp | Gly | Arg | Asn | Val | Ala | Ile | Asp | Asp | Arg | Val | Ser | Asp | Leu | His | |
| 1 | | | | 5 | | | | | 10 | | | | | 15 | | |

| tct | atg | ttc | ttc | gat | att | gct | tgc | tgt | aac | aat | cct | acc | tgt | aaa | gaa | 96 |
| Ser | Met | Phe | Phe | Asp | Ile | Ala | Cys | Cys | Asn | Asn | Pro | Thr | Cys | Lys | Glu | |
| | | | | 20 | | | | | 25 | | | | | 30 | | | acg tat ggt tgt tgatcgttgg ttttgaagac gctgatgctc caggaccctc    148
Thr Tyr Gly Cys
          35 tgaaccacga cgt                                                  161

<210> SEQ ID NO 264
<211> LENGTH: 36
<212> TYPE: PRT
<213> ORGANISM: Conus musicus

<400> SEQUENCE: 264

Ser Asp Gly Arg Asn Val Ala Ile Asp Asp Arg Val Ser Asp Leu His
 1               5                  10                  15

Ser Met Phe Phe Asp Ile Ala Cys Cys Asn Asn Pro Thr Cys Lys Glu
            20                  25                  30

Thr Tyr Gly Cys
         35

<210> SEQ ID NO 265
<211> LENGTH: 161
<212> TYPE: DNA
<213> ORGANISM: Conus musicus
<220> FEATURE:
<221> NAME/KEY: CDS
<222> LOCATION: (1)..(108)

<400> SEQUENCE: 265

| tct | gat | ggc | agg | aat | gtc | gca | atc | gag | gac | aga | gtg | tct | gac | ctg | ctc | 48 |
| Ser | Asp | Gly | Arg | Asn | Val | Ala | Ile | Glu | Asp | Arg | Val | Ser | Asp | Leu | Leu | |
| 1 | | | | 5 | | | | | 10 | | | | | 15 | | |

| tct | atg | ctc | ttc | gat | gtt | gct | tgc | tgt | agc | aat | cct | gtc | tgt | aaa | gaa | 96 |
| Ser | Met | Leu | Phe | Asp | Val | Ala | Cys | Cys | Ser | Asn | Pro | Val | Cys | Lys | Glu | |
| | | | | 20 | | | | | 25 | | | | | 30 | | | acg tat ggt tgt tgatcgttgg ttttgaagac gctgatgctc caggaccctc    148
Thr Tyr Gly Cys
          35 tgaaccacga cgt                                                  161

<210> SEQ ID NO 266
<211> LENGTH: 36
<212> TYPE: PRT
<213> ORGANISM: Conus musicus

<400> SEQUENCE: 266

Ser Asp Gly Arg Asn Val Ala Ile Glu Asp Arg Val Ser Asp Leu Leu
 1               5                  10                  15

Ser Met Leu Phe Asp Val Ala Cys Cys Ser Asn Pro Val Cys Lys Glu
            20                  25                  30

Thr Tyr Gly Cys
         35

<210> SEQ ID NO 267
<211> LENGTH: 154

-continued

```
<212> TYPE: DNA
<213> ORGANISM: Conus betulinus
<220> FEATURE:
<221> NAME/KEY: CDS
<222> LOCATION: (1)..(123)

<400> SEQUENCE: 267 tat gat ggc agg aat gct gcc gcc gac gac aaa gct ttt gac ctg ctg      48
Tyr Asp Gly Arg Asn Ala Ala Ala Asp Asp Lys Ala Phe Asp Leu Leu
 1               5                  10                  15 gct atg acc ata agg gga gga tgc tgt tcc tat cct ccc tgt atc gcg      96
Ala Met Thr Ile Arg Gly Gly Cys Cys Ser Tyr Pro Pro Cys Ile Ala
             20                  25                  30 agt aat cct aaa tgt ggt gga aga cgc tgatgctcca ggaccctctg           143
Ser Asn Pro Lys Cys Gly Gly Arg Arg
         35                  40 aaccacaacg t                                                          154

<210> SEQ ID NO 268
<211> LENGTH: 41
<212> TYPE: PRT
<213> ORGANISM: Conus betulinus

<400> SEQUENCE: 268

Tyr Asp Gly Arg Asn Ala Ala Ala Asp Asp Lys Ala Phe Asp Leu Leu
 1               5                  10                  15

Ala Met Thr Ile Arg Gly Gly Cys Cys Ser Tyr Pro Pro Cys Ile Ala
             20                  25                  30

Ser Asn Pro Lys Cys Gly Gly Arg Arg
         35                  40

<210> SEQ ID NO 269
<211> LENGTH: 151
<212> TYPE: DNA
<213> ORGANISM: Conus lividus
<220> FEATURE:
<221> NAME/KEY: CDS
<222> LOCATION: (1)..(111)

<400> SEQUENCE: 269 ttt gat ggc agg aat gct gca ggc aac gcc aaa atg tcc gcc ctg atg      48
Phe Asp Gly Arg Asn Ala Ala Gly Asn Ala Lys Met Ser Ala Leu Met
 1               5                  10                  15 gcc ctg acc atc agg gga tgc tgt tcc cat cct gtc tgt agc gcg atg      96
Ala Leu Thr Ile Arg Gly Cys Cys Ser His Pro Val Cys Ser Ala Met
             20                  25                  30 agt cca atc tgt ggc tgaagacgct gatgcccag gaccctctga accacgacgt     151
Ser Pro Ile Cys Gly
         35

<210> SEQ ID NO 270
<211> LENGTH: 37
<212> TYPE: PRT
<213> ORGANISM: Conus lividus

<400> SEQUENCE: 270

Phe Asp Gly Arg Asn Ala Ala Gly Asn Ala Lys Met Ser Ala Leu Met
 1               5                  10                  15

Ala Leu Thr Ile Arg Gly Cys Cys Ser His Pro Val Cys Ser Ala Met
             20                  25                  30

Ser Pro Ile Cys Gly
         35
```

```
<210> SEQ ID NO 271
<211> LENGTH: 196
<212> TYPE: DNA
<213> ORGANISM: Conus musicus
<220> FEATURE:
<221> NAME/KEY: CDS
<222> LOCATION: (1)..(165)

<400> SEQUENCE: 271 atc aag aat gct gca gct gac gac aaa gca tct gac ctg ctc tct cag      48
Ile Lys Asn Ala Ala Ala Asp Asp Lys Ala Ser Asp Leu Leu Ser Gln
 1               5                  10                  15 atc gtc agg aat gct gca tcc aat gac aaa ggg tct gac ctg atg act      96
Ile Val Arg Asn Ala Ala Ser Asn Asp Lys Gly Ser Asp Leu Met Thr
             20                  25                  30 ctt gcc ctc agg gga tgc tgt aaa aat cct tac tgt ggt gcg tcg aaa     144
Leu Ala Leu Arg Gly Cys Cys Lys Asn Pro Tyr Cys Gly Ala Ser Lys
         35                  40                  45 aca tat tgt ggt aga aga cgc tgatgctcca ggaccctctg aaccacgacg t      196
Thr Tyr Cys Gly Arg Arg Arg
     50                  55

<210> SEQ ID NO 272
<211> LENGTH: 55
<212> TYPE: PRT
<213> ORGANISM: Conus musicus

<400> SEQUENCE: 272

Ile Lys Asn Ala Ala Ala Asp Asp Lys Ala Ser Asp Leu Leu Ser Gln
 1               5                  10                  15

Ile Val Arg Asn Ala Ala Ser Asn Asp Lys Gly Ser Asp Leu Met Thr
             20                  25                  30

Leu Ala Leu Arg Gly Cys Cys Lys Asn Pro Tyr Cys Gly Ala Ser Lys
         35                  40                  45

Thr Tyr Cys Gly Arg Arg Arg
     50                  55

<210> SEQ ID NO 273
<211> LENGTH: 139
<212> TYPE: DNA
<213> ORGANISM: Conus omaria
<220> FEATURE:
<221> NAME/KEY: CDS
<222> LOCATION: (40)..(108)

<400> SEQUENCE: 273
tctgatggca ggaatgccgc agcgtctgac ctgatggat ctg acc atc aag gga       54
                                           Leu Thr Ile Lys Gly
                                            1               5 tgc tgt tct tat cct ccc tgt ttc gcg act aat cca gac tgt ggt cga     102
Cys Cys Ser Tyr Pro Pro Cys Phe Ala Thr Asn Pro Asp Cys Gly Arg
             10                  15                  20 cga cgc tgatgctcca ggaccctctg aaccacgacg t                          139
Arg Arg

<210> SEQ ID NO 274
<211> LENGTH: 23
<212> TYPE: PRT
<213> ORGANISM: Conus omaria

<400> SEQUENCE: 274

Leu Thr Ile Lys Gly Cys Cys Ser Tyr Pro Pro Cys Phe Ala Thr Asn
 1               5                  10                  15
```

```
Pro Asp Cys Gly Arg Arg Arg
            20

<210> SEQ ID NO 275
<211> LENGTH: 126
<212> TYPE: DNA
<213> ORGANISM: Conus radiatus
<220> FEATURE:
<221> NAME/KEY: CDS
<222> LOCATION: (1)..(123)

<400> SEQUENCE: 275 ttt gat ggc agg aat gcc gca gcc gac tac aaa ggg tct gaa ttg ctc        48
Phe Asp Gly Arg Asn Ala Ala Ala Asp Tyr Lys Gly Ser Glu Leu Leu
 1               5                  10                  15 gct atg acc gtc agg gga gga tgc tgt tcc tat cct ccc tgt atc gca        96
Ala Met Thr Val Arg Gly Gly Cys Cys Ser Tyr Pro Pro Cys Ile Ala
            20                  25                  30 aat aat cct ctt tgt gct gga aga cgc tga                               126
Asn Asn Pro Leu Cys Ala Gly Arg Arg
        35                  40

<210> SEQ ID NO 276
<211> LENGTH: 41
<212> TYPE: PRT
<213> ORGANISM: Conus radiatus

<400> SEQUENCE: 276

Phe Asp Gly Arg Asn Ala Ala Ala Asp Tyr Lys Gly Ser Glu Leu Leu
 1               5                  10                  15

Ala Met Thr Val Arg Gly Gly Cys Cys Ser Tyr Pro Pro Cys Ile Ala
            20                  25                  30

Asn Asn Pro Leu Cys Ala Gly Arg Arg
        35                  40

<210> SEQ ID NO 277
<211> LENGTH: 126
<212> TYPE: DNA
<213> ORGANISM: Conus radiatus
<220> FEATURE:
<221> NAME/KEY: CDS
<222> LOCATION: (1)..(123)

<400> SEQUENCE: 277 ttt gat ggc agg aat gcc gca gcc gac tac aaa ggg tct gaa ttg ctc        48
Phe Asp Gly Arg Asn Ala Ala Ala Asp Tyr Lys Gly Ser Glu Leu Leu
 1               5                  10                  15 gct atg acc gtc agg gga gga tgc tgt tcc tat cct ccc tgt atc gca        96
Ala Met Thr Val Arg Gly Gly Cys Cys Ser Tyr Pro Pro Cys Ile Ala
            20                  25                  30 aat aat cct ttt tgt gct gga aga cgc tga                               126
Asn Asn Pro Phe Cys Ala Gly Arg Arg
        35                  40

<210> SEQ ID NO 278
<211> LENGTH: 41
<212> TYPE: PRT
<213> ORGANISM: Conus radiatus

<400> SEQUENCE: 278

Phe Asp Gly Arg Asn Ala Ala Ala Asp Tyr Lys Gly Ser Glu Leu Leu
 1               5                  10                  15

Ala Met Thr Val Arg Gly Gly Cys Cys Ser Tyr Pro Pro Cys Ile Ala
```

```
                    20                  25                  30

Asn Asn Pro Phe Cys Ala Gly Arg Arg
         35                  40

<210> SEQ ID NO 279
<211> LENGTH: 155
<212> TYPE: DNA
<213> ORGANISM: Conus virgo
<220> FEATURE:
<221> NAME/KEY: CDS
<222> LOCATION: (1)..(114)

<400> SEQUENCE: 279 tct tat gac agg tat gcc tcg ccc gtc gac aga gcg tct gcc ctg atc      48
Ser Tyr Asp Arg Tyr Ala Ser Pro Val Asp Arg Ala Ser Ala Leu Ile
 1               5                  10                  15 gct cag gcc atc ctt cga gat tgc tgt tcc aat cct ccc tgt tcc caa      96
Ala Gln Ala Ile Leu Arg Asp Cys Cys Ser Asn Pro Pro Cys Ser Gln
             20                  25                  30 aat aat cca gac tgt atg taaagacgct gcttgctcca ggaccctctg            144
Asn Asn Pro Asp Cys Met
         35 aaccacgacg t                                                        155

<210> SEQ ID NO 280
<211> LENGTH: 38
<212> TYPE: PRT
<213> ORGANISM: Conus virgo

<400> SEQUENCE: 280

Ser Tyr Asp Arg Tyr Ala Ser Pro Val Asp Arg Ala Ser Ala Leu Ile
 1               5                  10                  15

Ala Gln Ala Ile Leu Arg Asp Cys Cys Ser Asn Pro Pro Cys Ser Gln
             20                  25                  30

Asn Asn Pro Asp Cys Met
         35

<210> SEQ ID NO 281
<211> LENGTH: 155
<212> TYPE: DNA
<213> ORGANISM: Conus virgo
<220> FEATURE:
<221> NAME/KEY: CDS
<222> LOCATION: (1)..(114)

<400> SEQUENCE: 281 tct tat ggc agg tat gcc tca ccc gtc gac aga gcg tct gcc ctg atc      48
Ser Tyr Gly Arg Tyr Ala Ser Pro Val Asp Arg Ala Ser Ala Leu Ile
 1               5                  10                  15 gct cag gcc atc ctt cga gat tgc tgc tcc aat cct cct tgt gcc cat      96
Ala Gln Ala Ile Leu Arg Asp Cys Cys Ser Asn Pro Pro Cys Ala His
             20                  25                  30 aat aat cca gac tgt cgt taaagacgct gcttgctcca ggaccctctg            144
Asn Asn Pro Asp Cys Arg
         35 aaccacgacg t                                                        155

<210> SEQ ID NO 282
<211> LENGTH: 38
<212> TYPE: PRT
<213> ORGANISM: Conus virgo

<400> SEQUENCE: 282
```

```
Ser Tyr Gly Arg Tyr Ala Ser Pro Val Asp Arg Ala Ser Ala Leu Ile
 1               5                  10                  15

Ala Gln Ala Ile Leu Arg Asp Cys Cys Ser Asn Pro Pro Cys Ala His
             20                  25                  30

Asn Asn Pro Asp Cys Arg
         35
```

<210> SEQ ID NO 283
<211> LENGTH: 126
<212> TYPE: DNA
<213> ORGANISM: Conus achatinus
<220> FEATURE:
<221> NAME/KEY: CDS
<222> LOCATION: (1)..(123)

<400> SEQUENCE: 283

```
tct gat ggc agg aat gcc gca gcc aac gac aaa gcg tct ggc atg agc      48
Ser Asp Gly Arg Asn Ala Ala Ala Asn Asp Lys Ala Ser Gly Met Ser
 1               5                  10                  15 gcg ctg gcc gtc aat gaa tgc tgt acc aac cct gtc tgt cac gcg gaa      96
Ala Leu Ala Val Asn Glu Cys Cys Thr Asn Pro Val Cys His Ala Glu
             20                  25                  30 cat caa gaa ctt tgt gct aga aga cgc tga                              126
His Gln Glu Leu Cys Ala Arg Arg Arg
         35                  40
```

<210> SEQ ID NO 284
<211> LENGTH: 41
<212> TYPE: PRT
<213> ORGANISM: Conus achatinus

<400> SEQUENCE: 284

```
Ser Asp Gly Arg Asn Ala Ala Ala Asn Asp Lys Ala Ser Gly Met Ser
 1               5                  10                  15

Ala Leu Ala Val Asn Glu Cys Cys Thr Asn Pro Val Cys His Ala Glu
             20                  25                  30

His Gln Glu Leu Cys Ala Arg Arg Arg
         35                  40
```

<210> SEQ ID NO 285
<211> LENGTH: 126
<212> TYPE: DNA
<213> ORGANISM: Conus achatinus
<220> FEATURE:
<221> NAME/KEY: CDS
<222> LOCATION: (1)..(123)

<400> SEQUENCE: 285

```
tct gat ggc agg aat gcc gca gcc aac gac aaa gcg tct gac gtg atc      48
Ser Asp Gly Arg Asn Ala Ala Ala Asn Asp Lys Ala Ser Asp Val Ile
 1               5                  10                  15 acg ctg gcc ctc aag gga tgc tgt tcc aac cct gtc tgt cac ttg gag      96
Thr Leu Ala Leu Lys Gly Cys Cys Ser Asn Pro Val Cys His Leu Glu
             20                  25                  30 cat tca aac ctt tgt ggt aga aga cgc tga                              126
His Ser Asn Leu Cys Gly Arg Arg Arg
         35                  40
```

<210> SEQ ID NO 286
<211> LENGTH: 41
<212> TYPE: PRT
<213> ORGANISM: Conus achatinus -continued

<400> SEQUENCE: 286

Ser Asp Gly Arg Asn Ala Ala Ala Asn Asp Lys Ala Ser Asp Val Ile
1               5                   10                  15

Thr Leu Ala Leu Lys Gly Cys Cys Ser Asn Pro Val Cys His Leu Glu
            20                  25                  30

His Ser Asn Leu Cys Gly Arg Arg Arg
        35                  40

<210> SEQ ID NO 287
<211> LENGTH: 126
<212> TYPE: DNA
<213> ORGANISM: Conus achatinus
<220> FEATURE:
<221> NAME/KEY: CDS
<222> LOCATION: (1)..(123)

<400> SEQUENCE: 287 tct gat ggc agg aat gcc gca gcc aac gac aaa gcg tct ggc atg agc     48
Ser Asp Gly Arg Asn Ala Ala Ala Asn Asp Lys Ala Ser Gly Met Ser
1               5                   10                  15 gcg ctg gcc gtc aat gaa tgc tgt acc aac cct gtc tgt cac gtg gaa     96
Ala Leu Ala Val Asn Glu Cys Cys Thr Asn Pro Val Cys His Val Glu
            20                  25                  30 cat caa gaa ctt tgt gct aga aga cgc tga                            126
His Gln Glu Leu Cys Ala Arg Arg Arg
        35                  40

<210> SEQ ID NO 288
<211> LENGTH: 41
<212> TYPE: PRT
<213> ORGANISM: Conus achatinus

<400> SEQUENCE: 288

Ser Asp Gly Arg Asn Ala Ala Ala Asn Asp Lys Ala Ser Gly Met Ser
1               5                   10                  15

Ala Leu Ala Val Asn Glu Cys Cys Thr Asn Pro Val Cys His Val Glu
            20                  25                  30

His Gln Glu Leu Cys Ala Arg Arg Arg
        35                  40

<210> SEQ ID NO 289
<211> LENGTH: 220
<212> TYPE: DNA
<213> ORGANISM: Conus ammiralis
<220> FEATURE:
<221> NAME/KEY: CDS
<222> LOCATION: (1)..(180)

<400> SEQUENCE: 289 atg ttc acc gtg ttt ctg ttg gtt gtc ttg gca acc acc gtc gtt tcc     48
Met Phe Thr Val Phe Leu Leu Val Val Leu Ala Thr Thr Val Val Ser
1               5                   10                  15 ttc act tca gat cgt gca ttt cgt ggc agg aat gcc gca gcc aaa gcg     96
Phe Thr Ser Asp Arg Ala Phe Arg Gly Arg Asn Ala Ala Ala Lys Ala
            20                  25                  30 tct ggc ctg gtc ggt ctg acc gac aag agg caa gaa tgc tgt tct tat    144
Ser Gly Leu Val Gly Leu Thr Asp Lys Arg Gln Glu Cys Cys Ser Tyr
        35                  40                  45 cct gcc tgt aac cta gat cat cca gaa ctt tgt ggt tgaagacgct         190
Pro Ala Cys Asn Leu Asp His Pro Glu Leu Cys Gly
        50                  55                  60 gatgctccag gaccctctga accacgacgt                                   220

```
<210> SEQ ID NO 290
<211> LENGTH: 60
<212> TYPE: PRT
<213> ORGANISM: Conus ammiralis

<400> SEQUENCE: 290

Met Phe Thr Val Phe Leu Leu Val Val Leu Ala Thr Thr Val Val Ser
 1               5                  10                  15

Phe Thr Ser Asp Arg Ala Phe Arg Gly Arg Asn Ala Ala Ala Lys Ala
                20                  25                  30

Ser Gly Leu Val Gly Leu Thr Asp Lys Arg Gln Glu Cys Cys Ser Tyr
            35                  40                  45

Pro Ala Cys Asn Leu Asp His Pro Glu Leu Cys Gly
        50                  55                  60

<210> SEQ ID NO 291
<211> LENGTH: 223
<212> TYPE: DNA
<213> ORGANISM: Conus ammiralis
<220> FEATURE:
<221> NAME/KEY: CDS
<222> LOCATION: (1)..(192)

<400> SEQUENCE: 291 atg ttc acc gtg ttt ctg ttg gtt gtc ttg gca acc act gtc gtt tcc      48
Met Phe Thr Val Phe Leu Leu Val Val Leu Ala Thr Thr Val Val Ser
 1               5                  10                  15 tcc act tca ggt cgt cgt gca ttt cgt ggc agg aat gcc gca gcc aaa      96
Ser Thr Ser Gly Arg Arg Ala Phe Arg Gly Arg Asn Ala Ala Ala Lys
                20                  25                  30 gcg tct gga ctg gtc ggt ctg act gac agg aga cca gaa tgc tgt agt     144
Ala Ser Gly Leu Val Gly Leu Thr Asp Arg Arg Pro Glu Cys Cys Ser
            35                  40                  45 gat cct cgc tgt aac tcg act cat cca gaa ctt tgt ggt gga aga cgc     192
Asp Pro Arg Cys Asn Ser Thr His Pro Glu Leu Cys Gly Gly Arg Arg
        50                  55                  60 tgatgctcca ggaccctctg aaccacgacg t                                   223

<210> SEQ ID NO 292
<211> LENGTH: 64
<212> TYPE: PRT
<213> ORGANISM: Conus ammiralis

<400> SEQUENCE: 292

Met Phe Thr Val Phe Leu Leu Val Val Leu Ala Thr Thr Val Val Ser
 1               5                  10                  15

Ser Thr Ser Gly Arg Arg Ala Phe Arg Gly Arg Asn Ala Ala Ala Lys
                20                  25                  30

Ala Ser Gly Leu Val Gly Leu Thr Asp Arg Arg Pro Glu Cys Cys Ser
            35                  40                  45

Asp Pro Arg Cys Asn Ser Thr His Pro Glu Leu Cys Gly Gly Arg Arg
        50                  55                  60

<210> SEQ ID NO 293
<211> LENGTH: 151
<212> TYPE: DNA
<213> ORGANISM: Conus arenatus
<220> FEATURE:
<221> NAME/KEY: CDS
<222> LOCATION: (1)..(120)
```

```
<400> SEQUENCE: 293 tct gat ggc agg aat gcc gca gcc aac gcg ttt gac ctg atc gat ctg    48
Ser Asp Gly Arg Asn Ala Ala Ala Asn Ala Phe Asp Leu Ile Asp Leu
 1               5                  10                  15 acc gcc agg cta aat tgc tgt atg att ccc ccc tgt tgg aag aaa tat    96
Thr Ala Arg Leu Asn Cys Cys Met Ile Pro Pro Cys Trp Lys Lys Tyr
             20                  25                  30 gga gac aga tgt agt gaa gta cgc tgatgctcca ggaccctctg aaccacgacg   150
Gly Asp Arg Cys Ser Glu Val Arg
         35                  40 t                                                                  151

<210> SEQ ID NO 294
<211> LENGTH: 40
<212> TYPE: PRT
<213> ORGANISM: Conus arenatus

<400> SEQUENCE: 294

Ser Asp Gly Arg Asn Ala Ala Ala Asn Ala Phe Asp Leu Ile Asp Leu
 1               5                  10                  15

Thr Ala Arg Leu Asn Cys Cys Met Ile Pro Pro Cys Trp Lys Lys Tyr
             20                  25                  30

Gly Asp Arg Cys Ser Glu Val Arg
         35                  40

<210> SEQ ID NO 295
<211> LENGTH: 126
<212> TYPE: DNA
<213> ORGANISM: Conus arenatus
<220> FEATURE:
<221> NAME/KEY: CDS
<222> LOCATION: (1)..(93)

<400> SEQUENCE: 295 tct gat ggc agg aat gcc gca cgc aaa gcg ttt ggc tgc tgc gac tta    48
Ser Asp Gly Arg Asn Ala Ala Arg Lys Ala Phe Gly Cys Cys Asp Leu
 1               5                  10                  15 ata ccc tgt ttg gag aga tat ggt aac aga tgt aat gaa gtg cac        93
Ile Pro Cys Leu Glu Arg Tyr Gly Asn Arg Cys Asn Glu Val His
             20                  25                  30 tgatgctcca ggaccctctg aaccacgcga cgt                              126

<210> SEQ ID NO 296
<211> LENGTH: 31
<212> TYPE: PRT
<213> ORGANISM: Conus arenatus

<400> SEQUENCE: 296

Ser Asp Gly Arg Asn Ala Ala Arg Lys Ala Phe Gly Cys Cys Asp Leu
 1               5                  10                  15

Ile Pro Cys Leu Glu Arg Tyr Gly Asn Arg Cys Asn Glu Val His
             20                  25                  30

<210> SEQ ID NO 297
<211> LENGTH: 151
<212> TYPE: DNA
<213> ORGANISM: Conus arenatus
<220> FEATURE:
<221> NAME/KEY: CDS
<222> LOCATION: (1)..(120)

<400> SEQUENCE: 297
```

```
tct gat ggc agc aat gcc gca gcc aac gag ttt gac ctg atc gct ctg      48
Ser Asp Gly Ser Asn Ala Ala Ala Asn Glu Phe Asp Leu Ile Ala Leu
 1               5                  10                  15 acc gcc agg cta ggt tgc tgt aac gtt aca ccc tgt tgg gag aaa tat      96
Thr Ala Arg Leu Gly Cys Cys Asn Val Thr Pro Cys Trp Glu Lys Tyr
             20                  25                  30 gga gac aaa tgt aat gaa gta cgc tgatgcttca ggaccctctg aaccacgacg    150
Gly Asp Lys Cys Asn Glu Val Arg
         35                  40 t                                                                   151

<210> SEQ ID NO 298
<211> LENGTH: 40
<212> TYPE: PRT
<213> ORGANISM: Conus arenatus

<400> SEQUENCE: 298

Ser Asp Gly Ser Asn Ala Ala Ala Asn Glu Phe Asp Leu Ile Ala Leu
 1               5                  10                  15

Thr Ala Arg Leu Gly Cys Cys Asn Val Thr Pro Cys Trp Glu Lys Tyr
             20                  25                  30

Gly Asp Lys Cys Asn Glu Val Arg
         35                  40

<210> SEQ ID NO 299
<211> LENGTH: 148
<212> TYPE: DNA
<213> ORGANISM: Conus arenatus
<220> FEATURE:
<221> NAME/KEY: CDS
<222> LOCATION: (1)..(117)

<400> SEQUENCE: 299 tct gat ggc agg aat gtc gca gca aaa gcg ttt cac cgg atc ggc cgg      48
Ser Asp Gly Arg Asn Val Ala Ala Lys Ala Phe His Arg Ile Gly Arg
 1               5                  10                  15 acc atc agg gat gaa tgc tgt tcc aat cct gcc tgt agg gtg aat aat      96
Thr Ile Arg Asp Glu Cys Cys Ser Asn Pro Ala Cys Arg Val Asn Asn
             20                  25                  30 cca cac gtt tgt aga cga cgc tgatgctcca ggaccctctg aaccacgacg t      148
Pro His Val Cys Arg Arg Arg
         35

<210> SEQ ID NO 300
<211> LENGTH: 39
<212> TYPE: PRT
<213> ORGANISM: Conus arenatus

<400> SEQUENCE: 300

Ser Asp Gly Arg Asn Val Ala Ala Lys Ala Phe His Arg Ile Gly Arg
 1               5                  10                  15

Thr Ile Arg Asp Glu Cys Cys Ser Asn Pro Ala Cys Arg Val Asn Asn
             20                  25                  30

Pro His Val Cys Arg Arg Arg
         35

<210> SEQ ID NO 301
<211> LENGTH: 151
<212> TYPE: DNA
<213> ORGANISM: Conus arenatus
<220> FEATURE:
<221> NAME/KEY: CDS
<222> LOCATION: (1)..(120)
```

```
<400> SEQUENCE: 301 tct gat ggc agg aat gcc gca gcc aac gcg ttt gac ctg atg cct ctg     48
Ser Asp Gly Arg Asn Ala Ala Ala Asn Ala Phe Asp Leu Met Pro Leu
 1               5                  10                  15 acc gcc agg cta aat tgc tgt agc att ccc ggc tgt tgg aac gaa tat     96
Thr Ala Arg Leu Asn Cys Cys Ser Ile Pro Gly Cys Trp Asn Glu Tyr
                20                  25                  30 aaa gac aga tgt agt aaa gta cgc tgatgctcca ggaccctctg aaccacgacg   150
Lys Asp Arg Cys Ser Lys Val Arg
            35                  40 t                                                                  151

<210> SEQ ID NO 302
<211> LENGTH: 40
<212> TYPE: PRT
<213> ORGANISM: Conus arenatus

<400> SEQUENCE: 302

Ser Asp Gly Arg Asn Ala Ala Ala Asn Ala Phe Asp Leu Met Pro Leu
 1               5                  10                  15

Thr Ala Arg Leu Asn Cys Cys Ser Ile Pro Gly Cys Trp Asn Glu Tyr
                20                  25                  30

Lys Asp Arg Cys Ser Lys Val Arg
            35                  40

<210> SEQ ID NO 303
<211> LENGTH: 157
<212> TYPE: DNA
<213> ORGANISM: Conus aurisiacus
<220> FEATURE:
<221> NAME/KEY: CDS
<222> LOCATION: (52)..(126)

<400> SEQUENCE: 303
tctgatggca ggaatgccgc agccgacgac aaagcgtctg acctggtcgc t ctg gtc    57
                                                         Leu Val
                                                          1 gtc agg gga gga tgc tgt tcc cac cct gtc tgt tac ttt aat aat cca   105
Val Arg Gly Gly Cys Cys Ser His Pro Val Cys Tyr Phe Asn Asn Pro
         5                  10                  15 caa atg tgt cgt gga aga cgc tgatgctcca ggaccctctg aaccacgacg t    157
Gln Met Cys Arg Gly Arg Arg
        20                  25

<210> SEQ ID NO 304
<211> LENGTH: 25
<212> TYPE: PRT
<213> ORGANISM: Conus aurisiacus

<400> SEQUENCE: 304

Leu Val Val Arg Gly Gly Cys Cys Ser His Pro Val Cys Tyr Phe Asn
 1               5                  10                  15

Asn Pro Gln Met Cys Arg Gly Arg Arg
                20                  25

<210> SEQ ID NO 305
<211> LENGTH: 157
<212> TYPE: DNA
<213> ORGANISM: Conus aurisiacus
<220> FEATURE:
<221> NAME/KEY: CDS
<222> LOCATION: (52)..(126)
```

-continued

```
<400> SEQUENCE: 305
tctgatggca ggaatgccgc agccgacgac aaagcgtctg acctggtcgc t ctg gcc       57
                                                         Leu Ala
                                                           1 gtc agg gga gga tgc tgt tcc cac cct gtc tgt aac ttg aat aat cca      105
Val Arg Gly Gly Cys Cys Ser His Pro Val Cys Asn Leu Asn Asn Pro
        5                  10                  15 caa atg tgt cgt gga aga cgc tgatgctcca ggaccctctg aaccacgacg t       157
Gln Met Cys Arg Gly Arg Arg
 20              25

<210> SEQ ID NO 306
<211> LENGTH: 25
<212> TYPE: PRT
<213> ORGANISM: Conus aurisiacus

<400> SEQUENCE: 306

Leu Ala Val Arg Gly Gly Cys Cys Ser His Pro Val Cys Asn Leu Asn
  1               5                  10                  15

Asn Pro Gln Met Cys Arg Gly Arg Arg
             20                  25

<210> SEQ ID NO 307
<211> LENGTH: 157
<212> TYPE: DNA
<213> ORGANISM: Conus betulinus
<220> FEATURE:
<221> NAME/KEY: CDS
<222> LOCATION: (1)..(117)

<400> SEQUENCE: 307 ttt cgt ggc agg aat ccc gca gcc aac gac aaa agg tct gac ctg gcc       48
Phe Arg Gly Arg Asn Pro Ala Ala Asn Asp Lys Arg Ser Asp Leu Ala
  1               5                  10                  15 gct ctg agc gtc agg gga gga tgc tgt tcc cat cct gcc tgt agc gtg       96
Ala Leu Ser Val Arg Gly Gly Cys Cys Ser His Pro Ala Cys Ser Val
             20                  25                  30 act cat cca gag ctt tgt ggc tgaagacgct gatgcccag gaccctctga         147
Thr His Pro Glu Leu Cys Gly
             35 accacgacgt                                                          157

<210> SEQ ID NO 308
<211> LENGTH: 39
<212> TYPE: PRT
<213> ORGANISM: Conus betulinus

<400> SEQUENCE: 308

Phe Arg Gly Arg Asn Pro Ala Ala Asn Asp Lys Arg Ser Asp Leu Ala
  1               5                  10                  15

Ala Leu Ser Val Arg Gly Gly Cys Cys Ser His Pro Ala Cys Ser Val
             20                  25                  30

Thr His Pro Glu Leu Cys Gly
             35

<210> SEQ ID NO 309
<211> LENGTH: 151
<212> TYPE: DNA
<213> ORGANISM: Conus betulinus
<220> FEATURE:
<221> NAME/KEY: CDS
<222> LOCATION: (1)..(120)
```

```
<400> SEQUENCE: 309 tct gat ggc ggg aat gcc gca gcc aaa gcg tct gac ctg atc gct cag      48
Ser Asp Gly Gly Asn Ala Ala Ala Lys Ala Ser Asp Leu Ile Ala Gln
 1               5                  10                  15 acc atc agg gga gga tgc tgt tcc tat cct gcc tgt agc gtg gaa cat      96
Thr Ile Arg Gly Gly Cys Cys Ser Tyr Pro Ala Cys Ser Val Glu His
             20                  25                  30 caa gac ctt tgt gat gga aga cgc tgatgctcca ggaccctctg aaccacgacg    150
Gln Asp Leu Cys Asp Gly Arg Arg
         35                  40 t                                                                   151

<210> SEQ ID NO 310
<211> LENGTH: 40
<212> TYPE: PRT
<213> ORGANISM: Conus betulinus

<400> SEQUENCE: 310

Ser Asp Gly Gly Asn Ala Ala Ala Lys Ala Ser Asp Leu Ile Ala Gln
 1               5                  10                  15

Thr Ile Arg Gly Gly Cys Cys Ser Tyr Pro Ala Cys Ser Val Glu His
             20                  25                  30

Gln Asp Leu Cys Asp Gly Arg Arg
         35                  40

<210> SEQ ID NO 311
<211> LENGTH: 114
<212> TYPE: DNA
<213> ORGANISM: Conus caracteristicus
<220> FEATURE:
<221> NAME/KEY: CDS
<222> LOCATION: (1)..(111)

<400> SEQUENCE: 311 tct tat ggc agg aat gcc gca gcc aaa gcg ttt gaa gtg agt tgc tgt      48
Ser Tyr Gly Arg Asn Ala Ala Ala Lys Ala Phe Glu Val Ser Cys Cys
 1               5                  10                  15 gtc gtt cgc ccc tgt tgg att cgc tat caa gag gaa tgt ctt gaa gca      96
Val Val Arg Pro Cys Trp Ile Arg Tyr Gln Glu Glu Cys Leu Glu Ala
             20                  25                  30 gat ccc agg acc ctc tga                                             114
Asp Pro Arg Thr Leu
         35

<210> SEQ ID NO 312
<211> LENGTH: 37
<212> TYPE: PRT
<213> ORGANISM: Conus caracteristicus

<400> SEQUENCE: 312

Ser Tyr Gly Arg Asn Ala Ala Ala Lys Ala Phe Glu Val Ser Cys Cys
 1               5                  10                  15

Val Val Arg Pro Cys Trp Ile Arg Tyr Gln Glu Glu Cys Leu Glu Ala
             20                  25                  30

Asp Pro Arg Thr Leu
         35

<210> SEQ ID NO 313
<211> LENGTH: 123
<212> TYPE: DNA
<213> ORGANISM: Conus caracteristicus
```

```
<220> FEATURE:
<221> NAME/KEY: CDS
<222> LOCATION: (1)..(120)

<400> SEQUENCE: 313 tct gat ggc agg aat gcc gca gcc aac gcc ctt gac ctg atc act ctg    48
Ser Asp Gly Arg Asn Ala Ala Ala Asn Ala Leu Asp Leu Ile Thr Leu
 1               5                  10                  15 atc gcc agg caa aat tgc tgt agc att ccc ggc tgt tgg gag aaa tat    96
Ile Ala Arg Gln Asn Cys Cys Ser Ile Pro Gly Cys Trp Glu Lys Tyr
             20                  25                  30 gga gac aaa tgt agt gaa gta cgc tga                                123
Gly Asp Lys Cys Ser Glu Val Arg
         35                  40

<210> SEQ ID NO 314
<211> LENGTH: 40
<212> TYPE: PRT
<213> ORGANISM: Conus caracteristicus

<400> SEQUENCE: 314

Ser Asp Gly Arg Asn Ala Ala Ala Asn Ala Leu Asp Leu Ile Thr Leu
 1               5                  10                  15

Ile Ala Arg Gln Asn Cys Cys Ser Ile Pro Gly Cys Trp Glu Lys Tyr
             20                  25                  30

Gly Asp Lys Cys Ser Glu Val Arg
         35                  40

<210> SEQ ID NO 315
<211> LENGTH: 154
<212> TYPE: DNA
<213> ORGANISM: Conus catus
<220> FEATURE:
<221> NAME/KEY: CDS
<222> LOCATION: (1)..(123)

<400> SEQUENCE: 315 tct gat ggc agg aat gaa gca gcc aac gac gaa gcg tct gac gtg atc    48
Ser Asp Gly Arg Asn Glu Ala Ala Asn Asp Glu Ala Ser Asp Val Ile
 1               5                  10                  15 gag ctg gcc ctc aag gga tgc tgt tcc aac cct gtc tgt cac ttg gag    96
Glu Leu Ala Leu Lys Gly Cys Cys Ser Asn Pro Val Cys His Leu Glu
             20                  25                  30 cat cca aac gct tgt ggt aga aga cgc tgatgctcca ggaccctctg          143
His Pro Asn Ala Cys Gly Arg Arg Arg
         35                  40 aaccacgacg t                                                       154

<210> SEQ ID NO 316
<211> LENGTH: 41
<212> TYPE: PRT
<213> ORGANISM: Conus catus

<400> SEQUENCE: 316

Ser Asp Gly Arg Asn Glu Ala Ala Asn Asp Glu Ala Ser Asp Val Ile
 1               5                  10                  15

Glu Leu Ala Leu Lys Gly Cys Cys Ser Asn Pro Val Cys His Leu Glu
             20                  25                  30

His Pro Asn Ala Cys Gly Arg Arg Arg
         35                  40

<210> SEQ ID NO 317
```

<211> LENGTH: 154
<212> TYPE: DNA
<213> ORGANISM: Conus catus
<220> FEATURE:
<221> NAME/KEY: CDS
<222> LOCATION: (1)..(123)

<400> SEQUENCE: 317

```
tct gat ggc agg aat gcc gca gcc aac gac aaa gcg tct gac ctg gtc        48
Ser Asp Gly Arg Asn Ala Ala Ala Asn Asp Lys Ala Ser Asp Leu Val
 1               5                  10                  15 gct ctg gcc gtc agg gga tgc tgt tcc aac cct atc tgt tac ttt aat        96
Ala Leu Ala Val Arg Gly Cys Cys Ser Asn Pro Ile Cys Tyr Phe Asn
                20                  25                  30 aat cca cga att tgt cgt gga aga cgc tgatgctcca ggaccctctg             143
Asn Pro Arg Ile Cys Arg Gly Arg Arg
                35                  40 aaccacgacg t                                                          154
```

<210> SEQ ID NO 318
<211> LENGTH: 41
<212> TYPE: PRT
<213> ORGANISM: Conus catus

<400> SEQUENCE: 318

```
Ser Asp Gly Arg Asn Ala Ala Ala Asn Asp Lys Ala Ser Asp Leu Val
 1               5                  10                  15

Ala Leu Ala Val Arg Gly Cys Cys Ser Asn Pro Ile Cys Tyr Phe Asn
                20                  25                  30

Asn Pro Arg Ile Cys Arg Gly Arg Arg
                35                  40
```

<210> SEQ ID NO 319
<211> LENGTH: 111
<212> TYPE: DNA
<213> ORGANISM: Conus episcopatus
<220> FEATURE:
<221> NAME/KEY: CDS
<222> LOCATION: (1)..(108)

<400> SEQUENCE: 319

```
tct cat ggc agg aat gcc gca cgc aaa gcg tct gac ctg atc gct ctg        48
Ser His Gly Arg Asn Ala Ala Arg Lys Ala Ser Asp Leu Ile Ala Leu
 1               5                  10                  15 acc gtc agg gaa tgc tgt tct cag cct ccc tgt cgc tgg aaa cat cca        96
Thr Val Arg Glu Cys Cys Ser Gln Pro Pro Cys Arg Trp Lys His Pro
                20                  25                  30 gaa ctt tgt agt tga                                                   111
Glu Leu Cys Ser
                35
```

<210> SEQ ID NO 320
<211> LENGTH: 36
<212> TYPE: PRT
<213> ORGANISM: Conus episcopatus

<400> SEQUENCE: 320

```
Ser His Gly Arg Asn Ala Ala Arg Lys Ala Ser Asp Leu Ile Ala Leu
 1               5                  10                  15

Thr Val Arg Glu Cys Cys Ser Gln Pro Pro Cys Arg Trp Lys His Pro
                20                  25                  30

Glu Leu Cys Ser
                35
```

<210> SEQ ID NO 321
<211> LENGTH: 151
<212> TYPE: DNA
<213> ORGANISM: Conus geographus
<220> FEATURE:
<221> NAME/KEY: CDS
<222> LOCATION: (1)..(120)

<400> SEQUENCE: 321

```
tct gat ggc agg aat gac gca gcc aaa gcg ttt gac ctg ata tct tcg         48
Ser Asp Gly Arg Asn Asp Ala Ala Lys Ala Phe Asp Leu Ile Ser Ser
 1               5                  10                  15 acc gtc aag aaa gga tgc tgt tcc cat cct gcc tgt gcg ggg aat aat         96
Thr Val Lys Lys Gly Cys Cys Ser His Pro Ala Cys Ala Gly Asn Asn
             20                  25                  30 caa cat att tgt ggc cga aga cgc tgatgctcca ggaccctctg aaccacgacg       150
Gln His Ile Cys Gly Arg Arg Arg
         35                  40 t                                                                      151
```

<210> SEQ ID NO 322
<211> LENGTH: 40
<212> TYPE: PRT
<213> ORGANISM: Conus geographus

<400> SEQUENCE: 322

```
Ser Asp Gly Arg Asn Asp Ala Ala Lys Ala Phe Asp Leu Ile Ser Ser
 1               5                  10                  15

Thr Val Lys Lys Gly Cys Cys Ser His Pro Ala Cys Ala Gly Asn Asn
             20                  25                  30

Gln His Ile Cys Gly Arg Arg Arg
         35                  40
```

<210> SEQ ID NO 323
<211> LENGTH: 154
<212> TYPE: DNA
<213> ORGANISM: Conus geographus
<220> FEATURE:
<221> NAME/KEY: CDS
<222> LOCATION: (1)..(123)

<400> SEQUENCE: 323

```
tct gat ggc agg aat gcc gca gcc aac gac caa gcg tct gac ctg atg         48
Ser Asp Gly Arg Asn Ala Ala Ala Asn Asp Gln Ala Ser Asp Leu Met
 1               5                  10                  15 gct gcg acc gtc agg gga tgc tgt gcc gtt cct tcc tgt cgc ctc cgt         96
Ala Ala Thr Val Arg Gly Cys Cys Ala Val Pro Ser Cys Arg Leu Arg
             20                  25                  30 aat cca gac ctt tgt ggt gga gga cgc tgatgctcca ggaccctctg              143
Asn Pro Asp Leu Cys Gly Gly Gly Arg
         35                  40 aaccacgacg t                                                           154
```

<210> SEQ ID NO 324
<211> LENGTH: 41
<212> TYPE: PRT
<213> ORGANISM: Conus geographus

<400> SEQUENCE: 324

```
Ser Asp Gly Arg Asn Ala Ala Ala Asn Asp Gln Ala Ser Asp Leu Met
 1               5                  10                  15
```

Ala Ala Thr Val Arg Gly Cys Cys Ala Val Pro Ser Cys Arg Leu Arg
            20                  25                  30

Asn Pro Asp Leu Cys Gly Gly Arg
        35                  40

<210> SEQ ID NO 325
<211> LENGTH: 120
<212> TYPE: DNA
<213> ORGANISM: Conus imperialis
<220> FEATURE:
<221> NAME/KEY: CDS
<222> LOCATION: (1)..(117)

<400> SEQUENCE: 325 ctt gat gaa agg aat gcc gca gcc gac gac aaa gcg tct gac ctg atc        48
Leu Asp Glu Arg Asn Ala Ala Ala Asp Asp Lys Ala Ser Asp Leu Ile
 1               5                  10                  15 gct caa atc gtc agg aga gga tgc tgt tcc cat cct gcc tgt aac gtg        96
Ala Gln Ile Val Arg Arg Gly Cys Cys Ser His Pro Ala Cys Asn Val
            20                  25                  30 aat aat cca cac att tgt ggt tga                                       120
Asn Asn Pro His Ile Cys Gly
        35

<210> SEQ ID NO 326
<211> LENGTH: 39
<212> TYPE: PRT
<213> ORGANISM: Conus imperialis

<400> SEQUENCE: 326

Leu Asp Glu Arg Asn Ala Ala Ala Asp Asp Lys Ala Ser Asp Leu Ile
 1               5                  10                  15

Ala Gln Ile Val Arg Arg Gly Cys Cys Ser His Pro Ala Cys Asn Val
            20                  25                  30

Asn Asn Pro His Ile Cys Gly
        35

<210> SEQ ID NO 327
<211> LENGTH: 142
<212> TYPE: DNA
<213> ORGANISM: Conus lividus
<220> FEATURE:
<221> NAME/KEY: CDS
<222> LOCATION: (1)..(111)

<400> SEQUENCE: 327 tct gat ggc agg aat act gca gcc aaa gtc aaa tat tct aag acg ccg        48
Ser Asp Gly Arg Asn Thr Ala Ala Lys Val Lys Tyr Ser Lys Thr Pro
 1               5                  10                  15 gag gaa tgc tgt ccc aat cct ccc tgt ttc gcg aca aat tcg gat att        96
Glu Glu Cys Cys Pro Asn Pro Pro Cys Phe Ala Thr Asn Ser Asp Ile
            20                  25                  30 tgt ggc gga aga cgc tgatgctcca ggaccctctg aaccacgacg t               142
Cys Gly Gly Arg Arg
        35

<210> SEQ ID NO 328
<211> LENGTH: 37
<212> TYPE: PRT
<213> ORGANISM: Conus lividus

<400> SEQUENCE: 328

Ser Asp Gly Arg Asn Thr Ala Ala Lys Val Lys Tyr Ser Lys Thr Pro
 1               5                  10                  15

Glu Glu Cys Cys Pro Asn Pro Pro Cys Phe Ala Thr Asn Ser Asp Ile
            20                  25                  30

Cys Gly Gly Arg Arg
        35

<210> SEQ ID NO 329
<211> LENGTH: 157
<212> TYPE: DNA
<213> ORGANISM: Conus lividus
<220> FEATURE:
<221> NAME/KEY: CDS
<222> LOCATION: (1)..(117)

<400> SEQUENCE: 329 tct aat ggc agg aat gcc gca gcc aaa ttc aaa gcg cct gcc ctg atg       48
Ser Asn Gly Arg Asn Ala Ala Ala Lys Phe Lys Ala Pro Ala Leu Met
 1               5                  10                  15 aag cgg acc gtc agg gat gct tgc tgt tca gac cct cgc tgt tcc ggg       96
Lys Arg Thr Val Arg Asp Ala Cys Cys Ser Asp Pro Arg Cys Ser Gly
            20                  25                  30 aaa cat caa gac ctg tgt ggc tgaagacgct gatgctccag gaccctctga        147
Lys His Gln Asp Leu Cys Gly
        35 accacgacgt                                                          157

<210> SEQ ID NO 330
<211> LENGTH: 39
<212> TYPE: PRT
<213> ORGANISM: Conus lividus

<400> SEQUENCE: 330

Ser Asn Gly Arg Asn Ala Ala Ala Lys Phe Lys Ala Pro Ala Leu Met
 1               5                  10                  15

Lys Arg Thr Val Arg Asp Ala Cys Cys Ser Asp Pro Arg Cys Ser Gly
            20                  25                  30

Lys His Gln Asp Leu Cys Gly
        35

<210> SEQ ID NO 331
<211> LENGTH: 157
<212> TYPE: DNA
<213> ORGANISM: Conus lividus
<220> FEATURE:
<221> NAME/KEY: CDS
<222> LOCATION: (1)..(117)

<400> SEQUENCE: 331 tct aat ggc agg aat gcc gca gcc aaa ttc aaa gcg cct gcc ctg atg       48
Ser Asn Gly Arg Asn Ala Ala Ala Lys Phe Lys Ala Pro Ala Leu Met
 1               5                  10                  15 gag ctg acc gtc agg gaa gat tgc tgt tca gac cct cgc tgt tcc gtg       96
Glu Leu Thr Val Arg Glu Asp Cys Cys Ser Asp Pro Arg Cys Ser Val
            20                  25                  30 gga cat caa gac ctg tgt ggc tgaagacgct gatgctccag gaccctctga        147
Gly His Gln Asp Leu Cys Gly
        35 accacgacgt                                                          157

<210> SEQ ID NO 332
<211> LENGTH: 39
<212> TYPE: PRT
<213> ORGANISM: Conus lividus

```
<400> SEQUENCE: 332

Ser Asn Gly Arg Asn Ala Ala Lys Phe Lys Ala Pro Ala Leu Met
1               5                   10                  15

Glu Leu Thr Val Arg Glu Asp Cys Cys Ser Asp Pro Arg Cys Ser Val
                20                  25                  30

Gly His Gln Asp Leu Cys Gly
            35

<210> SEQ ID NO 333
<211> LENGTH: 157
<212> TYPE: DNA
<213> ORGANISM: Conus lividus
<220> FEATURE:
<221> NAME/KEY: CDS
<222> LOCATION: (1)..(126)

<400> SEQUENCE: 333 gca ttt gat ggc agg aat gct gca gcc agc gac aaa gcg tcc gag ctg      48
Ala Phe Asp Gly Arg Asn Ala Ala Ala Ser Asp Lys Ala Ser Glu Leu
1               5                   10                  15 atg gct ctg gcc gtc agg gga tgc tgt tcc cat cct gcc tgt gct ggg      96
Met Ala Leu Ala Val Arg Gly Cys Cys Ser His Pro Ala Cys Ala Gly
                20                  25                  30 agt aat gca cat atc tgt ggc aga aga cgc tgatgctcca ggaccctctg       146
Ser Asn Ala His Ile Cys Gly Arg Arg Arg
            35                  40 aaccacgacg t                                                         157

<210> SEQ ID NO 334
<211> LENGTH: 42
<212> TYPE: PRT
<213> ORGANISM: Conus lividus

<400> SEQUENCE: 334

Ala Phe Asp Gly Arg Asn Ala Ala Ala Ser Asp Lys Ala Ser Glu Leu
1               5                   10                  15

Met Ala Leu Ala Val Arg Gly Cys Cys Ser His Pro Ala Cys Ala Gly
                20                  25                  30

Ser Asn Ala His Ile Cys Gly Arg Arg Arg
            35                  40

<210> SEQ ID NO 335
<211> LENGTH: 157
<212> TYPE: DNA
<213> ORGANISM: Conus lividus
<220> FEATURE:
<221> NAME/KEY: CDS
<222> LOCATION: (1)..(117)

<400> SEQUENCE: 335 tct aat ggc agg aat gcc gca gcc aaa ttc aaa gcg cct gcc ctg atg      48
Ser Asn Gly Arg Asn Ala Ala Ala Lys Phe Lys Ala Pro Ala Leu Met
1               5                   10                  15 aag ctg acc gtc agg gag gat tgc tgt tca gac cct cgc tgt tcc gtg      96
Lys Leu Thr Val Arg Glu Asp Cys Cys Ser Asp Pro Arg Cys Ser Val
                20                  25                  30 gga cat caa gac atg tgt ggc tgaagacgct gatgctccag gaccctctga        147
Gly His Gln Asp Met Cys Gly
            35 atcacgacgt                                                           157
```

<210> SEQ ID NO 336
<211> LENGTH: 39
<212> TYPE: PRT
<213> ORGANISM: Conus lividus

<400> SEQUENCE: 336

Ser Asn Gly Arg Asn Ala Ala Lys Phe Lys Ala Pro Ala Leu Met
1               5                   10                  15

Lys Leu Thr Val Arg Glu Asp Cys Cys Ser Asp Pro Arg Cys Ser Val
            20                  25                  30

Gly His Gln Asp Met Cys Gly
        35

<210> SEQ ID NO 337
<211> LENGTH: 154
<212> TYPE: DNA
<213> ORGANISM: Conus lividus
<220> FEATURE:
<221> NAME/KEY: CDS
<222> LOCATION: (1)..(114)

<400> SEQUENCE: 337 ttt gaa tgc agg aat gct gca ggc aac gac aaa gcg act gac ctg atg      48
Phe Glu Cys Arg Asn Ala Ala Gly Asn Asp Lys Ala Thr Asp Leu Met
1               5                   10                  15 gct ctg act gtc agg gga tgc tgt tcc cat cct gcc tgt gct ggg aat      96
Ala Leu Thr Val Arg Gly Cys Cys Ser His Pro Ala Cys Ala Gly Asn
            20                  25                  30 aat cca cat atc tgc ggc tgaagacgct gatgctccag gaccctctga            144
Asn Pro His Ile Cys Gly
        35 accacgacgt                                                          154

<210> SEQ ID NO 338
<211> LENGTH: 38
<212> TYPE: PRT
<213> ORGANISM: Conus lividus

<400> SEQUENCE: 338

Phe Glu Cys Arg Asn Ala Ala Gly Asn Asp Lys Ala Thr Asp Leu Met
1               5                   10                  15

Ala Leu Thr Val Arg Gly Cys Cys Ser His Pro Ala Cys Ala Gly Asn
            20                  25                  30

Asn Pro His Ile Cys Gly
        35

<210> SEQ ID NO 339
<211> LENGTH: 154
<212> TYPE: DNA
<213> ORGANISM: Conus lividus
<220> FEATURE:
<221> NAME/KEY: CDS
<222> LOCATION: (1)..(114)

<400> SEQUENCE: 339 ttt gat ggc agg aac gcc gca gcc aac aac aaa gcg act gat ctg atg      48
Phe Asp Gly Arg Asn Ala Ala Ala Asn Asn Lys Ala Thr Asp Leu Met
1               5                   10                  15 gct ctg act gtc aga gga tgc tgt ggc aat cct tca tgt agc atc cat      96
Ala Leu Thr Val Arg Gly Cys Cys Gly Asn Pro Ser Cys Ser Ile His
            20                  25                  30 att cct tac gtt tgt aat tagagacact gatgctccag gaccctctga            144

```
Ile Pro Tyr Val Cys Asn
         35 accacgacgt                                                              154

<210> SEQ ID NO 340
<211> LENGTH: 38
<212> TYPE: PRT
<213> ORGANISM: Conus lividus

<400> SEQUENCE: 340

Phe Asp Gly Arg Asn Ala Ala Ala Asn Asn Lys Ala Thr Asp Leu Met
 1               5                  10                  15

Ala Leu Thr Val Arg Gly Cys Cys Gly Asn Pro Ser Cys Ser Ile His
            20                  25                  30

Ile Pro Tyr Val Cys Asn
         35

<210> SEQ ID NO 341
<211> LENGTH: 157
<212> TYPE: DNA
<213> ORGANISM: Conus lividus
<220> FEATURE:
<221> NAME/KEY: CDS
<222> LOCATION: (1)..(126)

<400> SEQUENCE: 341 tct aat ggc agg aat gcc gca gcc aaa ttc aaa gcg cct gcc ctg atg      48
Ser Asn Gly Arg Asn Ala Ala Ala Lys Phe Lys Ala Pro Ala Leu Met
 1               5                  10                  15 aag cgg acc gac agc gaa gaa tgc tgt tta gac tct cgc tgt gcc ggg      96
Lys Arg Thr Asp Ser Glu Glu Cys Cys Leu Asp Ser Arg Cys Ala Gly
            20                  25                  30 caa cat caa gac ctg tgt ggc gga aga cgc tgatgctcca ggaccctctg      146
Gln His Gln Asp Leu Cys Gly Gly Arg Arg
         35                  40 aaccacgacg t                                                           157

<210> SEQ ID NO 342
<211> LENGTH: 42
<212> TYPE: PRT
<213> ORGANISM: Conus lividus

<400> SEQUENCE: 342

Ser Asn Gly Arg Asn Ala Ala Ala Lys Phe Lys Ala Pro Ala Leu Met
 1               5                  10                  15

Lys Arg Thr Asp Ser Glu Glu Cys Cys Leu Asp Ser Arg Cys Ala Gly
            20                  25                  30

Gln His Gln Asp Leu Cys Gly Gly Arg Arg
         35                  40

<210> SEQ ID NO 343
<211> LENGTH: 126
<212> TYPE: DNA
<213> ORGANISM: Conus marmoreus
<220> FEATURE:
<221> NAME/KEY: CDS
<222> LOCATION: (1)..(123)

<400> SEQUENCE: 343 tct gat ggc agg aat gcc gca gcc aag gac aaa gcg tct gac ctg gtc      48
Ser Asp Gly Arg Asn Ala Ala Ala Lys Asp Lys Ala Ser Asp Leu Val
 1               5                  10                  15
```

```
gct ctg acc gtc aag gga tgc tgt tct aat cct ccc tgt tac gcg aat    96
Ala Leu Thr Val Lys Gly Cys Cys Ser Asn Pro Pro Cys Tyr Ala Asn
         20                  25                  30 aat caa gcc tat tgt aat gga aga cgc tga                           126
Asn Gln Ala Tyr Cys Asn Gly Arg Arg
         35                  40

<210> SEQ ID NO 344
<211> LENGTH: 41
<212> TYPE: PRT
<213> ORGANISM: Conus marmoreus

<400> SEQUENCE: 344

Ser Asp Gly Arg Asn Ala Ala Lys Asp Lys Ala Ser Asp Leu Val
 1               5                  10                  15

Ala Leu Thr Val Lys Gly Cys Cys Ser Asn Pro Pro Cys Tyr Ala Asn
         20                  25                  30

Asn Gln Ala Tyr Cys Asn Gly Arg Arg
         35                  40

<210> SEQ ID NO 345
<211> LENGTH: 117
<212> TYPE: DNA
<213> ORGANISM: Conus marmoreus
<220> FEATURE:
<221> NAME/KEY: CDS
<222> LOCATION: (1)..(114)

<400> SEQUENCE: 345 tct gat ggc agg aat gcc gca gcc aag gac aaa gcg tct gac ctg gtc    48
Ser Asp Gly Arg Asn Ala Ala Ala Lys Asp Lys Ala Ser Asp Leu Val
 1               5                  10                  15 gct ctg acc gtc aag gga tgc tgt tct cat cct gcc tgt agc gtg aat    96
Ala Leu Thr Val Lys Gly Cys Cys Ser His Pro Ala Cys Ser Val Asn
         20                  25                  30 aat cca gac att tgt ggt tga                                       117
Asn Pro Asp Ile Cys Gly
         35

<210> SEQ ID NO 346
<211> LENGTH: 38
<212> TYPE: PRT
<213> ORGANISM: Conus marmoreus

<400> SEQUENCE: 346

Ser Asp Gly Arg Asn Ala Ala Lys Asp Lys Ala Ser Asp Leu Val
 1               5                  10                  15

Ala Leu Thr Val Lys Gly Cys Cys Ser His Pro Ala Cys Ser Val Asn
         20                  25                  30

Asn Pro Asp Ile Cys Gly
         35

<210> SEQ ID NO 347
<211> LENGTH: 145
<212> TYPE: DNA
<213> ORGANISM: Conus musicus
<220> FEATURE:
<221> NAME/KEY: CDS
<222> LOCATION: (1)..(114)

<400> SEQUENCE: 347 tct gat ggc agg aat gct gca gcc aac aac aaa gtg gct ttg acc atg    48
Ser Asp Gly Arg Asn Ala Ala Ala Asn Asn Lys Val Ala Leu Thr Met
 1               5                  10                  15
```

```
agg gga aaa tgc tgt atc aat gat gcg tgt cgc tcg aaa cat cca cag      96
Arg Gly Lys Cys Cys Ile Asn Asp Ala Cys Arg Ser Lys His Pro Gln
            20                  25                  30 tac tgt tct gga aga cgc tgatactcca ggaccctctg aaccacgacg t           145
Tyr Cys Ser Gly Arg Arg
        35
```

<210> SEQ ID NO 348
<211> LENGTH: 38
<212> TYPE: PRT
<213> ORGANISM: Conus musicus

<400> SEQUENCE: 348

```
Ser Asp Gly Arg Asn Ala Ala Ala Asn Asn Lys Val Ala Leu Thr Met
  1               5                  10                  15

Arg Gly Lys Cys Cys Ile Asn Asp Ala Cys Arg Ser Lys His Pro Gln
            20                  25                  30

Tyr Cys Ser Gly Arg Arg
        35
```

<210> SEQ ID NO 349
<211> LENGTH: 154
<212> TYPE: DNA
<213> ORGANISM: Conus musicus
<220> FEATURE:
<221> NAME/KEY: CDS
<222> LOCATION: (1)..(123)

<400> SEQUENCE: 349

```
tct gat ggc agg aat gct gca gcc aac gac aaa gtg tct gac cag atg      48
Ser Asp Gly Arg Asn Ala Ala Ala Asn Asp Lys Val Ser Asp Gln Met
  1               5                  10                  15 gct ctg gtt gtc agg gga tgc tgt tac aat att gcc tgt aga att aat      96
Ala Leu Val Val Arg Gly Cys Cys Tyr Asn Ile Ala Cys Arg Ile Asn
            20                  25                  30 aat cca cgg tac tgt cgt gga aaa cgc tgatgttcca ggaccctctg           143
Asn Pro Arg Tyr Cys Arg Gly Lys Arg
        35                  40 aaccacgacg t                                                         154
```

<210> SEQ ID NO 350
<211> LENGTH: 41
<212> TYPE: PRT
<213> ORGANISM: Conus musicus

<400> SEQUENCE: 350

```
Ser Asp Gly Arg Asn Ala Ala Ala Asn Asp Lys Val Ser Asp Gln Met
  1               5                  10                  15

Ala Leu Val Val Arg Gly Cys Cys Tyr Asn Ile Ala Cys Arg Ile Asn
            20                  25                  30

Asn Pro Arg Tyr Cys Arg Gly Lys Arg
        35                  40
```

<210> SEQ ID NO 351
<211> LENGTH: 154
<212> TYPE: DNA
<213> ORGANISM: Conus obscurus
<220> FEATURE:
<221> NAME/KEY: CDS
<222> LOCATION: (52)..(123)

<400> SEQUENCE: 351

```
tctgaaggca ggaatgccgc agccaacgac aaagcgtctg acctgatggc t ctg aac    57
                                                         Leu Asn
                                                           1 gtc agg gga tgc tgt tcc cat cct gtc tgt cgc ttc aat tat cca aaa    105
Val Arg Gly Cys Cys Ser His Pro Val Cys Arg Phe Asn Tyr Pro Lys
      5                  10                  15 tat tgt ggt gga aga cgc tgatggtcca ggaccctctg aaccacgacg t         154
Tyr Cys Gly Gly Arg Arg
         20
```

<210> SEQ ID NO 352
<211> LENGTH: 24
<212> TYPE: PRT
<213> ORGANISM: Conus obscurus

<400> SEQUENCE: 352

Leu Asn Val Arg Gly Cys Cys Ser His Pro Val Cys Arg Phe Asn Tyr
 1               5                  10                  15

Pro Lys Tyr Cys Gly Gly Arg Arg
             20

<210> SEQ ID NO 353
<211> LENGTH: 151
<212> TYPE: DNA
<213> ORGANISM: Conus obscurus
<220> FEATURE:
<221> NAME/KEY: CDS
<222> LOCATION: (46)..(111)

<400> SEQUENCE: 353

```
tctgatggcg ggaatgccgc agcaaaagcg tttgatctaa tcact ctg gcc ctc agg    57
                                                 Leu Ala Leu Arg
                                                              1 gat gaa tgc tgt gcc agt cct ccc tgt cgt ttg aat aat cca tac gta    105
Asp Glu Cys Cys Ala Ser Pro Pro Cys Arg Leu Asn Asn Pro Tyr Val
  5                  10                  15                  20 tgt cat tgacgacgct gatgctccag gaccctctga accacgacgt               151
Cys His
```

<210> SEQ ID NO 354
<211> LENGTH: 22
<212> TYPE: PRT
<213> ORGANISM: Conus obscurus

<400> SEQUENCE: 354

Leu Ala Leu Arg Asp Glu Cys Cys Ala Ser Pro Pro Cys Arg Leu Asn
 1               5                  10                  15

Asn Pro Tyr Val Cys His
             20

<210> SEQ ID NO 355
<211> LENGTH: 217
<212> TYPE: DNA
<213> ORGANISM: Conus obscurus
<220> FEATURE:
<221> NAME/KEY: CDS
<222> LOCATION: (1)..(186)

<400> SEQUENCE: 355

```
atg ttc acc gtg ttt ctg ttg gtt gtc ttg gca acc acc gtc gtt tcc    48
Met Phe Thr Val Phe Leu Leu Val Val Leu Ala Thr Thr Val Val Ser
 1               5                  10                  15 ccc act tca gat cgt gca tct gat agg agg aat gcc gca gcc aaa gcg    96
Pro Thr Ser Asp Arg Ala Ser Asp Arg Arg Asn Ala Ala Ala Lys Ala
```

```
                    20                  25                  30
ttt gac ctg aga tat tcg acc gcc aag aga gga tgc tgt tcc aat cct       144
Phe Asp Leu Arg Tyr Ser Thr Ala Lys Arg Gly Cys Cys Ser Asn Pro
            35                  40                  45 gtc tgt tgg cag aat aat gca gaa tac tgt cgt gaa agt ggc               186
Val Cys Trp Gln Asn Asn Ala Glu Tyr Cys Arg Glu Ser Gly
        50                  55                  60 taatgctcca ggaccctctg aaccacgacg t                                    217

<210> SEQ ID NO 356
<211> LENGTH: 62
<212> TYPE: PRT
<213> ORGANISM: Conus obscurus

<400> SEQUENCE: 356

Met Phe Thr Val Phe Leu Leu Val Val Leu Ala Thr Thr Val Val Ser
 1               5                  10                  15

Pro Thr Ser Asp Arg Ala Ser Asp Arg Arg Asn Ala Ala Ala Lys Ala
                20                  25                  30

Phe Asp Leu Arg Tyr Ser Thr Ala Lys Arg Gly Cys Cys Ser Asn Pro
            35                  40                  45

Val Cys Trp Gln Asn Asn Ala Glu Tyr Cys Arg Glu Ser Gly
        50                  55                  60

<210> SEQ ID NO 357
<211> LENGTH: 208
<212> TYPE: DNA
<213> ORGANISM: Conus obscurus
<220> FEATURE:
<221> NAME/KEY: CDS
<222> LOCATION: (1)..(168)

<400> SEQUENCE: 357 atg ttc acc gtg ttt ctg ttg gtt gtc ttg gca acc acc gtc gtt tcc       48
Met Phe Thr Val Phe Leu Leu Val Val Leu Ala Thr Thr Val Val Ser
 1               5                  10                  15 ttc act tca gat cgt gca tct gat ggc ggg aat gtc gca gcg tct cac       96
Phe Thr Ser Asp Arg Ala Ser Asp Gly Gly Asn Val Ala Ala Ser His
                20                  25                  30 ctg atc gct ctg acc atc aag gga tgc tgt tct cac cct ccc tgt gcc       144
Leu Ile Ala Leu Thr Ile Lys Gly Cys Cys Ser His Pro Pro Cys Ala
            35                  40                  45 cag aat aat caa gac tat tgt ggt tgacgacgct gatgctccag accctctga       198
Gln Asn Asn Gln Asp Tyr Cys Gly
        50                  55 accacgacgt                                                            208

<210> SEQ ID NO 358
<211> LENGTH: 56
<212> TYPE: PRT
<213> ORGANISM: Conus obscurus

<400> SEQUENCE: 358

Met Phe Thr Val Phe Leu Leu Val Val Leu Ala Thr Thr Val Val Ser
 1               5                  10                  15

Phe Thr Ser Asp Arg Ala Ser Asp Gly Gly Asn Val Ala Ala Ser His
                20                  25                  30

Leu Ile Ala Leu Thr Ile Lys Gly Cys Cys Ser His Pro Pro Cys Ala
            35                  40                  45

Gln Asn Asn Gln Asp Tyr Cys Gly
```

<210> SEQ ID NO 359
<211> LENGTH: 217
<212> TYPE: DNA
<213> ORGANISM: Conus obscurus
<220> FEATURE:
<221> NAME/KEY: CDS
<222> LOCATION: (1)..(186)

<400> SEQUENCE: 359

| | | | | | | | | | | | | | | | | |
|---|---|---|---|---|---|---|---|---|---|---|---|---|---|---|---|---|
| atg | ttc | acc | gtg | ttt | ctg | ttg | gtt | gtc | tta | tca | acc | acc | gtc | gtt | tcc | 48 |
| Met | Phe | Thr | Val | Phe | Leu | Leu | Val | Val | Leu | Ser | Thr | Thr | Val | Val | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | act | tca | gat | cgt | gca | tct | gat | agg | agg | aat | gcc | gca | gcc | aaa | gcg | 96 |
| Ser | Thr | Ser | Asp | Arg | Ala | Ser | Asp | Arg | Arg | Asn | Ala | Ala | Ala | Lys | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| tct | gac | ctg | atg | tat | tcg | acc | gtc | aag | aaa | gga | tgt | tgt | tcc | cat | cct | 144 |
| Ser | Asp | Leu | Met | Tyr | Ser | Thr | Val | Lys | Lys | Gly | Cys | Cys | Ser | His | Pro | |
| | | | 35 | | | | | 40 | | | | | 45 | | | |

| | | | | | | | | | | | | |
|---|---|---|---|---|---|---|---|---|---|---|---|---|
| gcc | tgt | tcg | ggg | aat | aat | cga | gaa | tat | tgt | cgt | gaa | agt | ggc | 186 |
| Ala | Cys | Ser | Gly | Asn | Asn | Arg | Glu | Tyr | Cys | Arg | Glu | Ser | Gly | |
| | 50 | | | | | 55 | | | | | 60 | | | | taatgctcca ggaccctctg aaccacgacg t    217

<210> SEQ ID NO 360
<211> LENGTH: 62
<212> TYPE: PRT
<213> ORGANISM: Conus obscurus

<400> SEQUENCE: 360

Met Phe Thr Val Phe Leu Leu Val Val Leu Ser Thr Thr Val Val Ser
1               5                   10                  15

Ser Thr Ser Asp Arg Ala Ser Asp Arg Arg Asn Ala Ala Ala Lys Ala
            20                  25                  30

Ser Asp Leu Met Tyr Ser Thr Val Lys Lys Gly Cys Cys Ser His Pro
        35                  40                  45

Ala Cys Ser Gly Asn Asn Arg Glu Tyr Cys Arg Glu Ser Gly
    50                  55                  60

<210> SEQ ID NO 361
<211> LENGTH: 157
<212> TYPE: DNA
<213> ORGANISM: Conus omaria
<220> FEATURE:
<221> NAME/KEY: CDS
<222> LOCATION: (52)..(126)

<400> SEQUENCE: 361
tttgatggca ggaatgcctc agccgacagc aaagtggctg cccggatcgc t cag atc    57
                                                        Gln Ile
                                                        1

| | | | | | | | | | | | | | | | |
|---|---|---|---|---|---|---|---|---|---|---|---|---|---|---|---|---|
| gac | agg | gat | cca | tgc | tgt | tcc | tat | cct | gac | tgt | ggc | gcg | aat | cat | cca | 105 |
| Asp | Arg | Asp | Pro | Cys | Cys | Ser | Tyr | Pro | Asp | Cys | Gly | Ala | Asn | His | Pro | |
| | | 5 | | | | | 10 | | | | | 15 | | | | |

| | | | | | | | | | |
|---|---|---|---|---|---|---|---|---|---|
| gag | att | tgt | ggt | gga | aaa | cgc | tgatgctcca ggaccctctg aaccacgacg t | | 157 |
| Glu | Ile | Cys | Gly | Gly | Lys | Arg | | | |
| | 20 | | | | | 25 | | | |

<210> SEQ ID NO 362
<211> LENGTH: 25
<212> TYPE: PRT
<213> ORGANISM: Conus omaria

```
<400> SEQUENCE: 362

Gln Ile Asp Arg Asp Pro Cys Cys Ser Tyr Pro Asp Cys Gly Ala Asn
 1               5                  10                  15

His Pro Glu Ile Cys Gly Gly Lys Arg
            20                  25

<210> SEQ ID NO 363
<211> LENGTH: 128
<212> TYPE: DNA
<213> ORGANISM: Conus omaria
<220> FEATURE:
<221> NAME/KEY: CDS
<222> LOCATION: (26)..(88)

<400> SEQUENCE: 363
tctcatggca ggaatgccgc acgct ctg acc gtc agg gaa tgc tgt tct cag        52
                           Leu Thr Val Arg Glu Cys Cys Ser Gln
                            1               5 cct cct tgt cgc tgg aaa cat cca gaa ctt tgt agt tgaagacgct             98
Pro Pro Cys Arg Trp Lys His Pro Glu Leu Cys Ser
 10              15                  20 gatgctccag gaccctctga accacgacgt                                      128

<210> SEQ ID NO 364
<211> LENGTH: 21
<212> TYPE: PRT
<213> ORGANISM: Conus omaria

<400> SEQUENCE: 364

Leu Thr Val Arg Glu Cys Cys Ser Gln Pro Pro Cys Arg Trp Lys His
 1               5                  10                  15

Pro Glu Leu Cys Ser
            20

<210> SEQ ID NO 365
<211> LENGTH: 154
<212> TYPE: DNA
<213> ORGANISM: Conus omaria
<220> FEATURE:
<221> NAME/KEY: CDS
<222> LOCATION: (52)..(123)

<400> SEQUENCE: 365
tttgatggca ggaatgctgc agccagcgac aaagcgtctg agctgatggc t ctg gcc       57
                                                       Leu Ala
                                                        1 gtc agg gga tgc tgt tcc cat cct gcc tgt gct ggg aat aat cca cat      105
Val Arg Gly Cys Cys Ser His Pro Ala Cys Ala Gly Asn Asn Pro His
     5                  10                  15 atc tgt ggc aga aga cgc tgatgctcca ggaccctctg aaccacgacg t            154
Ile Cys Gly Arg Arg Arg
         20

<210> SEQ ID NO 366
<211> LENGTH: 24
<212> TYPE: PRT
<213> ORGANISM: Conus omaria

<400> SEQUENCE: 366

Leu Ala Val Arg Gly Cys Cys Ser His Pro Ala Cys Ala Gly Asn Asn
 1               5                  10                  15

Pro His Ile Cys Gly Arg Arg Arg
            20
```

```
<210> SEQ ID NO 367
<211> LENGTH: 142
<212> TYPE: DNA
<213> ORGANISM: Conus omaria
<220> FEATURE:
<221> NAME/KEY: CDS
<222> LOCATION: (40)..(102)

<400> SEQUENCE: 367
tctggtgtca ggaaagacgc agcgcctggc ctgatcgct ctg acc atc aag gga      54
                                            Leu Thr Ile Lys Gly
                                              1               5 tgc tgt tct gat cct agc tgt aac gtg aat aat cca gac tat tgt ggt    102
Cys Cys Ser Asp Pro Ser Cys Asn Val Asn Asn Pro Asp Tyr Cys Gly
             10                  15                  20 tgacgacgct gatgctccag gaccctctga accacgacgt                         142

<210> SEQ ID NO 368
<211> LENGTH: 21
<212> TYPE: PRT
<213> ORGANISM: Conus omaria

<400> SEQUENCE: 368

Leu Thr Ile Lys Gly Cys Cys Ser Asp Pro Ser Cys Asn Val Asn Asn
  1               5                  10                  15

Pro Asp Tyr Cys Gly
             20

<210> SEQ ID NO 369
<211> LENGTH: 157
<212> TYPE: DNA
<213> ORGANISM: Conus omaria
<220> FEATURE:
<221> NAME/KEY: CDS
<222> LOCATION: (52)..(117)

<400> SEQUENCE: 369
tctaatggca ggaatgccgc agccaaattc aaagcgcctg ccctgatgga g ctg acc    57
                                                        Leu Thr
                                                          1 gtc agg gaa gaa tgc tgt tca gac cct cgc tgt tcc gtg gga cat caa   105
Val Arg Glu Glu Cys Cys Ser Asp Pro Arg Cys Ser Val Gly His Gln
      5                  10                  15 gat atg tgt cgg tgaagcacgt gatgctccag gaccctctga accacgacgt       157
Asp Met Cys Arg
         20

<210> SEQ ID NO 370
<211> LENGTH: 22
<212> TYPE: PRT
<213> ORGANISM: Conus omaria

<400> SEQUENCE: 370

Leu Thr Val Arg Glu Glu Cys Cys Ser Asp Pro Arg Cys Ser Val Gly
  1               5                  10                  15

His Gln Asp Met Cys Arg
             20

<210> SEQ ID NO 371
<211> LENGTH: 151
<212> TYPE: DNA
<213> ORGANISM: Conus purpurascens
```

-continued

```
<220> FEATURE:
<221> NAME/KEY: CDS
<222> LOCATION: (1)..(120)

<400> SEQUENCE: 371 act gat ggc agg aat gct gca gcc ata gcg ctt gac ctg atc gct ccg      48
Thr Asp Gly Arg Asn Ala Ala Ala Ile Ala Leu Asp Leu Ile Ala Pro
 1               5                  10                  15 gcc gtc agg gga gga tgc tgt tcc aat cct gcc tgt tta gtg aat cat      96
Ala Val Arg Gly Gly Cys Cys Ser Asn Pro Ala Cys Leu Val Asn His
             20                  25                  30 cta gaa atg tgt ggt aaa aga cgc tgatgcccca ggaccctctg aaccacgacg    150
Leu Glu Met Cys Gly Lys Arg Arg
         35                  40 t                                                                   151

<210> SEQ ID NO 372
<211> LENGTH: 40
<212> TYPE: PRT
<213> ORGANISM: Conus purpurascens

<400> SEQUENCE: 372

Thr Asp Gly Arg Asn Ala Ala Ala Ile Ala Leu Asp Leu Ile Ala Pro
 1               5                  10                  15

Ala Val Arg Gly Gly Cys Cys Ser Asn Pro Ala Cys Leu Val Asn His
             20                  25                  30

Leu Glu Met Cys Gly Lys Arg Arg
         35                  40

<210> SEQ ID NO 373
<211> LENGTH: 160
<212> TYPE: DNA
<213> ORGANISM: Conus purpurascens
<220> FEATURE:
<221> NAME/KEY: CDS
<222> LOCATION: (1)..(120)

<400> SEQUENCE: 373 tct gat ggc agg gat gcc gca gcc aac gac aaa gcg tct gac ctg atc      48
Ser Asp Gly Arg Asp Ala Ala Ala Asn Asp Lys Ala Ser Asp Leu Ile
 1               5                  10                  15 gct ctg acc gcc agg aga gat cca tgc tgt ttc aat cct gcc tgt aac      96
Ala Leu Thr Ala Arg Arg Asp Pro Cys Cys Phe Asn Pro Ala Cys Asn
             20                  25                  30 gtg aat aat cca cag att tgt ggt tgaagacgct gatgctccag gaccctctga   150
Val Asn Asn Pro Gln Ile Cys Gly
         35                  40 accacgacgt                                                         160

<210> SEQ ID NO 374
<211> LENGTH: 40
<212> TYPE: PRT
<213> ORGANISM: Conus purpurascens

<400> SEQUENCE: 374

Ser Asp Gly Arg Asp Ala Ala Ala Asn Asp Lys Ala Ser Asp Leu Ile
 1               5                  10                  15

Ala Leu Thr Ala Arg Arg Asp Pro Cys Cys Phe Asn Pro Ala Cys Asn
             20                  25                  30

Val Asn Asn Pro Gln Ile Cys Gly
         35                  40
```

```
<210> SEQ ID NO 375
<211> LENGTH: 151
<212> TYPE: DNA
<213> ORGANISM: Conus purpurascens
<220> FEATURE:
<221> NAME/KEY: CDS
<222> LOCATION: (1)..(120)

<400> SEQUENCE: 375 tct gat ggc agg gat gct gag aaa aca ggc ttt gac acg acc att gtg      48
Ser Asp Gly Arg Asp Ala Glu Lys Thr Gly Phe Asp Thr Thr Ile Val
 1               5                  10                  15 ccg gaa gac tgc tgt tcg gat cct tcc tgt tgg agg ctg cat agt tta      96
Pro Glu Asp Cys Cys Ser Asp Pro Ser Cys Trp Arg Leu His Ser Leu
             20                  25                  30 gct tgt act gga att gta aac cgc tgatgctcca ggaccctctg aaccacgacg    150
Ala Cys Thr Gly Ile Val Asn Arg
         35                  40 t                                                                    151

<210> SEQ ID NO 376
<211> LENGTH: 40
<212> TYPE: PRT
<213> ORGANISM: Conus purpurascens

<400> SEQUENCE: 376

Ser Asp Gly Arg Asp Ala Glu Lys Thr Gly Phe Asp Thr Thr Ile Val
 1               5                  10                  15

Pro Glu Asp Cys Cys Ser Asp Pro Ser Cys Trp Arg Leu His Ser Leu
             20                  25                  30

Ala Cys Thr Gly Ile Val Asn Arg
         35                  40

<210> SEQ ID NO 377
<211> LENGTH: 142
<212> TYPE: DNA
<213> ORGANISM: Conus purpurascens
<220> FEATURE:
<221> NAME/KEY: CDS
<222> LOCATION: (1)..(111)

<400> SEQUENCE: 377 act gat ggc agg agt gct gca gcc ata gcg ttt gcc ctg atc gct ccg      48
Thr Asp Gly Arg Ser Ala Ala Ala Ile Ala Phe Ala Leu Ile Ala Pro
 1               5                  10                  15 acc gtc tgc tgt act aat cct gcc tgt ctc gtg aat aat ata cgc ttt      96
Thr Val Cys Cys Thr Asn Pro Ala Cys Leu Val Asn Asn Ile Arg Phe
             20                  25                  30 tgt ggt gga aga cgc tgatgcccca ggaccctctg aaccacgacg t              142
Cys Gly Gly Arg Arg
         35

<210> SEQ ID NO 378
<211> LENGTH: 37
<212> TYPE: PRT
<213> ORGANISM: Conus purpurascens

<400> SEQUENCE: 378

Thr Asp Gly Arg Ser Ala Ala Ala Ile Ala Phe Ala Leu Ile Ala Pro
 1               5                  10                  15

Thr Val Cys Cys Thr Asn Pro Ala Cys Leu Val Asn Asn Ile Arg Phe
             20                  25                  30
```

```
Cys Gly Gly Arg Arg
        35

<210> SEQ ID NO 379
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 379 tct gat gga aga aat gcc gca agc gac gcc aaa gcg ttt ccc cgg atc         48
Ser Asp Gly Arg Asn Ala Ala Ser Asp Ala Lys Ala Phe Pro Arg Ile
 1               5                  10                  15 gct cca atc gtc agg gac gaa tgc tgt agc gat cct agg tgt cac ggg         96
Ala Pro Ile Val Arg Asp Glu Cys Cys Ser Asp Pro Arg Cys His Gly
            20                  25                  30 aat aat cgg gac cac tgt gct tgaagacgct gctgctccag gaccctctga          147
Asn Asn Arg Asp His Cys Ala
        35 accacgacgt                                                             157

<210> SEQ ID NO 380
<211> LENGTH: 39
<212> TYPE: PRT
<213> ORGANISM: Conus regius

<400> SEQUENCE: 380

Ser Asp Gly Arg Asn Ala Ala Ser Asp Ala Lys Ala Phe Pro Arg Ile
 1               5                  10                  15

Ala Pro Ile Val Arg Asp Glu Cys Cys Ser Asp Pro Arg Cys His Gly
            20                  25                  30

Asn Asn Arg Asp His Cys Ala
        35

<210> SEQ ID NO 381
<211> LENGTH: 156
<212> TYPE: DNA
<213> ORGANISM: Conus regius
<220> FEATURE:
<221> NAME/KEY: CDS
<222> LOCATION: (1)..(117)

<400> SEQUENCE: 381 tct gat ggc agg aat acc gcg gcc gac gaa aaa gcg tcc gac ctg atc         48
Ser Asp Gly Arg Asn Thr Ala Ala Asp Glu Lys Ala Ser Asp Leu Ile
 1               5                  10                  15 tct caa act gtc aag aga gat tgc tgt tcc cat cct ctc tgt aga tta         96
Ser Gln Thr Val Lys Arg Asp Cys Cys Ser His Pro Leu Cys Arg Leu
            20                  25                  30 ttt gtt cca gga ctt tgt att tgaagacgct gctgctccag gaccctctga         147
Phe Val Pro Gly Leu Cys Ile
        35 accacgact                                                             156

<210> SEQ ID NO 382
<211> LENGTH: 39
<212> TYPE: PRT
<213> ORGANISM: Conus regius

<400> SEQUENCE: 382

Ser Asp Gly Arg Asn Thr Ala Ala Asp Glu Lys Ala Ser Asp Leu Ile
```

```
                1               5                  10                 15
Ser Gln Thr Val Lys Arg Asp Cys Cys Ser His Pro Leu Cys Arg Leu
                        20                  25                 30

Phe Val Pro Gly Leu Cys Ile
                35
```

<210> SEQ ID NO 383
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 383

```
tct gat ggc agg aat gcc gca gcc gac aac aaa gcg tct gac cta atc        48
Ser Asp Gly Arg Asn Ala Ala Ala Asp Asn Lys Ala Ser Asp Leu Ile
  1               5                  10                 15 gct caa atc gtc agg aga gga tgc tgt tcc cat cct gtc tgt aaa gtg        96
Ala Gln Ile Val Arg Arg Gly Cys Cys Ser His Pro Val Cys Lys Val
            20                  25                 30 agg tat cca gac ctg tgt cgt tgaagacgct gctgctccag gaccctctga          147
Arg Tyr Pro Asp Leu Cys Arg
        35 accacgacgt                                                             157
```

<210> SEQ ID NO 384
<211> LENGTH: 39
<212> TYPE: PRT
<213> ORGANISM: Conus regius

<400> SEQUENCE: 384

```
Ser Asp Gly Arg Asn Ala Ala Ala Asp Asn Lys Ala Ser Asp Leu Ile
  1               5                  10                 15

Ala Gln Ile Val Arg Arg Gly Cys Cys Ser His Pro Val Cys Lys Val
            20                  25                 30

Arg Tyr Pro Asp Leu Cys Arg
        35
```

<210> SEQ ID NO 385
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 385

```
tct gat ggc agg aat gcc gca gcc gac aac aga gcg tct gac cta atc        48
Ser Asp Gly Arg Asn Ala Ala Ala Asp Asn Arg Ala Ser Asp Leu Ile
  1               5                  10                 15 gct caa atc gtc agg aga gga tgc tgt tcc cat cct gcc tgt aat gtg        96
Ala Gln Ile Val Arg Arg Gly Cys Cys Ser His Pro Ala Cys Asn Val
            20                  25                 30 aat aat cca cac att tgt ggt tgaagacgct gctgctccag gaccctctga          147
Asn Asn Pro His Ile Cys Gly
        35 accacgacgt                                                             157
```

<210> SEQ ID NO 386
<211> LENGTH: 39
<212> TYPE: PRT

<213> ORGANISM: Conus regius

<400> SEQUENCE: 386

Ser Asp Gly Arg Asn Ala Ala Ala Asp Asn Arg Ala Ser Asp Leu Ile
1               5                   10                  15

Ala Gln Ile Val Arg Arg Gly Cys Cys Ser His Pro Ala Cys Asn Val
            20                  25                  30

Asn Asn Pro His Ile Cys Gly
        35

<210> SEQ ID NO 387
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 387

```
tct gat ggc agg aat gcc gca gcc gac aac aaa ccg tct gac cta atc     48
Ser Asp Gly Arg Asn Ala Ala Ala Asp Asn Lys Pro Ser Asp Leu Ile
1               5                   10                  15 gct caa atc gtc agg aga gga tgc tgt tcg cat cct gtc tgt aaa gtg     96
Ala Gln Ile Val Arg Arg Gly Cys Cys Ser His Pro Val Cys Lys Val
            20                  25                  30 agg tat tca gac atg tgt ggt tgaagacgct gctgctccag daccctctga       147
Arg Tyr Ser Asp Met Cys Gly
        35 accacgacgt                                                          157
```

<210> SEQ ID NO 388
<211> LENGTH: 39
<212> TYPE: PRT
<213> ORGANISM: Conus regius

<400> SEQUENCE: 388

Ser Asp Gly Arg Asn Ala Ala Ala Asp Asn Lys Pro Ser Asp Leu Ile
1               5                   10                  15

Ala Gln Ile Val Arg Arg Gly Cys Cys Ser His Pro Val Cys Lys Val
            20                  25                  30

Arg Tyr Ser Asp Met Cys Gly
        35

<210> SEQ ID NO 389
<211> LENGTH: 154
<212> TYPE: DNA
<213> ORGANISM: Conus stercusmuscarum
<220> FEATURE:
<221> NAME/KEY: CDS
<222> LOCATION: (1)..(114)

<400> SEQUENCE: 389

```
tct gat ggc agg aat gca gag cga cga caa agc gtc tgt cct ggt cgc     48
Ser Asp Gly Arg Asn Ala Glu Arg Arg Gln Ser Val Cys Pro Gly Arg
1               5                   10                  15 tct ggc ccc agg gga gga tgt tgt tcc cac cct gcc tgt aag gtg cat     96
Ser Gly Pro Arg Gly Gly Cys Cys Ser His Pro Ala Cys Lys Val His
            20                  25                  30 ttt cca cac agt tgt ggt tgacgacgct gatgctccag daccctctga           144
Phe Pro His Ser Cys Gly
        35 accacgacgt                                                          154
```

<210> SEQ ID NO 390
<211> LENGTH: 38
<212> TYPE: PRT
<213> ORGANISM: Conus stercusmuscarum

<400> SEQUENCE: 390

```
Ser Asp Gly Arg Asn Ala Glu Arg Arg Gln Ser Val Cys Pro Gly Arg
 1               5                  10                  15

Ser Gly Pro Arg Gly Gly Cys Cys Ser His Pro Ala Cys Lys Val His
            20                  25                  30

Phe Pro His Ser Cys Gly
        35
```

<210> SEQ ID NO 391
<211> LENGTH: 145
<212> TYPE: DNA
<213> ORGANISM: Conus stercusmuscarum
<220> FEATURE:
<221> NAME/KEY: CDS
<222> LOCATION: (1)..(114)

<400> SEQUENCE: 391

```
tct gat ggc agg aat gcc gca gcc agc gac aga gcg tct gac gcg gcc      48
Ser Asp Gly Arg Asn Ala Ala Ala Ser Asp Arg Ala Ser Asp Ala Ala
 1               5                  10                  15 cac cag gta tgc tgt tcc aac cct gtc tgt cac gtg gat cat cca gaa      96
His Gln Val Cys Cys Ser Asn Pro Val Cys His Val Asp His Pro Glu
            20                  25                  30 ctt tgt cgt aga aga cgc tgatgctcca ggaccctctg aaccacgacg t          145
Leu Cys Arg Arg Arg Arg
        35
```

<210> SEQ ID NO 392
<211> LENGTH: 38
<212> TYPE: PRT
<213> ORGANISM: Conus stercusmuscarum

<400> SEQUENCE: 392

```
Ser Asp Gly Arg Asn Ala Ala Ala Ser Asp Arg Ala Ser Asp Ala Ala
 1               5                  10                  15

His Gln Val Cys Cys Ser Asn Pro Val Cys His Val Asp His Pro Glu
            20                  25                  30

Leu Cys Arg Arg Arg Arg
        35
```

<210> SEQ ID NO 393
<211> LENGTH: 154
<212> TYPE: DNA
<213> ORGANISM: Conus striatus
<220> FEATURE:
<221> NAME/KEY: CDS
<222> LOCATION: (1)..(123)

<400> SEQUENCE: 393

```
tct gat ggc agg aat gcc gcg gcc aac gac aaa gcg tct gac ctg gtc      48
Ser Asp Gly Arg Asn Ala Ala Ala Asn Asp Lys Ala Ser Asp Leu Val
 1               5                  10                  15 gct ccg gcc atc agg gga tgc tgt tcc cac cct gtc tgt aac ttg agt      96
Ala Pro Ala Ile Arg Gly Cys Cys Ser His Pro Val Cys Asn Leu Ser
            20                  25                  30 aat cca caa att tgt cgt gga aga cgc tgatgctcca ggaccctctg            143
Asn Pro Gln Ile Cys Arg Gly Arg Arg
```

```
                              35                  40 aaccacgacg t                                                              154

<210> SEQ ID NO 394
<211> LENGTH: 41
<212> TYPE: PRT
<213> ORGANISM: Conus striatus

<400> SEQUENCE: 394

Ser Asp Gly Arg Asn Ala Ala Asn Asp Lys Ala Ser Asp Leu Val
 1               5                  10                  15

Ala Pro Ala Ile Arg Gly Cys Cys Ser His Pro Val Cys Asn Leu Ser
             20                  25                  30

Asn Pro Gln Ile Cys Arg Gly Arg Arg
             35                  40

<210> SEQ ID NO 395
<211> LENGTH: 117
<212> TYPE: DNA
<213> ORGANISM: Conus textile
<220> FEATURE:
<221> NAME/KEY: CDS
<222> LOCATION: (1)..(114)

<400> SEQUENCE: 395 ttt cat ggc agg aat gcc gca gcc aaa gcg tct ggc ctg gtc ggt ctg       48
Phe His Gly Arg Asn Ala Ala Ala Lys Ala Ser Gly Leu Val Gly Leu
 1               5                  10                  15 acc gac aag agg caa gaa tgc tgt tct cat cct gcc tgt aac gta gat       96
Thr Asp Lys Arg Gln Glu Cys Cys Ser His Pro Ala Cys Asn Val Asp
             20                  25                  30 cat cca gaa att tgt cgt tga                                           117
His Pro Glu Ile Cys Arg
             35

<210> SEQ ID NO 396
<211> LENGTH: 38
<212> TYPE: PRT
<213> ORGANISM: Conus textile

<400> SEQUENCE: 396

Phe His Gly Arg Asn Ala Ala Ala Lys Ala Ser Gly Leu Val Gly Leu
 1               5                  10                  15

Thr Asp Lys Arg Gln Glu Cys Cys Ser His Pro Ala Cys Asn Val Asp
             20                  25                  30

His Pro Glu Ile Cys Arg
             35

<210> SEQ ID NO 397
<211> LENGTH: 151
<212> TYPE: DNA
<213> ORGANISM: Conus tulipa
<220> FEATURE:
<221> NAME/KEY: CDS
<222> LOCATION: (1)..(120)

<400> SEQUENCE: 397 act gat ggc agg agt gct gca gcc ata gcg ttt gcc ctg atc gct ccg       48
Thr Asp Gly Arg Ser Ala Ala Ala Ile Ala Phe Ala Leu Ile Ala Pro
 1               5                  10                  15 acc gtc tgg gaa gga tgc tgt tct aat cct gcc tgt ctc gtg aat cat       96
Thr Val Trp Glu Gly Cys Cys Ser Asn Pro Ala Cys Leu Val Asn His
             20                  25                  30
```

```
ata cgc ttt tgt ggt gga aga cgc tgatgcccca ggaccctctg aaccacgacg        150
Ile Arg Phe Cys Gly Gly Arg Arg
         35                  40 t                                                                       151
```

<210> SEQ ID NO 398
<211> LENGTH: 40
<212> TYPE: PRT
<213> ORGANISM: Conus tulipa

<400> SEQUENCE: 398

```
Thr Asp Gly Arg Ser Ala Ala Ile Ala Phe Ala Leu Ile Ala Pro
 1               5                  10                 15

Thr Val Trp Glu Gly Cys Cys Ser Asn Pro Ala Cys Leu Val Asn His
                20                  25                  30

Ile Arg Phe Cys Gly Gly Arg Arg
         35                  40
```

<210> SEQ ID NO 399
<211> LENGTH: 157
<212> TYPE: DNA
<213> ORGANISM: Conus virgo
<220> FEATURE:
<221> NAME/KEY: CDS
<222> LOCATION: (1)..(117)

<400> SEQUENCE: 399

```
tct aat ggc atg aat gcc gca gcc atc agg aaa gcg tct gcc ctg gtg         48
Ser Asn Gly Met Asn Ala Ala Ala Ile Arg Lys Ala Ser Ala Leu Val
 1               5                  10                  15 gct cag atc gcc cat cga gac tgc tgt gac gat cct gcc tgc acc gtg         96
Ala Gln Ile Ala His Arg Asp Cys Cys Asp Asp Pro Ala Cys Thr Val
                20                  25                  30 aat aat cca ggc ctt tgc act tgaagatgct gctgccccag gaccctctga           147
Asn Asn Pro Gly Leu Cys Thr
         35 accacgacgt                                                             157
```

<210> SEQ ID NO 400
<211> LENGTH: 39
<212> TYPE: PRT
<213> ORGANISM: Conus virgo

<400> SEQUENCE: 400

```
Ser Asn Gly Met Asn Ala Ala Ala Ile Arg Lys Ala Ser Ala Leu Val
 1               5                  10                  15

Ala Gln Ile Ala His Arg Asp Cys Cys Asp Asp Pro Ala Cys Thr Val
                20                  25                  30

Asn Asn Pro Gly Leu Cys Thr
         35
```

<210> SEQ ID NO 401
<211> LENGTH: 154
<212> TYPE: DNA
<213> ORGANISM: Conus geographus
<220> FEATURE:
<221> NAME/KEY: CDS
<222> LOCATION: (1)..(114)

<400> SEQUENCE: 401

```
tct gat ggc ggg aat gcc gca gca aaa gag tct gac gtg atc gct ctg         48
Ser Asp Gly Gly Asn Ala Ala Ala Lys Glu Ser Asp Val Ile Ala Leu
```

```
                    1               5                  10                 15
acc gtc tgg aaa tgc tgt acc att cct tcc tgt tat gag aaa aaa aaa        96
Thr Val Trp Lys Cys Cys Thr Ile Pro Ser Cys Tyr Glu Lys Lys Lys
                   20                 25                 30 att aaa gca tgt gtc ttt tgacgacgct gatgctccag gaccctctga               144
Ile Lys Ala Cys Val Phe
            35 accacgacgt                                                             154

<210> SEQ ID NO 402
<211> LENGTH: 38
<212> TYPE: PRT
<213> ORGANISM: Conus geographus

<400> SEQUENCE: 402

Ser Asp Gly Gly Asn Ala Ala Ala Lys Glu Ser Asp Val Ile Ala Leu
 1               5                  10                 15

Thr Val Trp Lys Cys Cys Thr Ile Pro Ser Cys Tyr Glu Lys Lys Lys
                   20                 25                 30

Ile Lys Ala Cys Val Phe
            35

<210> SEQ ID NO 403
<211> LENGTH: 154
<212> TYPE: DNA
<213> ORGANISM: Conus regius
<220> FEATURE:
<221> NAME/KEY: CDS
<222> LOCATION: (1)..(114)

<400> SEQUENCE: 403 tct gat ggc gca gtc gac gac aaa gcg ttg gat cga atc gct gaa atc        48
Ser Asp Gly Ala Val Asp Asp Lys Ala Leu Asp Arg Ile Ala Glu Ile
 1               5                  10                 15 gtc agg aga gga tgc tgt ggc aat cct gcc tgt agc ggc tcc tcg aaa        96
Val Arg Arg Gly Cys Cys Gly Asn Pro Ala Cys Ser Gly Ser Ser Lys
                   20                 25                 30 gat gca ccc tct tgt ggt tgaagacgct gctgctccag gaccctctga               144
Asp Ala Pro Ser Cys Gly
            35 accacgacgt                                                             154

<210> SEQ ID NO 404
<211> LENGTH: 38
<212> TYPE: PRT
<213> ORGANISM: Conus regius

<400> SEQUENCE: 404

Ser Asp Gly Ala Val Asp Asp Lys Ala Leu Asp Arg Ile Ala Glu Ile
 1               5                  10                 15

Val Arg Arg Gly Cys Cys Gly Asn Pro Ala Cys Ser Gly Ser Ser Lys
                   20                 25                 30

Asp Ala Pro Ser Cys Gly
            35
```

What is claimed is:

1. An isolated α-conotoxin peptide selected from the group consisting of
   (i) a peptide having the amino acid sequence Gly-Cys-Cys-Ser-Asp-Xaa$_5$-Arg-Cys-Arg-Xaa$_4$-Arg-Cys-Arg (SEQ ID NO:9), wherein Xaa$_4$ is Tyr, nor-Tyr, mono-halo-Tyr, di-halo-Tyr, O-sulpho-Tyr, O-phospho-Tyr or nitro-Tyr; and Xaa$_5$ is Pro or hydroxy-Pro; and the C-terminus contains a carboxyl or amide group, and or
   (ii) a derivative thereof, wherein the derivative is a peptide of (i) in which a Ser residue may be substituted with Thr or a Ser residue modified to contain an O-glycan; an Arg residue may be substituted by Lys, ornithine, homoarginine, N-methyl-Lys, N,N-dimethyl-Lys, N,N,N-trimethyl-Lys or an unnatural basic amino acid; a Tyr residue may be substituted with an unnatural hydroxy containing amino acid, a 3-hydroxyl or 2-hydroxyl isomer of Tyr or a corresponding O-sulpho-derivative or O-phospho-derivative; the Cys residues may be in D or L configuration or may be substituted with homocysteine in the D or L configuration or pairs of Cys residues may be replaced pairwise with a Ser/(Glu or Asp) combination or a Lys/(Glu or Asp) combination; an Asp residue may be substituted with a synthetic acidic bioisoteric amino acid surrogate; and
wherein the unnatural basic amino acid is selected from the group consisting of N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala; the unnatural hydroxy containing amino acid is selected from the group consisting of 4-hydroxymethyl-Phe, 4-hydroxyphenyl-Gly, 2,6-dimethyl-Tyr and 5-amino-Tyr; and the synthetic acidic bioisoteric amino acid surrogate is selected from the group of a tetrazolyl derivative of Gly and a tetrazolyl derivative of Ala.

2. The isolated α-conotoxin peptide of claim 1, wherein Xaa$_4$ is Tyr.

3. The isolated α-conotoxin peptide of claim 1, wherein Xaa$_4$ is mono-iodo-Tyr.

4. The isolated α-conotoxin peptide of claim 1, wherein Xaa$_4$ is di-iodo-Tyr.

5. The isolated α-conotoxin peptide of claim 1, which is modified to contain an O-glycan, an S-glycan or an N-glycan.

6. An isolated α-conotoxin peptide precursor having the amino acid sequence of SEQ ID NO:244.

7. The isolated α-conotoxin peptide of claim 1, wherein Xaa$_5$ is Pro.

8. The isolated α-conotoxin peptide of claim 1, wherein Xaa$_5$ is hydroxy-Pro.

\* \* \* \* \*